US012492184B2

(12) United States Patent
Dai

(10) Patent No.: US 12,492,184 B2
(45) Date of Patent: Dec. 9, 2025

(54) HETEROARYL COMPOUNDS, PREPARATION METHODS AND USES THEREOF

(71) Applicants: InventisBio Co., Ltd., Shanghai (CN); InventisBio LLC, Florham Park, NJ (US)

(72) Inventor: Xing Dai, Short Hills, NJ (US)

(73) Assignees: InventisBio Co., Ltd., Shanghai (CN); InventisBio LLC, Short Hills, NJ (US)

( * ) Notice: Subject to any disclaimer, the term of this patent is extended or adjusted under 35 U.S.C. 154(b) by 363 days.

(21) Appl. No.: 18/268,681

(22) PCT Filed: Dec. 22, 2021

(86) PCT No.: PCT/CN2021/140271

§ 371 (c)(1),
(2) Date: Jun. 21, 2023

(87) PCT Pub. No.: WO2022/135430

PCT Pub. Date: Jun. 30, 2022

(65) Prior Publication Data

US 2024/0140929 A1 May 2, 2024

(30) Foreign Application Priority Data

Dec. 22, 2020 (WO) ................ PCT/CN2020/138305
Apr. 9, 2021 (WO) ................ PCT/CN2021/086083

(51) Int. Cl.

| | |
|---|---|
| ***C07D 401/12*** | (2006.01) |
| ***C07D 213/75*** | (2006.01) |
| ***C07D 237/24*** | (2006.01) |
| ***C07D 253/075*** | (2006.01) |
| ***C07D 401/14*** | (2006.01) |
| ***C07D 405/14*** | (2006.01) |
| ***C07D 413/14*** | (2006.01) |
| ***C07D 417/12*** | (2006.01) |
| ***C07D 417/14*** | (2006.01) |
| ***C07D 471/04*** | (2006.01) |
| ***C07D 513/04*** | (2006.01) |

(52) U.S. Cl.

CPC ......... *C07D 401/12* (2013.01); *C07D 213/75* (2013.01); *C07D 237/24* (2013.01); *C07D 253/075* (2013.01); *C07D 401/14* (2013.01); *C07D 405/14* (2013.01); *C07D 413/14* (2013.01); *C07D 417/12* (2013.01); *C07D 417/14* (2013.01); *C07D 471/04* (2013.01); *C07D 513/04* (2013.01)

(58) Field of Classification Search

CPC ... C07D 401/12; C07D 213/75; C07D 237/24
USPC ........................................................ 514/210.2
See application file for complete search history.

(56) References Cited

U.S. PATENT DOCUMENTS

| | | | |
|---|---|---|---|
| 8,901,124 | B2 | 12/2014 | Hermann et al. |
| 10,000,480 | B2 | 6/2018 | Moslin et al. |
| 2024/0025876 | A1 | 1/2024 | Li et al. |
| 2024/0101548 | A1 | 3/2024 | Wang et al. |
| 2024/0182429 | A1 | 6/2024 | Wang |
| 2024/0382477 | A1 | 11/2024 | Zhang et al. |

FOREIGN PATENT DOCUMENTS

| | | |
|---|---|---|
| CN | 104159891 | 11/2014 |
| CN | 111315737 | 6/2020 |
| CN | 111484480 | 8/2020 |
| CN | 111757878 | 10/2020 |
| CN | 113490664 | 10/2021 |
| CN | 113773262 | 12/2021 |
| CN | 115141149 | 10/2022 |
| WO | 2013054351 | 4/2013 |
| WO | 2014/074661 | 5/2014 |
| WO | 2018/111787 | 6/2018 |
| WO | 2018/118842 | 6/2018 |
| WO | 2019/079485 | 4/2019 |
| WO | 2019103952 | 5/2019 |

(Continued)

OTHER PUBLICATIONS

EP Search Report in related EP Application No. 21909426.5-1102 dated Dec. 11, 2024, 9 pages.

(Continued)

*Primary Examiner* — Kahsay Habte

(74) *Attorney, Agent, or Firm* — NIXON & VANDERHYE, PC

(57) ABSTRACT

Provided herein are novel compounds, for example, compounds having a Formula (I), or a pharmaceutically acceptable salt thereof. Also provided herein are methods of preparing the compounds and methods of using the compounds, for example, in inhibiting TYK2, and/or function of IL-12, IL-23 and/or INF-alpha, and/or in treating various associated diseases or disorders.

(I)

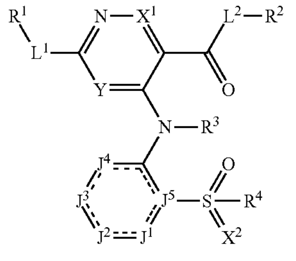

2 Claims, No Drawings

(56) References Cited

FOREIGN PATENT DOCUMENTS

| | | | | |
|---|---|---|---|---|
| WO | WO-2019103952 A1 * | 5/2019 | .............. | A61P 29/00 |
| WO | 2019/183186 | 9/2019 | | |
| WO | 2020086616 | 4/2020 | | |
| WO | 2020/092196 | 5/2020 | | |
| WO | 2020/159904 | 8/2020 | | |
| WO | 2020156311 | 8/2020 | | |
| WO | 2021/222153 | 11/2021 | | |
| WO | 2022/117016 | 6/2022 | | |
| WO | 2022/175745 | 8/2022 | | |
| WO | 2022/175747 | 8/2022 | | |
| WO | 2022/175752 | 8/2022 | | |
| WO | 2022/193499 | 9/2022 | | |
| WO | 2022/233286 | 11/2022 | | |
| WO | 2022/241171 | 11/2022 | | |
| WO | 2022/241172 | 11/2022 | | |
| WO | 2022/241173 | 11/2022 | | |
| WO | 2022/241174 | 11/2022 | | |
| WO | 2022/241175 | 11/2022 | | |

OTHER PUBLICATIONS

International Search Report in related PCT Application No. PCT/CN2021/140271 dated Mar. 22, 2022, 6 pages.

Track One U.S. Appl. No. 19/240,239, filed Jun. 17, 2025, 124 pages.

* cited by examiner

HETEROARYL COMPOUNDS, PREPARATION METHODS AND USES THEREOF

CROSS REFERENCE TO RELATED APPLICATIONS

This application claims priority of International Application Nos. PCT/CN2020/138305, filed on Dec. 22, 2020, and PCT/CN2021/086083, filed on Apr. 9, 2021, the content of each of which is incorporated herein by reference in its entirety.

BACKGROUND

Field of the Disclosure

In various embodiments, the present disclosure generally relates to novel heteroaryl compounds, compositions comprising the same, methods of preparing and methods of using the same, e.g., for inhibiting a kinase and/or for treating various diseases or disorders such as autoimmune diseases described herein.

Background

The cytokines are critical in mediating the pathobiology of a number of autoimmune diseases, including rheumatoid arthritis, multiple sclerosis, inflammatory bowel disease, and lupus. The heterodimeric cytokines interleukin IL-12 and IL-23 are produced by activated antigen-presenting cells and are critical in the differentiation and proliferation of Th1 and Th17 cells, two effector T cell lineages which play key roles in autoimmunity. IL-23 is essential for the survival and expansion of Th17 cells which produce pro-inflammatory cytokines such as IL-17A, IL-17F, IL-6 and TNF-a. IL-12 is essential for Th1 cell development and secretion of IFNg, a cytokine which plays a critical role in immunity by stimulating MHC expression, class switching of B cells to IgG subclasses, and the activation of macrophages. Genome-wide association studies have identified a number of loci associated with chronic inflammatory and autoimmune diseases that encode factors that function in the IL-23 and IL-12 pathways. These genes include IL23A, IL12A5, IL12B, IL12RB1, IL12RB2, IL23R, JAK2, TYK2, STAT3, and STAT4. Agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens. Genome-wide association studies have identified loci associated with lupus that encode factors that function in the type I interferon pathway, including IRF5, IKBKE, TYK2, and STAT4. In addition to lupus, there is evidence that aberrant activation of type I interferon-mediated pathways is important in the pathobiology of other autoimmune diseases such as Sjogren's syndrome and scleroderma. Agents which inhibit the action of type I interferon responses may be expected to have therapeutic benefit in human autoimmune disorders.

The Janus kinase (JAK) family is a small family of receptor-associated tyrosine kinases that are essential for the signal cascade downstream of type I and type II cytokine receptors. Type I and type II cytokine receptors—which compose a family of receptors bound by over 50 cytokines, interleukins, interferons (IFNs), colony-stimulating factors (CSFs) and hormones—share a distinct intracellular signaling pathway mediated by JAKs (JAK1, JAK2, JAK3 and tyrosine kinase 2 (TYK2)) that bind directly to the intracellular domains of type I and type II cytokine receptors and not to other classes of cytokine receptor. JAK-dependent cytokines are major contributors to immunopathology. The dependence of type I and type II cytokines on JAKs was established in a variety of genetic models from mutagenized cell lines and knockout mice to humans. Polymorphisms in JAK and signal transducer and activator of transcription (STAT) genes are associated with autoimmunity, and loss of function mutations cause immunodeficiency due to the inability of type I and type II cytokines to transmit signals through their receptors. The critical role of JAKs in type I and type II cytokine signaling strongly argues that interfering with the activity of these kinases could lead to a new class of immunomodulatory drugs.

Tyrosine kinase 2 (TYK2) is a member of the JAK family of nonreceptor tyrosine kinases and has been shown to be critical in regulating the signal transduction cascade downstream of receptors for IL-12, IL-23 and type I interferons in both mice and humans. TYK2 is the sole signaling messenger common to both IL12 and IL-23. TYK2 mediates the receptor-induced phosphorylation of members of the STAT family of transcription factors, an essential signal that leads to the dimerization of STAT proteins and the transcription of STAT dependent pro-inflammatory genes. TYK2-deficient mice are resistant to experimental models of colitis, psoriasis and multiple sclerosis, demonstrating the importance of TYK2-mediated signaling in autoimmunity and related disorders. In humans, individuals expressing an inactive variant of TYK2 are protected from multiple sclerosis and possibly other autoimmune disorders. Genome-wide association studies have shown variants of TYK2 active forms are associated with autoimmune disorders such as Crohn's Disease, psoriasis, systemic lupus erythematosus, and rheumatoid arthritis, further demonstrating the importance of TYK2 in autoimmunity.

Therapies have dramatically altered outcomes for a range of allergic, inflammatory and autoimmune disorders, including rheumatoid arthritis, psoriasis and inflammatory bowel disease (IBD). However, even for a disease such as rheumatoid arthritis, in which much progress has been made, most patients do not completely respond to currently available therapies, and there are relatively few examples of long-term remission after cessation of therapy. Therefore, despite substantial advances, there is still a major need for novel therapeutic strategies for immune and inflammatory diseases or disorders.

New compounds that inhibit the activity of TYK2 capable of modulating cytokines and/or interferons, such as IL-12, IL-23 and/or IFNα, should deliver a pharmacological response that favorably treats one or more of the conditions described herein and may provide substantial therapeutic benefits to a wide variety of patients in need thereof.

BRIEF SUMMARY

In various embodiments, the present disclosure provides novel compounds, pharmaceutical compositions, methods of preparing and using the same. Typically, the compounds herein are TYK2 inhibitors, which can modulate the function of IL-12, IL-23 and/or IFN-alpha. The compounds and compositions herein are useful for treating various diseases or disorders, such as an autoimmune and/or inflammatory disease, such as multiple sclerosis, rheumatoid arthritis, inflammatory bowel disease, systemic lupus erythematosus, psoriasis, psoriatic arthritis, Crohn's Disease, Sjogren's syndrome and/or scleroderma.

In some embodiments, the present disclosure provides a compound of Formula I, or a pharmaceutically acceptable salt thereof.

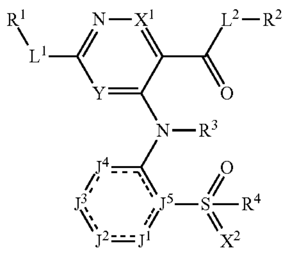

wherein $L^1$, $R^1$, $L^2$, $R^2$, $R^3$, $J^1$, $J^2$, $J^3$, $J^4$, $J^5$, $X^1$, Y, $X^2$, and $R^4$ are defined herein. In some embodiments, the present disclosure also provides compounds of subformulae of Formula I, such as Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1, as defined herein, or a pharmaceutically acceptable salt thereof. In some embodiments, the present disclosure also provides a specific compound selected from Compound Nos. 1-133, or a pharmaceutically acceptable salt thereof.

Certain embodiments of the present disclosure are directed to a pharmaceutical composition comprising one or more of the compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) and optionally a pharmaceutically acceptable excipient. The pharmaceutical composition described herein can be formulated for various routes of administration, such as oral administration or parenteral administration, etc.

Certain embodiments are directed to a method of treating a disease or disorder associated with TYK2, e.g., those mediated by IL-12, IL-23 and/or Interferon-alpha (INF-alpha). In some embodiments, the method comprises administering to a subject in need thereof a therapeutically effective amount of a compound of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) or a therapeutically effective amount of a pharmaceutical composition described herein. Diseases or disorders associated with TYK2 that can be treated with the methods herein include any of those known in the art and those described herein.

In some embodiments, a method of treating proliferative, metabolic, allergic, autoimmune and/or inflammatory disease or disorder is provided. In some embodiments, the method comprises administering to a subject in need thereof a therapeutically effective amount of a compound of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) or a therapeutically effective amount of a pharmaceutical composition described herein. Suitable proliferative, metabolic, allergic, autoimmune and/or inflammatory diseases or disorders that can be treated with the methods herein include any of those described herein.

In some embodiments, a method of treating an autoimmune and/or inflammatory disease or disorder is provided. In some embodiments, the method comprises administering to a subject in need thereof a therapeutically effective amount of a compound of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) or a therapeutically effective amount of a pharmaceutical composition described herein. Suitable autoimmune and/or inflammatory diseases or disorders that can be treated with the methods herein include any of those described herein.

In some embodiments, a method of treating a metabolic disease or disorder, e.g., described herein, such as type 2 diabetes or atherosclerosis, is provided. In some embodiments, the method comprises administering to a subject in need thereof a therapeutically effective amount of a compound of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) or a therapeutically effective amount of a pharmaceutical composition described herein.

In some embodiments, a method of treating cancer is provided. In some embodiments, the method comprises administering to a subject in need thereof a therapeutically effective amount of a compound of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) or a therapeutically effective amount of a pharmaceutical composition described herein.

In some embodiments, a method of treating multiple sclerosis, rheumatoid arthritis, inflammatory bowel disease, systemic lupus erythematosus, psoriasis, psoriatic arthritis, Crohn's Disease, Sjogren's syndrome and/or scleroderma is provided. In some embodiments, the method comprises administering to a subject in need thereof a therapeutically effective amount of a compound of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) or a therapeutically effective amount of a pharmaceutical composition described herein.

The administering in the methods herein is not limited to any particular route of administration. For example, in some embodiments, the administering can be orally, nasally, transdermally, pulmonary, inhalationally, buccally, sublingually, intraperitoneally, subcutaneously, intramuscularly, intravenously, rectally, intrapleurally, intrathecally and parenterally. The compounds of the present disclosure can be used as a monotherapy or in a combination therapy.

It is to be understood that both the foregoing summary and the following detailed description are exemplary and explanatory only, and are not restrictive of the invention herein.

DETAILED DESCRIPTION

In various embodiments, provided herein are novel heteroaryl compounds, pharmaceutical compositions, methods of preparation and methods of use. The compounds herein typically can be a TYK2 inhibitor and can be useful for treating various diseases or disorders, such as those described herein, e.g., an autoimmune and/or inflammatory disease, such as multiple sclerosis, rheumatoid arthritis, inflammatory bowel disease, systemic lupus erythematosus, psoriasis, psoriatic arthritis, Crohn's Disease, Sjogren's syndrome and/or scleroderma.

Compounds

In some embodiments, the present disclosure provides a compound of Formula I, or a pharmaceutically acceptable salt thereof:

Formula I

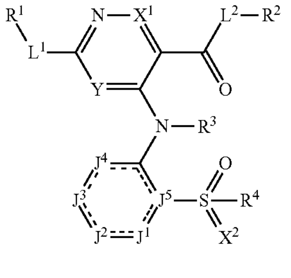

wherein:

$X^1$ is $CR^{10}$ or N;

Y is $CR^{10}$ or N;

$L^1$ is $NR^{11}$,

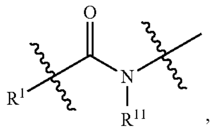,

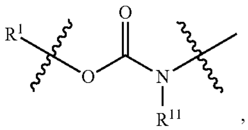,

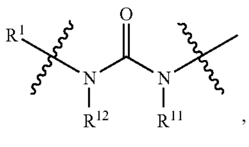, or null;

$L^2$ is optionally substituted $C_{1-4}$ alkylene, optionally substituted $C_{1-4}$ heteroalkylene, optionally substituted $C_{3-6}$ cycloalkylene, optionally substituted 4-6 membered heterocyclylene, or NH;

$X^2$ is O or $NR^{13}$;

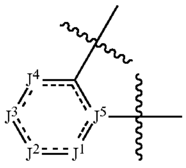

represents an optionally substituted phenyl or optionally substituted 6-membered heteroaryl ring, wherein:

$J^1$ is $CR^{14}$ or N;

$J^2$ is $CR^{15}$ or N;

$J^3$ is $CR^{16}$ or N;

$J^4$ is $CR^{17}$ or N; and $J^5$ is C;

or

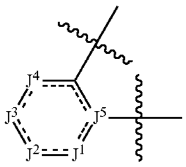

represents an optionally substituted 5-membered heteroaryl ring, wherein:

$J^P$ is $CR^8$, $NR^{19}$, O, S, or N;

$J^4$ is $CR^{20}$, $NR^{21}$, O, S, or N;

$J^5$ is C or N; and one of $J^2$ and $J^3$ does not exist, and the other of $J^2$ and $J^3$ is O, S, N, $NR^{22}$, or $CR^{23}$;

wherein:

$R^1$ is hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ heteroalkyl, an optionally substituted $C_{3-10}$ carbocyclic ring, an optionally substituted 4-10 membered heterocyclic ring, an optionally substituted phenyl, or an optionally substituted heteroaryl;

$R^2$ is hydrogen, $CD_3$, an optionally substituted $C_{1-4}$ alkyl, or an optionally substituted $C_{1-4}$ heteroalkyl;

$R^3$ is hydrogen, an optionally substituted $C_{1-6}$ alkyl, an optionally substituted $C_{1-6}$ heteroalkyl, or a nitrogen protecting group;

$R^4$ is hydrogen, an optionally substituted $C_{1-6}$ alkyl, or an optionally substituted $C_{1-6}$ heteroalkyl;

wherein:

$R^{10}$ at each occurrence is hydrogen, halogen, CN, OH, $C_{1-4}$ alkyl optionally substituted with F, $C_{1-4}$ alkoxy optionally substituted with F, or $C_{3-6}$ cycloalkyl optionally substituted with one or more substituents independently selected from F, methyl, and OH;

each of $R^{11}$, $R^{12}$, and $R^{13}$ is independently hydrogen, optionally substituted $C_{1-6}$ alkyl, optionally substituted $C_{1-4}$ heteroalkyl, or optionally substituted $C_{3-6}$ cycloalkyl; or $R^{11}$ and $R^{12}$, together with the intervening atoms, are joined to form an optionally substituted 5-8 membered ring structure;

$R^{14}$, $R^{15}$, $R^{16}$, $R^{17}$, $R^{18}$, $R^{20}$, and $R^{23}$ are each independently halogen, $R^A$, $OR^A$, $SR^A$, $S(O)R^A$, $S(O)_2R^A$, $COR^A$, $COOR^A$, CN, $NR^BR^C$, $CONR^BR^C$, $S(O)_2NR$-

${}^{B}R^{C}$, or $NO_2$, $R^{19}$, $R^{21}$, and $R^{22}$ are each independently $R^A$, $COR^A$, $COOR^A$, $S(O)_2R^A$, $S(O)_2NR^BR^C$, or $CONR^BR^C$, wherein $R^A$ at each occurrence is independently hydrogen, an optionally substituted $C_{1-6}$ alkyl, optionally substituted $C_{2-6}$ alkenyl, optionally substituted $C_{2-6}$ alkynyl, optionally substituted $C_{3-8}$ carbocyclyl, optionally substituted $C_{1-4}$ heteroalkyl, optionally substituted 4-8 membered heterocyclyl, optionally substituted 5 or 6 membered heteroaryl, or optionally substituted phenyl, wherein each of $R^B$ and $R^C$ at each occurrence is independently $R^A$, —C(O)—$R^A$, —$COOR^A$, $S(O)_2R^A$, $CONR^{B'}R^{C'}$, wherein each of $R^{B'}$ and $R^{C'}$ is independently $R^A$;

or $R^B$ and $R^C$ together with the nitrogen they are both attached to are joined to form an optionally substituted 4-8 membered ring structure;

or $R^4$ and $R^{13}$, as applicable, together with the intervening atoms, are joined to form an optionally substituted 5-8 membered ring structure;

or $R^4$ and $R^{13}$, $R^4$ and $R^{14}$, $R^{13}$ and $R^{14}$, $R^{14}$ and $R^{15}$, $R^{15}$ and $R^{16}$, or $R^{16}$ and $R^{17}$, as applicable, together with the respective intervening atoms, are joined to form an optionally substituted 5-8 membered ring structure; or $R^{13}$ and $R^{18}$, $R^{13}$ and $R^{19}$, $R^{18}$ and $R^{22}$, $R^{18}$ and $R^{23}$, $R^{19}$ and $R^{22}$, $R^{19}$ and $R^{23}$, $R^{20}$ and $R^{22}$, $R^{20}$ and $R^{23}$, $R^{21}$ and $R^{22}$, or $R^{21}$ and $R^{23}$, as applicable, together with the respective intervening atoms, are joined to form an optionally substituted 5-8 membered ring structure.

It should be clear to those skilled in the art that when "$\overline{\overline{---}}$" is used in a drawing to connect two atoms, it should be understood that the bond between the two atoms can be a single bond or a double bond as valency permits.

To be clear, when it is said that $R^4$ and $R^{14}$, $R^{13}$ and $R^{14}$, $R^{14}$ and $R^{15}$, $R^{15}$ and $R^{16}$, or $R^{16}$ and $R^{17}$, as applicable, together with the respective intervening atoms, are joined to form an optionally substituted 5-8 membered ring structure, it should be understood that only one of the described pairs that are present in a formula according to Formula I may form the optionally substituted ring structure. For example, when $R^{13}$ and $R^{14}$, together with the intervening atoms, are joined to form an optionally substituted 5-8 membered ring structure, then it should be understood that $R^4$ and $R^{14}$, $R^{14}$ and $R^{15}$, $R^{15}$ and $R^{16}$, and $R^{16}$ and $R^{17}$, as applicable, do not also form a ring structure; rather, in such embodiments, $R^{15}$, $R^{16}$, and $R^{17}$, as applicable, and $R^4$ should be understood as having the definition described herein without reference to its potential to forming a ring with another variable, for example, in such embodiments, $R^{15}$, $R^{16}$, and $R^{17}$, when present, should be understood as independently being halogen, $R^A$, $OR^A$, $SR^A$, $S(O)R^A$, $S(O)_2R^A$, $COR^A$, $COOR^A$, CN, $NR^BR^C$, $CONR^BR^C$, $S(O)_2NR^BR^C$, or $NO_2$ as defined herein. Also, when $R^4$ and $R^{13}$ are joined to form an optionally substituted 5-8 membered ring structure, $R^4$ and $R^{14}$ typically do not also form an optionally substituted 5-8 membered ring structure, and vice versa. Similarly, in Formula I herein, when it is said that $R^{13}$ and $R^{18}$, $R^{13}$ and $R^{19}$, $R^{18}$ and $R^{22}$, $R^{18}$ and $R^{23}$, $R^{19}$ and $R^{22}$, $R^{19}$ and $R^{23}$, $R^{20}$ and $R^{22}$, $R^{20}$ and $R^{23}$, $R^{21}$ and $R^{22}$, or $R^{21}$ and $R^{23}$, as applicable, together with the respective intervening atoms, are joined to form an optionally substituted 5-8 membered ring structure, it should be understood that only one of the described pairs that are present in a formula according to Formula I may form the optionally substituted ring structure.

The compound of Formula I (including any of the applicable sub-formulae as described herein) can exist in the form of an individual enantiomer, diastereomer, and/or geometric isomer, as applicable, or a mixture of stereoisomers, including racemic mixtures and mixtures enriched in one or more stereoisomers. In some embodiments, when applicable, the compound of Formula I (including any of the applicable sub-formulae as described herein) can exist as an isolated individual enantiomer substantially free (e.g., with less than 20%, less than 10%, less than 5%, less than 1%, by weight, by HPLC area, or both, or with a non-detectable amount) of the other enantiomer.

Typically, $X^1$ in Formula I is N.

In some embodiments, $X^1$ in Formula I can also be $CR^{10}$, wherein $R^{10}$ is defined herein. For example, $R^{10}$ can be hydrogen, F, Cl, CN, OH, $C_{1-4}$ alkyl optionally substituted with F, or $C_{1-4}$alkoxy optionally substituted with F. In some embodiments, $X^1$ in Formula I is CH.

In some embodiments, Y in Formula I is N.

In some embodiments, Y in Formula I is $CR^{10}$, wherein $R^{10}$ is defined herein. For example, $R^{10}$ can be hydrogen, F, Cl, CN, OH, $C_{1-4}$ alkyl optionally substituted with F, or $C_{1-4}$ alkoxy optionally substituted with F.

Typically, Y in Formula I is CH.

Typically, $X^1$ is N and Y is CH, and the compound of Formula I can be characterized as having Formula I-1:

Formula I-1

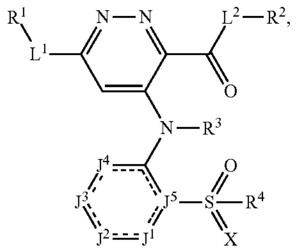

wherein the variables $L^1$, $R^1$, $L^2$, $R^2$, $R^3$, $J^1$, $J^2$, $J^3$, $J^4$, $J^5$, $X^2$, and $R^4$ include any of those described herein in any combination.

In some embodiments, $X^1$ and Y can both be CH and the compound of Formula I can be characterized as having Formula I-2:

Formula I-2

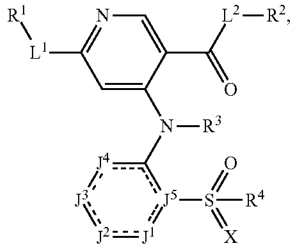

wherein the variables $L^1$, $R^1$, $L^2$, $R^2$, $R^3$, $J^1$, $J^2$, $J^3$, $J^4$, $J^5$, $X^2$, and $R^4$ include any of those described herein in any combination.

In some embodiments, $X^1$ and Y can both be N and the compound of Formula I can be characterized as having Formula I-3:

Formula I-3

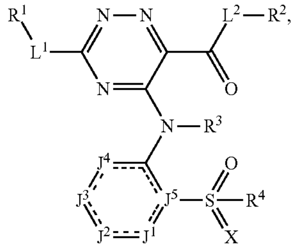

wherein the variables $L^1$, $R^1$, $L^2$, $R^2$, $R^3$, $J^1$, $J^2$, $J^3$, $J^4$, $J^5$, $X^2$, and $R^4$ include any of those described herein in any combination.

The

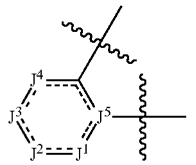

moiety (alternatively referred to herein as M-10) in Formula I (e.g., Formula I-1, I-2, or I-3) typically represents an optionally substituted phenyl or optionally substituted 6-membered heteroaryl ring. In such embodiments, $J^1$ can be $CR^{14}$ or N; $J^2$ can be $CR^{15}$ or N; $J^3$ can be $CR^{16}$ or N; $J^4$ can be $CR^{17}$ or N; and $J^5$ is C, wherein $R^{14}$, $R^{15}$, $R^{16}$, and $R^{17}$ include any of those described herein in any combination.

In embodiments wherein M-10 represents an optionally substituted phenyl or optionally substituted 6-membered heteroaryl ring, $J^1$ is typically $CR^{14}$, wherein $R^{14}$ is defined herein. However, in some embodiments wherein M-10 represents an optionally substituted 6-membered heteroaryl ring, $J^1$ can also be N. In some embodiments, $J^1$ is $CR^{14}$, and $R^{14}$ can be hydrogen, halogen, OH, CN, or $R^A$, wherein $R^A$ is defined herein, for example, in some embodiments, $R^{14}$ can be an optionally substituted $C_{1-6}$ alkyl, optionally substituted $C_{3-6}$ cycloalkyl, optionally substituted $C_{1-4}$ heteroalkyl, or optionally substituted 4-8 membered heterocyclyl having 1-2 ring heteroatoms independently selected from N, O, and S. In some embodiments, $J^1$ is $CR^{14}$, and $R^{14}$ can be hydrogen, halogen (e.g., F or Cl), $G^E$, —($C_{1-4}$ alkylene)-$G^E$, OH, CN, $OG^E$, or O—($C_{1-4}$ alkylene)-$G^E$, wherein $G^E$ is $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $J^1$ is $CR^{14}$, and $R^{14}$ can be $G^E$ as defined herein. In some embodiments, $J^1$ is $CR^{14}$, and $R^{14}$ is hydrogen, F, Cl, CN, $C_{1-4}$ alkyl (e.g., methyl, ethyl, n-propyl, isopropyl), hydroxyl substituted $C_{1-4}$ alkyl (e.g., hydroxymethyl, hydroxyethyl, etc.), fluorine substituted $C_{1-4}$ alkyl (e.g., fluoromethyl, difluoromethyl, trifluoromethyl, etc.), OH, cyclopropyl, cyclobutyl, azetidinyl, $C_{1-4}$ alkoxy (e.g., methoxy, ethoxy, isopropoxy, etc.), fluorine substituted $C_{1-4}$ alkoxy (e.g., $CF_3O$—, $CF_3CH_2O$—, etc.), cyclopropoxy or cyclobutoxy. As used herein, hydroxyl substituted $C_{1-4}$ alkyl refers to a $C_{1-4}$ alkyl which is substituted with one or two hydroxyl groups, such as —$CH_2$—OH, —$CH(CH_3)$—OH or —$CH_2CH_2OH$. As used herein, fluorine substituted $C_{1-4}$ alkyl refers to a $C_{1-4}$ alkyl which is substituted with 1-3 fluorines, e.g., —$CF_3$, —$CH_2F$, —$CHF_2$, etc. As used herein, fluorine substituted $C_{1-4}$ alkoxy refers to a $C_{1-4}$ alkoxy substituted with 1-3 fluorines, e.g., $CF_3O$—, $CF_3CH_2O$—, etc. In some embodiments, $J^1$ is $CR^{14}$, and $R^{14}$ can be joined with $R^4$, $X^2$, or $R^{15}$, together with the respective intervening atoms, to form an optionally substituted 5-8 membered ring structure, such as a 5-8 membered monocyclic carbocyclic or monocyclic heterocyclic ring, which is optionally substituted with one or more permissible substituents described herein. In any of the embodiments described herein, unless otherwise specified or contrary from context, when $J^1$ is $CR^{14}$, $R^{14}$ can be hydrogen, F, $CH_3$, $CH_2OH$, $OCH_3$, or cyclopropyl.

In embodiments wherein M-10 represents an optionally substituted phenyl or optionally substituted 6-membered heteroaryl ring, $J^2$ is typically $CR^{15}$, wherein $R^{15}$ is defined herein. However, in some embodiments wherein M-10 represents an optionally substituted 6-membered heteroaryl ring, $J^2$ can also be N. In some embodiments, $J^2$ is $CR^{15}$, and $R^{15}$ can be hydrogen, halogen, OH, CN, or $R^A$, wherein $R^A$ is defined herein, for example, in some embodiments, $R^{15}$ can be an optionally substituted $C_{1-6}$ alkyl, optionally substituted $C_{3-6}$ cycloalkyl, optionally substituted $C_{1-4}$ heteroalkyl, or optionally substituted 4-8 membered heterocyclyl having 1-2 ring heteroatoms independently selected from N, O, and S. In some embodiments, $J^2$ is $CR^{15}$ and $R^{15}$ can be hydrogen, halogen (e.g., F or Cl), $G^E$, —($C_{1-4}$ alkylene)-$G^E$, OH, CN, $OG^E$, O—($C_{1-4}$ alkylene)-$G^E$, $SG^E$, S(O)-$G^E$, or $S(O)_2$-$G^E$, wherein $G^E$ is $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $J^2$ is $CR^{15}$, and $R^{15}$ can be $G^E$ as defined herein. In some embodiments, $J^2$ is $CR^{15}$, and $R^{15}$ can be an optionally substituted 4-6 membered heterocyclyl having 1-2 ring heteroatoms independently selected from N, O, and S, such as an oxetanyl, morpholinyl, or azetidinyl, optionally substituted with one or more (e.g., 1, 2, or 3) substituents independently selected from F, $C_{1-4}$ alkyl (e.g., methyl), and OH. In some embodiments, $J^2$ is $CR^{15}$, and $R^{15}$ can be $OG^E$, wherein $G^E$ is a $C_{1-4}$ alkyl, hydroxyl substituted $C_{1-4}$ alkyl (e.g., hydroxymethyl, hydroxyethyl, etc.), fluorine substituted $C_{1-4}$ alkyl (e.g., fluoromethyl, difluoromethyl, trifluoromethyl, etc.), or 4-6 membered heterocyclyl having 1-2 ring heteroatoms independently selected from N, O, and S, such as oxetanyl, which is optionally substituted with one or more (e.g., 1, 2, or 3) substituents independently selected from F, $C_{1-4}$ alkyl (e.g., methyl), and OH. In some embodiments, $J^2$ is $CR^{15}$, and $R^{15}$ can be O—($C_{1-4}$ alkylene)-$G^F$, wherein $G^F$ is OH, $NH_2$, an optionally substituted $C_{1-4}$ alkyl, optionally substituted $C_{1-4}$ heteroalkyl, optionally substituted $C_{3-6}$ cycloalkyl, or optionally substituted 4-6 membered heterocyclyl having 1-2 ring heteroatoms independently selected from N, O, and S. In some embodiments, $J^2$ is $CR^{15}$, and $R^{15}$ can be O—($C_{1-4}$ alkylene)-$G^F$, wherein $G^F$ is OH, $NH_2$, NH($C_{1-4}$ alkyl), N($C_{1-4}$ alkyl)($C_{1-4}$ alkyl), $C_{1-4}$ alkoxy (e.g., methoxy, ethoxy, isopropoxy, etc.), fluorine substituted $C_{1-4}$alkoxy (e.g., $CF_3O$—, $CHF_2O$—, $CF_3CH_2O$—, etc.), hydroxyl substituted $C_{1-4}$ alkoxy (e.g., —O—$CH_2CH_2OH$), alkoxy substituted $C_{1-4}$ alkoxy (e.g., —O—$CH_2CH_2OMe$), O-Acyl (such as O—CH(O), O—C(O)$CH_3$), NH-Acyl, N($C_{1-4}$ alkyl)-Acyl, or 4-6 membered heterocyclyl having 1-2 ring heteroatoms independently selected from N, O, and S, such as oxetanyl, which is optionally substituted with one or more (e.g., 1, 2, or 3) substituents independently selected from F, $C_{1-4}$ alkyl (e.g., methyl), and OH. As used herein, it should be understood that the two $C_{1-4}$ alkyl groups in the expression "N($C_{1-4}$ alkyl)($C_{1-4}$ alkyl)" can be the same or different. In some embodiments, $J^2$ is $CR^{15}$, and $R^{15}$ can be O—($C_{1-4}$ alkylene)-$G^F$, wherein the $C_{1-4}$ alkylene (connection from left (O) to right ($G^F$)) is —$CH_2CH_2$—, —$CH(CH_3)CH_2$—, —$CH_2CH(CH_3)$—, or —$CH_2C(CH_3)_2$—, and $G^F$ is OH, $NH_2$, NH($C_{1-4}$ alkyl), N($C_{1-4}$ alkyl)($C_{1-4}$ alkyl), $C_{1-4}$ alkoxy (e.g., methoxy, ethoxy, isopropoxy, etc.), fluorine substituted $C_{1-4}$ alkoxy (e.g., $CF_3O$—, $CHF_2O$—, $CF_3CH_2O$—, etc.), hydroxyl substituted $C_{1-4}$ alkoxy (e.g., —O—$CH_2CH_2OH$), or alkoxy substituted $C_{1-4}$ alkoxy (e.g., —O—$CH_2CH_2OMe$). In some embodiments, $J^2$ is $CR^{15}$, and $R^{15}$ is hydrogen, F, Cl, CN, $C_{1-4}$ alkyl (e.g., methyl, ethyl, n-propyl, isopropyl), hydroxyl substituted $C_{1-4}$ alkyl (e.g., hydroxymethyl, hydroxyethyl, etc.), fluorine substituted $C_{1-4}$ alkyl (e.g., fluoromethyl, difluoromethyl, trifluoromethyl, etc.), OH, cyclopropyl, cyclobutyl, azetidinyl, $C_{1-4}$ alkoxy (e.g., methoxy, ethoxy, isopropoxy, etc.), fluorine substituted $C_{1-4}$alkoxy (e.g., $CF_3O$—, $CF_3CH_2O$—, etc.), $C_{1-4}$ alkylthio (e.g., $CH_3S$—), fluorine substituted $C_{1-4}$ alkylthio (e.g., $CF_3S$—), cyclopropoxy or cyclobutoxy. As would be understood by those skilled in the art, an alkylthio group refers to a group having a general structure of R—S—, wherein R is an alkyl. As used herein, fluorine substituted $C_{1-4}$ alkylthio refers to a $C_{1-4}$ alkylthio group wherein the $C_{1-4}$ alkyl portion is substituted with 1-3 fluorines, such as $CF_3S$—. In some embodiments, $J^2$ is $CR^{15}$, and $R^{15}$ can be joined with $R^{14}$ or $R^{16}$, together with the respective intervening atoms, to form an optionally substituted 5-8 membered ring structure, such as a 5-8 membered monocyclic carbocyclic or monocyclic heterocyclic ring, which is optionally substituted with one or more permissible substituent described herein. For example, in some embodiments, $J^2$ is $CR^{15}$, and can be joined with $R^{16}$, together with the intervening atoms, to form

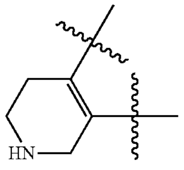

or

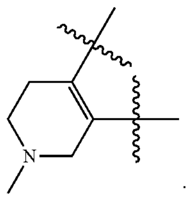

.

In any of the embodiments described herein, unless otherwise specified or contrary from context, when $J^2$ is $CR^{15}$, $R^{15}$ can be hydrogen, F, Cl, CN, $CH_3$, $CH_2CH_3$, $CHF_2$, $CF_3$, $OCH_3$, $OCH_2CH_3$, O—$CH(CH_3)_2$, $OCF_3$, $SCF_3$, cyclopropyl, or

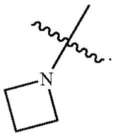 [SMILES: *N1CCC1]

.

In any of the embodiments described herein, unless otherwise specified or contrary from context, when $J^2$ is $CR^{15}$, $R^{15}$ can be selected from:

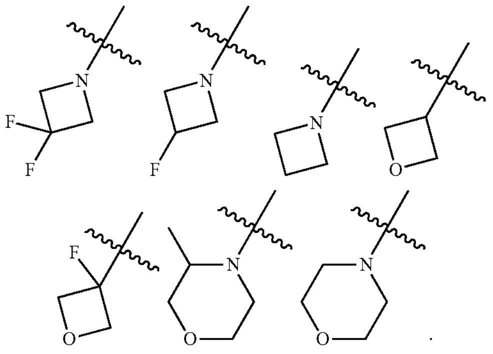

.

In any of the embodiments described herein, unless otherwise specified or contrary from context, when $J^2$ is $CR^{15}$, $R^{15}$ can be selected from:

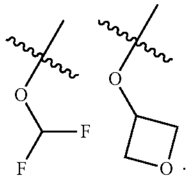

.

In any of the embodiments described herein, unless otherwise specified or contrary from context, when $J^2$ is $CR^5$, $R^{15}$ can be selected from:

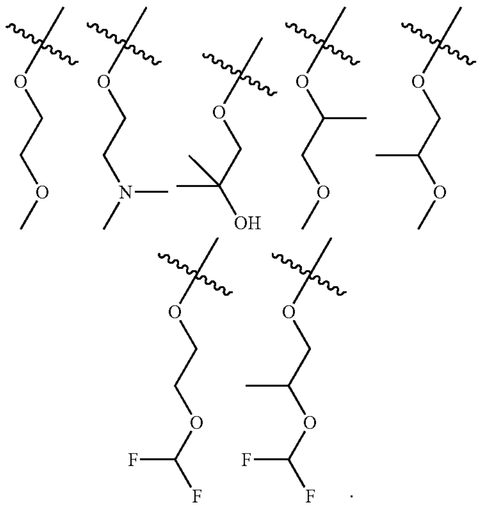

.

When $R^{15}$ contains one or more chiral centers, all of the potential stereoisomers and mixtures thereof (such as racemic mixtures) are contemplated by this disclosure. For example, in some embodiments, the $J^2$ is $CR^{15}$, $R^{15}$ can be selected from the following stereoisomers:

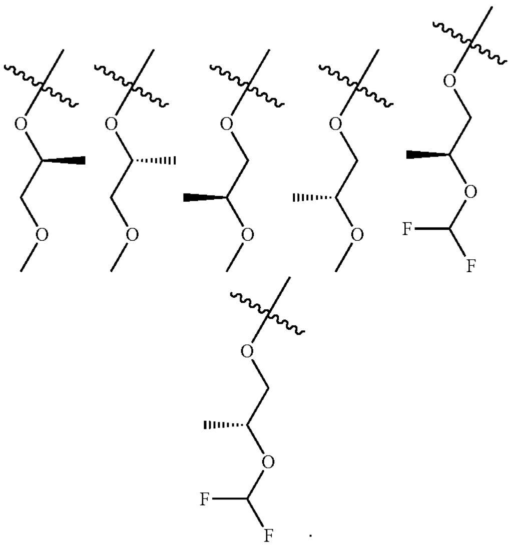

In some embodiments, with respect to the foregoing as-drawn chiral center, the compound can exist predominantly as the as-drawn enantiomer, such as having less than 20%, less than 10%, less than 5%, less than 1%, by weight, by HPLC area, or both, or having a non-detectable amount of the other corresponding enantiomer.

In embodiments wherein M-10 represents an optionally substituted phenyl or optionally substituted 6-membered heteroaryl ring, $J^3$ is typically $CR^{16}$, wherein $R^{16}$ is defined herein. However, in some embodiments wherein M-10 represents an optionally substituted 6-membered heteroaryl ring, $J^{16}$ can also be N. In some embodiments, $J^3$ is $CR^{16}$, and $R^{16}$ can be hydrogen, halogen, OH, CN, or $R^A$, wherein $R^A$ is defined herein, for example, in some embodiments, $R^{16}$ can be an optionally substituted $C_{1-6}$ alkyl, optionally substituted $C_{3-6}$ cycloalkyl, optionally substituted $C_{1-4}$ heteroalkyl, or optionally substituted 4-8 membered heterocyclyl having 1-2 ring heteroatoms independently selected from N, O, and S. In some embodiments, $J^3$ is $CR^{16}$, and $R^{16}$ can be hydrogen, F, Cl, $G^E$, —($C_{1-4}$ alkylene)-$G^E$, OH, CN, $OG^E$, or O—($C_{1-4}$ alkylene)-$G^E$, wherein $G^E$ is $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $J^3$ is $CR^{16}$, and $R^{16}$ can be $G^E$ as defined herein. In some embodiments, $J^3$ can be $CR^{16}$ and $R^{16}$ can be hydrogen, F, Cl, CN, $C_{1-4}$ alkyl (e.g., methyl, ethyl, n-propyl, isopropyl), fluorine substituted $C_{1-4}$ alkyl (e.g., fluoromethyl, difluoromethyl, trifluoromethyl, etc.), OH, $C_{3-6}$ cycloalkyl (e.g., cyclopropyl, cyclobutyl, etc.), $C_{1-4}$ alkoxy (e.g., methoxy, ethoxy etc.), fluorine substituted $C_{1-4}$ alkoxy (e.g., $CF_3O$—, $CF_3CH_2O$—, etc.), cyclopropoxy or cyclobutoxy. In some embodiments, $J^3$ is $CR^{16}$, and $R^{16}$ can be joined with $R^{15}$ or $R^{17}$, together with the respective intervening atoms, to form an optionally substituted 5-8 membered ring structure, such as a 5-8 membered monocyclic carbocyclic or monocyclic heterocyclic ring, which is optionally substituted with one or more permissible substituent described herein. In any of the embodiments described herein, unless otherwise specified or contrary from context, when $J^3$ is $CR^{16}$, $R^{16}$ can be hydrogen, F, Cl, CN, $C_{1-4}$ alkyl, $C_{1-4}$ alkoxy, cyclopropyl, or cyclobutyl.

In embodiments wherein M-10 represents an optionally substituted 6-membered heteroaryl ring, $J^4$ is typically N. However, in some embodiments M-10 represents an optionally substituted 6-membered heteroaryl ring, $J^4$ can also be $CR^{17}$, wherein $R^{17}$ is defined herein, such as hydrogen.

In embodiments wherein M-10 represents an optionally substituted phenyl or optionally substituted 6-membered heteroaryl ring, the combination of $J^1$, $J^2$, $J^3$, and $J^4$ is not particularly limited. For example, in some embodiments, the

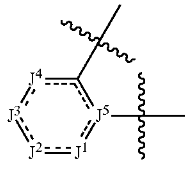

moiety in Formula I can be an optionally substituted phenyl. In some embodiments, the

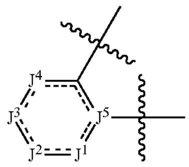

moiety in Formula I can be an optionally substituted pyridine.

In some preferred embodiments, the

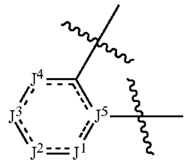

moiety in Formula I can be an optionally substituted pyridyl with $J^4$ being N. For example, in some embodiments, the compound of Formula I can be characterized as having Formula I-1-A:

Formula I-1-A

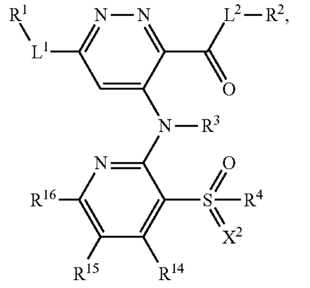

wherein the variables $L^1$, $R^1$, $L^2$, $R^2$, $R^3$, $R^4$, $R^{15}$, $R^{16}$, $X^2$, and $R^4$ include any of those described herein in any combination.

For example, in some embodiments, in Formula I-1-A, $R^{14}$ can be hydrogen. In some embodiments, in Formula I-1-A, $R^{15}$ can be hydrogen. In some embodiments, in Formula I-1-A, $R^{16}$ can be hydrogen. In some embodiments, in Formula I-1-A, one of $R^{14}$ and $R^{15}$ is hydrogen and the other of $R^{14}$ and $R^{15}$ is not hydrogen, for example, in some embodiments, $R^{14}$ is hydrogen and $R^{15}$ is not hydrogen. In some embodiments, in Formula I-1-A, both $R^{14}$ and $R^{15}$ are not hydrogen. In some embodiments, in Formula I-1-A, both $R^{14}$ and $R^{15}$ are hydrogen. In some embodiments, in Formula I-1-A, both $R^{14}$ and $R^{16}$ are hydrogen, and $R^{15}$ is not hydrogen. In some embodiments, in Formula I-1-A, all of $R^{14}$, $R^{15}$, and $R^{16}$ are hydrogen. In some embodiments, in Formula I-1-A, $R^{14}$ and $R^{15}$, together with the intervening atoms, are joined to form a 5-8 membered ring, such as a 5-8 membered carbocyclic or heterocyclic ring, which is optionally substituted. In some embodiments, in Formula I-1-A, $R^{15}$ and $R^{16}$, together with the intervening atoms, are joined to form a 5-8 membered ring, such as a 5-8 membered carbocyclic or heterocyclic ring, which is optionally substituted. In some embodiments, in Formula I-1-A, $X^2$ is $NR^{13}$, and $R^{14}$ and $R^{13}$, together with the intervening atoms, are joined to form a 5-8 membered heterocyclic ring, which is optionally substituted.

For example, in some embodiments, the compound of Formula I-1-A can be characterized as having a Formula I-1-A-1, I-1-A-2, I-1-A-3, I-1-A-4, I-1-A-5, or I-1-A-6:

Formula I-1-A-1

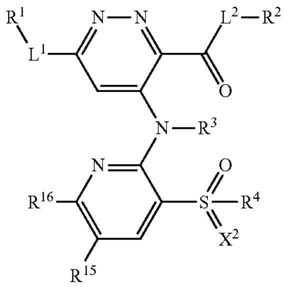

Formula I-1-A-2

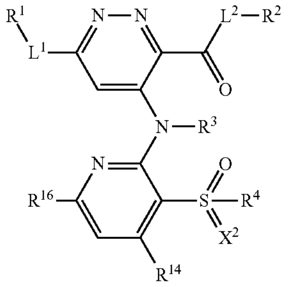

Formula I-1-A-3

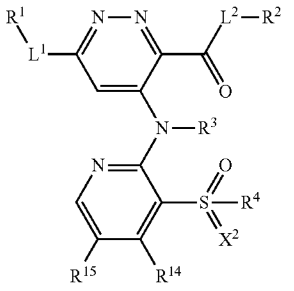

-continued

Formula I-1-A-4

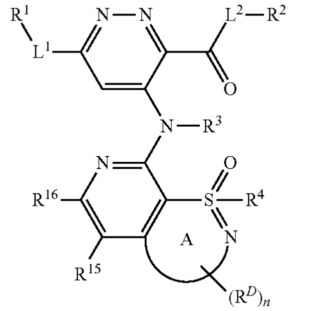

Formula I-1-A-5

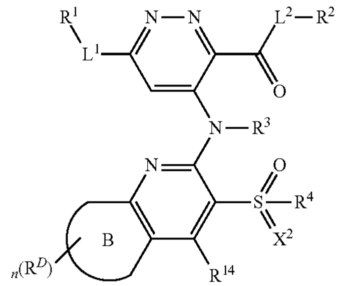

Formula I-1-A-6

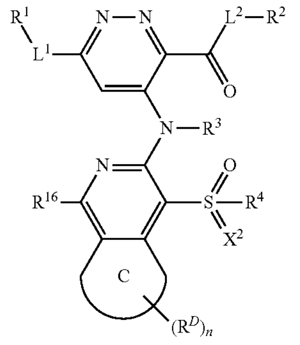

wherein:

ring A in Formula I-1-A-4 is a 5-8 membered ring, optionally containing one or more ring heteroatoms independently selected from N, O, or S, in addition to the ring S and N atoms shown therein, ring B in Formula I-1-A-5 is a 5-8 membered ring, optionally containing one or more ring heteroatoms independently selected from N, O, or S, ring C in Formula I-1-A-6 is a 5-8 membered ring, optionally containing one or more ring heteroatoms independently selected from N, O, or S, wherein:

n is an integer of 0-6 (e.g., 0, 1, or 2), as valency permits;

$R^D$ at each occurrence is independently halogen, $G^A$, $OG^A$, OH, CN, or $NG^BG^C$, or two $R^D$ form a bond, oxo, or a ring structure;

wherein $G^A$ at each occurrence is independently an optionally substituted $C_{1-6}$ alkyl, optionally substituted $C_{3-6}$ cycloalkyl, optionally substituted $C_{1-4}$ heteroalkyl, or optionally substituted 4-8 membered heterocyclyl, wherein $G^B$ and $G^C$ at each occurrence are independently hydrogen, $G^A$, $COG^A$, or $S(O)_2G^A$, wherein the variables $L^1$, $R^1$, $L^2$, $R^2$, $R^3$, $R^{14}$, $R^{15}$, $R^{16}$, $X^2$, and $R^4$ include any of those described herein in any combination. In some embodiments, ring A in Formula I-1-A-4 is a 5, 6, or 7 membered ring, containing no additional ring heteroatoms or one additional ring nitrogen or ring oxygen. In some embodiments, ring B in Formula I-1-A-5 is a 5, 6, or 7 membered ring, which can be an aryl or heteroaryl ring, or a carbocyclic or heterocyclic ring, which can contain no ring heteroatoms in the case of aryl or carbocyclic ring, or 1-3 ring heteroatoms independently selected from N, O, and S in the case of heteroaryl or heterocyclic ring. In some embodiments, ring C in Formula I-1-A-6 is a 5, 6, or 7 membered ring, which can be an aryl or heteroaryl ring, or a carbocyclic or heterocyclic ring, which can contain no ring heteroatoms in the case of aryl or carbocyclic ring, or 1-3 ring heteroatoms independently selected from N, O, and S in the case of heteroaryl or heterocyclic ring. In some embodiments, in Formula I-1-A-4, I-1-A-5, or I-1-A-6, n is 0, i.e., ring A, B, or C is not substituted with $R^D$. In some embodiments, in Formula I-1-A-4, I-1-A-5, or I-1-A-6, n is 1 or 2, wherein each $R^D$ is defined herein. In some embodiments, in Formula I-1-A-4, I-1-A-5, or I-1-A-6, $R^D$ at each occurrence is independently F, Cl, OH, $NH_2$, CN, or $G^A$ (e.g., described herein), or two $R^D$ form a bond or oxo. In some embodiments, in Formula I-1-A-4, I-1-A-5, or I-1-A-6, $R^D$ at each occurrence is independently F, Cl, OH, $NH_2$, CN, $C_{1-4}$ alkyl optionally substituted with 1-3 F, or $C_{1-4}$ heteroalkyl optionally substituted with 1-3 F, or two $R^D$ form a bond or oxo. To be clear, it should be noted the drawing of ring B or ring C in Formula I-1-A-5 or I-1-A-6, respectively, does not require that the two ring atoms directly connected to the pyridine ring to be carbon atoms. For example, in some embodiments, when ring B in Formula I-1-A-5 contains one or more ring heteroatoms, one or two ring heteroatoms can be directly bonded to the pyridine ring in Formula I-1-A-5.

In some embodiments, the compound of Formula I-1-A can be characterized as having Formula I-1-A-7, I-1-A-8, I-1-A-9, I-1-A-10, I-1-A-11, I-1-A-12, I-1-A-13, I-1-A-14, or I-1-A-15:

Formula I-1-A-7

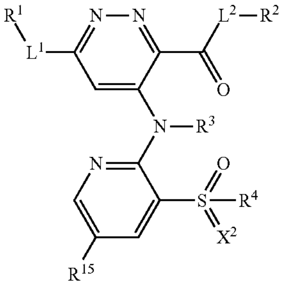

Formula I-1-A-8

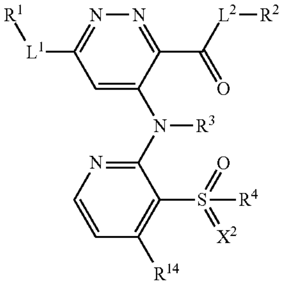

-continued

Formula I-1-A-9

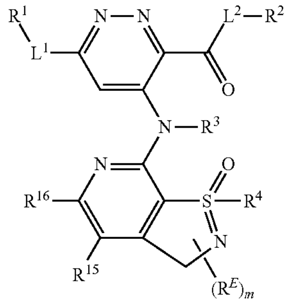

Formula I-1-A-10

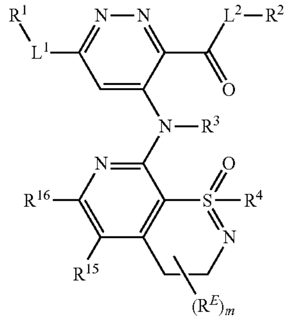

Formula I-1-A-11

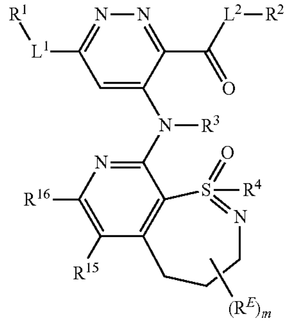

Formula I-1-A-12

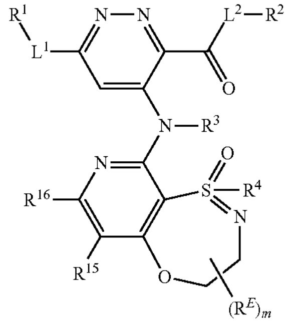

Formula I-1-A-13

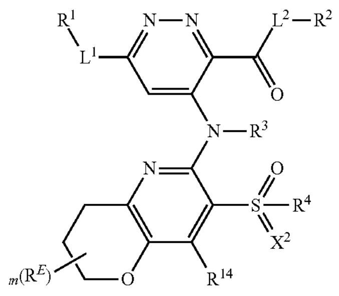

-continued

Formula I-1-A-14

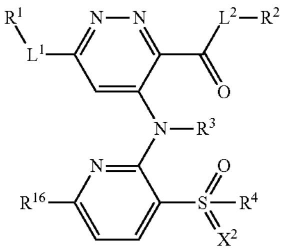

Formula I-1-A-15

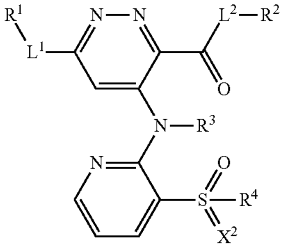

wherein:

m is an integer of 0-4 (e.g., 0, 1, or 2), as valency permits;

$R^E$ at each occurrence is independently F, Cl, $G^D$, $OG^D$, OH, or CN, or two $R^E$ form a bond, oxo, or a ring structure;

wherein $G^D$ at each occurrence is independently an optionally substituted $C_{1-4}$ alkyl, optionally substituted $C_{3-6}$ cycloalkyl, optionally substituted $C_{1-4}$ heteroalkyl, or optionally substituted 4-8 membered heterocyclyl, wherein the variables $L^1$, $R^1$, $L^2$, $R^2$, $R^3$, $R^{14}$, $R^{15}$, $R^{16}$, $X^2$, and $R^4$ include any of those described herein in any combination. In some embodiments, in Formula I-1-A-9, I-1-A-10, I-1-A-11, I-1-A-12, or I-1-A-13, m is 0. In some embodiments, in Formula I-1-A-9, I-1-A-10, I-1-A-11, I-1-A-12, or I-1-A-13, m is 1 or 2, wherein each $R^E$ is defined herein. In some embodiments, in Formula I-1-A-9, I-1-A-10, I-1-A-11, I-1-A-12, or I-1-A-13, $R^E$ at each occurrence is independently F, Cl, OH, $NH_2$, CN, or $G^D$ (e.g., described herein), or two $R^E$ form a bond or oxo. In some embodiments, in Formula I-1-A-9, I-1-A-10, I-1-A-11, I-1-A-12, or I-1-A-13, $R^E$ at each occurrence is independently F, Cl, OH, $NH_2$, CN, $C_{1-4}$ alkyl optionally substituted with 1-3 F, or $C_{1-4}$ heteroalkyl optionally substituted with 1-3 F, or two $R^E$ form a bond or oxo. To be clear, when it is said that two $R^E$ form a bond, it is meant that two adjacent ring atoms are connected by an additional bond, typically, a double bond; using Formula I-1-A-13 as an example, when two $R^E$ form a bond, the ring may have a structure such as

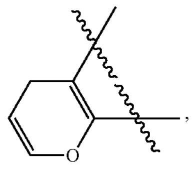

which may be further substituted with one or more $R^E$ as defined herein. When it is said that two $R^E$ form an oxo, it is meant that one ring atom is substituted with oxo group. Also using Formula I-1-A-13 as an example, when two $R^E$ form an oxo, the ring may have a structure such as

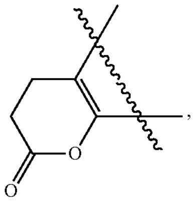

which may be further substituted with one or more $R^E$ as defined herein. Other similar expressions herein should be understood similarly.

In some embodiments, the

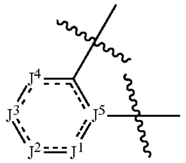

moiety in Formula I can also be an optionally substituted phenyl or 6-membered heteroaryl other than the pyridyl in Formula I-1-A. For example, in some embodiments, the compound of Formula I can be characterized as having Formula I-1-B, Formula I-1-C, or Formula I-1-D:

Formula I-1-B

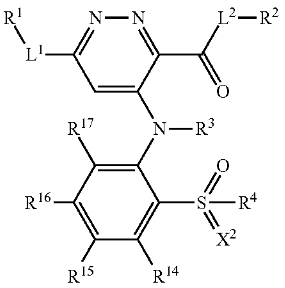

Formula I-1-C

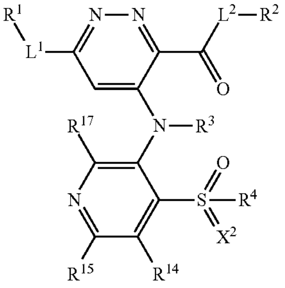

Formula I-1-D

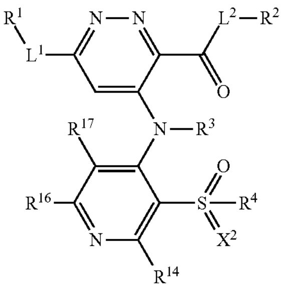

wherein the variables $L^1$, $R^1$, $L^2$, $R^2$, $R^3$, $R^{14}$, $R^{15}$, $R^{16}$, $R^{17}$, $X^2$, and $R^4$ include any of those described herein in any combination.

As discussed herein, various groups are suitable $R^{14}$, $R^{15}$, $R^{16}$, or $R^{17}$ for compounds of Formula I. Typically, in Formula I-1-A (e.g., Formula I-1-A-2, I-1-A-3, I-1-A-5, I-1-A-8, or I-1-A-13), Formula I-1-B, Formula I-1-C, or Formula I-1-D, or Formula I-1-H-1 as described below, $R^{14}$ can be hydrogen, halogen (e.g., F or Cl), $G^E$, —($C_{1-4}$ alkylene)-$G^E$, OH, CN, $OG^E$, or O—($C_{1-4}$ alkylene)-$G^E$, wherein $G^E$ is $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $G^E$ is $C_{1-4}$ alkyl optionally substituted with one or more (e.g., 1, 2, or 3) substituents independently selected from F and OH. In some embodiments, $G^E$ is $C_{1-4}$ heteroalkyl, such as $C_1$ heteroalkyl (e.g., $CH_2OH$ or $CH_2NH_2$), optionally substituted with one or more (e.g., 1, 2, or 3) substituents independently selected from F, $C_{1-4}$ alkyl (e.g., methyl), and OH. In some embodiments, $G^E$ is $C_{3-6}$ cycloalkyl such as cyclopropyl optionally substituted with one or more (e.g., 1, 2, or 3) substituents independently selected from F, $C_{1-4}$ alkyl (e.g., methyl), and OH. In some embodiments, $G^E$ is 4-6 membered heterocyclyl having 1-2 ring heteroatoms independently selected from N, O, and S such as azetidinyl, optionally substituted with one or more (e.g., 1, 2, or 3) substituents independently selected from F, $C_{1-4}$ alkyl (e.g., methyl), and OH. In some embodiments, in Formula I-1-A (e.g., Formula I-1-A-2, I-1-A-3, I-1-A-5, I-1-A-8, or I-1-A-13), Formula I-1-B, Formula I-1-C, Formula I-1-D, or Formula I-1-H-1, $R^{14}$ can be hydrogen, F, Cl, OH, CN, or $G^E$ (e.g., any of those described herein). In some embodiments, in Formula I-1-A (e.g., Formula I-1-A-2, I-1-A-3, I-1-A-5, I-1-A-8, or I-1-A-13), Formula I-1-B, Formula I-1-C, Formula I-1-D, or Formula I-1-H-1, $R^{14}$ can be hydrogen, F, Cl, CN, $C_{1-4}$ alkyl (e.g., methyl, ethyl, n-propyl, isopropyl), hydroxyl substituted $C_{1-4}$ alkyl (e.g., hydroxymethyl, hydroxyethyl, etc.), fluorine substituted $C_{1-4}$ alkyl (e.g., fluoromethyl, difluoromethyl, trifluoromethyl, etc.), OH, cyclopropyl, cyclobutyl, azetidinyl, $C_{1-4}$ alkoxy (e.g., methoxy, ethoxy, isopropoxy, etc.), fluorine substituted $C_{1-4}$alkoxy (e.g., $CF_3O$—, $CF_3CH_2O$—, etc.), cyclopropoxy or cyclobutoxy. In some preferred embodiments, in Formula I-1-A (e.g., Formula I-1-A-2, I-1-A-3, I-1-A-5, I-1-A-8, or I-1-A-13), Formula I-1-B, Formula I-1-C, Formula I-1-D, or Formula I-1-H-1, $R^{14}$ can be hydrogen. In some preferred embodiments, in Formula I-1-A (e.g., Formula I-1-A-2, I-1-A-3, I-1-A-5, I-1-A-8, or I-1-A-13), Formula I-1-B, Formula I-1-C, Formula I-1-D, or Formula I-1-H-1, $R^{14}$ can also be F, $CH_3$, $CH_2OH$, $OCH_3$, or cyclopropyl.

Typically, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be hydrogen, halogen (e.g., F or Cl), $G^E$, —($C_{1-4}$ alkylene)-$G^E$, OH, CN, $OG^E$, O—($C_{1-4}$ alkylene)-$G^E$, $SG^E$, S(O)-$G^E$, or $S(O)_2$-$G^E$, wherein $G^E$ is $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $G^E$ is $C_{1-4}$ alkyl optionally substituted with one or more (e.g., 1, 2, or 3) substituents independently selected from F and OH. In some embodiments, $G^E$ is $C_{1-4}$ heteroalkyl, such as $C_1$ heteroalkyl (e.g., $CH_2OH$ or $CH_2NH_2$), optionally substituted with one or more (e.g., 1, 2, or 3) substituents independently selected from F, $C_{1-4}$ alkyl (e.g., methyl), and OH. In some embodiments, $G^E$ is $C_{3-6}$ cycloalkyl such as cyclopropyl optionally substituted with one or more (e.g., 1, 2, or 3) substituents independently selected from F, $C_{1-4}$ alkyl (e.g., methyl), and OH. In some embodiments, $G^E$ is 4-6 membered heterocyclyl having 1-2 ring heteroatoms independently selected from N, O, and S such as azetidinyl, optionally substituted with one or more (e.g., 1, 2, or 3) substituents independently selected from F, $C_{1-4}$ alkyl (e.g., methyl), and OH.

In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be an optionally substituted 4-6 membered heterocyclyl having 1-2 ring heteroatoms independently selected from N, O, and S, such as an oxetanyl, morpholinyl, or azetidinyl, optionally substituted with one or more (e.g., 1, 2, or 3) substituents independently selected from F, $C_{1-4}$ alkyl (e.g., methyl), and OH.

In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be $OG^E$, wherein $G^E$ is a $C_{1-4}$ alkyl, hydroxyl substituted $C_{1-4}$ alkyl (e.g., hydroxymethyl, hydroxyethyl, etc.), fluorine substituted $C_{1-4}$ alkyl (e.g., fluoromethyl, difluoromethyl, trifluoromethyl, etc.), or 4-6 membered heterocyclyl having 1-2 ring heteroatoms independently selected from N, O, and S, such as oxetanyl, which is optionally substituted with one or more (e.g., 1, 2, or 3) substituents independently selected from F, $C_{1-4}$ alkyl (e.g., methyl), and OH.

In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be O—($C_{1-4}$ alkylene)-$G^F$, wherein $G^F$ is OH, $NH_2$, an optionally substituted $C_{1-4}$ alkyl, optionally substituted $C_{1-4}$ heteroalkyl, optionally substituted $C_{3-6}$ cycloalkyl, or optionally substituted 4-6 membered heterocyclyl having 1-2 ring heteroatoms independently selected from N, O, and S. For example, in some embodiments, $R^{15}$ can be O—($C_{1-4}$ alkylene)-$G^F$, wherein $G^F$ is OH, $NH_2$, NH($C_{1-4}$ alkyl), N($C_{1-4}$ alkyl)($C_{1-4}$ alkyl), $C_{1-4}$ alkoxy (e.g., methoxy, ethoxy, isopropoxy, etc.), fluorine substituted $C_{1-4}$ alkoxy (e.g., $CF_3O$—, $CHF_2O$—, $CF_3CH_2O$—, etc.), hydroxyl substituted $C_{1-4}$ alkoxy (e.g., —O—$CH_2CH_2OH$), alkoxy substituted $C_{1-4}$ alkoxy (e.g., —O—$CH_2CH_2OMe$), 0-Acyl (such as O—CH(O), O—C(O)$CH_3$), NH-Acyl, N($C_{1-4}$ alkyl)-Acyl, or 4-6 membered heterocyclyl having 1-2 ring heteroatoms independently selected from N, O, and S, such as oxetanyl, which is optionally substituted with one or more (e.g., 1, 2, or 3) substituents independently selected from F, $C_{1-4}$ alkyl (e.g., methyl), and OH. In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be O—($C_{1-4}$ alkylene)-$G^F$, wherein the $C_{1-4}$ alkylene (connection from left (0) to right ($G^F$)) is —$CH_2CH_2$—, —$CH(CH_3)CH_2$—, —$CH_2CH(CH_3)$—, or —$CH_2C(CH_3)_2$—, and $G^F$ is OH, $NH_2$, NH($C_{1-4}$ alkyl), N($C_{1-4}$ alkyl)($C_{1-4}$ alkyl), $C_{1-4}$ alkoxy (e.g., methoxy, ethoxy, isopropoxy, etc.), fluorine substituted $C_{1-4}$ alkoxy (e.g., $CF_3O$—, $CHF_2O$—, $CF_3CH_2O$—, etc.), hydroxyl substituted $C_{1-4}$ alkoxy (e.g., —O—$CH_2CH_2OH$), or alkoxy substituted $C_{1-4}$ alkoxy (e.g., —O—$CH_2CH_2OMe$).

In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be hydrogen, F, Cl, OH, CN, or $G^E$ (e.g., any of those described herein).

In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be hydrogen, F, Cl, CN, $C_{1-4}$ alkyl (e.g., methyl, ethyl, n-propyl, isopropyl), hydroxyl substituted $C_{1-4}$ alkyl (e.g., hydroxymethyl, hydroxyethyl, etc.), fluorine substituted $C_{1-4}$ alkyl (e.g., fluoromethyl, difluoromethyl, trifluoromethyl, etc.), OH, cyclopropyl, cyclobutyl, azetidinyl, $C_{1-4}$ alkoxy (e.g., methoxy, ethoxy, isopropoxy, etc.), fluorine substituted $C_{1-4}$ alkoxy (e.g., $CF_3O$—, $CF_3CH_2O$—, etc.), $C_{1-4}$ alkylthio (e.g., $CH_3S$—), fluorine substituted $C_{1-4}$ alkylthio (e.g., $CF_3S$—), cyclopropoxy or cyclobutoxy.

In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, or Formula I-1-C, $R^{15}$ can be hydrogen. In some embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ is not hydrogen.

In some preferred embodiments, in Formula I-1-A (in particular Formula I-1-A-1, I-1-A-3, I-1-A-4, I-1-A-7, I-1-A-9, I-1-A-10, I-1-A-11 or I-1-A-12), Formula I-1-B, Formula I-1-C, or Formula I-1-H-1, $R^{15}$ can be F, Cl, CN, $CH_3$, $CH_2CH_3$, $CHF_2$, $CF_3$, $OCH_3$, $OCH_2CH_3$, O—$CH(CH_3)_2$, $OCHF_2$, $OCF_3$, $SCF_3$, cyclopropyl or

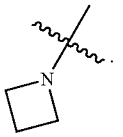 [SMILES: *N1CCC1]

In some preferred embodiments, $R^{15}$ can be

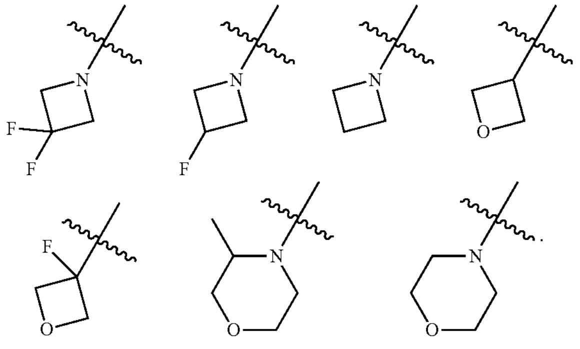

In some preferred embodiments, $R^{15}$ can be

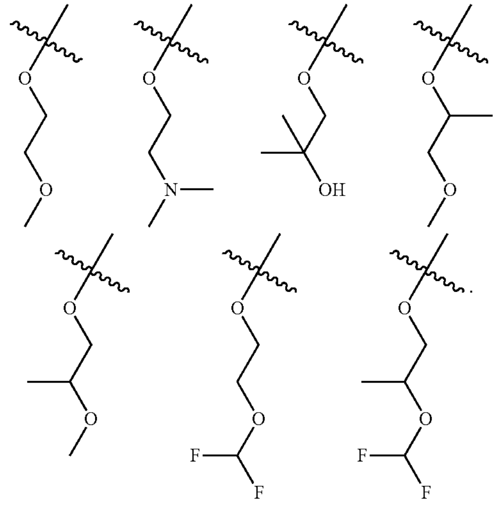

In some preferred embodiments, $R^{15}$ can be selected from the following stereoisomers:

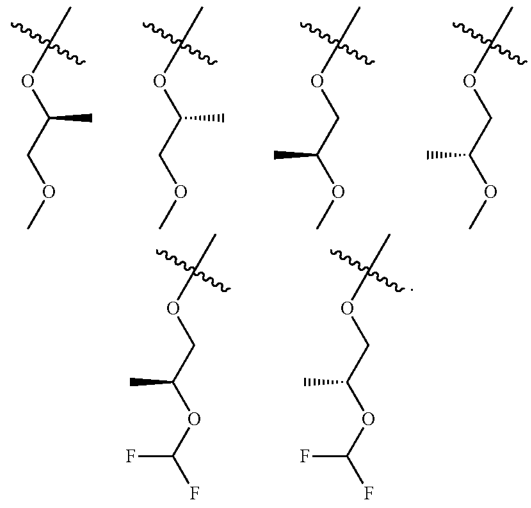

In some embodiments, with respect to the foregoing as-drawn chiral center, the compound can exist predominantly as the as-drawn enantiomer, such as having less than 20%, less than 10%, less than 5%, less than 1%, by weight, by HPLC area, or both, or having a non-detectable amount of the other corresponding enantiomer.

Typically, in Formula I-1-A (in particular I-1-A-1, I-1-A-2, I-1-A-4, I-1-A-6, I-1-A-9, I-1-A-10, I-1-A-11, I-1-A-12, or I-1-A-14), Formula I-1-B, Formula I-1-D, or Formula I-1-H-1, $R^{16}$ can be hydrogen, F, Cl, $G^E$, —($C_{1-4}$ alkylene)-$G^E$, OH, CN, $OG^E$, or O—($C_{1-4}$ alkylene)-$G^E$, wherein $G^E$ is $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $G^E$ is $C_{1-4}$ alkyl optionally substituted with one or more (e.g., 1, 2, or 3) substituents independently selected from F and OH. In some embodiments, $G^E$ is $C_{1-4}$ heteroalkyl, such as $C_1$ heteroalkyl (e.g., $CH_2OH$ or $CH_2NH_2$), optionally substituted with one or more (e.g., 1, 2, or 3) substituents independently selected from F, $C_{1-4}$ alkyl (e.g., methyl), and OH. In some embodiments, $G^E$ is $C_{3-6}$ cycloalkyl such as cyclopropyl optionally substituted with one or more (e.g., 1, 2, or 3) substituents independently selected from F, $C_{1-4}$ alkyl (e.g., methyl), and OH. In some embodiments, $G^E$ is 4-6 membered heterocyclyl having 1-2 ring heteroatoms independently selected from N, O, and S such as azetidinyl, optionally substituted with one or more (e.g., 1, 2, or 3) substituents independently selected from F, $C_{1-4}$ alkyl (e.g., methyl), and OH. In some embodiments, in Formula I-1-A (in particular I-1-A-1, I-1-A-2, I-1-A-4, I-1-A-6, I-1-A-9, I-1-A-10, I-1-A-11, I-1-A-12, or I-1-A-14), Formula I-1-B, Formula I-1-D, or Formula I-1-H-1, $R^{16}$ can be hydrogen, F, Cl, OH, CN, or $G^E$ (e.g., any of those described herein). In some embodiments, in Formula I-1-A (in particular I-1-A-1, I-1-A-2, I-1-A-4, I-1-A-6, I-1-A-9, I-1-A-10, I-1-A-11, I-1-A-12, or I-1-A-14), Formula I-1-B, Formula I-1-D, or Formula I-1-H-1, $R^{16}$ can be hydrogen, F, Cl, CN, $C_{1-4}$ alkyl (e.g., methyl, ethyl, n-propyl, isopropyl), fluorine substituted $C_{1-4}$ alkyl (e.g., fluoromethyl, difluoromethyl, trifluoromethyl, etc.), OH, $C_{3-6}$ cycloalkyl (e.g., cyclopropyl, cyclobutyl, etc.), $C_{1-4}$ alkoxy (e.g., methoxy, ethoxy etc.), fluorine substituted $C_{1-4}$alkoxy (e.g., $CF_3O$—, $CF_3CH_2O$—, etc.), cyclopropoxy or cyclobutoxy. In some preferred embodiments, in Formula I-1-A (in particular I-1-A-1, I-1-A-2, I-1-A-4, I-1-A-6, I-1-A-9, I-1-A-10, I-1-A-11, I-1-A-12, or I-1-A-14), Formula I-1-B, Formula I-1-D, or Formula I-1-H-1, $R^{16}$ can be hydrogen, F, Cl, CN, $C_{1-4}$ alkyl, $C_{1-4}$ alkoxy, cyclopropyl, or cyclobutyl. For example, in some preferred embodiments, in Formula I-1-A (in particular I-1-A-1, I-1-A-2, I-1-A-4, I-1-A-6, I-1-A-9, I-1-A-10, I-1-A-11, I-1-A-12, or I-1-A-14), Formula I-1-B, or Formula I-1-D, or Formula I-1-H-1, $R^{16}$ can be hydrogen.

When present, $R^{17}$ in Formula I (e.g., Formula I-1-B, I-1-C, or I-1-D) is typically hydrogen.

In some embodiments, in applicable Formula I (e.g., Formula I-1-A, such as Formula I-1-A-3, or I-1-H-1), at least one of $R^{14}$ and $R^{15}$ is not hydrogen.

In some embodiments, in applicable Formula I (e.g., Formula I-1-A or I-1-H-1), both $R^{14}$ and $R^{16}$ are hydrogen, and $R^{15}$ is not hydrogen.

In some embodiments, in applicable Formula I (e.g., Formula I-1-A or I-1-H-1), $R^{14}$, $R^1$, and $R^{16}$ are all hydrogen.

In some embodiments, the

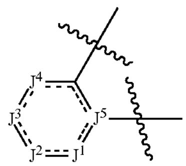

moiety (alternatively referred to herein as M-10) in Formula I (e.g., Formula I-1, I-2, or I-3) can also represent an optionally substituted 5-membered heteroaryl ring having 1-3 ring heteroatoms independently selected from S, O, and N, such as an optionally substituted pyrazole, optionally substituted thiazole, optionally substituted isothiazole, optionally substituted oxazole, optionally substituted isoxazole, optionally substituted imidazole, etc. In such embodiments, $J^1$ can be $CR^{18}$, $NR^{19}$, O, S, or N can be $CR^{14}$ or N; $J^4$ is $CR^{20}$, $NR^{21}$, O, S, or N; $J^5$ is C or N; and one of $J^2$ and $J^3$ does not exist, and the other of $J^2$ and $J^3$ is O, S, N, $NR^{22}$, or $CR^{23}$; wherein $R^{18}$, $R^{19}$, $R^{20}$, $R^{21}$, $R^{22}$, and $R^{23}$ include any of those described herein in any combination.

In embodiments wherein M-10 represents an optionally substituted 5-membered heteroaryl ring (e.g., described herein), $J^4$ is typically N. However, in some embodiments, $J^4$ can also be $CR^{20}$, $NR^{21}$, O, or S, wherein $R^{20}$ and $R^{21}$ are defined herein.

In embodiments wherein M-10 represents an optionally substituted 5-membered heteroaryl ring (e.g., described herein), $J^1$ can be $CR^{18}$, wherein $R^{18}$ is defined herein. In some preferred embodiments, $R^{18}$ is hydrogen, halogen (e.g., F, Cl), CN, $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $R^{18}$, together with the respective intervening atoms, can be joined with $R^{13}$, $R^{22}$, or $R^{23}$ to form an optionally substituted 5-8 membered ring structure.

In embodiments wherein M-10 represents an optionally substituted 5-membered heteroaryl ring (e.g., described herein), $J^1$ can also be $NR^{19}$, wherein $R^{19}$ is defined herein. For example, in some embodiments, $R^{19}$ can be hydrogen, $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $R^{19}$, together with the respective intervening atoms, can be joined with $R^{13}$, $R^{22}$, or $R^{23}$ to form an optionally substituted 5-8 membered ring structure.

In embodiments wherein M-10 represents an optionally substituted 5-membered heteroaryl ring (e.g., described herein), $J^1$ can also be O or S.

In embodiments wherein M-10 represents an optionally substituted 5-membered heteroaryl ring (e.g., described herein), $J^2$ can be $CR^{23}$, and $J^3$ does not exist, wherein $R^{23}$ is defined herein. For example, in some embodiments, $R^{23}$ can be hydrogen, halogen (e.g., F, Cl), CN, $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $R^{23}$, together with the respective intervening atoms, can be joined with $R^{18}$, $R^{19}$, $R^{20}$, or $R^{21}$ to form an optionally substituted 5-8 membered ring structure.

In embodiments wherein M-10 represents an optionally substituted 5-membered heteroaryl ring (e.g., described herein), $J^2$ can be $NR^{22}$, and $J^3$ does not exist, wherein $R^{22}$ is defined herein. For example, in some embodiments, $R^{22}$ can be hydrogen, $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $R^{22}$, together with the respective intervening atoms, can be joined with $R^{18}$, $R^{19}$, $R^{20}$, or $R^{21}$ to form an optionally substituted 5-8 membered ring structure.

In embodiments wherein M-10 represents an optionally substituted 5-membered heteroaryl ring (e.g., described herein), $J^2$ can also be O or S, and $J^3$ does not exist.

In some more specific embodiments, the compound of Formula I can be characterized as having a Formula I-1-E, I-1-F, or I-1-G:

Formula I-1-E

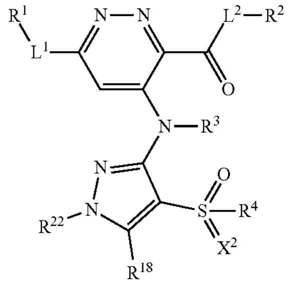

Formula I-1-F

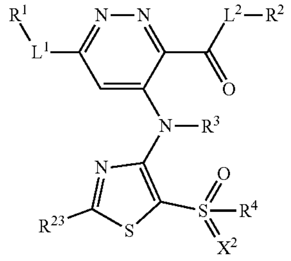

Formula I-1-G

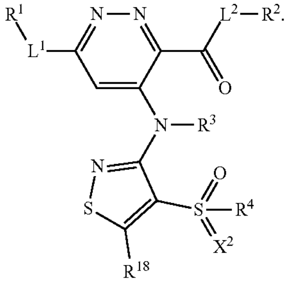

wherein the variables $L^1$, $R^1$, $L^2$, $R^2$, $R^3$, $R^{18}$, $R^{22}$, $R^{23}$, $X^2$, and $R^4$ include any of those described herein in any combination. For example, in some embodiments, $R^{18}$ in Formula I-1-E or I-1-G can be hydrogen, halogen (e.g., F, Cl), CN, $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $R^{22}$ in Formula I-1-E can be hydrogen, $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH. In some embodiments, $R^{23}$ in Formula I-1-F can be hydrogen, halogen (e.g., F, Cl), CN, $C_{1-6}$ alkyl, $C_{1-4}$ heteroalkyl, $C_{3-6}$ cycloalkyl, or 4-6 membered heterocyclyl having 1-2 ring heteroatoms independently selected from N, O, and S, wherein each of the $C_{1-6}$ alkyl, $C_{1-4}$ heteroalkyl, $C_{3-6}$ cycloalkyl, or 4-6 membered heterocyclyl is optionally substituted with one or more (e.g., 1, 2, or 3) substituents independently selected from F, $C_{1-4}$ alkyl (e.g., methyl), and OH.

Unless otherwise specified or contrary from context, $X^2$ in Formula I (e.g., Formula I-1, I-2, I-3, I-1-A, I-1-B, I-1-C, I-1-D, I-1-E, I-1-F, I-1-G, I-1-H, I-1-I, I-1-A-1, I-1-A-2, I-1-A-3, I-1-A-5, I-1-A-6, I-1-A-7, I-1-A-8, I-1-A-13, I-1-A-14, I-1-A-15, or I-1-H-1) is typically O.

In some embodiments, $X^2$ in Formula I (e.g., any of the applicable subformulae) can also be $NR^{13}$, wherein $R^{13}$ is defined herein. For example, in some embodiments, $X^2$ in Formula I (e.g., any of the applicable subformulae) can be NH. In some embodiments, $X^2$ in Formula I (e.g., any of the applicable subformulae) can be $NR^{13}$, wherein $R^{13}$ is a $C_{1-4}$ alkyl, such as methyl. As understood by those skilled in the art, when $X^2$ in Formula I is $NR^{13}$, the sulfur atom is an asymmetric center. In some embodiments, compounds of the present disclosure with $X^2$ being $NR^{13}$ can exist in racemic mixtures or mixtures enriched in a stereoisomer with either configuration with respect to the asymmetric sulfur center. For example, in some embodiments, the compound of Formula I (e.g., Formula I-1, 1-2, 1-3, I-1-A, I-1-B, I-1-C, I-1-D, I-1-E, I-1-F, I-1-G, I-1-H, I-1-I, I-1-A-1, I-1-A-2, I-1-A-3, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1) can be characterized as having Formula I-1-J-E1 or I-1-J-E2:

Formula I-1-J-E1

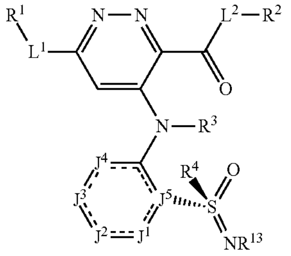

Formula I-1-J-E2

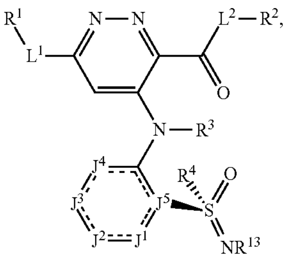

wherein the variables $L^1$, $R^1$, $L^2$, $R^2$, $R^3$, $J^1$, $J^2$, $J^3$, $J^4$, $J^5$, $R^{13}$, and $R^4$ include any of those described herein in any combination, such as those described herein in connection with Formula I-1-A and its subformulae I-1-A-1 to I-1-A-15. For example, in some embodiments, the compound of Formula I-1 with $X^2$ being $NR^{13}$ can be enriched in the stereoisomer of Formula I-1-J-E1, which can be substantially free of the stereoisomer of Formula I-1-J-E2, e.g., having less than 20%, less than 10%, less than 5%, less than 1%, by weight, by HPLC area, or both, or having a non-detectable amount of the stereoisomer of Formula I-1-J-E2. In some embodiments, the compound of Formula I-1 with $X^2$ being $NR^{13}$ can be enriched in the stereoisomer of Formula I-1-J-E2, which can be substantially free of the stereoisomer of Formula I-1-J-E1, e.g., having less than 20%, less than 10%, less than 5%, less than 1%, by weight, by HPLC area, or both, or having a non-detectable amount of the stereoisomer of Formula I-1-J-E1. In some embodiments, the compound of Formula I-1 with $X^2$ being $NR^{13}$ can be a mixture of stereoisomers of Formula I-1-J-E1 and Formula I-1-J-E2 in a 1:1 molar ratio, or any other ratio.

Unless otherwise specified or contrary from context, $R^4$ in Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1) is typically a $C_{1-4}$ alkyl optionally substituted with one or more substituents independently selected from F, OH, and $C_{1-4}$ heteroalkyl. For example, in any of the embodiments described herein, unless otherwise specified or contrary from context, $R^4$ in Formula I (e.g., any of the applicable subformulae) can be methyl.

In some embodiments, when $X^2$ is $NR^{13}$, $R^4$ and $R^{13}$ in Formula I (e.g., any of the applicable subformulae) can be joined together with the intervening atoms to form an optionally substituted 5-8 membered ring structure. For example, in some embodiments, the

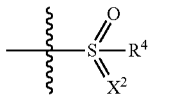

moiety in Formula I (including any of the applicable subformulae) can be

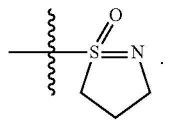 [SMILES: *S1(=O)=NCCC1 ; "."]

The combinations of M-10, $X^2$, and $R^4$ is not particularly limited. For example, unless otherwise specified or contrary from context, in any of the embodiments herein, the

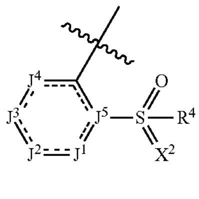

moiety in Formula I (including any of the applicable subformulae such as Formula I-1 (e.g., I-1-A or I-1-H), I-2, or I-3) can be selected from:

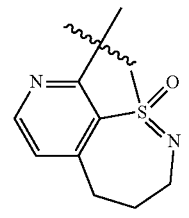
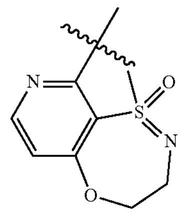
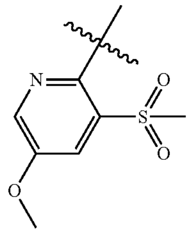
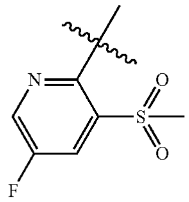
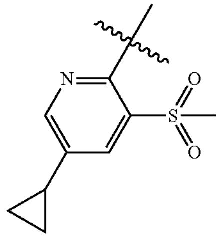
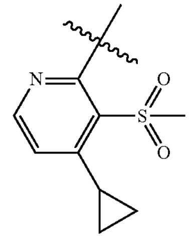
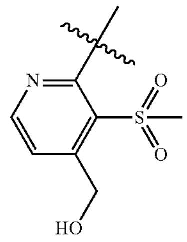
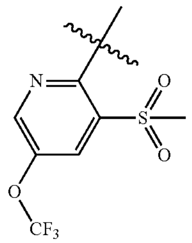
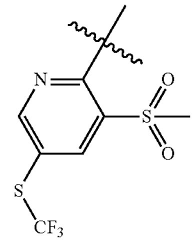
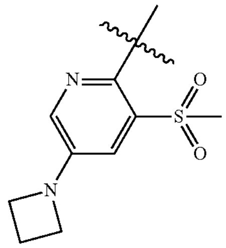
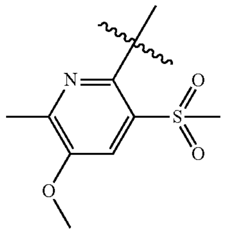
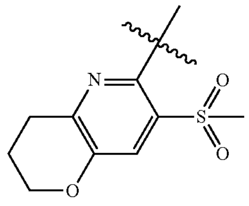
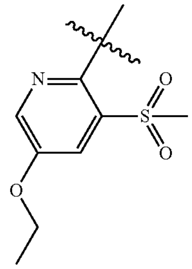
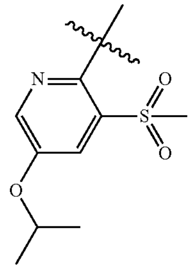

-continued
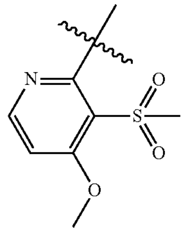
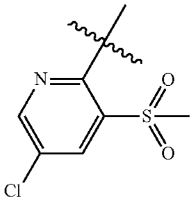
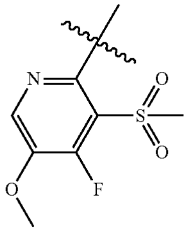
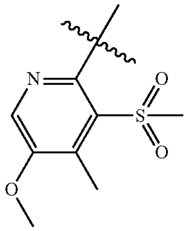
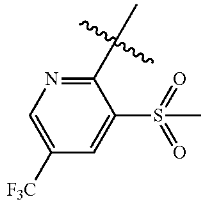
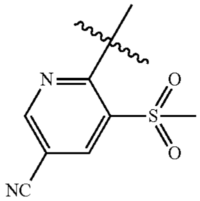
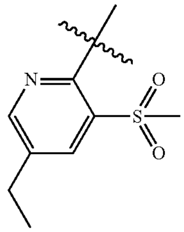
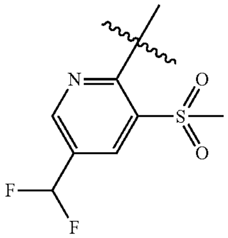
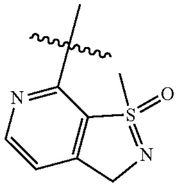
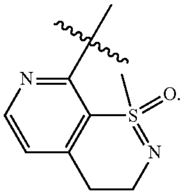
Unless otherwise specified or contrary from context, in any of the embodiments herein, the
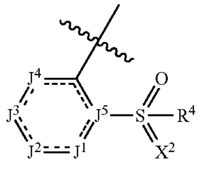
moiety in Formula I (including any of the applicable sub-formulae such as Formula I-1 (e.g., I-1-A or I-1-H), 1-2, or I-3) can also be selected from:
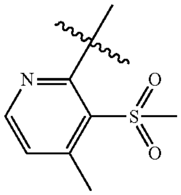
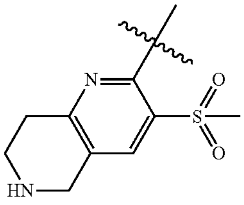
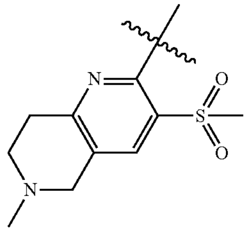
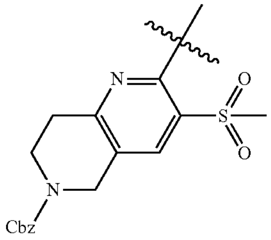
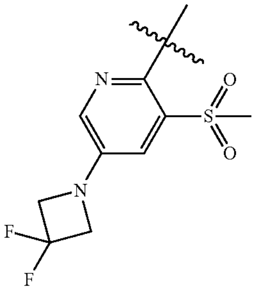
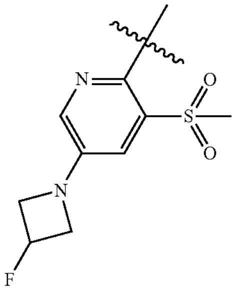
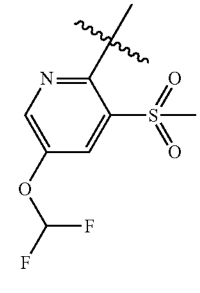
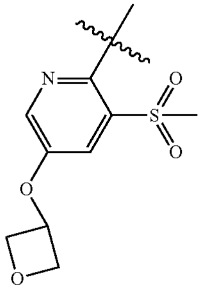
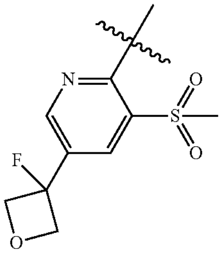
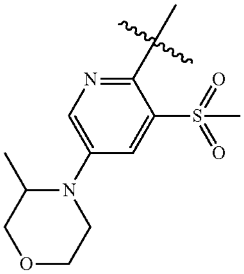
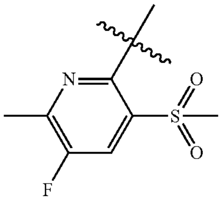
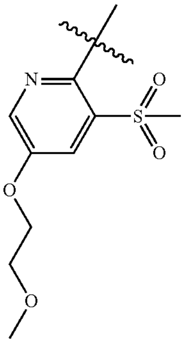

-continued

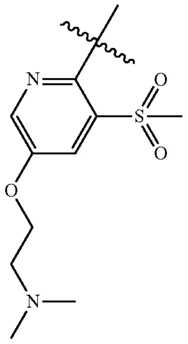

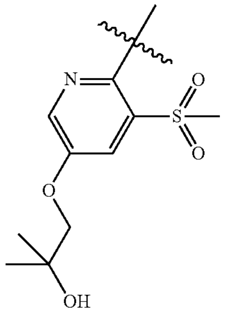

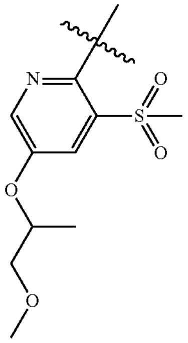

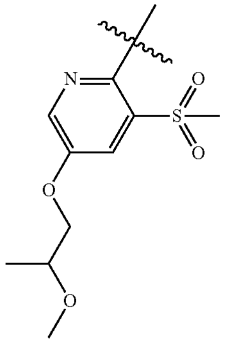

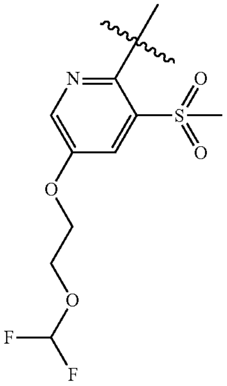

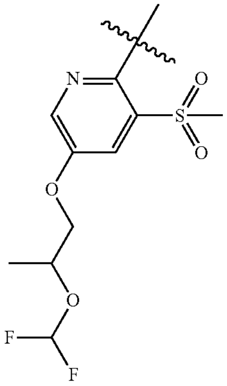

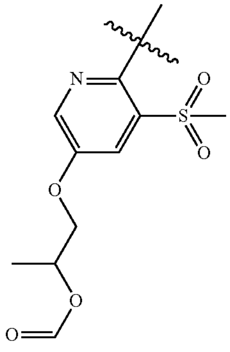

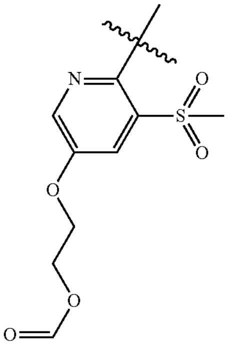

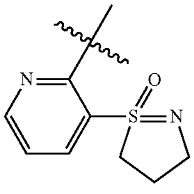

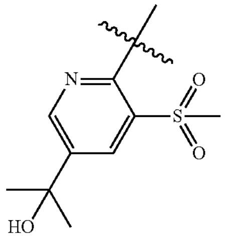

, wherein Cbz represents

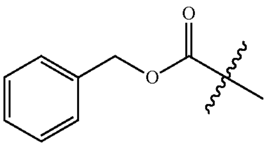

.

Unless otherwise specified or contrary from context, in any of the embodiments herein, the

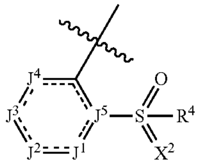

moiety in Formula I (including any of the applicable sub-formulae such as Formula I-1 (e.g., I-1-A or I-1-H), I-2, or I-3) can also be selected from:

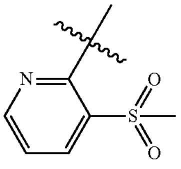

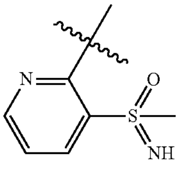

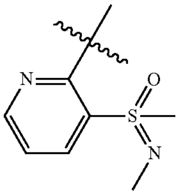

.

For example, in some embodiments, the

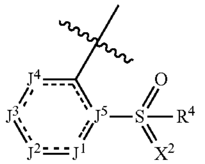

moiety in Formula I (including any of the applicable sub-formulae) can be

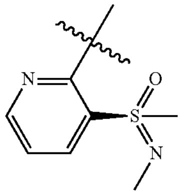

, which can be substantially enantiomerically pure with respect to the drawn chiral center, for example, having less than 20%, less than 10%, less than 5%, less than 1%, by weight, by HPLC area, or both, or having a non-detectable amount of the other corresponding enantiomer. In some embodiments, the

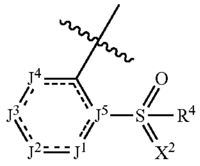

moiety in Formula I (including any of the applicable sub-formulae) can be

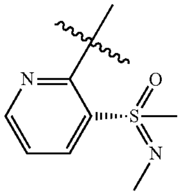,

Which can be substantially enantiomerically pure with respect to the drawn chiral center, for example, having less than 20%, less than 10%, less than 5%, less than 1%, by weight, by HPLC area, or both, or having a non-detectable amount of the other corresponding enantiomer.

Unless otherwise specified or contrary from context, in any of the embodiments herein, the

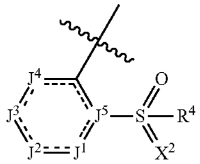

moiety in Formula I (including any of the applicable sub-formulae such as Formula I-1 (e.g., I-1-A or I-1-H), I-2, or I-3) can also be selected from:

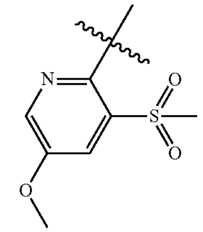
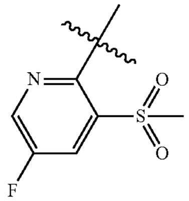
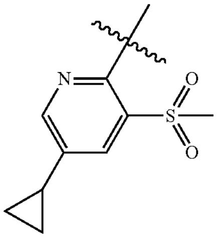
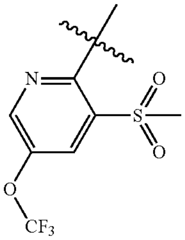

-continued

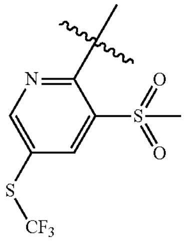
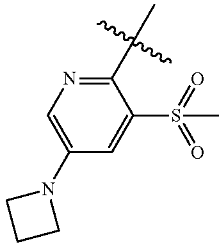
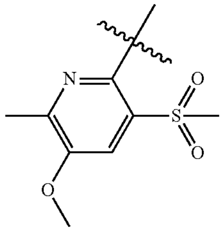
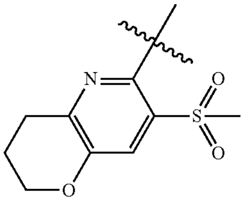
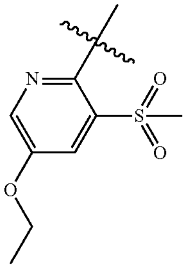
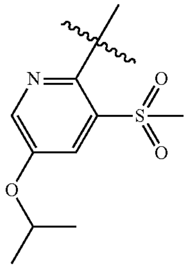
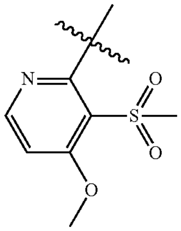
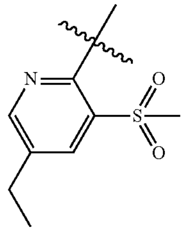
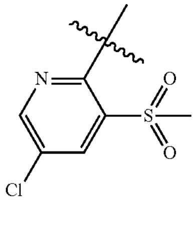
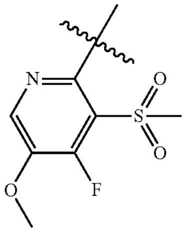
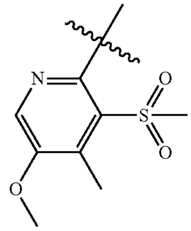
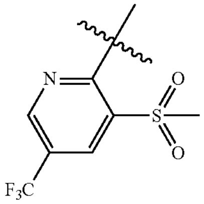
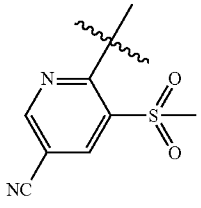
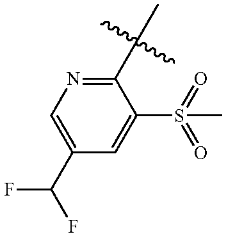.

Unless otherwise specified or contrary from context, in any of the embodiments herein, the
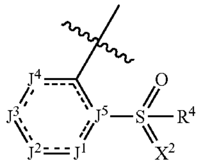
moiety in Formula I (including any of the applicable sub-formulae such as Formula I-1 (e.g., I-1-A or I-1-H), I-2, or I-3) can also be selected from:
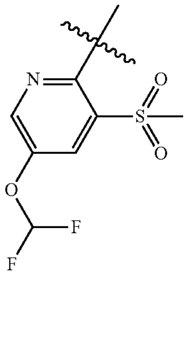
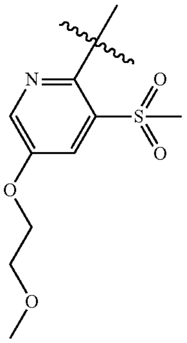
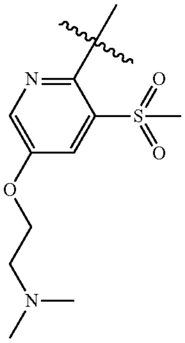
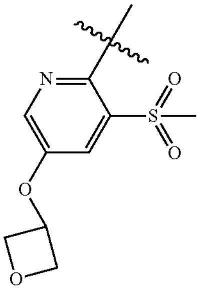
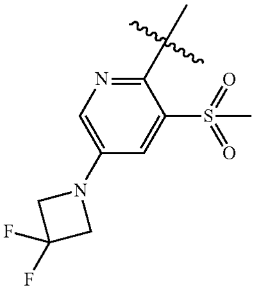
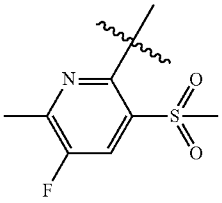
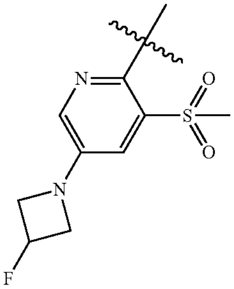
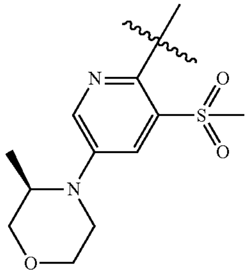
-continued
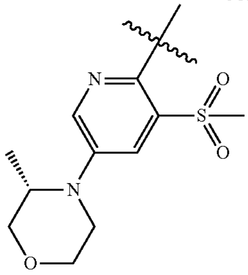
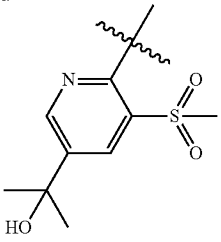
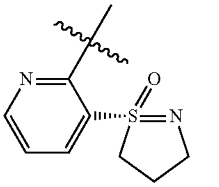
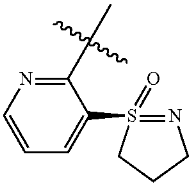
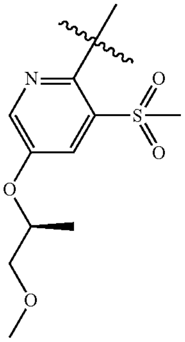
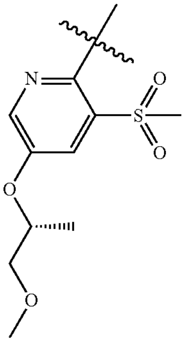
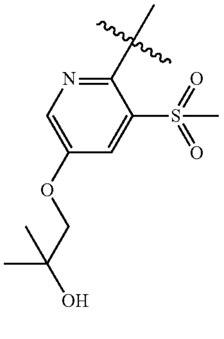
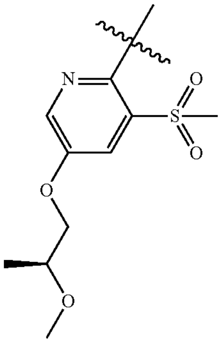
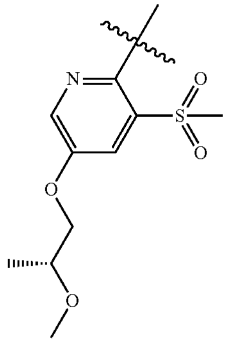
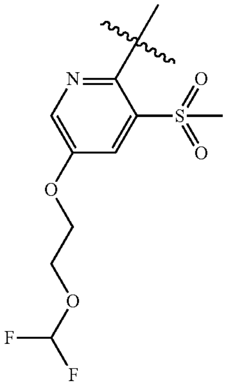

-continued

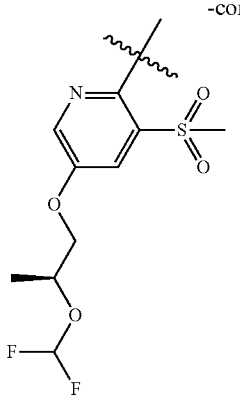

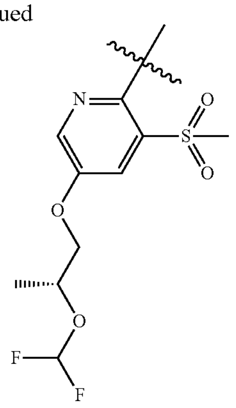

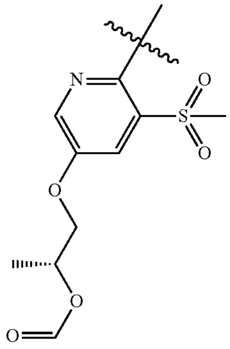

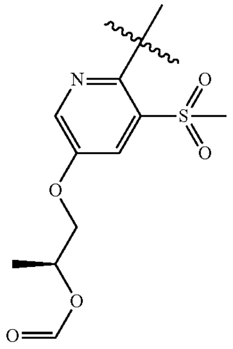

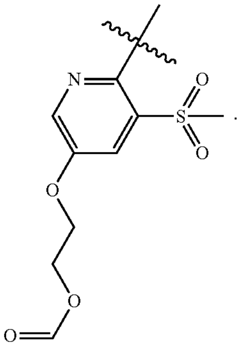

In some embodiments, with respect to the as-drawn chiral center above, the compound can exist predominantly as the as-drawn stereoisomer, such as with less than 20%, less than 10%, less than 5%, less than 1%, by weight, by HPLC area, or both, or with a non-detectable amount of the other stereoisomer(s).

Unless otherwise specified or contrary from context, in any of the embodiments herein, the

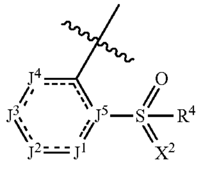

moiety in Formula I (including any of the applicable sub-formulae such as Formula I-1 (e.g., I-1-A, I-1-H, or I-1-J-E2), I-2, or 1-3) can also be selected from:

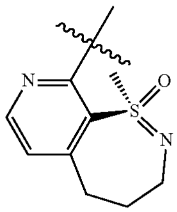

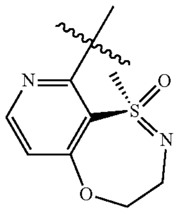

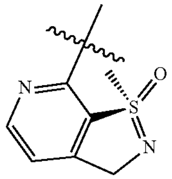

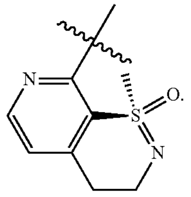

In some embodiments, with respect to the as-drawn chiral center above, the compound can exist predominantly as the as-drawn stereoisomer, such as with less than 20%, less than 10%, less than 5%, less than 1%, by weight, by HPLC area, or both, or with a non-detectable amount of the other stereoisomer(s).

Unless otherwise specified or contrary from context, in any of the embodiments herein, the

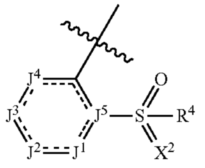

moiety in Formula I (including any of the applicable sub-formulae such as Formula I-1 (e.g., I-1-A, I-1-H, or I-1-J-E1), I-2, or 1-3) can also be selected from:

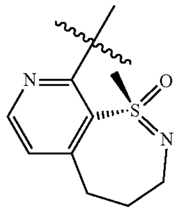

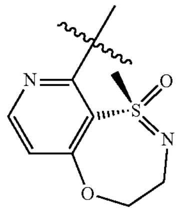

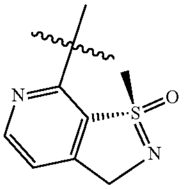

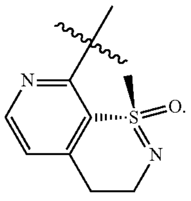

In some embodiments, with respect to the as-drawn chiral center above, the compound can exist predominantly as the as-drawn stereoisomer, such as with less than 20%, less than 10%, less than 5%, less than 1%, by weight, by HPLC area, or both, or with a non-detectable amount of the other stereoisomer(s).

Unless otherwise specified or contrary from context, in any of the embodiments herein, the

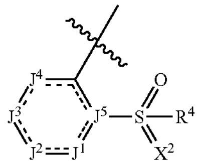

moiety in Formula I (including any of the applicable sub-formulae) can also be selected from:

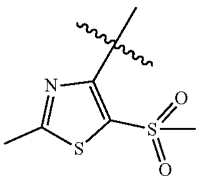
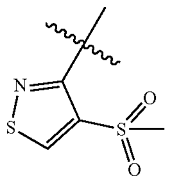
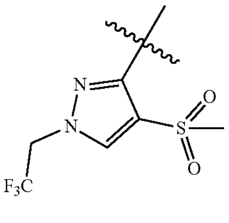
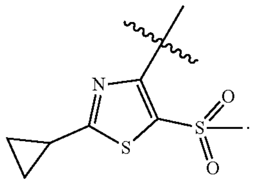

Typically, in Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15), $R^3$ is hydrogen.

Typically, in Formula I (e.g., Formula I-1, 1-2, 1-3, I-1-A, I-1-B, I-1-C, I-1-D, I-1-E, I-1-F, I-1-G, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15), $L^1$ is

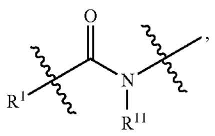

wherein $R^{11}$ is defined herein. In some preferred embodiments, $L^1$ is

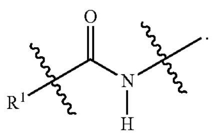

For example, in some embodiments, the compound of Formula I-1 (e.g., Formula I-1-A, I-1-B, I-1-C, I-1-D, I-1-E, I-1-F, I-1-G, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15) can be characterized as having Formula I-1-H:

Formula I-1-H

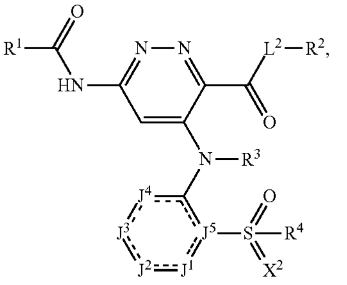

wherein the variables $R^1$, $L^2$, $R^2$, $R^3$, $J^1$, $J^2$, $J^3$, $J^4$, $J^5$, $X^2$, and $R^4$ include any of those described herein in any combination, such as those described in connection with Formula I-1 and its subformulae. In some specific embodiments, the compound of Formula I-1-H can be characterized as having the subformula of I-1-H-1:

Formula I-1-H-1

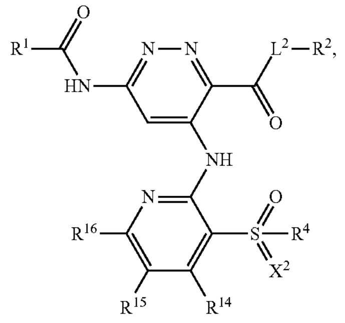

wherein the variables $R^1$, $L^2$, $R^2$, $R^{14}$, $R^{15}$, $R^{16}$, $X^2$, and $R^4$ include any of those described herein in any combination, such as those described in connection with Formula I-1-A (including any of the subformulae I-1-A-1 to I-1-A-15). For example, in some embodiments, in Formula I-1-H-1, $R^{14}$ can be hydrogen. In some embodiments, in Formula I-1-H-1, $R^{15}$ can be hydrogen. In some embodiments, in Formula I-1-H-1, $R^{16}$ can be hydrogen. In some embodiments, in Formula I-1-H-1, one of $R^{14}$ and $R^{15}$ is hydrogen and the other of $R^{14}$ and $R^{15}$ is not hydrogen, for example, in some embodiments, $R^{14}$ is hydrogen and $R^{15}$ is not hydrogen. In some embodiments, in Formula I-1-H-1, both $R^{14}$ and $R^{15}$ are not hydrogen. In some embodiments, in Formula I-1-H-1, both $R^{14}$ and $R^{15}$ are hydrogen. In some embodiments, in Formula I-1-H-1, both $R^{14}$ and $R^{16}$ are hydrogen, and $R^{15}$ is not hydrogen. In some embodiments, in Formula I-1-H-1, all of $R^{14}$, $R^{15}$, and $R^{16}$ are hydrogen. In some embodiments, in Formula I-1-H-1, $R^{14}$ and $R^{15}$, together with the intervening atoms, are joined to form a 5-8 membered ring, such as a 5-8 membered carbocyclic or heterocyclic ring, which is optionally substituted. In some embodiments, in Formula I-1-H-1, $X^2$ is $NR^{13}$ and $R^{14}$ and $R^{13}$, together with the intervening atoms, are joined to form a 5-8 membered heterocyclic ring, which is optionally substituted. Typically, $X^2$ in Formula I-1-H-1 is O, NH, or $NCH_3$. Typically, $R^4$ in Formula I-1-H-1 is $CH_3$. Suitable other definitions of the variables for Formula I-1-H-1 also include any of those described herein.

In some embodiments, in Formula I (e.g., Formula I-1-A, I-1-B, I-1-C, I-1-D, I-1-E, I-1-F, I-1-G, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15), $L^1$ is $NR^{11}$, wherein $R^{11}$ is defined herein. For example, in some embodiments, $L^1$ is NH. In some embodiments, $L^1$ is $NR^{11}$, wherein $R^{11}$ is hydrogen, $C_{1-4}$ alkyl, or $C_{3-6}$ cycloalkyl, wherein the $C_{1-4}$ alkyl or $C_{3-6}$ cycloalkyl is optionally substituted with one or more (e.g., 1, 2, or 3) substituents independently selected from F, $C_{1-4}$ alkyl (e.g., methyl), and OH.

In some embodiments, in Formula I (e.g., Formula I-1, I-2, I-3, I-1-A, I-1-B, I-1-C, I-1-D, I-1-E, I-1-F, I-1-G, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15), $L^1$ can also be

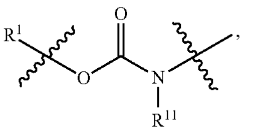

wherein $R^{11}$ is defined herein. For example, in some embodiments, $L^1$ can be

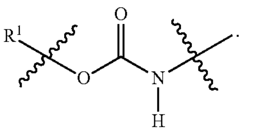

In some embodiments, in Formula I (e.g., Formula I-1, I-2, I-3, I-1-A, I-1-B, I-1-C, I-1-D, I-1-E, I-1-F, I-1-G, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15), $L^1$ can also be

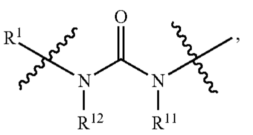

wherein $R^{11}$ and $R^{12}$ are defined herein. For example, in some embodiments, $L^1$ can be

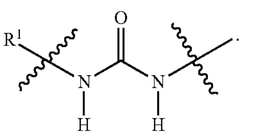

In some embodiments, in Formula I (e.g., Formula I-1, I-2, I-3, I-1-A, I-1-B, I-1-C, I-1-D, I-1-E, I-1-F, I-1-G, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15), $L^1$ can also be null. For example, in some embodiments, the compound of Formula I-1 can have a subformula of Formula I-1-I, wherein $R^1$ is directly attached to the pyridazine ring:

Formula I-1-I

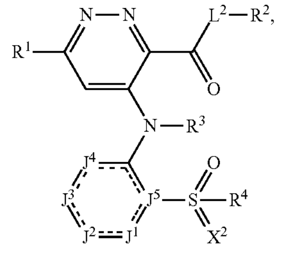

wherein the variables $R^1$, $L^2$, $R^2$, $R^3$, $J^1$, $J^2$, $J^3$, $J^4$, $J^5$, $X^2$, and $R^4$ include any of those described herein in any combination, such as those described in connection with Formula I-1 and its subformulae.

Various groups are suitable as $R^1$ in Formula I. In some embodiments, $R^1$ can be hydrogen. In some embodiments, $R^1$ can be an optionally substituted $C_{1-6}$ alkyl. In some embodiments, $R^1$ can be an optionally substituted $C_{3-10}$ carbocyclic ring, which can be a monocyclic, or a fused, bridged, or spiro bicyclic carbocyclic ring. Typically, the carbocyclic ring is fully saturated. However, in some embodiments, the carbocyclic ring can also be partially unsaturated. In some embodiments, $R^1$ can be an optionally substituted 4-10 membered heterocyclic ring, which can be a monocyclic or a fused, bridged, or spiro bicyclic heterocyclic ring. The heterocyclic ring can be fully saturated or partially unsaturated. In some embodiments, $R^1$ can be an optionally substituted phenyl. In some embodiments, $R^1$ can be an optionally substituted heteroaryl, such as a 5-10 membered monocyclic or bicyclic heteroaryl. In some embodiments, $R^1$ can be an optionally substituted 5- or 6-membered heteroaryl having 1-3 ring heteroatoms independently selected from N, O, and S. In some embodiments, $R^1$ can be an optionally substituted 8-10 membered bicyclic heteroaryl having 1-3 ring heteroatoms independently selected from N, O, and S.

In some embodiment, $R^1$ in Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1) can be selected from 1) a monocyclic $C_{3-6}$ cycloalkyl; 2) a spiro, fused, or bridged bicyclic $C_{4-10}$ cycloalkyl; 3) a monocyclic 4-8 membered heterocyclyl having 1-3 heteroatoms independently selected from O, N, and S; 4) a spiro, fused, or bridged bicyclic 5-10 membered heterocyclyl having 1-3 heteroatoms independently selected from O, N, and S; 5) phenyl; 6) a 6-membered heteroaryl having 1 or 2 ring nitrogen atoms; 7) a 5-membered heteroaryl having 1-3 ring heteroatoms independently selected from N, O, and S, 8) a 8-10 membered bicyclic heteroaryl having 1-3 ring heteroatoms independently selected from N, O, and S, and 9) a $C_{1-6}$ alkyl, wherein each of 1)-9) is optionally substituted, for example, with one or more independently selected $G^1$ as described herein. In some embodiments, $G^1$ at each occurrence is independently halogen (e.g., F or Cl), $G^{1A}$, $OG^{1A}$, ($C_{1-4}$ alkylene)-$G^{1A}$, O—($C_{1-4}$ alkylene)-$G^{1A}$, OH, CN, or $NG^{1B}G^{1C}$, or two $G^1$ form a bond, oxo, or a ring structure, wherein:

$G^{1A}$ at each occurrence is independently:

i) $C_{1-6}$ alkyl, ii) $C_{3-6}$ cycloalkyl, iii) $C_{1-4}$ heteroalkyl, iv) 4-8 membered heterocyclyl having 1-3 ring heteroatoms independently selected from O, N, and S, v) phenyl, or vi) 5-10 membered heteroaryl having 1-3 ring heteroatoms independently selected from O, N, and S, wherein each of i)-vi) is optionally substituted, e.g., with one or more substituents (e.g., 1, 2, or 3) each independently selected from F, Cl, CN, OH, oxo (as valency permits), $C_{1-4}$ alkyl, $C_{1-4}$ heteroalkyl, $C_{3-6}$ cycloalkyl, 4-6 membered heterocyclyl having 1 or 2 ring heteroatoms independently selected from O, N, and S, phenyl, or 5-6 membered heteroaryl having 1-3 ring heteroatoms independently selected from O, N, and S, wherein the $C_{1-4}$ alkyl, $C_{1-4}$ heteroalkyl, $C_{3-6}$ cycloalkyl, 4-6 membered heterocyclyl, phenyl, or 5-6 membered heteroaryl is independently optionally substituted with one or more substituents (e.g., 1, 2, or 3) each independently selected from F, Cl, CN, OH, oxo (as valency permits), $C_{1-4}$ alkyl optionally substituted with one or more (e.g., 1-3) $G^1D$, $C_{1-4}$ heteroalkyl optionally substituted with one or more (e.g., 1-3) $G^{1D}$, and $C_{3-6}$ cycloalkyl optionally substituted with one or more (e.g., 1-3) $G^{1D}$, wherein $G^{1D}$ at each occurrence is F, OH, or $C_{1-4}$ alkyl, $G^{1B}$ and $G^{1C}$ at each occurrence are independently hydrogen, $G^A$, ($C_{1-4}$ alkylene)-$G^A$, $COG^{1A}$, CO—($C_{1-4}$ alkylene)-$G^A$, $S(O)_2G^A$ or $S(O)_2$—($C_{1-4}$ alkylene)-$G^A$, wherein $G^{1A}$ is defined above.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a monocyclic $C_{3-6}$ cycloalkyl, such as cyclopropyl, cyclobutyl, or Cyclopentyl, which is unsubstituted or substituted with one or more (typically, 1 or 2) independently selected $G^1$ as described herein, such as F, OH, $C_{1-4}$ alkoxy, fluorine substituted $C_{1-4}$ alkoxy, $NH_2$, NH($C_{1-4}$ alkyl), N($C_{1-4}$ alkyl)($C_{1-4}$ alkyl), etc. In some preferred embodiments, $R^1$ in Formula I (e.g., Formula I-1 and its subformulae, such as Formula I-1-A (e.g., I-1-A-1 to I-1-A-15) or I-1-H (e.g., I-1-H-1)) can be cyclopropyl.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a spiro bicyclic $C_{5-8}$ cycloalkyl, such as

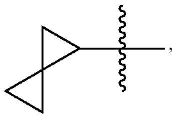 [SMILES: *C1CC12CC2], which is unsubstituted or substituted with one or more (typically, 1 or 2) independently selected $G^1$ as described herein, such as F, methyl, methoxy, etc.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a bridged bicyclic $C_{5-8}$ cycloalkyl, such as

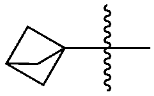,

Which is unsubstituted or substituted with one or more (typically, 1 or 2) independently selected $G^1$ as described herein.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a fused bicyclic $C_{5-8}$ cycloalkyl, which is unsubstituted or substituted with one or more (typically, 1 or 2) independently selected $G^1$ as described herein.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a monocyclic 4-6 membered heterocyclyl having 1-3 heteroatoms independently selected from O, N, and S, such as azetidinyl, pyrrolidinyl, etc., which is unsubstituted or substituted with one or more (typically, 1 or 2) independently selected $G^1$ as described herein, such as F or methyl.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a fused 6-8 membered heterocyclyl having 1-3 heteroatoms independently selected from O, N, and S, such as

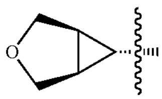, which is unsubstituted or substituted with one or more (typically, 1 or 2) independently selected $G^1$ as described herein, such as F, OH, or methyl.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a bridged or spiro 5-8 membered heterocyclyl having 1-3 heteroatoms independently selected from O, N, and S, which is unsubstituted or substituted with one or more (typically, 1 or 2) independently selected $G^1$ as described herein.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a phenyl, which is optionally substituted with one or more (typically, 1 or 2) independently selected $G^1$ as described herein, such as F, OH, Cl, CN, $C_{1-4}$ alkyl, hydroxyl substituted $C_{1-4}$ alkyl, fluorine substituted $C_{1-4}$ alkyl, $C_{1-4}$ alkoxy, fluorine substituted $C_{1-4}$ alkoxy, etc.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a 6-membered heteroaryl having 1 or 2 ring nitrogen atoms, such as pyridine, pyrimidine, etc., which is optionally substituted with one or more (typically, 1 or 2) independently selected $G^1$ as described herein, such as F, OH, Cl, CN, $C_{1-4}$ alkyl, hydroxyl substituted $C_{1-4}$ alkyl, fluorine substituted $C_{1-4}$ alkyl, $C_{1-4}$ alkoxy, fluorine substituted $C_{1-4}$ alkoxy, etc.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can be a 5-membered heteroaryl having 1-3 ring heteroatoms independently selected from N, O, and S, such as pyrazole, etc., which is optionally substituted with one or more (typically, 1 or 2) independently selected $G^1$ as described herein, such as F, OH, Cl, CN, $C_{1-4}$ alkyl, hydroxyl substituted $C_{1-4}$ alkyl, fluorine substituted $C_{1-4}$ alkyl, $C_{1-4}$ alkoxy, fluorine substituted $C_{1-4}$ alkoxy, etc.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can also be a 8-10 membered bicyclic heteroaryl having 1-3 ring heteroatoms independently selected from N, O, and S, which is optionally substituted with one or more (typically, 1 or 2) independently selected $G^1$ as described herein, such as F, OH, Cl, CN, $C_{1-4}$ alkyl, hydroxyl substituted $C_{1-4}$ alkyl, fluorine substituted $C_{1-4}$ alkyl, $C_{1-4}$ alkoxy, fluorine substituted $C_{1-4}$ alkoxy, etc.

In some embodiments, $R^1$ in Formula I (e.g., Formula I-1 and its subformulae, such as Formula I-1-A (e.g., I-1-A-1 to I-1-A-15) or I-1-H (e.g., I-1-H-1)) can also be a $C_{3-6}$ alkyl, such as isopropyl, which is optionally substituted with one or more (typically, 1 or 2) independently selected $G^1$ as described herein, such as F, OH, $C_{1-4}$ alkoxy, fluorine substituted $C_{1-4}$ alkoxy, etc.

When $L^1$ is null, such as those compounds of Formula I-1-I, $R^1$ is typically a heteroaryl, such as 5- or 6-membered heteroaryl. For example, in some embodiments, $R^1$ can be a 5-membered heteroaryl having 1-3 ring heteroatoms independently selected from N, O, and S, which is optionally substituted. In some embodiments, $R^1$ can be a 5-membered heteroaryl having 1-3 ring heteroatoms independently selected from N, O, and S, such as those 5-membered heteroaryl described herein, for example, pyrazole, which is optionally substituted with one or more $G^2$, wherein $G^2$ at each occurrence is independently halogen (e.g., F or Cl), $G^{2A}$, $OG^{2A}$, ($C_{1-4}$ alkylene)-$G^{2A}$, O—($C_{1-4}$ alkylene)-$G^{2A}$, OH, CN, or $NG^{2B}G^{2C}$, or two $G^2$ form a ring structure, wherein:

$G^{2A}$ at each occurrence is independently a $C_{1-6}$ alkyl, $C_{3-6}$ cycloalkyl, $C_{1-4}$ heteroalkyl, or 4-8 membered heterocyclyl having 1-3 heteroatoms independently selected from O, N, and S, wherein the $C_{1-6}$ alkyl, $C_{3-6}$ cycloalkyl, $C_{1-4}$ heteroalkyl, or 4-8 membered heterocyclyl is optionally substituted with one or more substituents (e.g., 1, 2, or 3) each independently selected from F, Cl, OH, $C_{1-4}$ alkyl, fluorine substituted $C_{1-4}$ alkyl, $C_{1-4}$ heteroalkyl, or fluorine substituted $C_{1-4}$ heteroalkyl, and $G^{2B}$ and $G^{2C}$ at each occurrence are independently hydrogen, $G^{2A}$, ($C_{1-4}$ alkylene)-$G^2$A, $COG^{2A}$, CO—($C_{1-4}$ alkylene)-$G^{2A}$, $S(O)_2G^{2A}$ or $S(O)_2$—($C_{1-4}$ alkylene)-$G^{2A}$, wherein $G^{1A}$ is defined above.

In some embodiments, $L^1$ is null, such as those compounds of Formula I-1-I, $R^1$ is pyrazole, which is optionally substituted with one or more (e.g., 1 or 2) independently selected $G^2$ as described herein, such as F, OH, Cl, CN, $C_{1-4}$ alkyl, fluorine substituted $C_{1-4}$ alkyl, $C_{1-4}$ alkoxy, fluorine substituted $C_{1-4}$ alkoxy, etc.

Suitable combinations of $L^1$ and $R^1$ for Formula I are not particularly limited. For example, unless otherwise specified or contrary from context, in any of the embodiments herein, $L^1$-$R^1$ in Formula I (e.g., Formula I-1, 1-2, 1-3, I-1-A, I-1-B, I-1-C, I-1-D, I-1-E, I-1-F, I-1-G, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, or I-1-A-15) can be selected from:

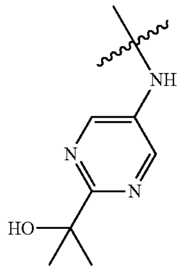
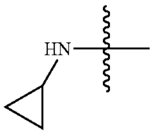
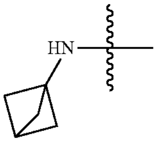
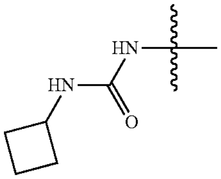
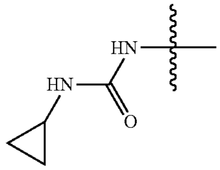
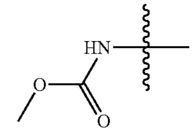
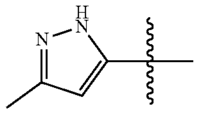
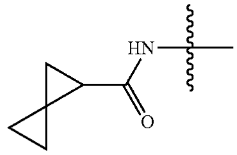
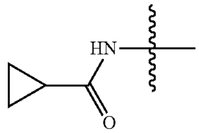
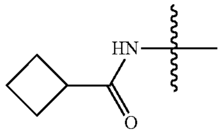
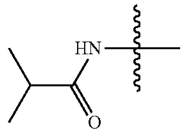
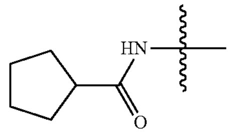
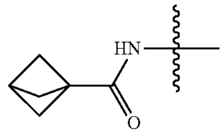
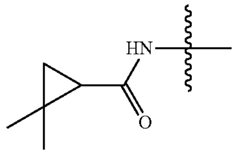
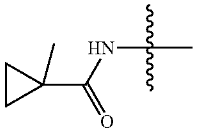
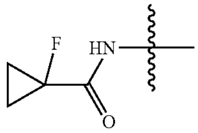
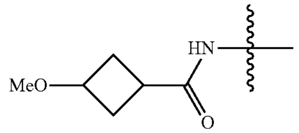
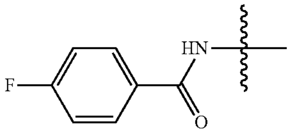
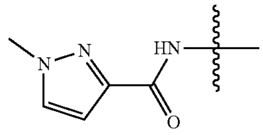
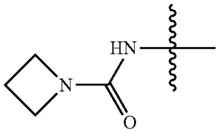
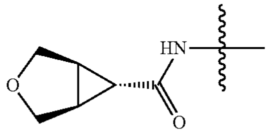

-continued

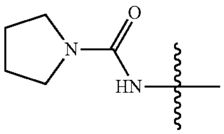
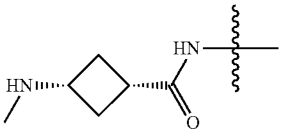
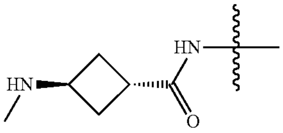
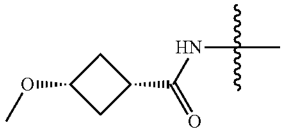
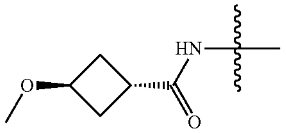
.

Unless otherwise specified or contrary from context, in any of the embodiments herein, $L^1$-$R^1$ in Formula I (e.g., Formula I-1, 1-2, 1-3, I-1-A, I-1-B, I-1-C, I-1-D, I-1-E, I-1-F, I-1-G, I-1-H, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1) can also be selected from:

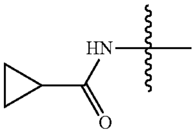
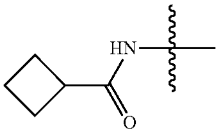
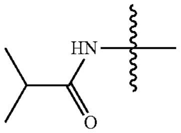
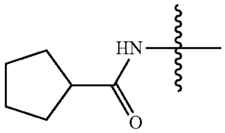
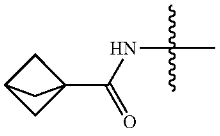
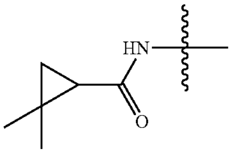
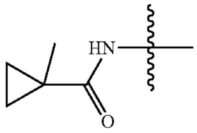
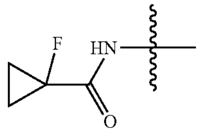
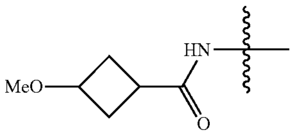
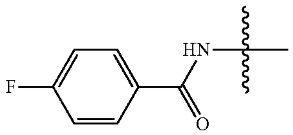
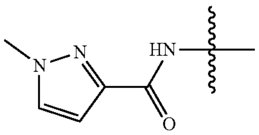
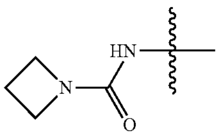
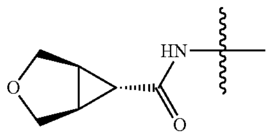

-continued

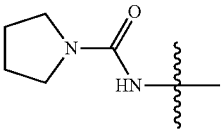
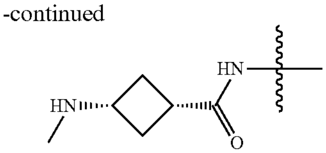
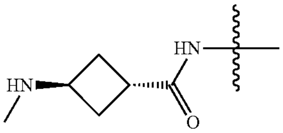
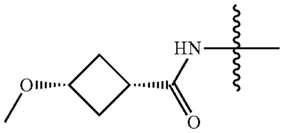
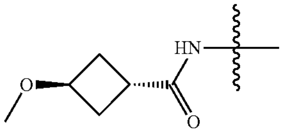
.

Unless otherwise specified or contrary from context, in any of the embodiments herein, $L^1$-$R^1$ in Formula I (e.g., Formula I-1, 1-2, 1-3, I-1-A, I-1-B, I-1-C, I-1-D, I-1-E, I-1-F, I-1-G, I-1-H, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1) can be:

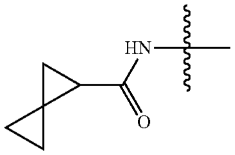
or
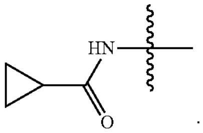
.

Unless otherwise specified or contrary from context, in any of the embodiments herein, $L^1$-$R^1$ in Formula I (e.g., Formula I-1, 1-2, 1-3, I-1-A, I-1-B, I-1-C, I-1-D, I-1-E, I-1-F, I-1-G, I-1-H, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1) can be selected from:

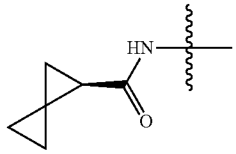
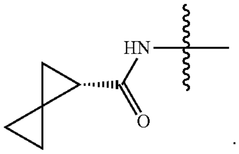
.

Typically, in Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), $L^2$ is NH.

In some embodiments, in Formula I (e.g., Formula I-1 and its subformulae), $L^2$ can be a $C_{1-4}$ alkylene, such as $CH_2$. In some embodiments, in Formula I (e.g., Formula I-1 and its subformulae), $L^2$ can be a $C_{1-4}$ heteroalkylene. In some embodiments, in Formula I (e.g., Formula I-1 and its subformulae), $L^2$ can be a $C_{3-6}$ cycloalkylene, such as cyclopropylene. In some embodiments, in Formula I (e.g., Formula I-1 and its subformulae), $L^2$ can be a 4-6 membered heterocyclylene having 1 or 2 ring heteroatoms independently selected from N, O, and S, which is optionally substituted, e.g., with F and/or methyl.

Typically, in Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), $R^2$ is hydrogen, $C_{1-4}$ alkyl, or $CD_3$.

In some embodiments, in Formula I (e.g., Formula I-1 and its subformulae), $R^2$ can also be a $C_{1-4}$ heteroalkyl.

Unless otherwise specified or contrary from context, in any of the embodiments herein, $L^2$-$R^2$ in Formula I (e.g., Formula I-1 and its subformulae) can be selected from:

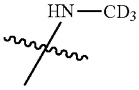
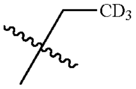
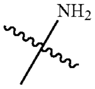
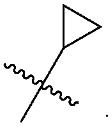

Unless otherwise specified or contrary from context, in any of the embodiments herein, $L^2$-$R^2$ in Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1) can be:

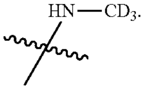

In some embodiments, the present disclosure also provides a compound selected from the following Compound Nos. 1-33 or a pharmaceutically acceptable salt thereof:

1

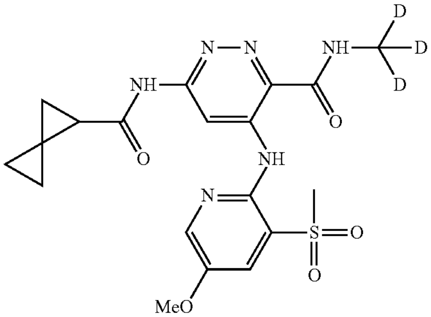

2

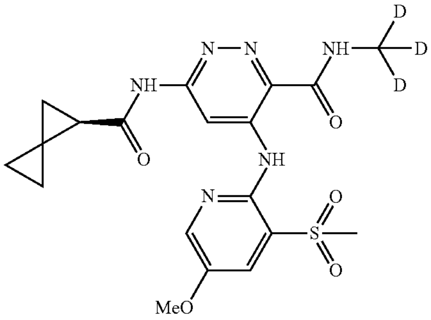

-continued

3

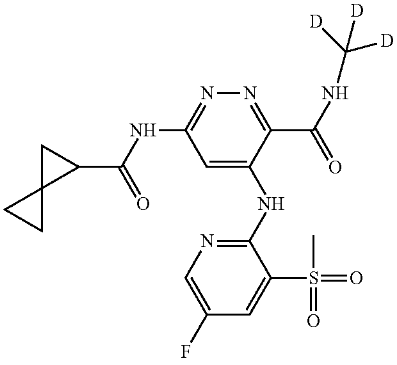

4

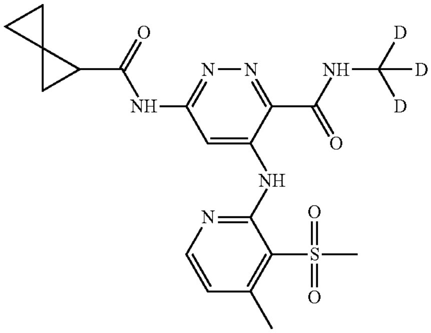

5

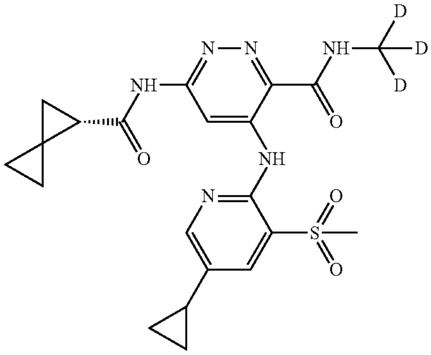

6

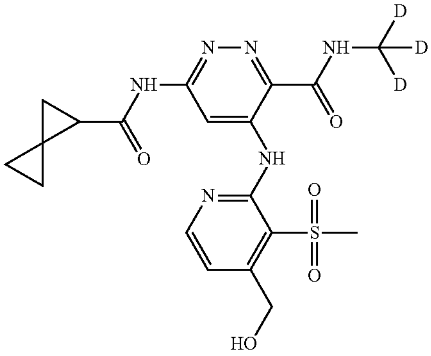

-continued
7
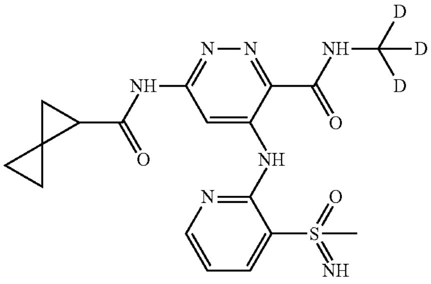
8
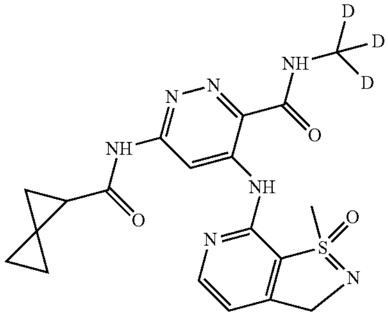
9
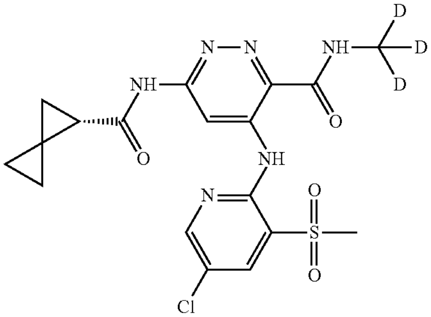
10
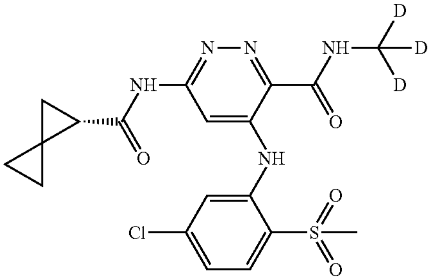
11
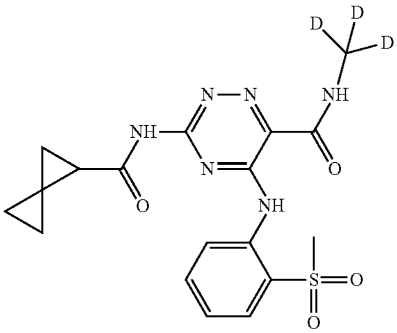
-continued
12
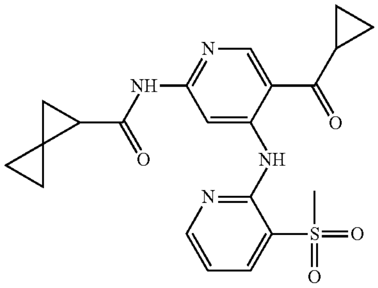
13
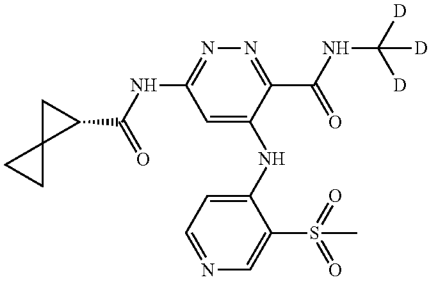
14
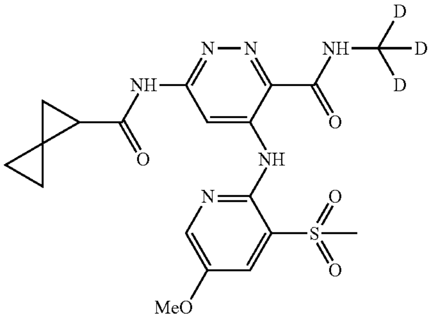
15
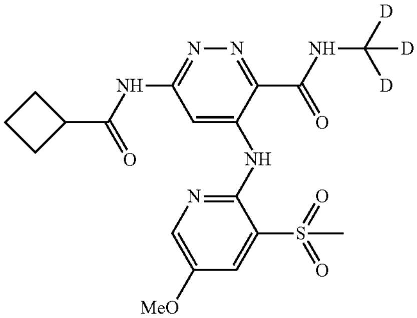
16
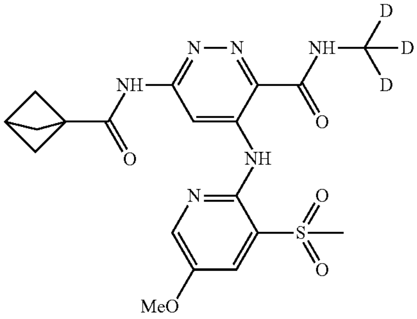

-continued
17
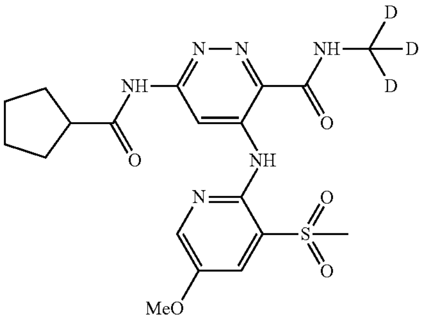
18
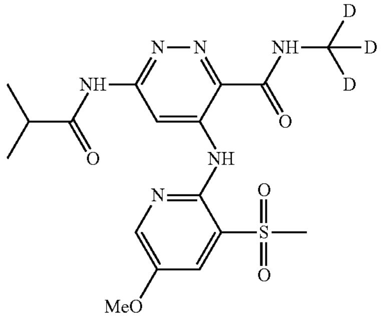
19
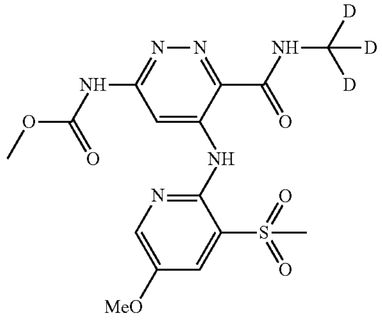
20
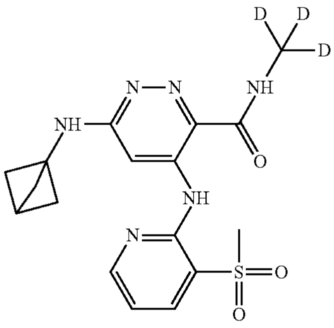
21
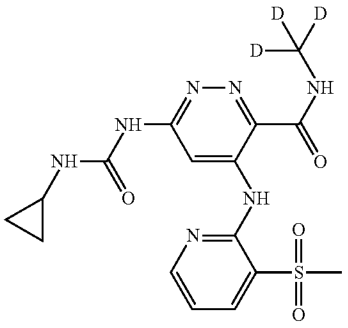
-continued
22
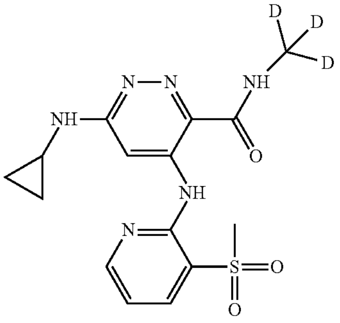
23
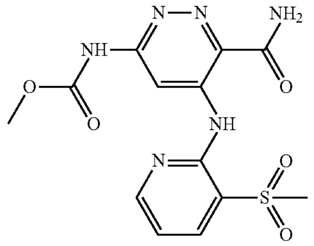
24
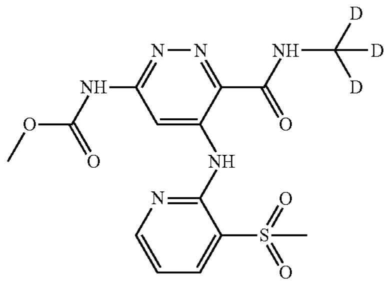
25
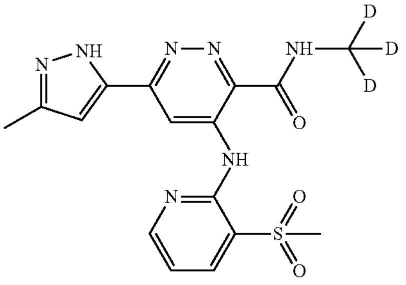
26
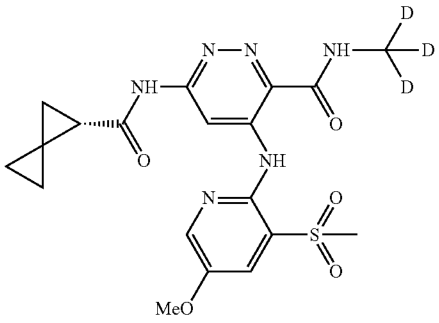

-continued
27
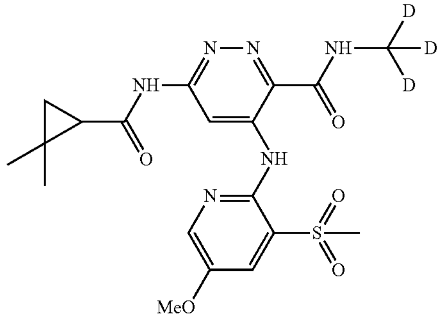
28
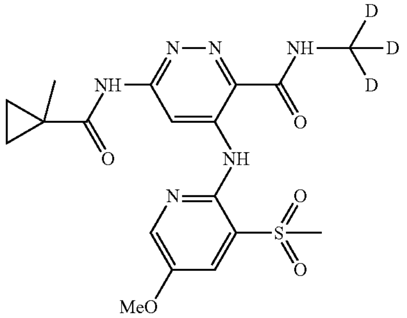
29
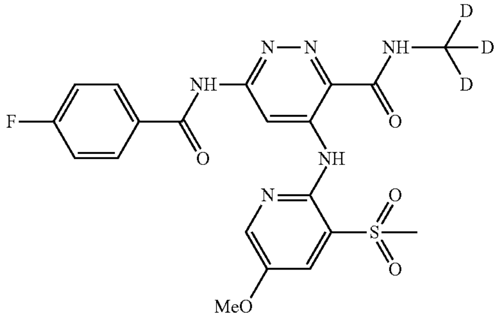
30
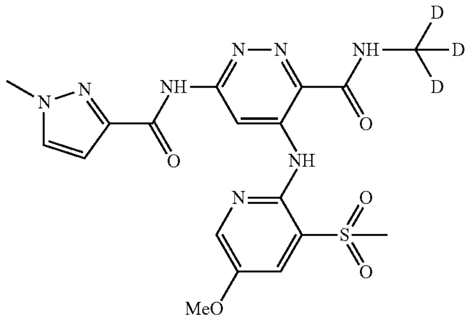
31
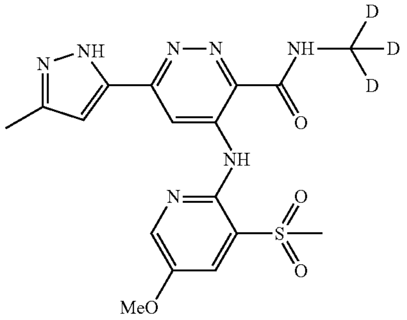
-continued
32
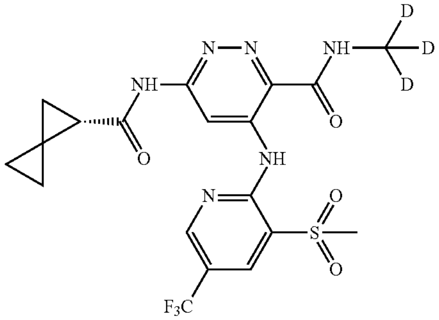
33
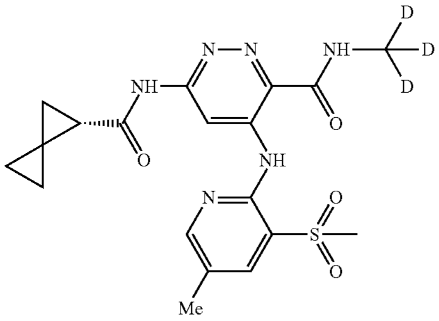
34
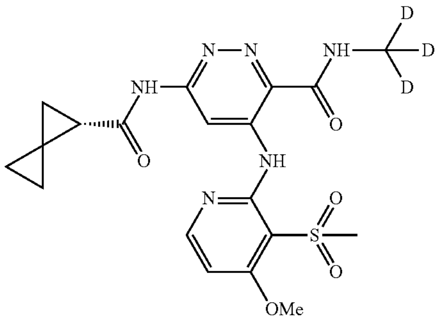
35
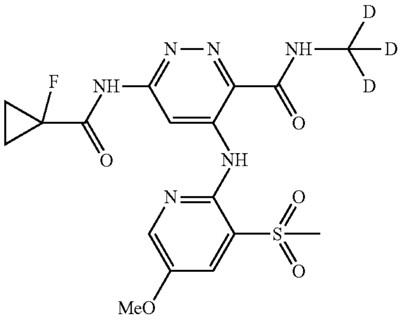
36
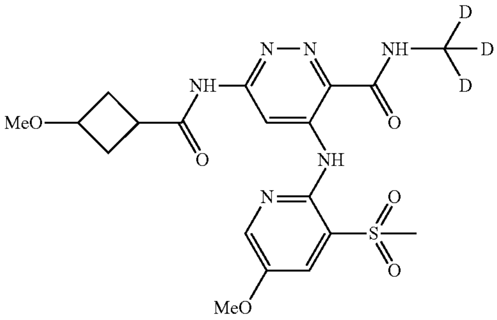

37
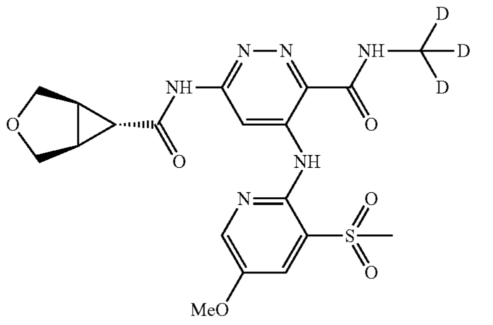
38
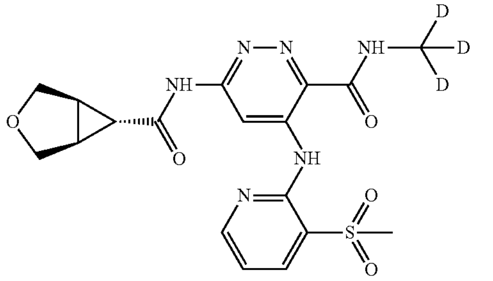
39
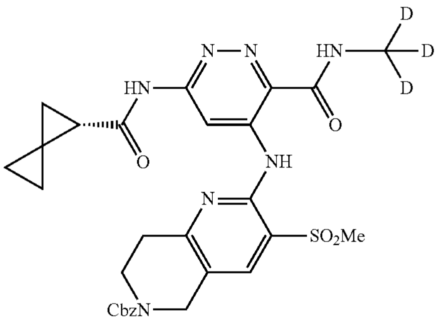
40
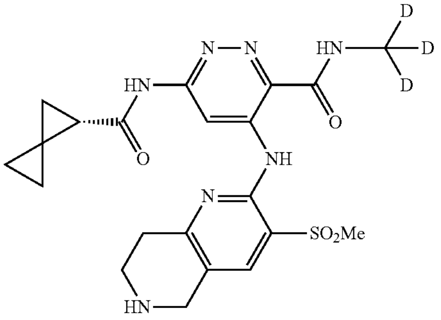
41
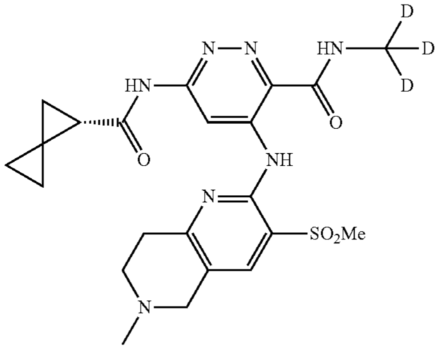
42
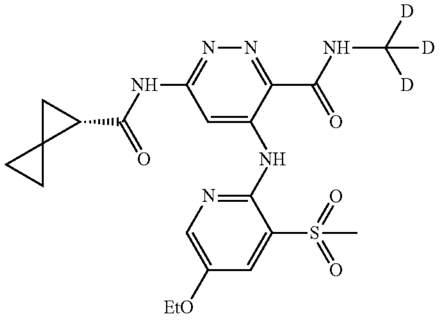
43
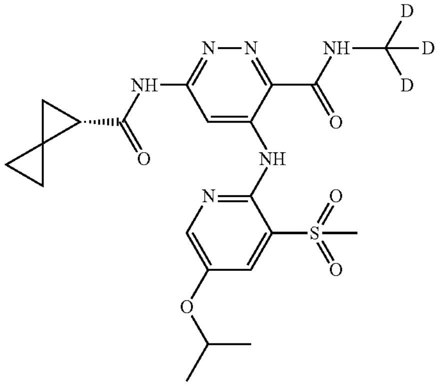
44
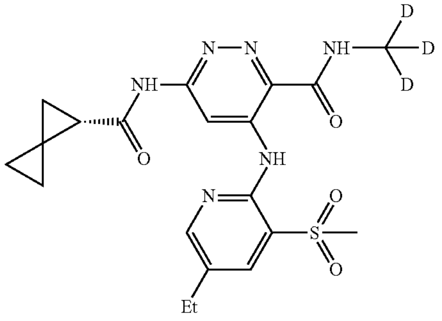

-continued
45
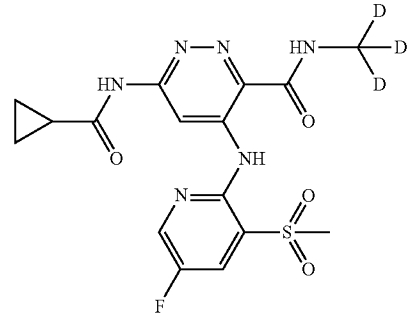
46
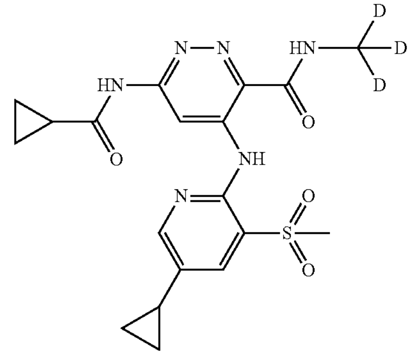
47
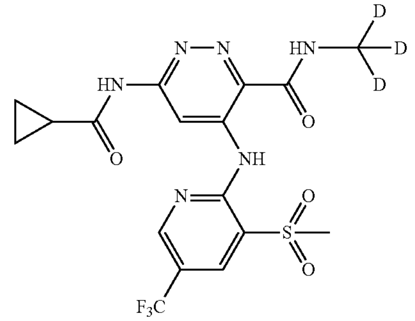
48
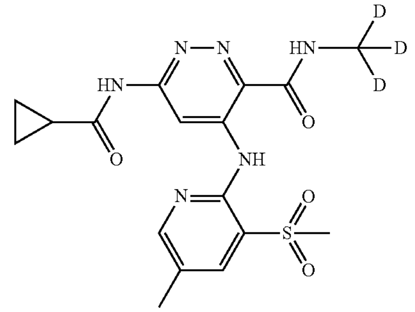
49
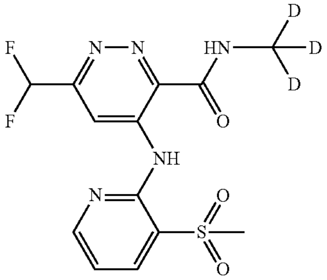
-continued
50
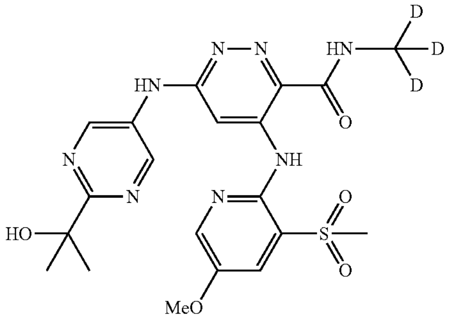
51
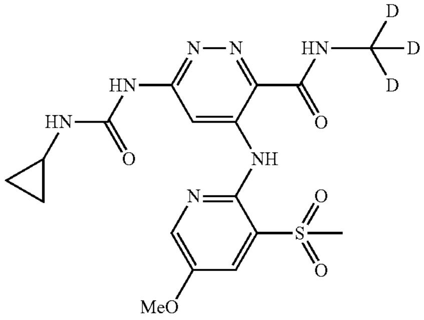
52
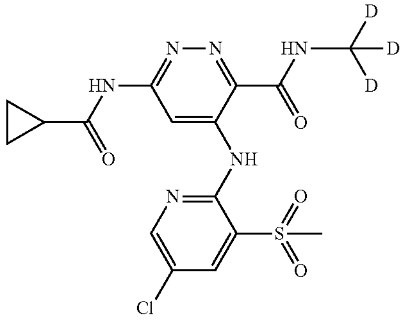
53
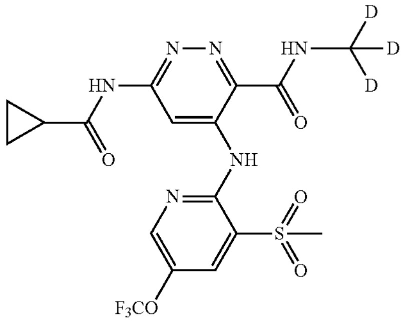
54
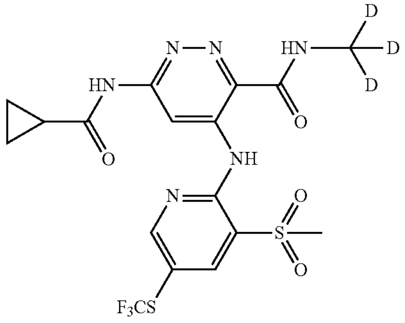

-continued
55
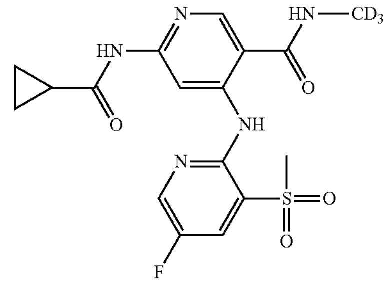
56
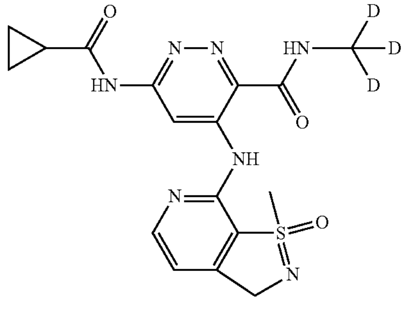
enantiomer 1
57
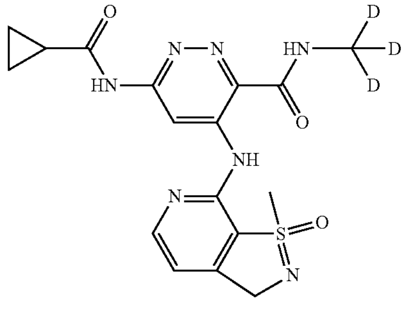
enantiomer 2
58
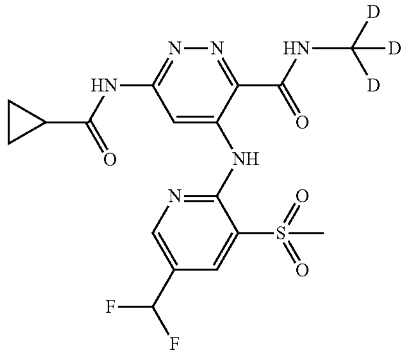
-continued
59
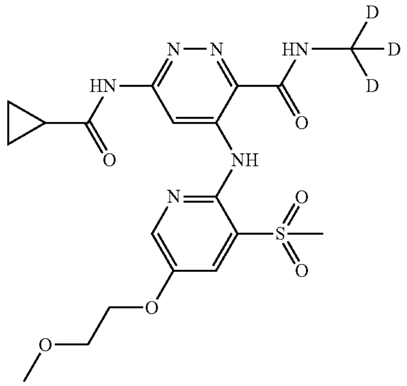
60
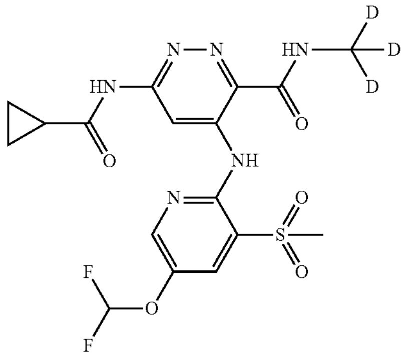
61
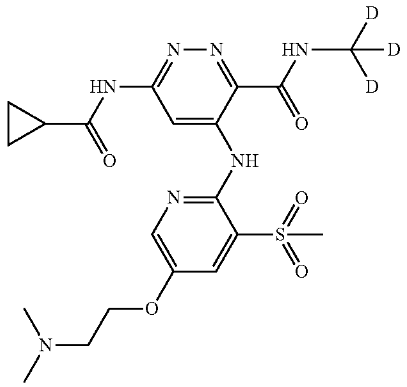
62
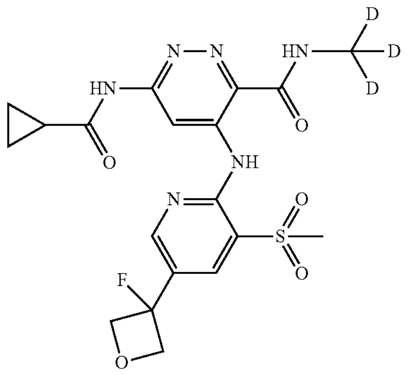

-continued
63
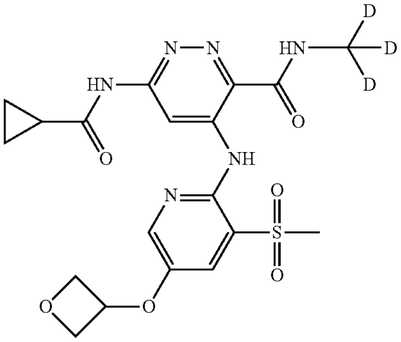
64
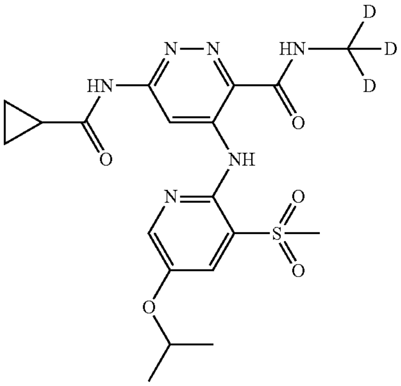
65
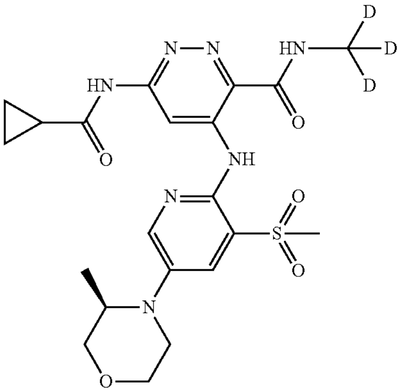
66
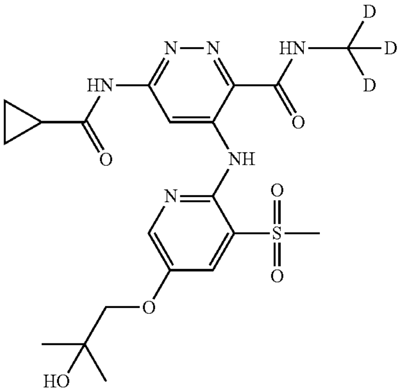
-continued
67
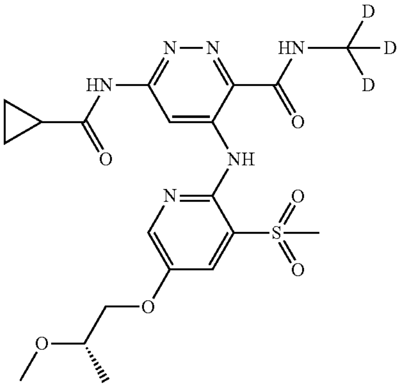
68
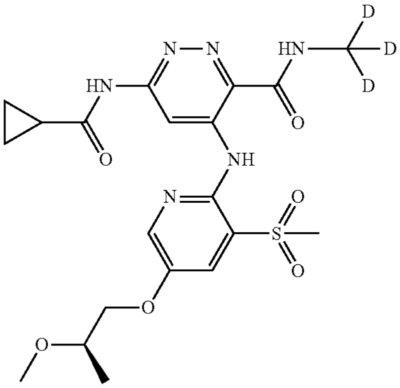
69
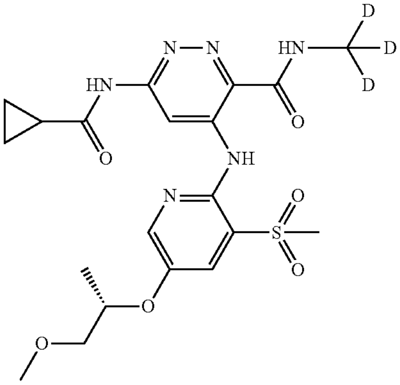
70
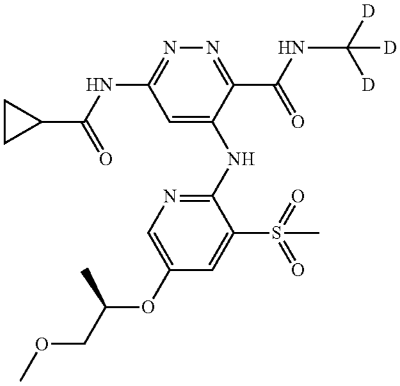

-continued
71
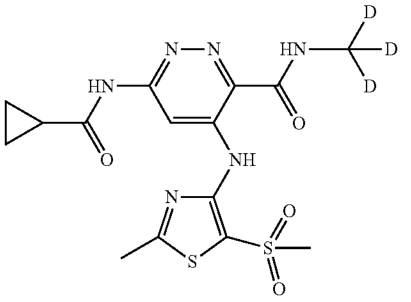
72
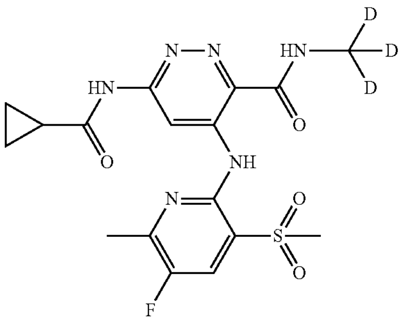
73
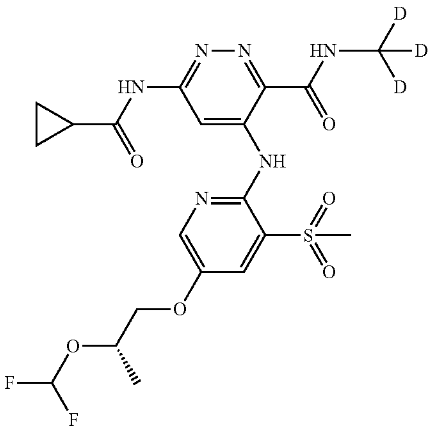
74
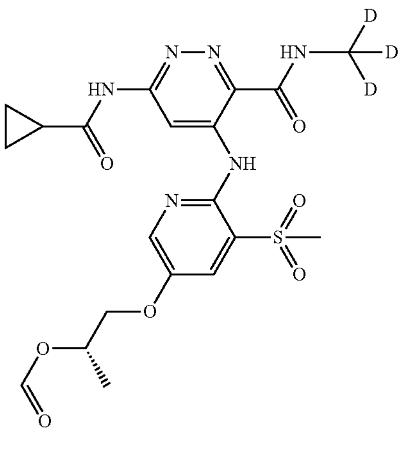
-continued
75
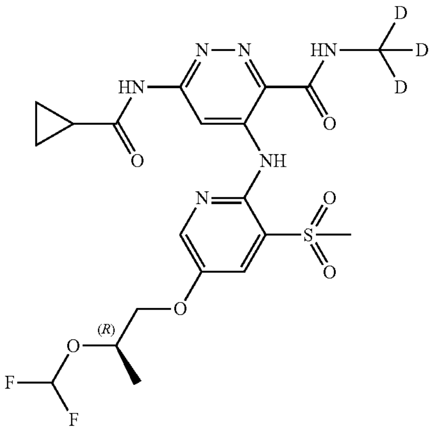
76
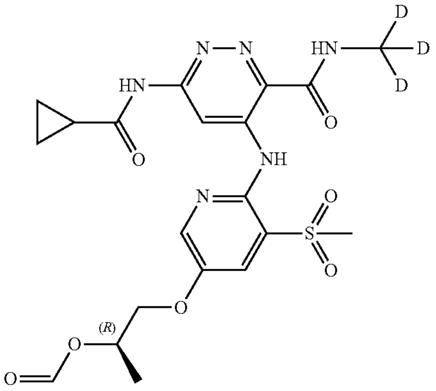
77
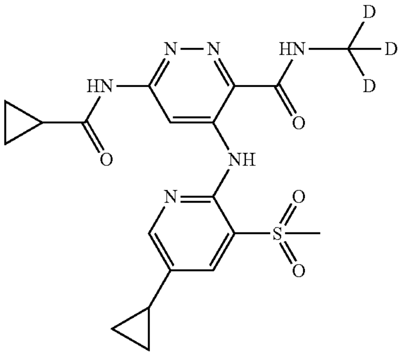
78
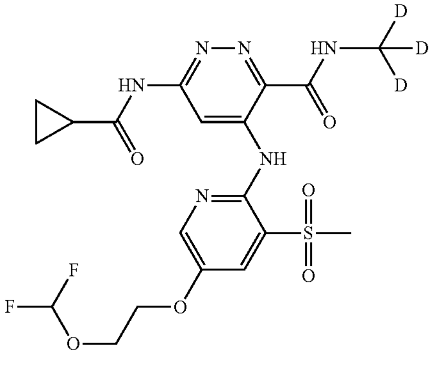

-continued
79
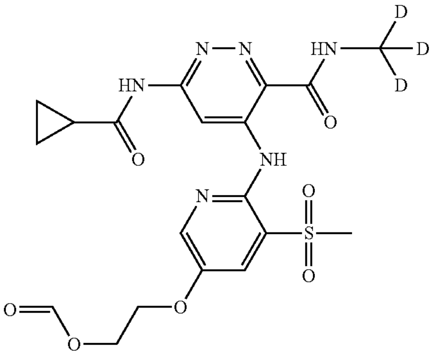
80
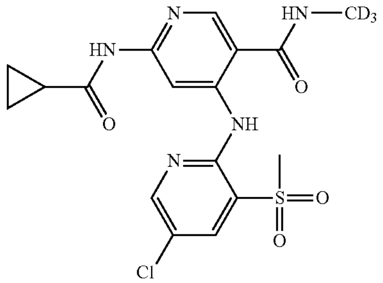
81
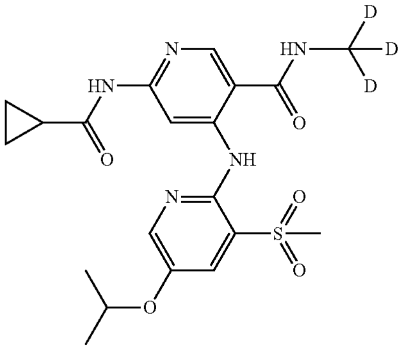
82
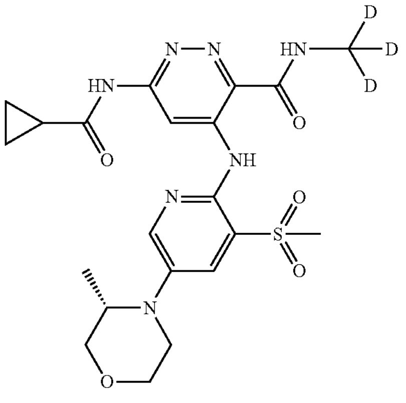
-continued
83
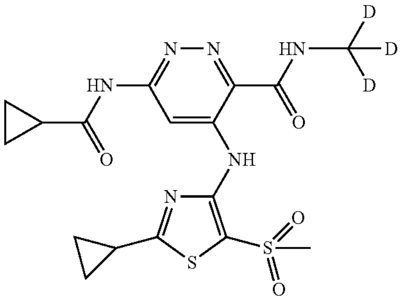
84
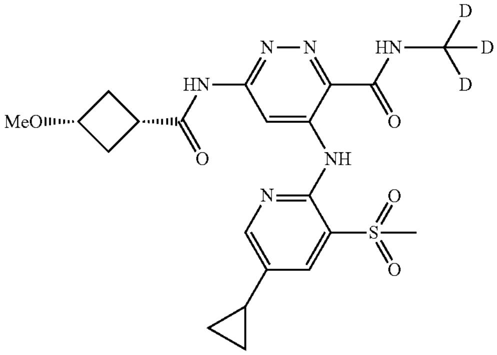
85
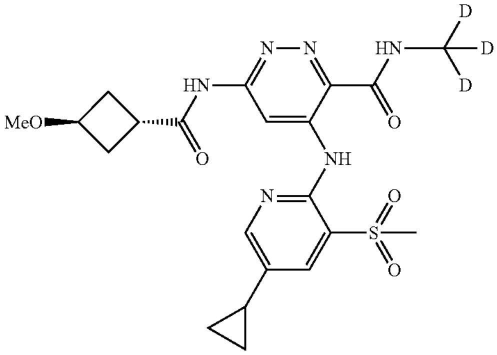
86
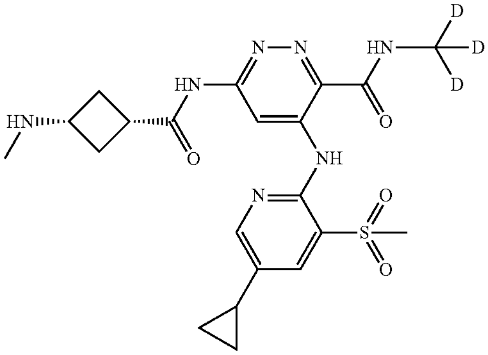

-continued
87
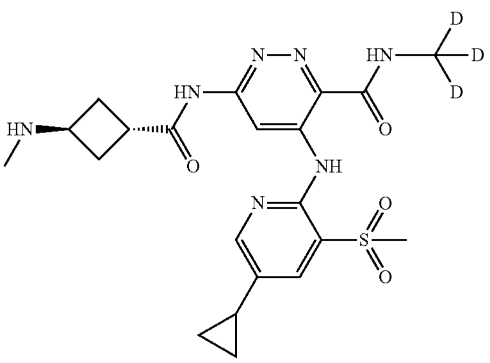
88
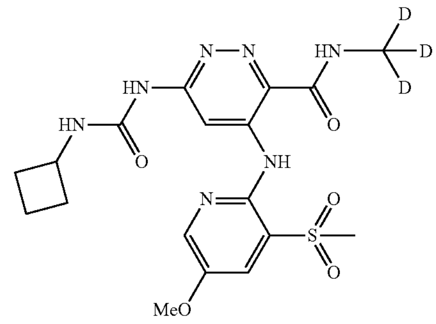
89
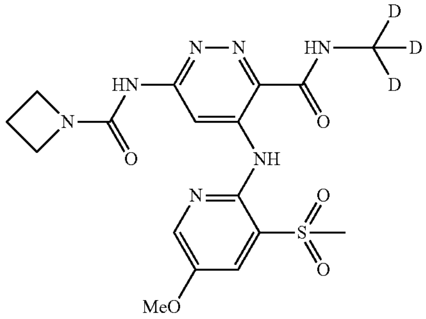
90
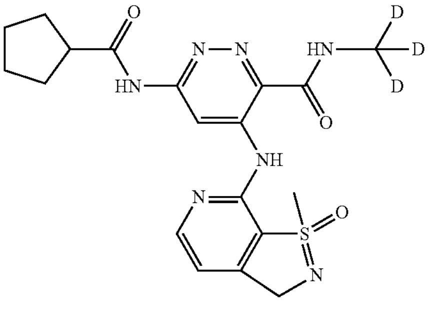
enantiomer 1
-continued
91
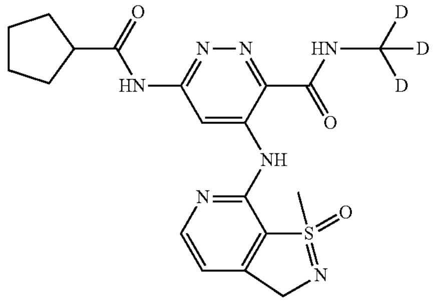
enantiomer 2
92
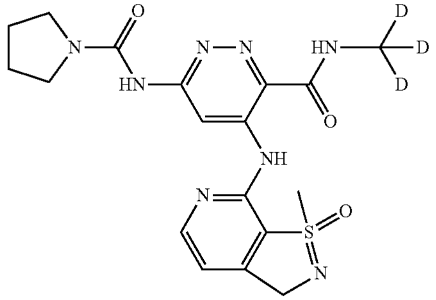
enantiomer 1
93
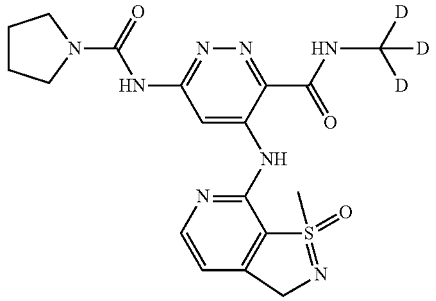
enantiomer 2
94
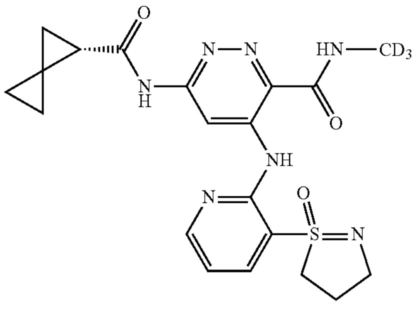
enantiomer 1

-continued
95
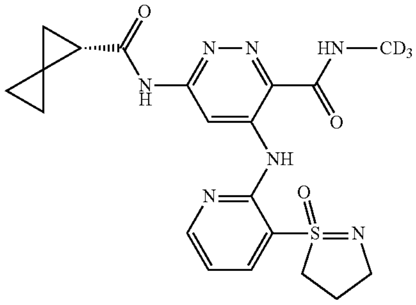
enantiomer 2
96
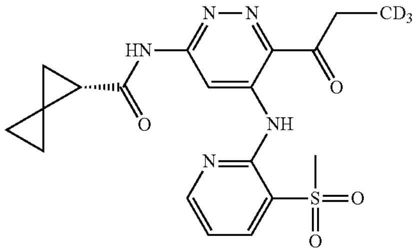
97
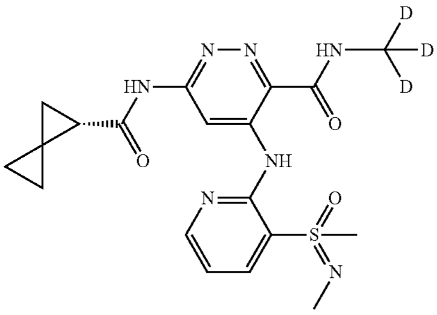
enantiomer 1
98
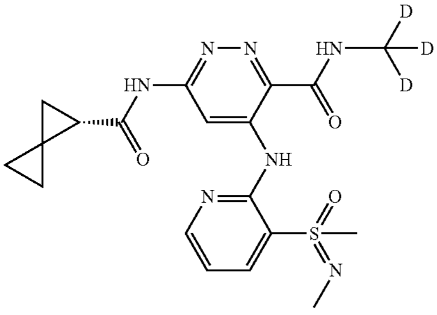
enantiomer 2
-continued
99
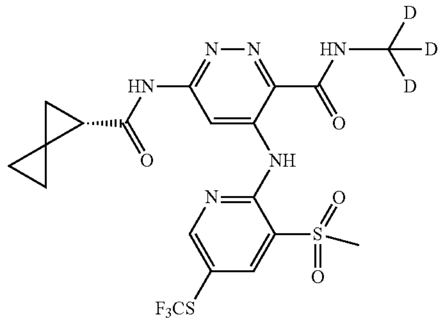
100
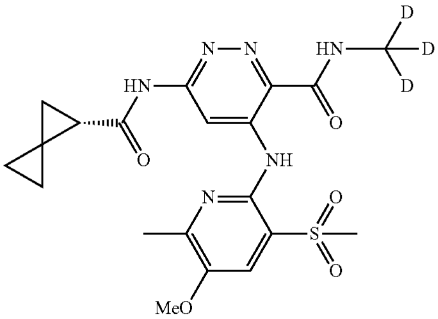
101
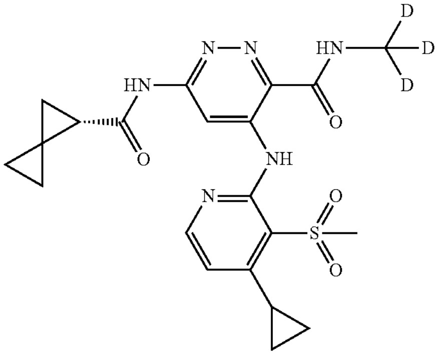
102
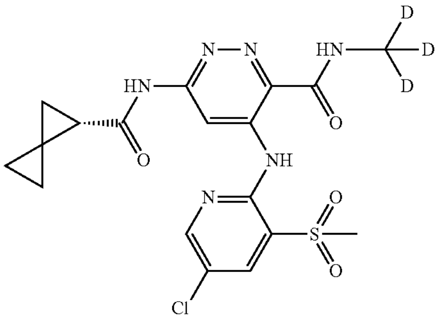
103
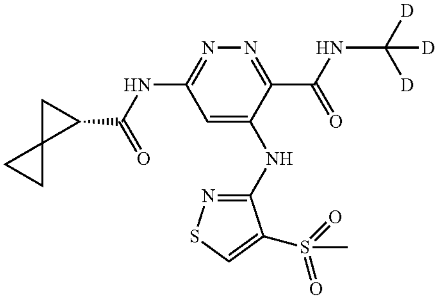

104
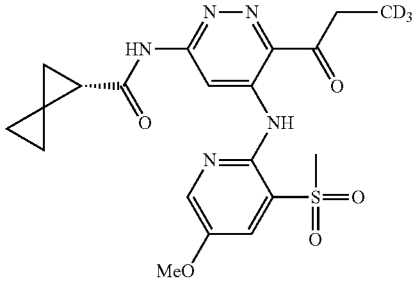
105
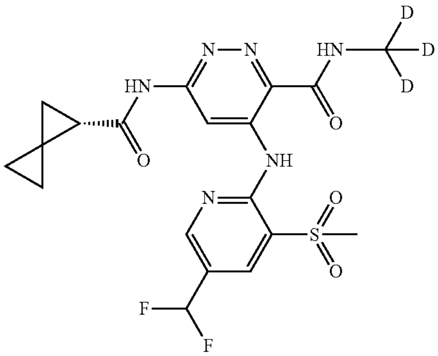
106
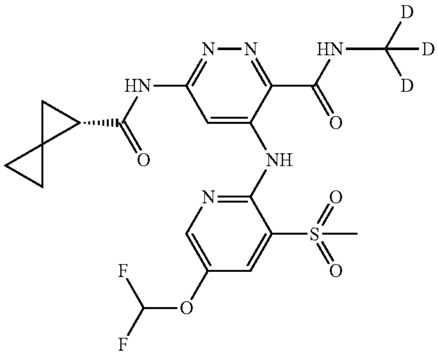
107
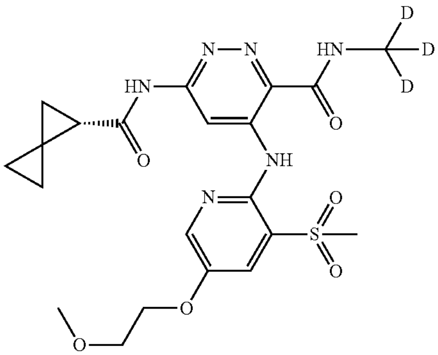
108
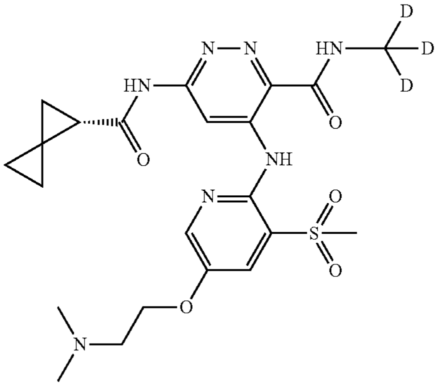
109
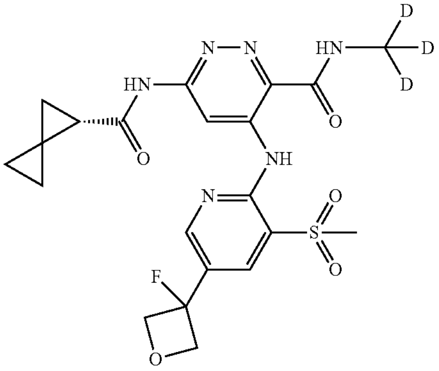
110
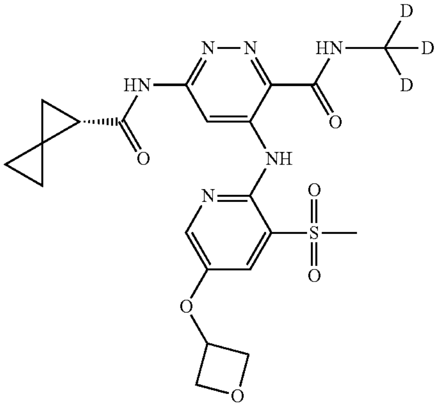
111
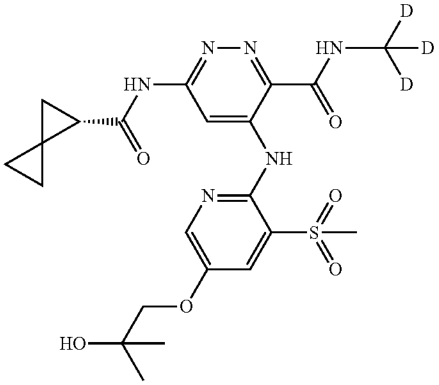

-continued
112
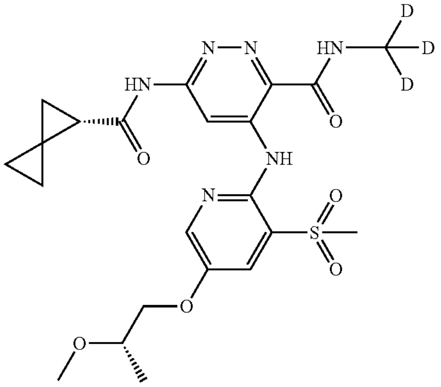
113
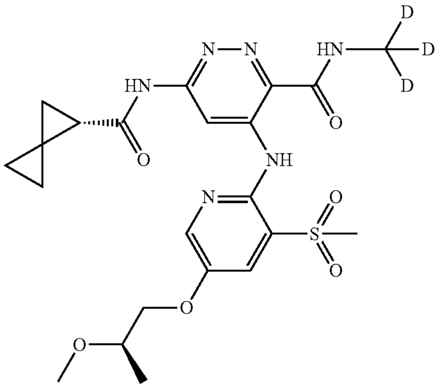
114
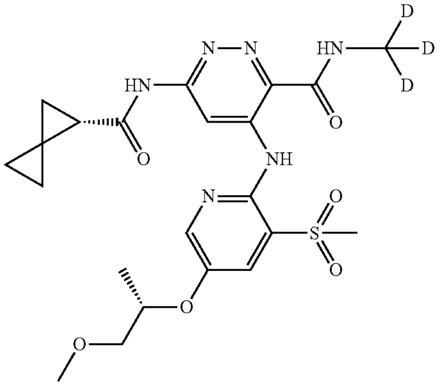
115
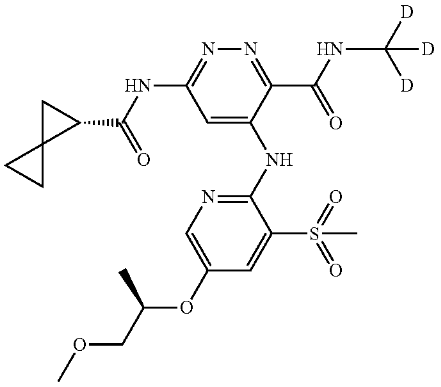
-continued
116
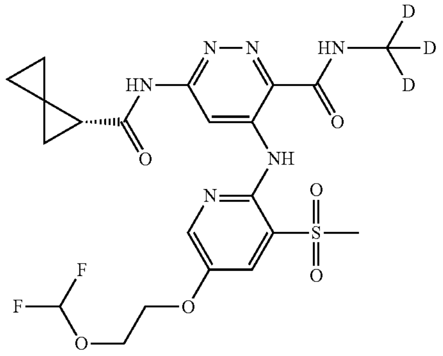
117
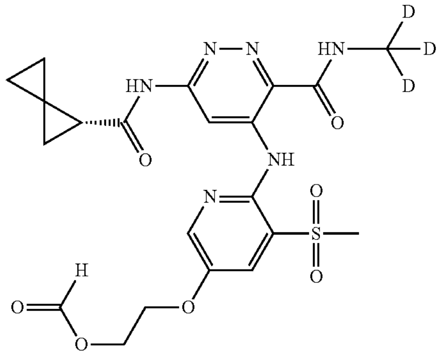
118
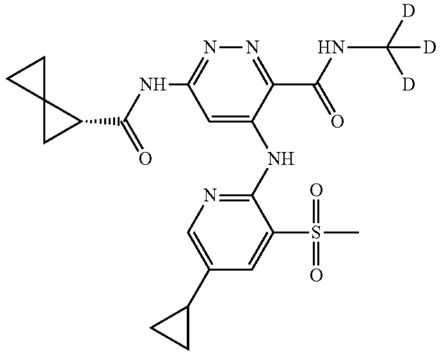
119
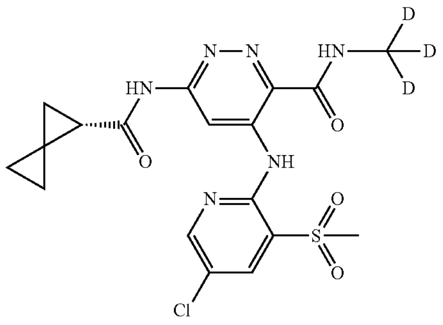

120
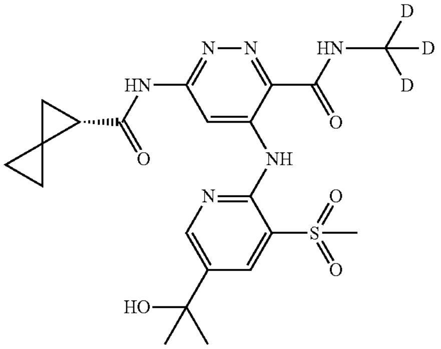
121
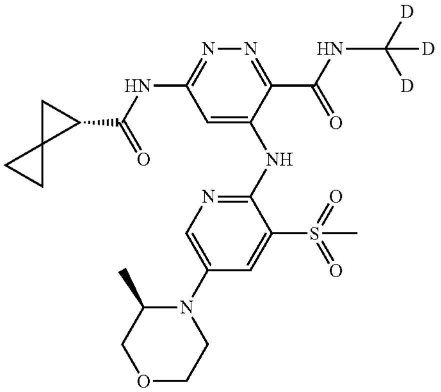
122
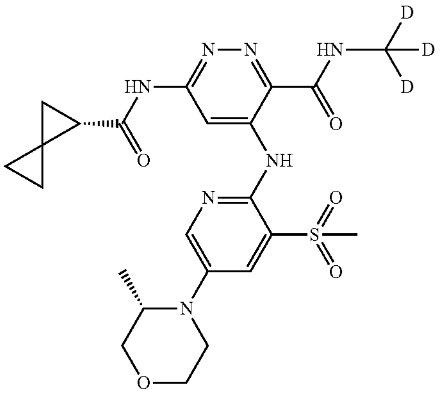
123
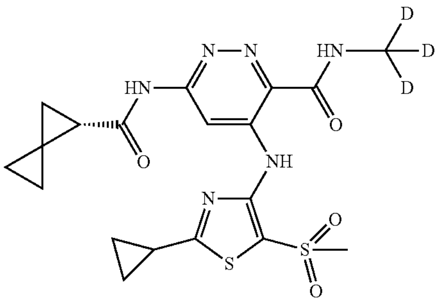
124
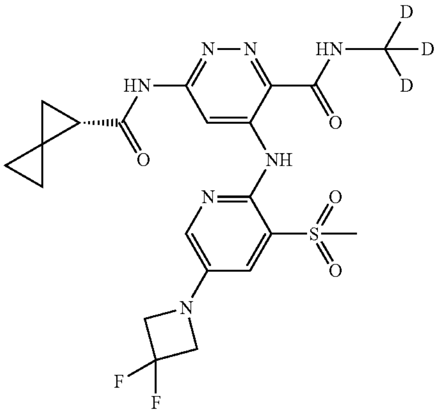
125
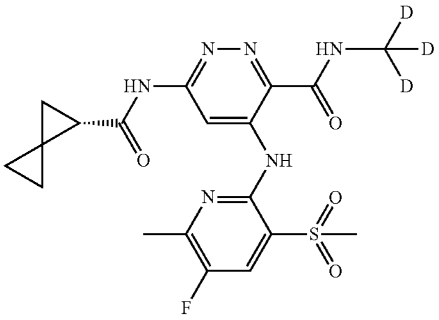
126
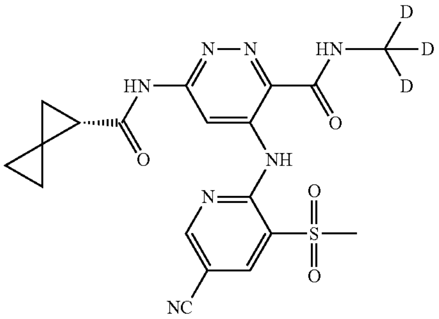
127
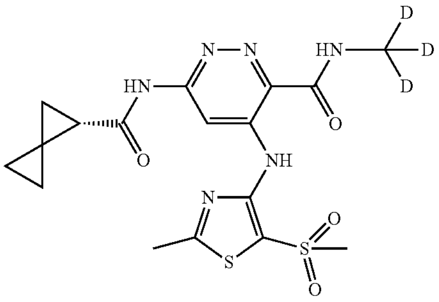

-continued

128

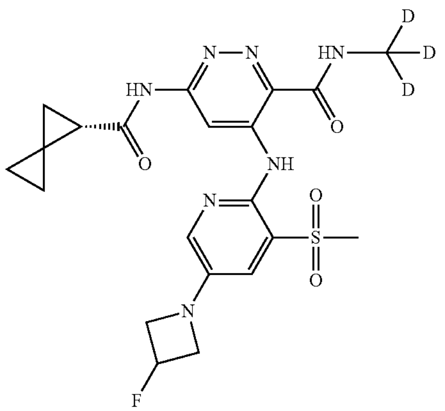

129

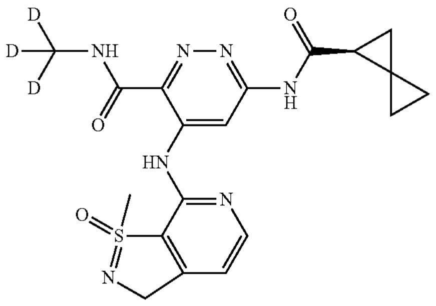

enantiomer 1

130

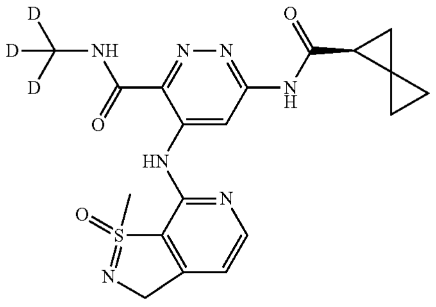

enantiomer 2

131

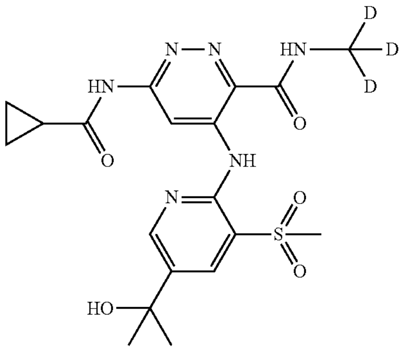

-continued

132

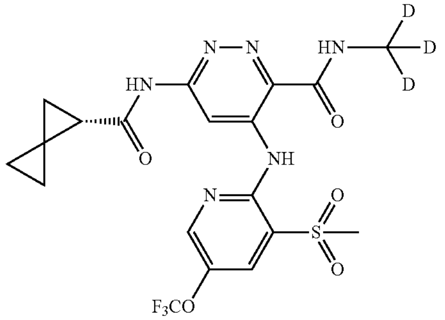

133

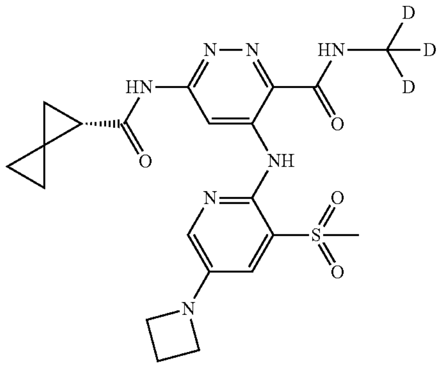

In some embodiments, to the extent applicable, the genus of compounds in the present disclosure also excludes any of the compounds specifically prepared and disclosed prior to this disclosure.

Method of Synthesis

The compounds of the present disclosure can be readily synthesized by those skilled in the art in view of the present disclosure. Exemplified synthesis are also shown in the Examples section.

The following synthetic process of Formula I-1-H-1 is illustrative, which can be applied similarly by those skilled in the art for the synthesis of other compounds of Formula I, by using a proper synthetic starting material and/or intermediate in view of the present disclosure. In some embodiments, the present disclosure also provides synthetic methods and synthetic intermediates for preparing the compounds of Formula I, as represented by the scheme herein.

As shown in Scheme 1, compounds of Formula I-1-H-1 can typically be synthesized through a series of coupling reactions and functional group transformations. In some embodiments, S-1 can be coupled with the pyridazine S-2 to form the compound S-3, wherein $Lg^1$ and $Lg^2$ can each independently be a leaving group described herein such as halogen (e.g., Cl). Typically, the reaction between S-1 and S-2 can be carried out under basic conditions, such as by using an alkali bis(trimethylsilyl)amide (e.g., LiHMDS) and the like. Compound S-3 can then be converted into S-5 by reacting with S-4. Typically, the reaction of S-3 and S-4 can be carried out in the presence of a transition metal catalyst, such as a palladium catalyst. Compound S-5 can then be transformed into the compound of Formula I-1-H-1 by converting the thioether function into $S(O)(X^2)$, typically by one or two steps of oxidation reaction (e.g., using an oxidizing agent and/or condition described herein), optionally also involving forming a ring between $X^2$ and $R^{14}$. Exemplary reaction conditions for converting a compound of S-1 into a compound of Formula I-1-H-1 are shown in the Examples section. The variables $R^1$, $L^2$, $R^2$, $R^4$, $R^{14}$, $R^{15}$, $R^{16}$, and $X^2$ in the formulae S-1, S-2, S-3, S-4, and S-5 of Scheme 1 include any of those defined hereinabove in connection with Formula I (e.g., any of the sub-formulae of Formula I) and protected derivatives thereof, when applicable.

Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7th Edition), and Larock's Comprehensive Organic Transformations (Wiley-VCH, 1999), and any of available updates as of this filing.

Scheme 1.

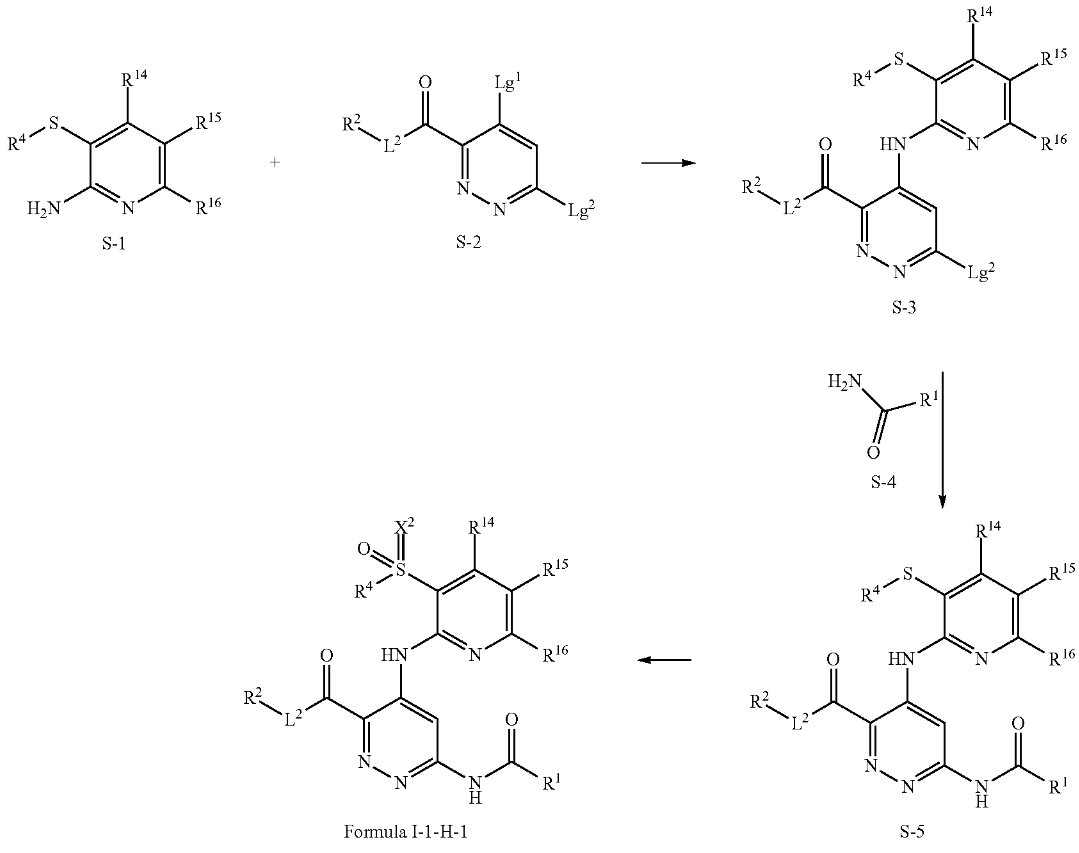

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", 4th ed. P. G. M. Wuts; T. W. Greene, John Wiley, 2007, and references cited therein. The reagents for the reactions described herein are generally known compounds or can be prepared by known procedures or obvious modifications thereof. For example, some of the reagents suitable for use in the reactions described herein may be prepared by following the respective procedures described in WO2019/103952, the content of which is incorporated by reference herein in its entirety. Also, many of the reagents are available from commercial suppliers such as Aldrich Chemical Co. (Milwaukee, Wisconsin, USA), Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Pharmaceutical Compositions Certain embodiments are directed to a pharmaceutical composition comprising one or more of the compounds of the present disclosure.

The pharmaceutical composition can optionally contain a pharmaceutically acceptable excipient. In some embodiments, the pharmaceutical composition comprises a compound of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof, e.g., in a therapeutically effective amount. In any of the embodiments described herein, the pharmaceutical composition can comprise a therapeutically effective amount of a compound selected from compound Nos. 1-133, or a pharmaceutically acceptable salt thereof.

The pharmaceutical composition can also be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof). In some embodiments, the pharmaceutical composition comprises a therapeutically effective amount of the compound of the present disclosure and a pharmaceutically acceptable excipient. As used herein, a therapeutically effective amount of a compound of the present disclosure is an amount effective to treat a disease or disorder as described herein, such as multiple sclerosis, rheumatoid arthritis, inflammatory bowel disease, systemic lupus erythematosus, psoriasis, psoriatic arthritis, Crohn's Disease, Sjogren's syndrome and/or scleroderma, which can depend on the recipient of the treatment, the disease or disorder being treated and the severity thereof, the composition containing the compound, the time of administration, the route of administration, the duration of treatment, the compound potency (e.g., for inhibiting TYK2), its rate of clearance and whether or not another drug is co-administered.

For veterinary use, a compound of the present disclosure can be administered as a suitably acceptable formulation in accordance with normal veterinary practice. The veterinarian can readily determine the dosing regimen and route of administration that is most appropriate for a particular animal.

In some embodiments, all the necessary components for the treatment of a disease or disorder associated with TYK2, e.g., those mediated by IL-12, IL-23 and/or Interferon-alpha (INF-alpha), using a compound of the present disclosure either alone or in combination with another agent or intervention traditionally used for the treatment of such disease can be packaged into a kit. Specifically, in some embodiments, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound of the present disclosure, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

Methods of Treatment/Uses

Compounds of the present disclosure are useful as therapeutic active substances for the treatment and/or prophylaxis of diseases or disorders that are associated with TYK2. In particular, compounds of the present disclosure are useful for treating conditions associated with the modulation of the function of IL-23, IL-12 and/or IFN-alpha, and particularly the inhibition of function of IL-23, IL-12 and/or IFN-alpha, by acting on Tyk2 to mediate signal transduction. Such conditions include IL-23-, IL-12-, and/or or IFN-alpha-associated diseases in which pathogenic mechanisms are mediated by these cytokines, which include any of those known in the art and those described herein.

In some embodiments, the present disclosure provides a method of inhibiting TYK2-mediated cell signaling comprising contacting a cell with an effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some embodiments, the present disclosure provides a method of inhibiting the function of IL-23, IL-12 and/or IFN-alpha in a subject in need thereof, the method comprising administering to the subject an effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some embodiments, the present disclosure provides a method of treating or preventing a disease or disorder mediated by TYK2 in a subject in need thereof, the method comprising administering to the subject an effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof). Suitable TYK2 mediated diseases or disorders that can be treated with the methods herein include any of those known in the art, such as those described in WO2019/103952 and WO2020/185755, the content of each of which is incorporated by reference in its entirety. Exemplary TYK2 mediated diseases or disorders that can be treated with the methods herein also include but not limited to those proliferative, metabolic, allergic, autoimmune and/or inflammatory diseases or disorders described herein.

In some embodiments, the present disclosure provides a method of treating or preventing a disease or disorder associated with IL-23, IL-12 and/or IFN-alpha in a subject in need thereof, the method comprising administering to the subject an effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof). Suitable diseases or disorders associated with IL-23, IL-12 and/or IFN-alpha that can be treated with the methods herein include any of those known in the art, such as those described in WO2019/103952 and WO2020/185755, the content of each of which is incorporated by reference in its entirety. Exemplary diseases or disorders associated with IL-23, IL-12 and/or IFN-alpha that can be treated with the methods herein also include but not limited to those proliferative, metabolic, allergic, autoimmune and/or inflammatory diseases or disorders described herein.

In some embodiments, the present disclosure provides a method of treating or preventing a proliferative, metabolic, allergic, autoimmune and/or inflammatory disease or disorder, e.g., described herein, in a subject in need thereof, the method comprising administering to the subject an effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some embodiments, the present disclosure provides a method of treating or preventing an autoimmune and/or inflammatory disease or disorder, e.g., described herein, in a subject in need thereof, the method comprising administering to the subject an effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some embodiments, the present disclosure provides a method of treating or preventing a metabolic disease or disorder, e.g., described herein, such as type 2 diabetes or atherosclerosis, in a subject in need thereof, the method comprising administering to the subject an effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some embodiments, the present disclosure provides a method of treating or preventing cancer in a subject in need thereof, the method comprising administering to the subject an effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some embodiments, the present disclosure provides a method of treating or preventing a disease or disorder in a subject in need thereof, the method comprising administering to the subject an effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof), wherein the disease or disorder can be one or more diseases or disorders selected from: inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

In some embodiments, the present disclosure provides a method of treating or preventing a disease or disorder in a subject in need thereof, the method comprising administering to the subject an effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof), wherein the disease or disorder that may be treated with the method include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic b-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoper oxidase syndase-2, and pemphigus vulgaris.

In some preferred embodiments, the present disclosure provides a method of treating or preventing a disease or disorder in a subject in need thereof, the method comprising administering to the subject an effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof), wherein the disease or disorder is one or more diseases or disorders selected from Crohn's disease, ulcerative colitis, allograft rejection, rheumatoid arthritis, psoriasis, ankylosing spondylitis, psoriatic arthritis, and pemphigus vulgaris.

In some preferred embodiments, the present disclosure provides a method of treating or preventing a disease or disorder in a subject in need thereof, the method comprising administering to the subject an effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof), wherein the disease or disorder is ischemia reperfusion injury, including cerebral ischemia reperfusions injury), arising from stroke and cardiac ischemia reperfusion injury arising from myocardial infarction.

In some preferred embodiments, the present disclosure provides a method of treating or preventing multiple myeloma in a subject in need thereof, the method comprising administering to the subject an effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating or preventing a disease or disorder in a subject in need thereof, the method comprising administering to the subject an effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof), wherein the disease or disorder is one or more disease or disorder selected from multiple sclerosis, rheumatoid arthritis, inflammatory bowel disease, systemic lupus erythematosus, psoriasis, psoriatic arthritis, Crohn's Disease, Sjogren's syndrome and scleroderma.

In some preferred embodiments, the present disclosure provides a method of treating multiple sclerosis in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating rheumatoid arthritis in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating inflammatory bowel disease in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating systemic lupus erythematosus in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating psoriasis in a subject in need thereof, the method comprising administering to the subject a therapeutically effective amount of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating psoriatic arthritis in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating Crohn's Disease in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating Sjogren's syndrome in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some preferred embodiments, the present disclosure provides a method of treating scleroderma in a subject in need thereof, the method comprising administering to the subject a therapeutically effective amount of one or more compounds of the present disclosure (e.g., a compound of Formula I (e.g., Formula I-1, 1-2, 1-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof).

In some embodiments, the present disclosure also provides a use of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) for the treatment or prevention of any of the diseases or disorders described herein, such as multiple sclerosis, rheumatoid arthritis, inflammatory bowel disease, systemic lupus erythematosus, psoriasis, psoriatic arthritis, Crohn's Disease, Sjogren's syndrome and/or scleroderma.

In some embodiments, the present disclosure also provides a use of one or more compounds of the present disclosure (e.g., a compound of Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, or a pharmaceutically acceptable salt thereof) in the manufacture of a medicament for the treatment or prevention of any of the diseases or disorders described herein, such as multiple sclerosis, rheumatoid arthritis, inflammatory bowel disease, systemic lupus erythematosus, psoriasis, psoriatic arthritis, Crohn's Disease, Sjogren's syndrome and/or scleroderma.

Compounds of the present disclosure can be used as a monotherapy or in a combination therapy. In some embodiments, the methods of treating IL-23-, IL-12 and/or IFNα-associated diseases or disorders can comprise administering compounds of the present disclosure alone or in combination with each other and/or other suitable therapeutic agents useful in treating such conditions. Exemplary of such other suitable therapeutic agents include corticosteroids, rolipram, calphostin, cytokine-suppressive anti-inflammatory drugs (CSAIDs), interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The administering herein is not limited to any particular route of administration. For example, in some embodiments, the administering can be orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the administering is orally.

Dosing regimen including doses can vary and can be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable atoms or groups for the variables herein are independently selected. The definitions of the variables can be combined. For example, any of the definitions of one or more of $L^1$, $R^1$, $L^2$, $R^2$, $R^3$, $J^1$, $J^2$, $J^3$, $J^4$, $J^5$, $X^1$, Y, $X^2$, and $R^4$ in Formula I can be combined with any of the definitions of the others of $L^1$, $R^1$, $L^2$, $R^2$, $R^3$, $J^1$, $J^2$, $J^3$, $J^4$, $J^5$, $X^1$, Y, $X^2$, and $R^4$ in Formula I. Such combination is contemplated and within the scope of the present disclosure.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

Compounds of the present disclosure can comprise one or more asymmetric centers and/or axial chirality, and thus can exist in various isomeric forms, e.g., enantiomers and/or diastereomers. For example, the compounds described herein can be in the form of an individual enantiomer, diastereomer, atropisomer, or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers including racemic mixtures. In embodiments herein, unless otherwise obviously contrary from context, when a stereochemistry is specifically drawn, it should be understood that with respect to that particular chiral center or axial chirality, the compound can exist predominantly as the as-drawn stereoisomer, such as with less than 20%, less than 10%, less than 5%, less than 1%, by weight, by HPLC area, or both, or with a non-detectable amount of the other stereoisomer(s). The presence and/or amounts of stereoisomers can be determined by those skilled in the art in view of the present disclosure, including through the use of chiral HPLC.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, the term "compound(s) of the present disclosure" refers to any of the compounds described herein according to Formula I (e.g., Formula I-1, I-2, I-3, I-1-A, I-1-B, I-1-C, I-1-D, I-1-E, I-1-F, I-1-G, I-1-H, I-1-I, I-1-J-E1, I-1-J-E2, I-1-A-1, I-1-A-2, I-1-A-3, I-1-A-4, I-1-A-5, I-1-A-6, I-1-A-7, I-1-A-8, I-1-A-9, I-1-A-10, I-1-A-11, I-1-A-12, I-1-A-13, I-1-A-14, I-1-A-15, or I-1-H-1), any of Compound Nos. 1-133, isotopically labeled compound(s) thereof (such as a deuterated analog wherein one or more of the hydrogen atoms is/are substituted with a deuterium atom with an abundance above its natural abundance), possible stereoisomers thereof (including diastereoisomers, enantiomers, and racemic mixtures), geometric isomers thereof, atropisomers thereof, tautomers thereof, conformational isomers thereof, and/or pharmaceutically acceptable salts thereof (e.g., acid addition salt such as HCl salt or base addition salt such as Na salt). For the avoidance of doubt, Compound Nos. 1-133 or Compounds 1-133 refers to the compounds described herein labeled as integers 1, 2, 3, . . . , 133, see for example the title compounds of the Examples and Table 1. For ease of description, synthetic starting materials or intermediates may be labeled with an integer (compound number) followed by a "-" and additional numeric values, such as 1-1, 1-2, etc., see examples for details. The labeling of such synthetic starting materials or intermediates should not be confused with the compounds labeled with an integer only. Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^{2}H$, $^{3}H$, $^{13}C$, $^{14}C$, $^{15}N$, $^{18}O$, $^{32}P$, $^{35}S$ $^{18}F$, $^{36}Cl$, and $^{125}I$. Compounds that contain other isotopes of these and/or other atoms are within the scope of this invention.

As used herein, the phrase "administration" of a compound, "administering" a compound, or other variants thereof means providing the compound or a prodrug of the compound to the individual in need of treatment.

As used herein, the term "alkyl" as used by itself or as part of another group refers to a straight- or branched-chain aliphatic saturated hydrocarbon. In some embodiments, the alkyl which can include one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. In one embodiment, the alkyl group is a $C_{1-4}$ alkyl group selected from methyl, ethyl, propyl (n-propyl), isopropyl, butyl (n-butyl), sec-butyl, tert-butyl, and iso-butyl. As used herein, the term "alkylene" as used by itself or as part of another group refers to a divalent radical derived from an alkyl group. For example, non-limiting straight chain alkylene groups include $—CH_2—CH_2—CH_2—CH_2—$, $—CH_2—CH_2—CH_2—$, $—CH_2—CH_2—$, and the like.

As used herein, the term "heteroalkyl," by itself or in combination with another term, means, unless otherwise stated, a stable straight or branched-chain alkyl group, e.g., having from 2 to 14 carbons, such as 2 to 10 carbons in the chain, one or more of which has been replaced by a heteroatom selected from S, O, P and N, and wherein the nitrogen, phosphine, and sulfur atoms can optionally be oxidized and the nitrogen heteroatom can optionally be quaternized. The heteroatom(s) S, O, P and N may be placed at any interior position of the heteroalkyl group or at the position at which the alkyl group is attached to the remainder of the molecule. Examples of $C_{1-4}$ heteroalkyl include, but are not limited to, $C_4$ heteroalkyl such as $—CH_2—CH_2—N(CH_3)—CH_3$, $C_3$ heteroalkyl such as $—CH_2—CH_2—O—CH_3$, $—CH_2—CH_2—NH—CH_3$, $—CH_2—S—CH_2—CH_3$, $—CH_2—CH_2—S(O)—CH_3$, or $—CH_2—CH_2—S(O)_2—CH_3$, $C_2$ heteroalkyl such as $—O—CH_2—CH_3$ and $C_1$ heteroalkyl such as $—O—CH_3$. Similarly, the term "heteroalkylene" by itself or as part of another substituent means a divalent radical derived from heteroalkyl, as exemplified, but not limited by, $—CH_2—CH_2—O—CH_2—CH_2—$ and $—O—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

As used herein, the term "alkenyl" as used by itself or as part of another group refers to a straight- or branched-chain aliphatic hydrocarbon containing one or more, such as one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to a straight- or branched-chain aliphatic hydrocarbon containing one or more, such as one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "alkoxy" as used by itself or as part of another group refers to a radical of the formula $OR^{a1}$, wherein $R^{a1}$ is an alkyl.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms. In one embodiment, the haloalkyl group is a $C_{1-4}$haloalkyl group.

"Carbocyclyl" or "carbocyclic" as used by itself or as part of another group refers to a radical of a non-aromatic cyclic hydrocarbon group having from 3 to 10 ring carbon atoms ("$C_{3-10}$ carbocyclyl") and zero heteroatoms in the non-aromatic ring system. The carbocyclyl group can be either monocyclic ("monocyclic carbocyclyl"), bicyclic or polycyclic, which may contain a fused, bridged or spiro ring system and can be saturated or can be partially unsaturated. As used herein, a bicyclic or polycyclic carbocyclyl group may have one or more of the rings being an aryl ring, provided that the bicyclic or polycyclic carbocyclyl group as a whole is not an aromatic ring system, and the point of attachment can be on any of the rings of the bicyclic or polycyclic carbocyclyl group. For example, a fused bicyclic carbocyclyl group can include those fused ring systems wherein one of the two rings is phenyl, wherein the point of attachment can be on either of the two rings. Non-limiting exemplary carbocyclyl groups include cyclopropyl, cyclobutyl, cyclopentyl, cyclohexyl, cycloheptyl, cyclooctyl, norbornyl, decalin, adamantyl, cyclopentenyl, and cyclohexenyl.

In some embodiments, "carbocyclyl" is fully saturated, which is also referred to as cycloalkyl. In some embodiments, the cycloalkyl can have from 3 to 10 ring carbon atoms ("$C_{3-10}$ cycloalkyl"). In some embodiments, the cycloalkyl is a monocyclic ring. In some embodiments, the cycloalkyl can be a bicyclic ring, which can be a fused, bridged or spiro bicyclic ring.

Unless otherwise specified or contrary from context, "heterocyclyl" or "heterocyclic" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). Heterocyclyl or heterocyclic ring that has a ring size different from the 3-10 membered heterocyclyl is specified with a different ring size designation when applicable. Those skilled in the art would understand that such different ring-sized heterocyclyl is also a non-aromatic ring system having ring carbon atoms and 1 to 4 ring heteroatoms, wherein each heteroatom is independently selected from nitrogen, oxygen, sulfur, boron, phosphorus, and silicon. In heterocyclyl groups that contain one or more nitrogen atoms, the point of attachment can be a carbon or nitrogen atom, as valency permits. A heterocyclyl group can either be monocyclic ("monocyclic heterocyclyl"), bicyclic or polycyclic, including a fused, bridged, or spiro ring system, such as a fused, bridged, or spiro bicyclic system ("bicyclic heterocyclyl"), and can be saturated or can be partially unsaturated. Heterocyclyl bicyclic ring systems can include one or more ring heteroatoms in one or both rings, wherein the point of attachment is on either of the two rings. For example, a fused heterocyclyl bicyclic ring system includes those fused bicyclic systems with one of the rings being a monocyclic carbocyclyl ring defined herein, wherein the point of attachment can be on the carbocyclyl ring or the ring having one or more ring heteroatoms. As used herein, a bicyclic or polycyclic heterocyclyl group may have one or more of the rings being an aryl or heteroaryl ring, provided that the bicyclic or polycyclic heterocyclyl group as a whole is not a heteroaromatic ring system, and the point of attachment can be on any of the rings of the bicyclic or polycyclic heterocyclyl group. For example, a fused heterocyclyl ring system also includes those fused ring systems with one or more of the rings being an aryl or heteroaryl ring, provided that the fused ring system as a whole is not a heteroaromatic ring, wherein the point of attachment can be on any of the rings.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to a phenyl ring (also referred to herein as a 6,6-bicyclic heterocyclic ring) include, without limitation, tetrahydroquinolinyl, tetrahydroisoquinolinyl, and the like.

"Aryl" as used by itself or as part of another group refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl).

"Aralkyl" as used by itself or as part of another group refers to an alkyl substituted with one or more aryl groups, preferably, substituted with one aryl group. Examples of aralkyl include benzyl, phenethyl, etc. When an aralkyl is said to be optionally substituted, either the alkyl portion or the aryl portion of the aralkyl can be optionally substituted.

Unless otherwise specified or contrary from context, "heteroaryl" as used by itself or as part of another group refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). Heteroaryl that has a ring size different from the 5-10 membered heteroaryl is specified with a different ring size designation when applicable. Those skilled in the art would understand that such different ring-sized heteroaryl is also a 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings, wherein the point of attachment can be on either ring. For example, in bicyclic heteroaryl groups wherein one ring does not contain a heteroatom (e.g., indolyl, quinolinyl, and the like), the point of attachment can be on either the ring bearing a heteroatom (e.g., 2-indolyl) or the ring that does not contain a heteroatom (e.g., 5-indolyl).

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzothiazolyl, benzisothiazolyl, benzothiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" as used by itself or as part of another group refers to an alkyl substituted with one or more heteroaryl groups, preferably, substituted with one heteroaryl group. When a heteroaralkyl is said to be optionally substituted, either the alkyl portion or the heteroaryl portion of the heteroaralkyl can be optionally substituted.

As commonly understood by those skilled in the art, alkylene, alkenylene, alkynylene, carbocyclylene, heterocyclylene, arylene, and heteroarylene refer to the corresponding divalent radicals of alkyl, alkenyl, alkynyl, carbocyclyl, heterocyclyl, aryl, and heteroaryl groups, respectively.

An "optionally substituted" group, such as an optionally substituted alkyl, optionally substituted alkenyl, optionally substituted alkynyl, optionally substituted carbocyclyl, optionally substituted heterocyclyl, optionally substituted aryl, and optionally substituted heteroaryl groups, refers to the respective group that is unsubstituted or substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. In some embodiments, two substituents can together with the intervening atoms form an optionally substituted ring system, such as an optionally substituted 3-8 membered carbocyclic, optionally substituted 3-8 membered heterocyclic, optionally substituted aryl, or optionally substituted heteroaryl ring. Substituents can be a carbon atom substituent, a nitrogen atom substituent, an oxygen atom substituent or a sulfur atom substituent, as applicable.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

In some embodiments, the "optionally substituted" alkyl, alkenyl, alkynyl, carbocyclic, cycloalkyl, alkoxy, cycloalkoxy, or heterocyclic group herein can be unsubstituted or substituted with 1, 2, 3, or 4 substituents independently selected from F, Cl, —OH, protected hydroxyl, oxo (as applicable), $NH_2$, protected amino, $NH(C_{1-4}$ alkyl) or a protected derivative thereof, $N(C_{1-4}$ alkyl(($C_{1-4}$ alkyl), $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1, 2, or 3 ring heteroatoms independently selected from O, S, and N, 3-7 membered heterocyclyl containing 1 or 2 ring heteroatoms independently selected from O, S, and N, wherein each of the alkyl, alkenyl, alkynyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl (e.g., $CF_3$), $C_{1-4}$ alkoxy and fluoro-substituted $C_{1-4}$ alkoxy. In some embodiments, the "optionally substituted" aryl or heteroaryl group herein can be unsubstituted or substituted with 1, 2, 3, or 4 substituents independently selected from F, Cl, —OH, —CN, $NH_2$, protected amino, $NH(C_{1-4}$ alkyl) or a protected derivative thereof, $N(C_{1-4}$ alkyl(($C_{1-4}$ alkyl), —S(═O)($C_{1-4}$ alkyl), —$SO_2$($C_{1-4}$ alkyl), $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1, 2 or 3 ring heteroatoms independently selected from O, S, and N, 3-7 membered heterocyclyl containing 1 or 2 ring heteroatoms independently selected from O, S, and N, wherein each of the alkyl, alkenyl, alkynyl, alkoxy, cycloalkyl, cycloalkoxy, phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl, $C_{1-4}$ alkoxy and fluoro-substituted $C_{1-4}$ alkoxy.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(═O)$R^{aa}$, —$CO_2H$, —CHO, —C($OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —Si$(R^{aa})_3$, —OSi$(R^{aa})_3$—C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$(R^{aa})_2$, —P(═O)$(OR^{cc})_2$, —OP(═O)$(R^{aa})_2$, —OP(═O)$(OR^{cc})_2$, —P(═O)$(N(R^{bb})_2)_2$, —OP(═O)$(N(R^{bb})_2)_2$, —$NR^{bb}$P(═O)$(R^{aa})_2$, —$NR^{bb}$P(═O)$(OR^{cc})_2$, —$NR^{bb}$P(═O)$(N(R^{bb})_2)_2$, —P$(R^{cc})_2$, —P$(OR^{cc})_2$, —P$(R^{cc})_3^+X^-$, —P$(OR^{cc})_3^+X^-$, —P$(R^{cc})_4$, —P$(OR^{cc})_4$, —OP$(R^{cc})_2$, —OP$(R^{cc})_3^+X^-$, —OP$(OR^{cc})_2$, —OP$(OR^{cc})_3^+X^-$, —OP$(R^{cc})_4$, —OP$(OR^{cc})_4$, —B$(R^a)_2$, —B$(OR^{cc})_2$, —$BR^{aa}(OR^{cc})$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion; or two geminal hydrogens on a carbon atom are replaced with the group ═O, ═S, ═NN$(R^{bb})_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$; each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^a$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^a$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$)$OR^{aa}$, —C(═$NR^{cc}$)$N(R^{cc})_2$, —$SO_2N(R^C)_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^a)_2$, —P(═O)$(OR^{cc})_2$, —P(═O)$(N(R^{cc})_2)_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{cc}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —C(═O)$R^{ee}$, —$CO_2H$, —$CO_2R^{cc}$, —OC(═O)$R^{ee}$, —$OCO_2R^{ee}$, —C(═O)$N(R^{E})_2$, —OC(═O)$N(R^{ff})_2$, —$NR^{ff}$C(═O)$R^{ee}$, —$NR^{ff}C_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —NRC(═$NR^{ff}$)$N(R^{ff})_2$,—$NR^{ff}SO_2R^{ee}$, —$SO_2N(R^{ff})_2$, —$SO_2R^{cc}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$—OP(═O)$(R^{ee})_2$, —OP(═O)$(OR^{ee})_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2(C_{1-6}$ alkyl), —OC(═O)($C_{1-6}$ alkyl), —$OCO_2(C_{1-6}$ alkyl), —C(═O)$NH_2$, —C(═O)$N(C_{1-6}$ alkyl$)_2$, —OC(═O)NH($C_{1-6}$ alkyl), —NHC(═O)($C_{1-6}$ alkyl), —$N(C_{1-6}$ alkyl)C(═O)($C_{1-6}$ alkyl), —$NHCO_2(C_{1-6}$ alkyl), —NHC(═O)$N(C_{1-6}$ alkyl$)_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)$N(C_{1-6}$ alkyl$)_2$, —C(═NH)NH($C_{1-6}$ alkyl), —C(═NH)$NH_2$, —OC(═NH)$N(C_{1-6}$ alkyl$)_2$, —OC(NH)NH($C_{1-6}$ alkyl), —OC(NH)$NH_2$, —NHC(NH)$N(C_{1-6}$ alkyl$)_2$, —NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$-C(═S)$N(C_{1-6}$ alkyl$)_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)$(OC_{1-6}$ alkyl$)_2$, —P(═O)$(C_{1-6}$ alkyl$)_2$, —OP(═O)$(C_{1-6}$ alkyl$)_2$, —OP(═O)$(OC_{1-6}$ alkyl$)_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $BPh_4^-$, $Al(OC(CF_3)_3)_4^-$, and a carborane anion (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(═O)$R^{aa}$, —CHO, —$CO_2$R—, —C(═O)$N(R^{bb})_2$, —C(═$NR^{bb}$)$R^{aa}$, —C(═$NR^{bb}$)$OR^{aa}$, —C(═$NR^{bb}$)$N(R^{bb})_2$, —C(═O)$NR^{bb}SO_2R^{aa}$, —C(═S)$N(R^{bb})_2$, —C(═O)$SR^{aa}$, or —C(═S)$SR^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —C(═O)$R^{aa}$, —C(═O)$N(R^{cc})_2$, —$CO_2R^{11}$, —$SO_2R^{aa}$, —C(═$NR^{bb}$)$R^{11}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(OR^{cc})_2$, —P(═O)$(R^{aa})_2$, —P(═O)$(N(R^{cc})_2)_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups are well known in the art and include those described in detail in *Protective Groups in Organic Synthesis*, T. W. Greene and P. G. M. Wuts, 3rd edition, John Wiley & Sons, 1999, incorporated by reference herein. Exemplary nitrogen protecting groups include, but not limited to, those forming carbamates, such as Carbobenzyloxy (Cbz) group, p-Methoxybenzyl carbonyl (Moz or MeOZ) group, tert-Butyloxycarbonyl (BOC) group, Troc, 9-Fluorenylmethyloxycarbonyl (Fmoc) group, etc., those forming an amide, such as acetyl, benzoyl, etc., those forming a benzylic amine, such as benzyl, p-methoxybenzyl, 3,4-dimethoxybenzyl, etc., those forming a sulfonamide, such as tosyl, Nosyl, etc., and others such as p-methoxyphenyl.

Exemplary oxygen atom substituents include, but are not limited to, $-R^{aa}$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protective Groups in Organic Synthesis*, T. W. Greene and P. G. M. Wuts, 3rd edition, John Wiley & Sons, 1999, incorporated herein by reference. Exemplary oxygen protecting groups include, but are not limited to, alkyl ethers or substituted alkyl ethers such as methyl, allyl, benzyl, substituted benzyls such as 4-methoxybenzyl, methoxymethyl (MOM), benzyloxymethyl (BOM), 2-methoxyethoxymethyl (MEM), etc., silyl ethers such as trimethylsilyl (TMS), triethylsilyl (TES), triisopropylsilyl (TIPS), t-butyldimethylsilyl (TBDMS), etc., acetals or ketals, such as tetrahydropyranyl (THP), esters such as formate, acetate, chloroacetate, dichloroacetate, trichloroacetate, trifluoroacetate, methoxyacetate, etc., carbonates, sulfonates such as methanesulfonate (mesylate), benzylsulfonate, and tosylate (Ts), etc.

The term "leaving group" is given its ordinary meaning in the art of synthetic organic chemistry, for example, it can refer to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

As used herein, the singular form "a", "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

Example 1 Synthesis of Compound 1

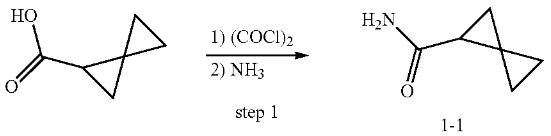

1-1

-continued

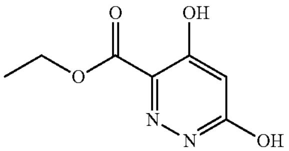

LiOH
step 2

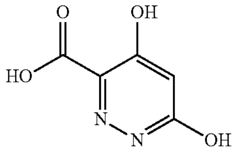

1-2

1) $POCl_3$
2) $D_3C$—$NH_2$ HCl
step 3

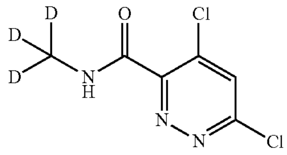

1-3

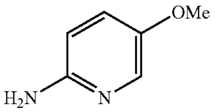

PivCl
step 4

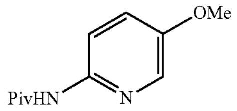

1-4

1) t-BuLi
2) 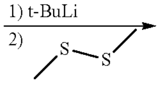
step 5

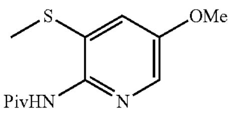

1-5

2N HCl
step 6

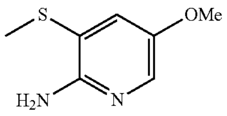

1-6

1-3
step 7

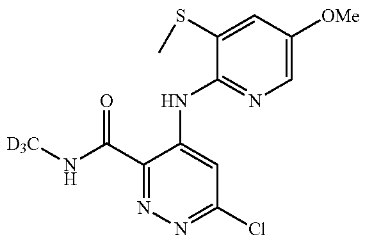

1-7

1-1
step 8

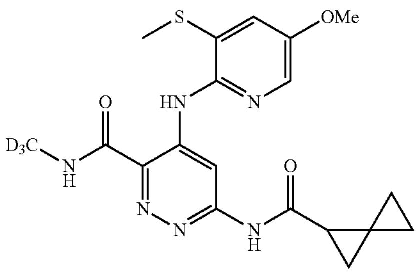

1-8

$H_2O_2$,
$Na_2WO_4$
step 9

-continued

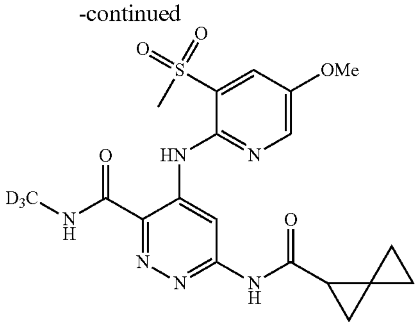

1

Step 1: To a solution of spiro[2.2]pentane-1-carboxylic acid (6.16 g, 55 mmol) in dichloromethane (100 mL) was added oxalyl chloride (21 g, 165 mmol) at 0° C. The reaction mixture was stirred for 4 hours at room temperature, then concentrated under vacuum. The residue was dissolved in dichloromethane, and a 7M solution of ammonia in methanol was added at 0° C. The reaction mixture was stirred for 2 hours at room temperature. The solvent was removed under vacuum to afford 1-1.

Step 2: To a solution of ethyl 4,6-dihydroxypyridazine-3-carboxylate (23.2 g, 126 mmol) in tetrahydrofuran (230 mL) and methanol (130 mL) was added a solution of lithium hydroxide (7.57 g, 315 mmol) in water (90 mL) at room temperature. The reaction mixture was stirred for 4 hours. The volatiles were removed under vacuum. The residue was acidified with 6N hydrochloric acid solution at 0° C. (pH<1) and stirred at room temperature for 30 minutes. The precipitate was filtered, washed with 1N hydrochloric acid, and dried under vacuum for 2 hours. This material was dissolved in dichloromethane/methanol (3/1) and stirred at room temperature for 30 minutes. The mixture was filtered and washed with dichloromethane/methanol (3/1) to afford 1-2.

Step 3: To a mixture of 1-2 (14.4 g, 92.3 mmol) in phosphorus oxychloride (200 mL) was added N, N-diethylaniline (13.8 g, 92.3 mmol) at room temperature. The mixture was stirred for 2 hours at 110° C. The phosphorus oxychloride was removed in a rotary evaporator and the remaining crude was co-evaporated with 1,2-dichloroethane. The reaction mixture was dissolved in tetrahydrofuran (200 mL) and methan-$d_3$-amine hydrochloride (6.51 g, 92.3 mmol) and N, N-diisopropylethylamine (29.8 g, 230.7 mmol) were added at 0° C. The mixture was stirred for 1 hour. The mixture was diluted with ethyl acetate, washed with saturated aqueous sodium bicarbonate and brine, dried over anhydrous sodium sulfate, filtered and concentrated. The residue was purified by column chromatography on silica gel (petroleum ether to petroleum ether/ethyl acetate=1/1) to afford 1-3.

Step 4: To a solution of 5-methoxypyridin-2-amine (25 g, 202 mmol) in dichloromethane (500 mL) were added triethylamine (24.4 g, 242 mmol) and pivaloyl chloride (25.6 g, 212 mmol) dropwise at 0° C. The reaction was stirred for 1 hour at room temperature. The mixture was washed with water. The organic layer was dried over anhydrous sodium sulfate, filtered and concentrated. The residue was purified by column chromatography on silica gel (petroleum ether to petroleum ether/ethyl acetate=4/1) to afford 1-4.

Step 5: To a solution of 1-4 (4.16 g, 20 mmol) in diethyl ether (120 mL) was added tert-butyllithium (38 mL, 50 mmol) dropwise at −78° C. under $N_2$ atmosphere. The reaction was stirred at −78° C. for 3 hours. To above mixture was added 1,2-dimethyldisulfane (2.82 g, 30 mmol) dropwise at −78° C. The reaction mixture was allowed to warm to room temperature and stirred for 1 hour. The reaction was quenched with water, and extracted with ethyl acetate. The combined organic layers were dried over anhydrous sodium sulfate, filtered and concentrated. The residue was purified by column chromatography on silica gel (petroleum ether to petroleum ether/ethyl acetate=4/1) to afford 1-5.

Step 6: A mixture of 1-5 (3.3 g, 13 mmol) and 2N HCl (65 mL, 130 mmol) was stirred at 100° C. overnight. The mixture was cooled to room temperature, and extracted with methyl tert-butyl ether. The aqueous layer was adjusted to pH 7 with saturated aqueous sodium carbonate solution, and then extracted with ethyl acetate. The combined organic layers were dried over anhydrous sodium sulfate, filtered and concentrated to afford 1-6.

Step 7: To a mixture of 1-3 (518 mg, 2.5 mmol) and 1-6 (447 mg, 2.6 mmol) in tetrahydrofuran (25 mL) was added a 1M solution of lithium bis(trimethylsilyl)amide in tetrahydrofuran (6.2 mL, 6.2 mmol) dropwise at 0° C. under $N_2$ atmosphere. The reaction mixture was allowed to warm to room temperature and stirred for 1 hour. The mixture was diluted with water and then filtered. The crude filter cake was slurried with acetonitrile, filtered and dried to afford 1-7.

Step 8: To a mixture of 1-7 (230 mg, 0.67 mmol) in dioxane (3 mL) were added 1-1 (112 mg, 1 mmol), cesium carbonate (434 mg, 1.34 mmol), tris(dibenzylideneacetone)dipalladium (184 mg, 0.2 mmol) and 4,5-bis(diphenylphosphino)-9,9-dimethylxanthene (116 mg, 0.2 mmol). The reaction mixture was stirred at 145° C. for 1 hour under $N_2$ atmosphere and microwave condition. The mixture was diluted with dichloromethane and washed with water. The organic layer was dried over anhydrous sodium sulfate, filtered and concentrated. The residue was purified by column chromatography on silica gel (dichloromethane to dichloromethane/ethyl acetate=1/1) to afford 1-8.

Step 9: To a mixture of 1-8 (122 mg, 0.29 mmol) in acetic acid (15 mL) were added sodium tungstate (86 mg, 0.29 mmol), and 30% aqueous hydrogen peroxide (657 mg, 5.8 mmol) dropwise at room temperature. The reaction mixture was stirred for 3 hours. The reaction was diluted with water and quenched with saturated aqueous sodium thiosulfate. The mixture was adjusted to pH~8 with saturated aqeuous sodium carbonate solution and extracted with dichloromethane. The combined organic layers were dried over anhydrous sodium sulfate, filtered and concentrated. The residue was purified by prep-HPLC (acetonitrile/0.05% formic acid in water: 5%~95%) to afford 1. LCMS (ESI, m/z): $[M+H]^+$=450.1; $^1$H-NMR (400 MHz, DMSO-$d_6$, ppm): δ 11.80 (s, 1H), 11.12 (s, 1H), 9.11-9.08 (m, 2H), 8.35 (d, J=2.8 Hz, 1H), 7.76 (d, J=3.2 Hz, 1H), 3.89 (s, 3H), 3.30-3.29 (m, 3H), 2.42-2.39 (m, 1H), 1.37-1.31 (m, 2H), 0.88-0.70 (m, 4H).

Example 2 Synthesis of Compound 2

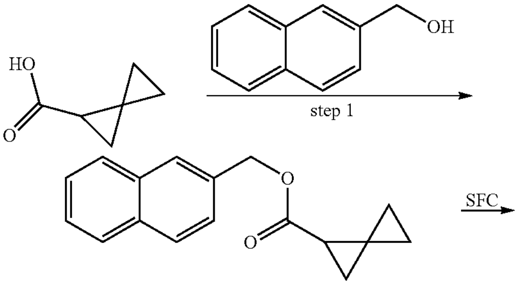

2-0

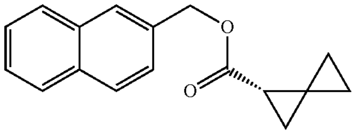

+

2-1

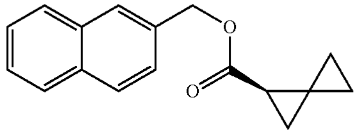

2-2

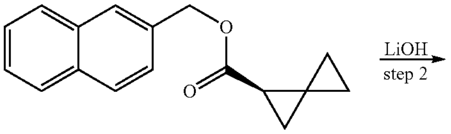

2-2

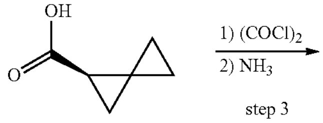

2-3

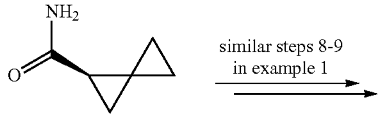

2-4

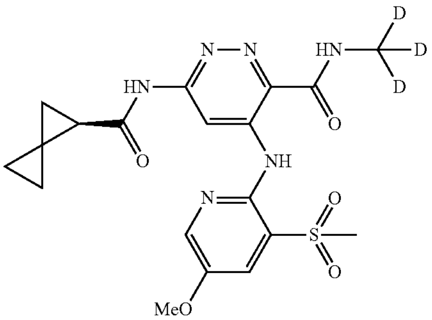

2

Step 1: To a solution of spiro[2.2]pentane-1-carboxylic acid (2.9 g, 25.9 mmol) and naphthalen-2-ylmethanol (4.91 g, 31.1 mmol) in tetrahydrofuran (80 mL) were added triphenylphosphine (8.14 g, 31.1 mmol) and di-tert-butyl azodicarboxylate (7.15 g, 31.1 mmol). The reaction mixture was stirred at room temperature for 16 hours. The mixture was concentrated and purified by column chromatography on silica gel (petroleum ether to petroleum ether/ethyl acetate=10/1) to afford 2-0. The racemic product was separated by prep-SFC (DAICELCHIRALPAK® IG with Supercritical $CO_2$/MeOH) to afford 2-1 and 2-2.

2-1: Optical rotation: $[\alpha]_D^{20}$ 77.3 (c 0.8, MeOH). Chiral SFC analysis: 99.46% ee. Retention time 1.578 min on Reprosil Chiral-AM (Similar to Daicel chiralpak AD) 100×3 mm 3 μm (35° C.); mobile phase: EtOH(+0.1% DEA) in $CO_2$, 1800 psi, 1.5 mL/min.

2-2: Optical rotation: $[\alpha]_D^{20}$ −78.4 (c 0.8, MeOH). Chiral SFC analysis: 98.2% ee. Retention time 1.841 min on Reprosil Chiral-AM (Similar to Daicel chiralpak AD) 100×3 mm 3 μm (35° C.); mobile phase: EtOH(+0.1% DEA) in $CO_2$, 1800 psi, 1.5 mL/min.

Step 2: To a solution of 2-2 (2.9 g, 11.5 mmol) in tetrahydrofuran (20 mL) and methanol (10 mL) was added 1N aqueous lithium hydroxide solution (34.5 mL, 34.5 mmol) at 0° C. The mixture was warmed to room temperature and stirred for 3 hours. The volatiles were removed under vacuum and the residue was diluted with water. The aqueous layer was washed with dichloromethane, acidified with 1N hydrochloric acid and then extracted with dichloromethane. The combined organic layers were dried over anhydrous sodium sulfate, filtered and concentrated to afford 2-3.

Step 3: To a solution of 2-3 (1.0 g, 8.9 mmol) in dichloromethane (30 mL) was added oxalyl chloride (1.47 g, 1.16 mmol) at room temperature. The mixture was stirred for 3 hours. The volatiles were removed under vacuum. The resulting mixture was dissolved in dichloromethane, followed by addition of a 7M solution of ammonia in methanol (30 mL) at 0° C. The reaction mixture was stirred for 16 hours at room temperature. The solvent was removed under vacuum to afford 2-4.

Compound 2 was prepared from 2-4 following the procedure for the synthesis of compound 1 in example 1. LCMS (ESI, m/z): $[M+H]^+$=450.2; $^1$H-NMR (400 MHz, DMSO-$d_6$, ppm): δ 11.80 (s, 1H), 11.12 (s, 1H), 9.10 (s, 1H), 9.09 (s, 1H), 8.36 (d, J=3.2 Hz, 1H), 7.76 (d, J=3.2 Hz, 1H), 3.89 (s, 3H), 3.30 (s, 3H), 2.44-2.39 (m, 1H), 1.39-1.31 (m, 2H), 0.89-0.79 (m, 3H), 0.76-0.68 (m, 1H).

Example 3 Synthesis of Compound 3

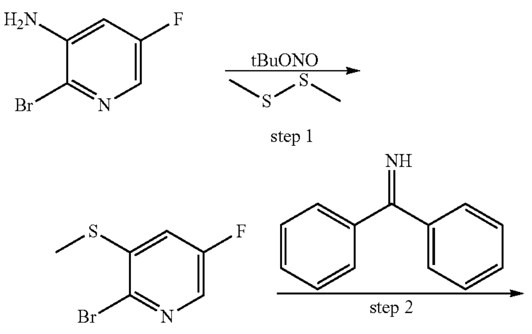

3-1

-continued

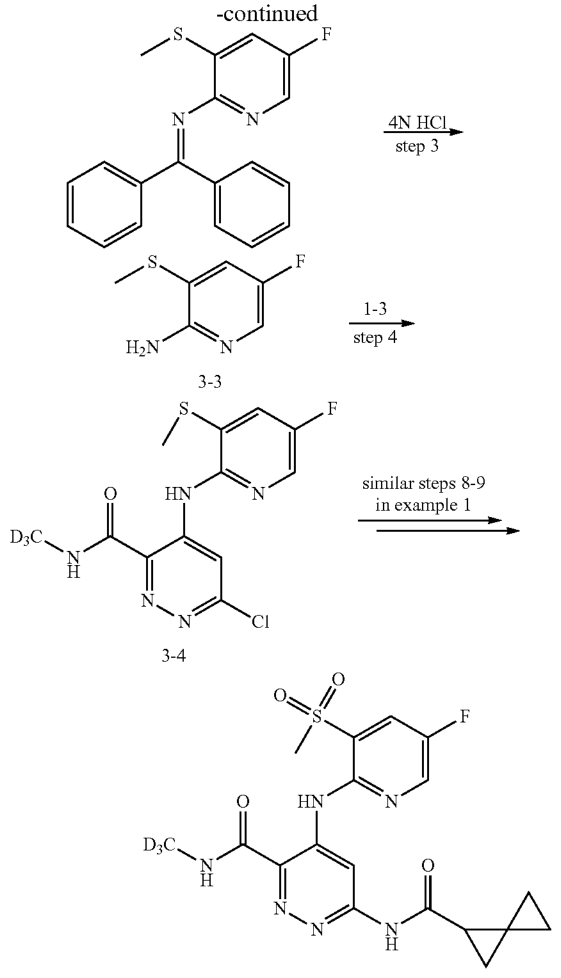

3-3

3-4

3

Step 1: To a solution of 3-amino-2-bromo-5-fluoropyridine (19.1 g, 100 mmol) and dimethyl disulfide (18.8 g, 200 mmol) in dichloroethane (300 mL) was added tert-butyl nitrite (15.5 g, 150 mmol) dropwise at 40° C. under $N_2$ atmosphere over 1 hour. The reaction mixture was stirred for 1 hour. The mixture was washed with brine. The organic layer was dried over anhydrous sodium sulfate, filtered and concentrated. The residue was purified by column chromatography on silica gel (petroleum ether to petroleum ether/ethyl acetate=4/1) to afford 3-1.

Step 2: A mixture of 3-1 (3.7 g, 6.7 mmol), diphenylmethanimine (3.63 g, 20 mmol), sodium tert-butoxide (2.4 g, 25 mmol), tris(dibenzylideneacetone)dipalladium (1.53 g, 1.67 mmol) and 1.1'-binaphthyl-2.2'-diphenyl phosphine (1.04 g, 1.67 mmol) in toluene (50 mL) was stirred for 3 hours at 100° C. under $N_2$ atmosphere. The mixture was filtered and concentrated. The residue was purified by column chromatography on silica gel (petroleum ether to petroleum ether/ethyl acetate=10/1) to afford 3-2.

Step 3: To a suspension of 3-2 (3.1 g, 9.63 mmol) in dioxane (24 mL) was added 4N HCl solution (24 mL, 96.3 mmol). The reaction mixture was stirred for 1 hour at room temperature. The mixture was concentrated and diluted with ethyl acetate. The mixture was adjusted to pH~8 with saturated aqueous sodium bicarbonate. The organic layer was dried over anhydrous sodium sulfate, filtered and concentrated. The residue was purified by column chromatography on silica gel (petroleum ether to petroleum ether/ethyl acetate=1/1) to afford 3-3.

Step 4: To a mixture of 1-3 (628 mg, 3 mmol) and 3-3 (501 mg, 3.15 mmol) in tetrahydrofuran (25 mL) was added a 1M solution of lithium bis(trimethylsilyl)amide in tetrahydrofuran (8 mL, 8 mmol) dropwise at 0° C. under $N_2$ atmosphere. The reaction mixture was stirred for 1 hour at room temperature. The mixture was diluted with water and filtered. The filter cake was slurried with acetonitrile, filtered and dried to afford 3-4.

Followed similar steps in example 1 to synthesize 3. LCMS (ESI, m/z): $[M+H]^+$=438.1; $^1$H-NMR (400 MHz, DMSO-$d_6$, ppm): δ 12.02 (s, 1H), 11.19 (s, 1H), 9.26 (s, 1H), 9.14 (s, 1H), 8.67 (d, J=2.8 Hz, 1H), 8.13 (dd, J=7.6, 2.8 Hz, 1H), 3.35 (s, 3H), 2.43-2.41 (m, 1H), 1.38-1.32 (m, 2H), 0.88-0.65 (m, 4H). $^{19}$F-NMR (376 MHz, DMSO-$d_6$, ppm): δ −133.11 (1F).

Example 4 Synthesis of Compound 5

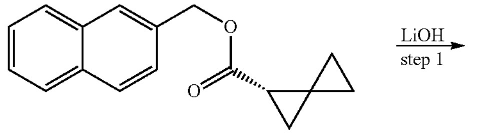

2-1

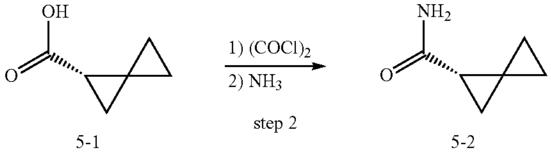

5-1 5-2

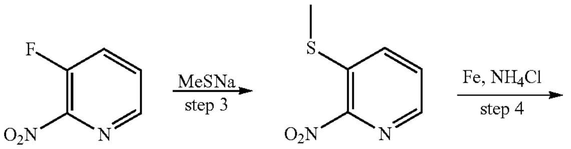

5-3

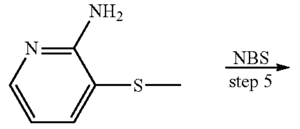

5-4

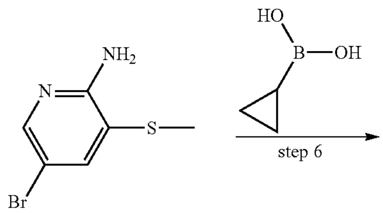

5-5

-continued

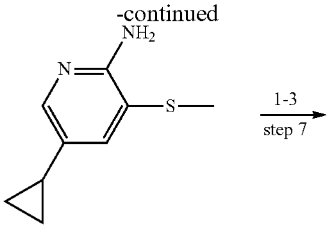

5-6

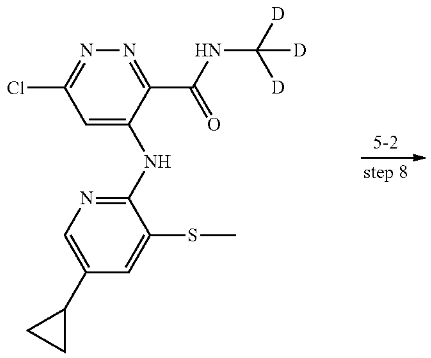

5-7

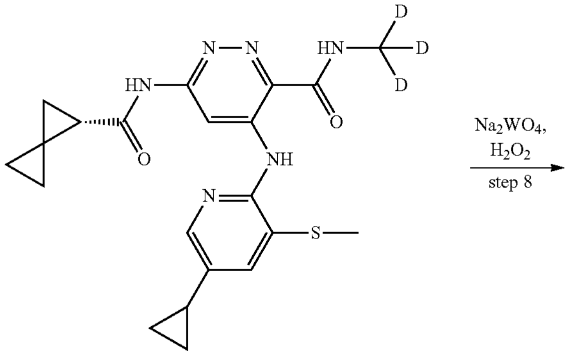

5-8

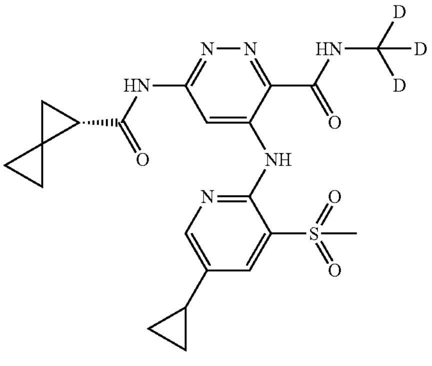

5

Step 1: To a solution of 2-1 (2.7 g, 10.7 mmol) in tetrahydrofuran (20 mL) and methanol (10 mL) was added a 1N solution of lithium hydroxide in water (32 mL, 32.1 mmol) at 0° C., then warmed to room temperature and stirred for 3 hours. The volatiles were removed under vacuum and diluted with water. The aqueous layer was washed with dichloromethane, and then acidified with 1N hydrochloric acid, extracted with dichloromethane. The combined organic layers were dried over anhydrous sodium sulfate, filtered and concentrated to give 5-1.

Step 2: To a solution of 5-1 (1.0 g, 8.9 mmol) in dichloromethane (30 mL) was added oxalyl chloride (1.47 g, 1.16 mmol) at room temperature, then stirred for 3 hours. The volatiles were removed under vacuum. The resulting mixture was dissolved in dichloromethane (10 mL), followed by the addition of a 7M solution of ammonia in methanol (30 mL) at 0° C. The reaction mixture was stirred for 16 hours at room temperature. The solvent was removed under vacuum to give 5-2.

Step 3: To a solution of 3-fluoro-2-nitropyridine (30 g, 211.3 mmol) in dimethyl formamide (300 mL) was added sodium methyl mercaptide (111 g, 317 mmol, 20% in water) dropwise at room temperature. The mixture was stirred for 1 hour. The mixture was diluted with ethyl acetate, washed with brine, dried over anhydrous sodium sulfate, filtered and concentrated to afford 5-3.

Step 4: To a mixture of 5-3 (42 g, 211.3 mmol) in methanol (500 mL) was added water (125 mL), ammonium chloride (56.5 g, 1057 mmol) and iron powder (60.9 g, 1057 mmol) portion-wised. The reaction mixture was stirred at 65° C. for 1 hour. The mixture was diluted with ethyl acetate and filtered. The organic layer was washed with water, brine, dried over anhydrous sodium sulfate, filtered and concentrated. The residue was purified by column chromatography on silica gel (petroleum ether to petroleum ether/ethyl acetate=1/1) to afford 5-4.

Step 5: To a solution of 5-4 (1.4 g, 10 mmol) in dichloromethane (30 mL) was added N-bromosuccinimide (2.14 g, 12 mmol). The mixture was stirred at room temperature for 1 hour. The mixture was diluted was water and extracted with dichloromethane. The organic layer was dried over anhydrous sodium sulfate, filtered and concentrated. The residue was purified by column chromatography on silica gel (petroleum ether to petroleum ether/ethyl acetate=10/1) to afford 5-5.

Step 6: To a mixture of 5-5 (766 mg, 3.5 mol), cyclopropylboronic acid (1.2 g, 14 mmol), tricyclohexyl phosphine (196 mg, 0.7 mmol), tris(dibenzylideneacetone) dipalladium (320 mg, 0.35 mmol) in toluene/water (25 mL/4 mL) was added potassium phosphate tribasic (3.71 g, 17.5 mmol). The mixture was stirred at 100° C. for 6 hours under $N_2$ atmosphere. The mixture was extracted with ethyl acetate. The organic layer was dried over anhydrous sodium sulfate, filtered and concentrated. The residue was purified by column chromatography on silica gel (petroleum ether to petroleum ether/ethyl acetate=5/1) to afford 5-6.

Step 7: To a mixture of 1-3 (209 mg, 1 mmol) and 5-6 (189 mg, 1.05 mmol) in tetrahydrofuran (10 mL) was added a 1 M solution of lithium bis(trimethylsilyl) amide in tetrahydrofuran (2.5 mL, 2.5 mmol) at 0° C. The mixture was warmed to room temperature and stirred for 1 hour. The mixture was diluted with water, acidified with 1N hydrochloric acid to pH~9 at 0° C., filtered and washed with water. The precipitate was dried to afford 5-7.

Step 8: To a mixture of 5-7 (127 mg, 0.36 mmol) in dioxane (5 mL) was added 5-2 (60 mg, 0.54 mmol), tris(dibenzylideneacetone)dipalladium (50 mg, 0.054 mmol), cesium carbonate (235 mg, 0.72 mmol) and 4,5-bis(diphenylphosphino)-9,9-dimethylxanthene (63 mg, 0.108 mmol). The reaction mixture was stirred at 145° C. for 1 hour under $N_2$ atmosphere and microwave condition. The mixture diluted with dichloromethane, washed with water. Organic layer was dried over anhydrous sodium sulfate, filtered and concentrated. The residue was purified by column chromatography on silica gel (dichloromethane to dichloromethane/ethyl acetate=1:1) to afford 5-8.

Step 9: To a mixture of 5-8 (100 mg, 0.234 mmol) in acetic acid (4 mL) was added sodium tungstate (69 mg, 0.234 mmol), 30% aqueous hydrogen peroxide (531 mg, 4.68 mmol) dropwise at room temperature. The reaction mixture was stirred for 1 hour. The reaction was diluted with water, quenched with saturated aqueous sodium thiosulfate, adjusted to pH~9 with sodium carbonate, extracted with dichloromethane. The combined organic lays were dried over anhydrous sodium sulfate, filtered and concentrated. The residue was purified by column chromatography on silica gel (dichloromethane to dichloromethane/methanol=40:1) to afford 5. LCMS (ESI, m/z): $[M+H]^+$=460.2; $^1$H-NMR (400 MHz, DMSO-$d_6$, ppm): δ 11.94 (s, 1H), 11.17 (s, 1H), 9.33 (s, 1H), 9.12 (s, 1H), 8.43 (d, J=1.6 Hz, 1H), 7.81 (d, J=2.0 Hz, 1H), 3.28 (s, 3H), 2.45-2.39 (m, 1H), 2.13-2.02 (m, 1H), 1.40-1.31 (m, 2H), 1.04-0.95 (m, 2H), 0.89-0.70 (m, 6H).

Example 5 Synthesis of Compound 6

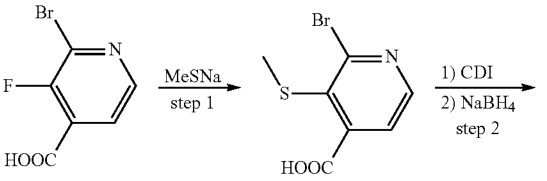

6-1

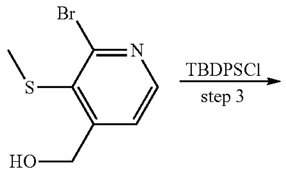

6-2

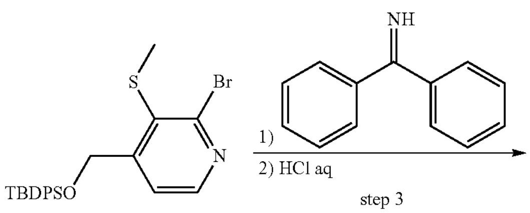

6-3

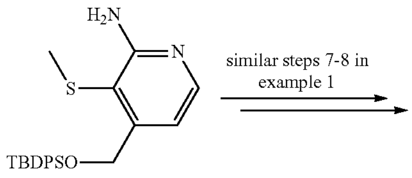

6-4

-continued

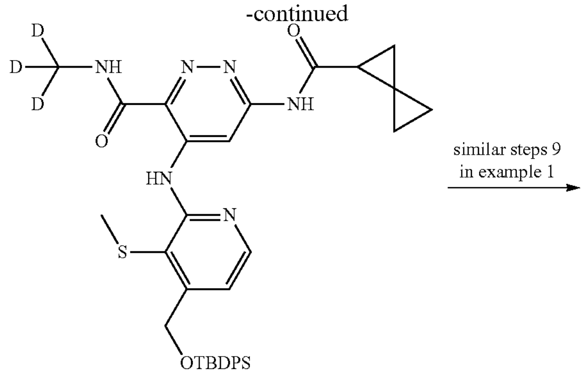

6-6

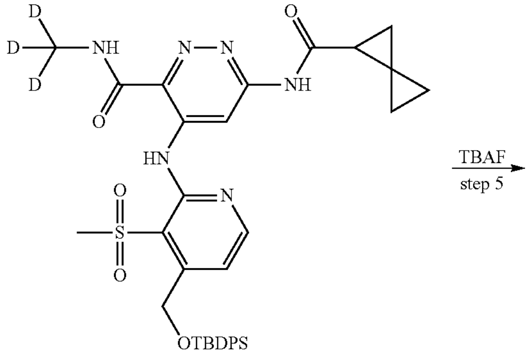

6-7

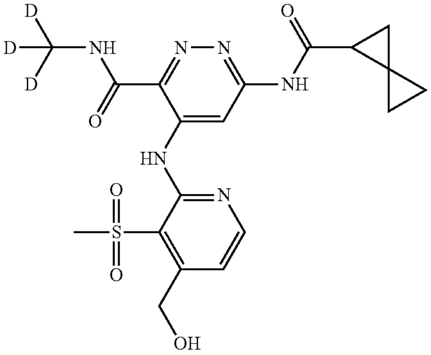

6

Step 1: To a solution of 2-bromo-3-fluoroisonicotinic acid (24.8 g, 113 mmol) in dimethylacetamide (150 mL) was added 20% aqueous sodium methyl mercaptide (98.9 g, 282.5 mmol) dropwise at 0° C. The mixture was stirred for 16 hours at room temperature. The mixture was diluted with water, adjusted to pH~2 with 1M aqueous hydrochloride and then extracted with ethyl acetate. The combined organic layers were dried over anhydrous sodium sulfate, filtered and concentrated to afford 6-1.

Step 2: To a solution of 6-1 (23 g, 93 mmol) in tetrahydrofuran (200 mL) was added N,N'-carbonyldiimidazole (22.6 g, 139.5 mmol) at room temperature. The mixture was stirred for 3 hours. The mixture was poured into a solution of sodium borohydride (17.67 g, 465 mmol) in water (200 mL) dropwise at 0° C. After being stirred for 1 hour, the reaction was quenched with 2M aqueous hydrochloride, adjusted to pH~8 with saturated aqueous sodium carbonate and extracted with ethyl acetate. The combined organic layers were dried over anhydrous sodium sulfate, filtered and concentrated to afford 6-2.

Step 3: To a solution of 6-2 (17.8 g, 43 mmol) and imidazole (6.2 g, 91.2 mmol) in dichloromethane (200 mL) was added tert-butylchlorodiphenylsilane (23 g, 83.6 mmol) dropwise at 0° C. under $N_2$ atmosphere. The mixture was warmed to room temperature and stirred for 1 hour. The mixture was washed with water, saturated aqueous sodium bicarbonate and brine. The organic layer was dried over anhydrous sodium sulfate, filtered and concentrated. The residue was purified by column chromatography on silica gel (petroleum ether to petroleum ether/ethyl acetate=4/1) to afford 6-3.

Step 4: A mixture of 6-3 (23.9 g, 50.5 mmol), diphenylmethanimine (10 g, 55.6 mmol), sodium tert-butoxide (6.3 g, 65.15 mmol), tris(dibenzylideneacetone)dipalladium (1.39 g, 1.52 mmol) and 1.1'-binaphthyl-2.2'-diphenyl phosphine (1.88 g, 3.03 mmol) in toluene (200 mL) was stirred for 3 hours at 100° C. under $N_2$ atmosphere. The mixture was washed with water and brine. The organic layer was dried over anhydrous sodium sulfate, filtered and concentrated. The residue was dissolved in dioxane and 3M aqueous hydrochloride. The mixture was stirred for 1 hour at room temperature. The mixture was adjusted to pH~8 with saturated aqueous sodium carbonate and extracted with ethyl acetate. The combined organic layers were dried over anhydrous sodium sulfate, filtered and concentrated. The crude product was purified by column chromatography on silica gel (petroleum ether to petroleum ether/ethyl acetate=1/1) to afford 6-4.

Compound 6-6 was prepared from 6-4 following the procedure for the synthesis of compound 1-8 in example 1.

Compound 6-7 was prepared from 6-6 following the procedure for the synthesis of compound 1 in example 1.

Step 5: To a solution of 6-7 (20 mg, 0.029 mmol) in tetrahydrofuran (0.5 mL) was added a 1M solution of tetrabutylammonium fluoride in tetrahydrofuran (0.03 mL, 0.03 mmol) dropwise at room temperature. The mixture was stirred for 1 hour. The mixture was diluted with water and stirred for 10 minutes, filtered and washed with water. The residue was purified by prep-HPLC (acetonitrile/0.05% formic acid in water: 5%~95%) to afford 6. LCMS (ESI, m/z): $[M+H]^+$ =450.2; $^1$H-NMR (400 MHz, DMSO-$d_6$, ppm): δ 11.86 (s, 1H), 11.15 (s, 1H), 9.08 (s, 1H), 9.06 (s, 1H), 8.51 (d, J=5.2 Hz, 1H), 7.55 (d, J=4.8 Hz, 1H), 5.61 (s, 1H), 4.93 (s, 2H), 3.30 (s, 3H), 2.42-2.39 (m, 1H), 1.39-1.28 (m, 2H), 0.91-0.65 (m, 4H).

Example 6 Synthesis of Compound 7

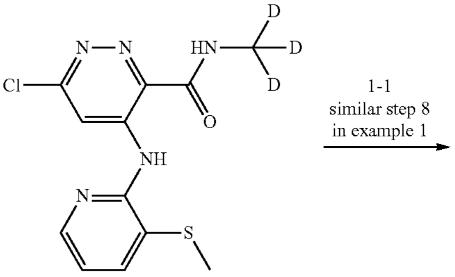

20-1

-continued

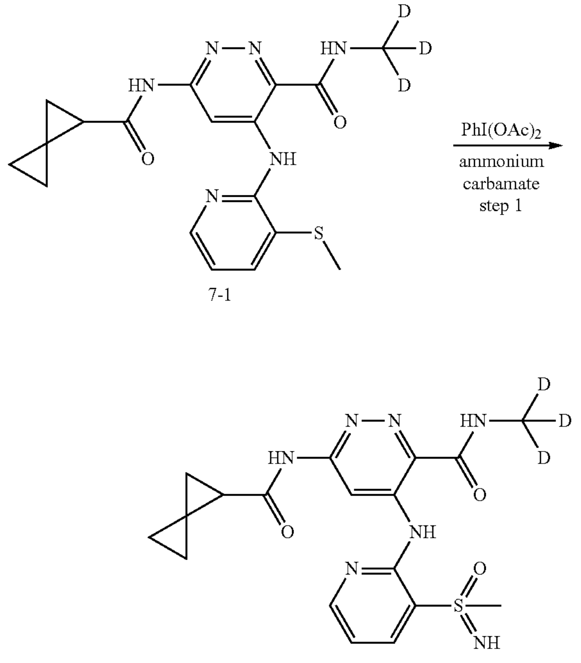

7-1

7

Compound 7-1 was prepared from 20-1 following the procedure for the synthesis of compound 1-8 in example 1.

Step 1: To a suspension of 7-1 (40 mg, 0.103 mmol) in methanol (100 mL) and dichloromethane (5 mL) was added (diacetoxyiodo)benzene (83 mg, 0.258 mmol) and ammonium carbonate (20 mg, 0.258 mmol). The mixture was stirred at room temperate for 2 hours. The mixture was concentrated and purified by prep-HPLC (acetonitrile/0.05% formic acid in water: 5%~95%) to afford 7. LCMS (ESI, m/z): $[M+H]^+$=419.1; $^1$H-NMR (400 MHz, DMSO-$d_6$, ppm): δ 11.96 (s, 1H), 11.19 (s, 1H), 9.45 (s, 1H), 9.09 (s, 1H), 8.54 (dd, J=4.8, 1.6 Hz, 1H), 8.29 (dd, J=8.0, 1.6 Hz, 1H), 7.30 (dd, J=8.0, 4.8 Hz, 1H), 4.81 (s, 1H), 3.20 (s, 3H), 2.48-2.44 (m, 1H), 1.45-1.32 (m, 2H), 0.98-0.83 (m, 3H), 0.80-0.68 (m, 1H).

Example 7 Synthesis of Compound 8

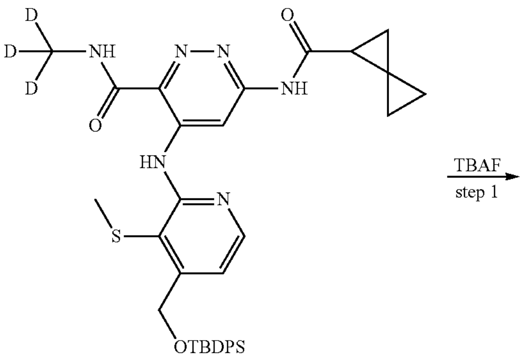

6-6

-continued

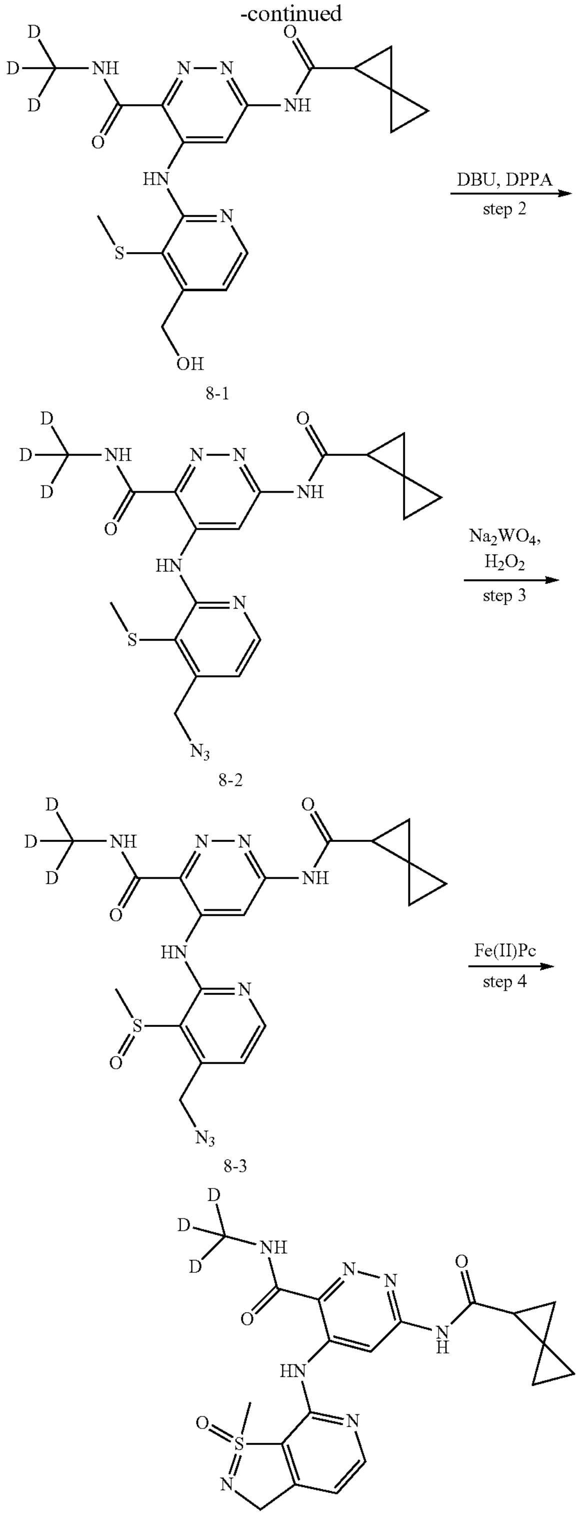

8-1

8-2

8-3

8

Step 1: To a solution of 6-6 (2.1 g, 3.2 mmol) in tetrahydrofuran (20 mL) was added a 1M solution of tetrabutylammonium fluoride in THF (3.2 mL, 3.2 mmol) at room temperature. The mixture was stirred for 1 hour. The reaction was diluted with water, filtered and washed with water. The filter cake was slurried with methanol, filtered and dried to afford 8-1.

Step 2: To a suspension of 8-1 (834 mg, 2 mmol) in tetrahydrofuran (100 mL) was added 1,8-diazabicyclo[5.4.0]undec-7-ene (1.22 g, 8 mmol) and diphenylphosphoryl azide (1.1 g, 4 mmol) at room temperature. The mixture was stirred for 3 hours under $N_2$ atmosphere. The mixture was diluted with water, filtered and washed with water. The filter cake was slurried with methanol, filtered and dried to afford 8-2.

Step 3: To a mixture of 8-2 (221 mg, 0.5 mmol) in acetic acid (20 mL) was added sodium tungstate (147 mg, 0.5 mmol), 30% aqueous hydrogen peroxide (1.13 g, 10 mmol) dropwise at room temperature, then stirred for 0.5 hour. The mixture was diluted with water, adjusted to pH~8 with sodium carbonate, quenched with saturated aqueous sodium thiosulfate. The crude product was filtered and washed with water. The filter cake was slurried with methanol to give 8-3.

Step 4: A suspension of 8-3 (115 mg, 0.25 mmol) and iron phthalocyanine (14 mg, 0.025 mmol) in dioxane (30 mL) was stirred for 3 hours at 100° C. under $N_2$ atmosphere. The mixture was concentrated and the residue was purified by column chromatography on silica gel (dichloromethane to dichloromethane/methanol=10/1) to afford 8. LCMS (ESI, m/z): $[M+H]^+$=431.2; 1H-NMR (400 MHz, $CDCl_3$, ppm): δ 12.63 (s, 1H), 10.07 (s, 1H), 8.94 (s, 1H), 8.56 (d, J=5.2 Hz, 1H), 8.22 (s, 1H), 7.06 (d, J=5.2 Hz, 1H), 4.92-4.69 (m, 2H), 3.68-3.66 (m, 3H), 2.22-2.18 (m, 1H), 1.69-1.64 (m, 1H), 1.53-1.49 (m, 1H), 1.16-0.94 (m, 4H).

Example 8 Synthesis of Compound 9

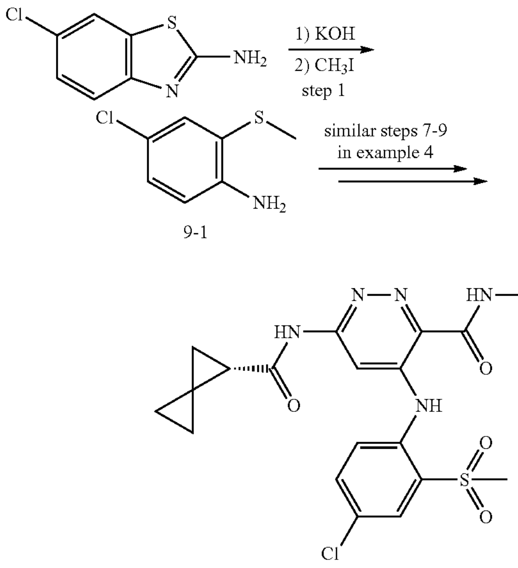

9-1

9

Step 1: To a solution of potassium hydroxide (60.5 g, 1.08 mol) in water (100 mL) was added 6-chlorobenzo[d]thiazol-2-amine (10.0 g, 54.1 mmol). The mixture was stirred at 100° C. for 6 hours. The mixture was cooled to room temperature. Then iodomethane was added (8.4 g, 59.5 mmol) and the mixture was stirred at room temperature for 1 hour. The mixture was extracted with tert-butyl methyl ether. The combined organic layers were dried over anhydrous sodium sulfate, filtered and concentrated. The residue was purified by column chromatography on silica gel (petroleum ether to petroleum ether/ethyl acetate=5/1) to afford 9-1.

Compound 9 was prepared from 9-1 following the procedure for the synthesis of compound 5 in example 4. LCMS (ESI, m/z): $[M+H]^+$=453.1; $^1$H-NMR (400 MHz, DMSO-$d_6$, ppm): δ 11.20 (s, 1H), 11.10 (s, 1H), 9.09 (s, 1H), 8.06 (s, 1H), 7.91-7.78 (m, 2H), 7.73 (d, J=8.4 Hz, 1H), 3.20 (s, 3H), 2.41-2.35 (m, 1H), 1.35-1.27 (m, 2H), 0.88-0.76 (m, 3H), 0.74-0.65 (m, 1H).

Example 9 Synthesis of Compound 10

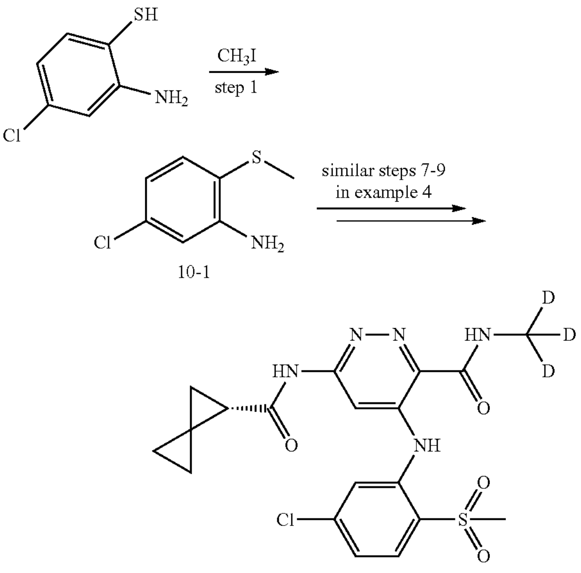

10-1

10

Step 1: To a solution of 2-amino-4-chlorobenzenethiol (6.4 g, 40 mmol) in ethanol (80 mL) was added potassium tert-butoxide (4.93 g, 44 mmol) at 0° C. The mixture was stirred for 75 minutes. Then iodomethane was added (11.36 g, 80 mmol) and the reaction mixture was stirred for 16 hours. The mixture was filtered and concentrated. The residue was purified by column chromatography on silica gel (petroleum ether to petroleum ether/ethyl acetate=5/1) to afford 10-1.

Compound 10 was prepared from 10-1 following the procedure for the synthesis of compound 5 in example 4. LCMS (ESI, m/z): $[M+H]^+$=453.1; $^1$H-NMR (400 MHz, DMSO-$d_6$, ppm): δ 11.21 (s, 1H), 11.15 (s, 1H), 9.09 (s, 1H), 8.12 (s, 1H), 7.91 (d, J=8.4 Hz, 1H), 7.82 (s, 1H), 7.48 (d, J=8.0 Hz, 1H), 3.17 (s, 3H), 2.41-2.37 (m, 1H), 1.36-1.28 (m, 2H), 0.88-0.78 (m, 3H), 0.73-0.66 (m, 1H).

Example 10 Synthesis of Compound 11

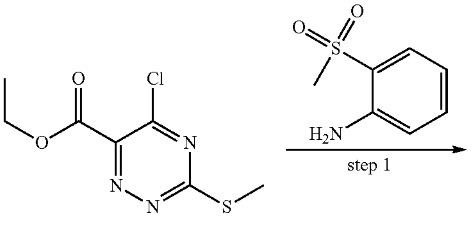

-continued

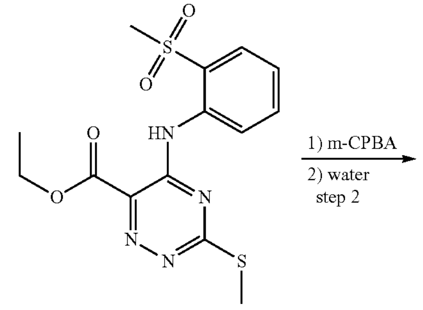

11-1

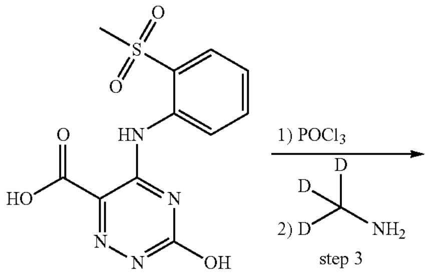

11-2

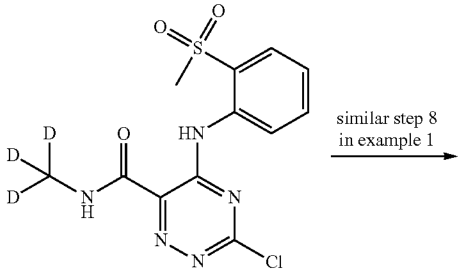

11-3

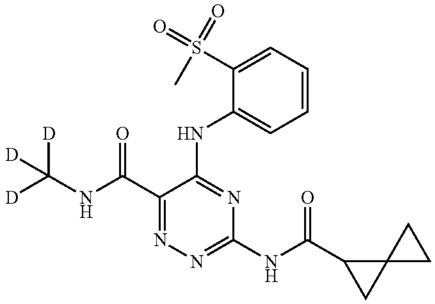

11

Step 1: To a mixture of ethyl 5-chloro-3-(methylthio)-1,2,4-triazine-6-carboxylate (702 mg, 3 mmol) and 2-(methylsulfonyl)aniline (567 mg, 3.3 mmol) in acetonitrile (15 mL) was added N,N-diisopropylethylamine (503 mg, 3.9 mmol) at 25° C. The mixture was stirred for 2 minutes under $N_2$ atmosphere and then purified by prep-HPLC (acetonitrile/0.05% TFA in water/: 5%~95%) to afford 11-1.

Step 2: To a solution of 11-1 (450 mg, 1.2 mmol) in dichloromethane (10 mL) was added 3-chloroperoxybenzoic acid (621 mg, 3.0 mmol). The reaction mixture was stirred at 25° C. for 30 minutes. The mixture was concentrated, and then dissolved in ethanol and water. To above mixture was added sodium hydroxide (240 mg, 6 mmol) at 0° C. The mixture was stirred for 30 minutes at 25° C. The mixture was diluted with water and washed with dichloromethane. The aqueous layer was neutralized with acetic acid to pH~7 and purified by prep-HPLC (acetonitrile/0.05% TFA in water/: 5%~95%) to afford 11-2.

Step 3: A mixture of 11-2 (104 mg, 0.33 mmol) and N, N-diethylaniline (50 mg, 0.33 mmol) in phosphorus oxychloride (2 mL) was stirred at 80° C. for 2 hours under $N_2$ atmosphere. After removal of solvent, the residue was dissolved in tetrahydrofuran (2 mL). To above mixture was added methyl-$d_3$-ammonium hydrochloride (23.6 mg, 0.33 mmol) and N, N-diisopropylethylamine (213 mg, 1.65 mmol) at 0° C. The reaction mixture was stirred at 25° C. for 30 minutes under $N_2$ atmosphere. The mixture was diluted with ethyl acetate, washed with water, brine, dried over anhydrous sodium sulfate, filtered and concentrated. The residue was purified by prep-HPLC (acetonitrile/0.05% TFA in water: 5%~95%) to afford 11-3.

Compound 11 was prepared from 11-3 following the procedure for the synthesis of compound 1-8 in example 1. LCMS (ESI, m/z): $[M+H]^+$=420.1; $^1$H-NMR (400 MHz, DMSO-$d_6$, ppm): δ 11.70 (s, 1H), 11.02 (s, 1H), 9.13 (s, 1H), 8.65-8.54 (m, 1H), 7.93-7.82 (m, 1H), 7.72-7.59 (m, 1H), 7.42-7.28 (m, 1H), 3.19 (s, 3H), 2.52-2.44 (m, 1H), 1.41-1.37 (m, 1H), 1.31-1.25 (m, 1H), 0.88-0.76 (m, 3H), 0.73-0.66 (m, 1H).

Example 11 Synthesis of Compound 12

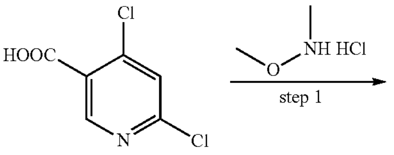

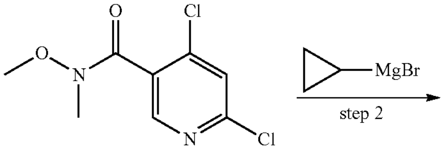

12-1

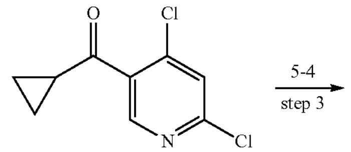

12-2

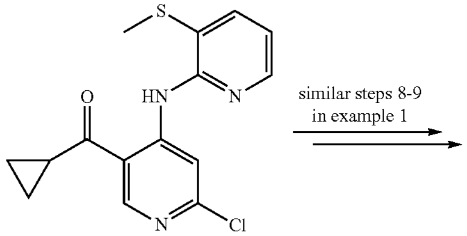

12-3

-continued

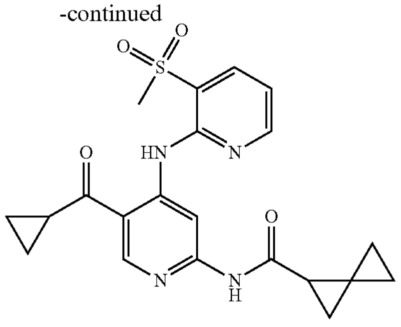

12

Step 1: To a solution of 4,6-dichloronicotinic acid (5 g, 26 mmol) in acetonitrile (50 mL) was added N,O-dimethylhydroxylamine hydrochloride (3.8 g, 39 mmol), N,N-diisopropylethylamine (10 g, 77.5 mmol) and 2-(7-azabenzotriazol-1-yl)-N,N,N',N'-tetramethyluronium hexafluorophosphate (10.4 g, 27.4 mmol). The mixture was diluted with ethyl acetate, washed with water, brine, dried over anhydrous sodium sulfate, filtered and concentrated. The residue was purified by column chromatography on silica gel (petroleum ether to petroleum ether/ethyl acetate=4/1) to afford 12-1.

Step 2: To a solution of 12-1 (5.68 g, 24.2 mmol) in tetrahydrofuran (25 mL) was added a 1M solution of cyclopropylmagnesium bromide in THF (73 mL, 73 mmol) dropwise at −15° C. under $N_2$ atmosphere. The mixture was allowed to warm to room temperature and stirred for 0.5 hour. Then the mixture was poured into saturated aqueous ammonium chloride and extracted with ethyl acetate. The combined organic layers were washed with water, brine, dried over anhydrous sodium sulfate, filtered and concentrated. The residue was purified by column chromatography on silica gel (petroleum ether to petroleum ether/ethyl acetate=10/1) to afford 12-2.

Step 3: To a solution of 5-4 (1.2 g, 8.7 mmol) in dimethyl formamide (30 mL) was added sodium hydride (1.74 g, 43.5 mmol, 60% in mineral oil) in portions at 0° C. The mixture was stirred for 0.5 hour at 0° C., followed by addition of a solution of 12-2 (1.7 g, 7.9 mmol) in dimethyl formamide (10 mL). The mixture was stirred for 1 hour at room temperature. Then the mixture was poured into saturated aqueous ammonium chloride and extracted with ethyl acetate. The combined organic layers were washed with water, brine, dried over anhydrous sodium sulfate, filtered and concentrated. The residue was purified by column chromatography on silica gel (petroleum ether to petroleum ether/ethyl acetate=4/1) to afford 12-3.

Compound 12 was prepared from 12-3 following the procedure for the synthesis of compound 1 in example 1. LCMS (ESI, m/z): $[M+H]^+$=427.2; $^1$H-NMR (400 MHz, DMSO-$d_6$, ppm): δ 11.70 (s, 1H), 10.77 (s, 1H), 9.12 (s, 1H), 9.01 (s, 1H), 8.56 (dd, J=4.8, 2.0 Hz, 1H), 8.22 (dd, J=8.0, 2.0 Hz, 1H), 7.28 (dd, J=7.6, 4.8 Hz, 1H), 3.24 (s, 3H), 2.94-2.90 (m, 1H), 2.37-2.34 (m, 1H), 1.35-1.28 (m, 2H), 1.06-0.97 (m, 4H), 0.86-0.68 (m, 4H).

Example 12 Synthesis of Compound 13

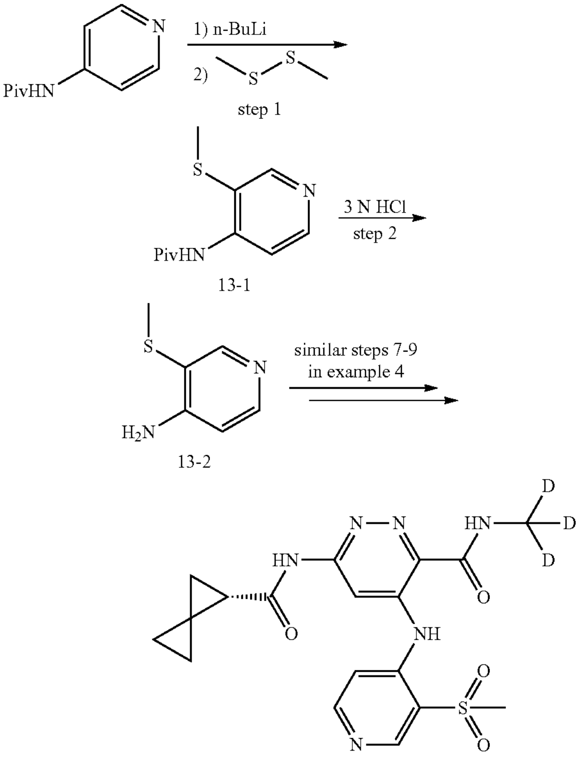

13-1
13-2
13

Step 1: To a suspension of N-(pyridin-4-yl) pivalamide (7 g, 39 mmol) in tetrahydrofuran (150 mL) was added n-butyllithium (39 mL, 98 mmol) dropwise at −78° C. under $N_2$ atmosphere. The mixture was allowed to warm to 0° C. and stirred for 3 hours. To above mixture was added dimethyl disulfide (11 g, 118 mmol) dropwise at −78° C. The mixture was allowed to warm to room temperature and stirred for 0.5 hour. The reaction was quenched with water and extracted with ethyl acetate. The combined organic layers were washed with brine, dried over anhydrous sodium sulfate, filtered and concentrated. The residue was purified by column chromatography on silica gel (petroleum ether to petroleum ether/ethyl acetate=5/1) to afford 13-1.

Step 2: A mixture of 13-1 (2 g, 8.9 mmol) in 3 N aqueous hydrochloride (30 mL) was stirred at reflux for 4 hours. After being cooled to room temperature, the mixture was diluted with water and washed with tert-butyl methyl ether. The aqueous layer was adjusted to pH~8 with 2N aqueous sodium hydroxide and extracted with ethyl acetate. The combined organic layers were combined and dried over anhydrous sodium sulfate, filtered and concentrated to afford 13-2.

Compound 13 was prepared from 13-2 following the procedure for the synthesis of compound 5 in example 4. LCMS (ESI, m/z): $[M+H]^+$=420.2; $^1$H-NMR (400 MHz, DMSO-$d_6$, ppm): δ 11.48 (s, 1H), 11.36 (s, 1H), 9.18 (s, 1H), 8.92-8.58 (m, 2H), 8.46-8.35 (m, 1H), 7.76-7.61 (m, 1H), 3.26 (s, 3H), 2.43-2.37 (m, 1H), 1.40-1.28 (m, 2H), 0.88-0.79 (m, 3H), 0.74-0.66 (m, 1H).

Example 13 Synthesis of Compound 16

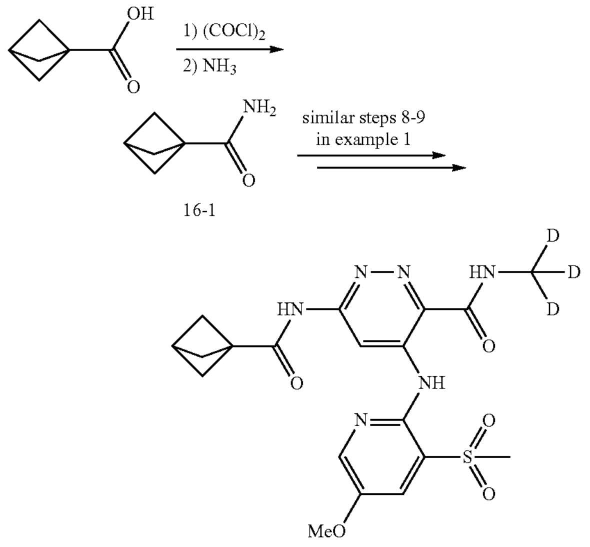

16-1

16

To a solution of bicyclo[1.1.1]pentane-1-carboxylic acid (224 mg, 2.0 mmol) in dichloromethane (4 mL) was added oxalyl chloride (762 mg, 6.0 mmol) at 0° C. The mixture was stirred for 2 hours at room temperature. The mixture was concentrated under vacuum. The resulting mixture was dissolved in dichloromethane (4 mL), followed by addition of a 7M solution of ammonia in methanol (6 mL, 42 mmol) at 0° C. The reaction mixture was allowed to warm to room temperature and stirred for 0.5 hour. The solvent was removed under vacuum to afford 16-1.

Compound 16 was prepared from 16-1 following the procedure for the synthesis of compound 1 in example 1. LCMS (ESI, m/z): $[M+H]^+$=450.2; $^1$H-NMR (400 MHz, DMSO-$d_6$, ppm): δ 11.83 (s, 1H), 10.82 (s, 1H), 9.14 (s, 1H), 9.10 (s, 1H), 8.37 (d, J=2.8 Hz, 1H), 7.76 (d, J=2.8 Hz, 1H), 3.89 (s, 3H), 3.30 (s, 3H), 2.40 (s, 1H), 2.10 (s, 6H).

Example 14 Synthesis of Compound 20

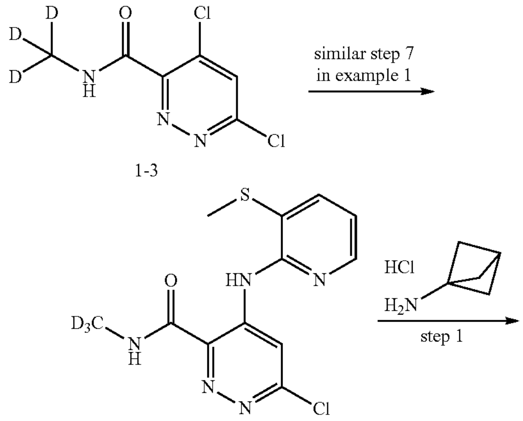

1-3

20-1

-continued

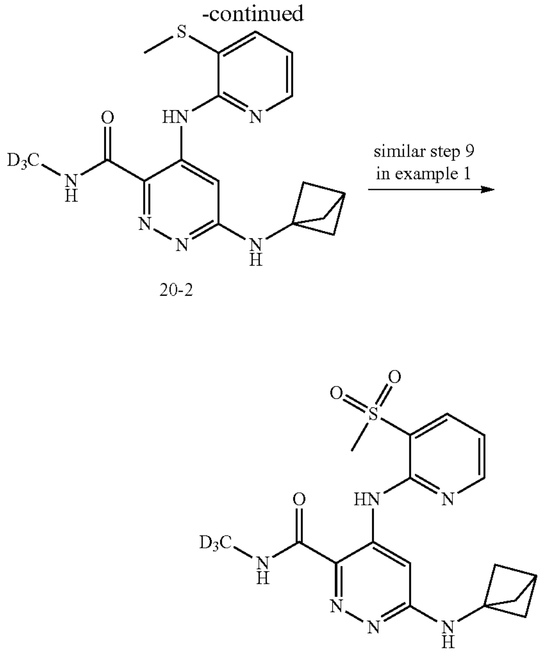

20-2

20

Compound 20-1 was prepared from 1-3 following the procedure for the synthesis of compound 1-7 in example 1.

Step 1: To a mixture of 20-1 (700 mg, 2.24 mmol) and N,N-diisopropylethylamine (5.8 g, 44.9 mmol) in 1-methyl-2-pyrrolidinone (5 mL) was added bicyclo[1.1.1]pentan-1-amine hydrochloride (4.04 g, 33.4 mmol) at room temperature. The mixture was stirred at 150° C. for 24 hours in a sealed tube. The mixture was cooled, diluted with ethyl acetate, washed with water and brine. The organic layer was dried over anhydrous sodium sulfate, filtered and concentrated. The residue was purified by prep-TLC (dichloromethane/methanol=15/1) to afford 20-2.

Compound 20 was prepared from 20-2 following the procedure for the synthesis of compound 1 in example 1. LCMS (ESI, m/z): $[M+H]^+$=392.1; $^1$H-NMR (400 MHz, DMSO-$d_6$, ppm): δ 11.99 (s, 1H), 9.04 (s, 1H), 8.55 (dd, J=4.8, 2.0 Hz, 1H), 8.21 (dd, J=7.6, 1.6 Hz, 1H), 8.16 (s, 1H), 7.97 (s, 1H), 7.22 (dd, J=8.0, 4.8 Hz, 1H), 3.32 (s, 3H), 2.47-2.45 (m, 1H), 2.09 (s, 6H).

Example 15 Synthesis of Compounds 21 and 22

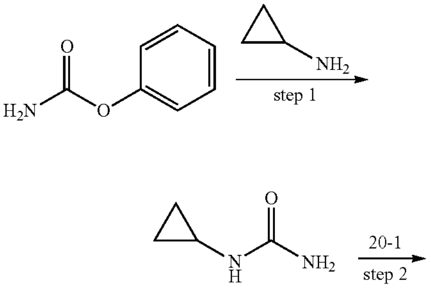

21-1

-continued

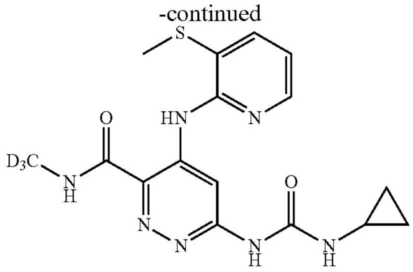

21-2

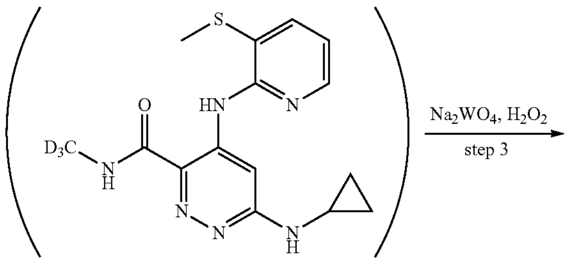

22-2

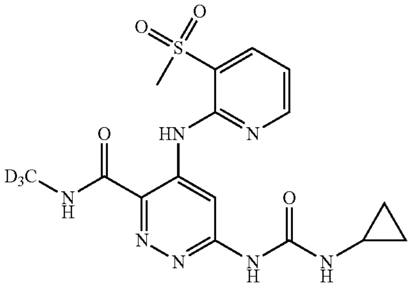

21

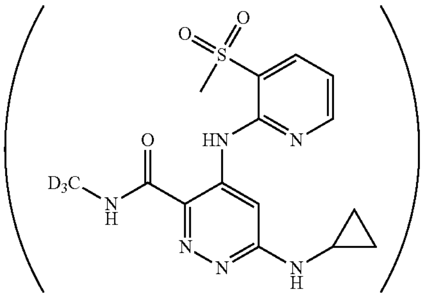

22

Step 1: To a solution of phenyl carbamate (2.1 g, 15.3 mmol) in dioxane (30 mL) was added cyclopropanamine (2.2 g, 38.3 mmol). The mixture was stirred at room temperature for 16 hours and concentrated. The residue was suspended in dichloromethane and sonicated. The resulting precipitate was collected by filtration to afford 21-1.

Step 2: To a mixture of 20-1 (156 mg, 0.5 mmol) in dioxane (5 mL) was added 21-1 (125 mg, 1.25 mmol), tris(dibenzylideneacetone)dipalladium (68 mg, 0.075 mmol), sodium tert-butoxide (286 mg, 3.0 mmol) and 1.1'-binaphthyl-2.2'-diphenyl phosphine (46 mg, 0.10 mmol). Then reaction mixture was stirred at 110° C. for 1 h under $N_2$ atmosphere. The mixture was diluted with ethyl acetate, washed with water and brine. The organic layer was dried over anhydrous sodium sulfate, filtered and concentrated. The residue was purified by prep-HPLC (acetonitrile/0.05% TFA in water: 10%~95%) to afford 21-2/22-2(20%).

Step 3: To a mixture of 21-2 (160 mg, 0.41 mmol, mixed with ~20% 22-2) in acetic acid (10 mL) was added sodium tungstate (122 mg, 0.41 mmol), 30% aqueous hydrogen peroxide (937 mg, 8.3 mmol) dropwise at room temperature. The reaction mixture was stirred for 1 hour. The mixture was diluted with water, quenched with saturated aqueous sodium thiosulfate, adjusted to pH~9 with sodium carbonate, extracted with dichloromethane/methanol (10/1). The combined organic layers were dried over anhydrous sodium sulfate, filtered and concentrated. The residue was purified by prep-HPLC (acetonitrile/0.05% formic acid in water: 10%~95%) to afford 21 as a 2.0 eq formic acid salt, and 22 as a 2.0 eq formic acid salt.

2.0 eq formic acid salt of 21: LCMS (ESI, m/z): $[M+H]^+$=409.1; $^1$H-NMR (400 MHz, DMSO-$d_6$, ppm): δ 12.02 (s, 1H), 9.62 (s, 1H), 9.12 (s, 1H), –9.06 (s, 1H), 8.58 (d, J=3.2 Hz, 1H), 8.42 (s, 2H), 8.23 (d, J=7.6 Hz, 1H), 7.68 (s, 1H), 7.30-7.26 (m, 1H), 3.30 (s, 3H), 2.59-2.51 (m, 1H), 0.66-0.59 (m, 2H), 0.40-0.38 (s, 2H).

2.0 eq formic acid salt of 22: LCMS (ESI, m/z): $[M+H]^+$=366.1; $^1$H-NMR (400 MHz, DMSO-$d_6$, ppm): δ 12.00 (s, 1H), 8.94 (s, 1H), 8.58-8.55 (m, 1H), 8.42 (s, 2H), 8.22-8.18 (m, 2H), 7.62 (s, 1H), 7.22 (dd, J=8.0, J=4.8 Hz, 1H), 3.32 (s, 3H), 2.61-2.53 (m, 1H), 0.75-0.70 (m, 2H), 0.50-0.44 (m, 2H).

Example 16 Synthesis of Compound 25

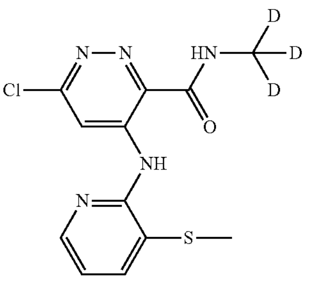

20-1

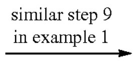

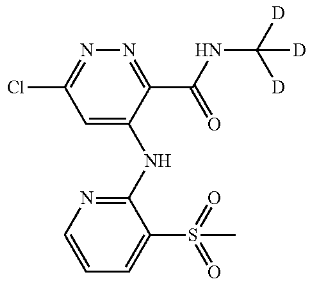

25-1

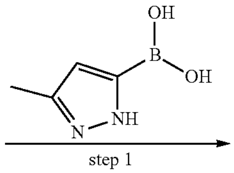

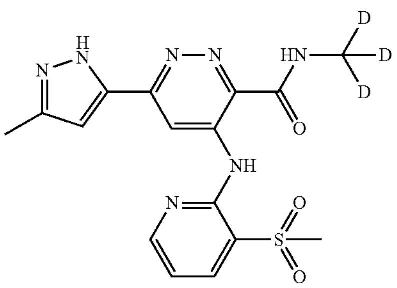

25

Compound 25-1 was prepared from 20-1 following the procedure for the synthesis of compound 1 in example 1.

Step 1: To a mixture of 25-1 (173 mg, 0.5 mmol) in dimethyl sulfoxide (4 mL)/water (0.4 mL) was added (3-methyl-1H-pyrazol-5-yl)boronic acid (157.5 mg, 1.25 mmol), [1,1'-bis(diphenylphosphino)ferrocene]dichloropalladium (I) (73 mg, 0.1 mmol) and potassium carbonate (207 mg, 1.5 mmol). The reaction mixture was stirred at 130° C. for 1 hour under $N_2$ atmosphere and microwave condition. The mixture was diluted with ethyl acetate and washed with water. The organic layer was dried over anhydrous sodium sulfate, filtered and concentrated. The residue was purified by prep-HPLC (acetonitrile/0.05% formic acid in water: 15%~95%) to afford 25 as a 2.0 eq formic acid salt. LCMS (ESI, m/z): $[M+H]^+$=391.1; $^1$H-NMR (400 MHz, DMSO-$d_6$, ppm): δ 13.00 (s, 1H), 12.07 (s, 1H), 9.34 (s, 1H), 9.16 (s, 1H), 8.64 (d, J=3.6 Hz, 1H), 8.40 (s, 2H), 8.25 (d, J=7.6 Hz, 1H), 7.34-7.25 (m, 1H), 6.74 (s, 1H), 3.30 (s, 3H), 2.29 (s, 3H).

Example 17 Synthesis of Compound 37

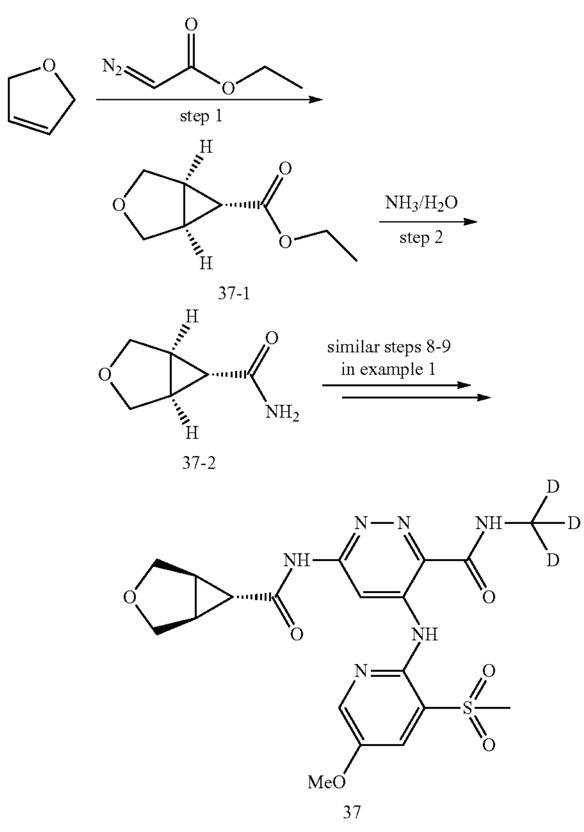

37-1

37-2

37

Step 1: To a solution of 2,5-dihydrofuran (1.08 mL, 14.2 mmol) in dichloromethane (15 mL) was added Rhodium (II) acetate dimer (31.53 mg, 0.071 mmol). To above solution was added a solution of ethyl 2-diazoacetate (1.5 mL, 14.2 mmol) in dichloromethane (7 mL) dropwise over 0.5 hour. The reaction mixture was stirred at room temperature for 15 hours. The mixture was concentrated and the residue was purified by column chromatography on silica gel (petroleum ether to petroleum ether/ethyl acetate=10/1)) to afford 37-1.

Step 2: A mixture of 37-1 (200 mg, 1.28 mmol) and ammonia (10 mL) was stirred at room temperature for 72 hours. The mixture was concentrated to afford 37-2.

Compound 37 was prepared from 37-2 following the procedure for the synthesis of compound 1 in example 1. LCMS (ESI, m/z): $[M+H]^+$=466.2; $^1$H-NMR (400 MHz, DMSO-$d_6$, ppm): δ 11.85 (s, 1H), 11.30 (s, 1H), 9.16 (s, 1H), 9.12 (s, 1H), 8.38 (d, J=2.8 Hz, 1H), 7.80 (d, J=2.8 Hz, 1H), 3.93 (s, 3H), 3.83 (d, J=8.4 Hz, 2H), 3.66 (d, J=8.4 Hz, 2H), 3.34 (s, 3H), 2.25-1.97 (m, 3H).

Example 18 Synthesis of Compounds 39-41

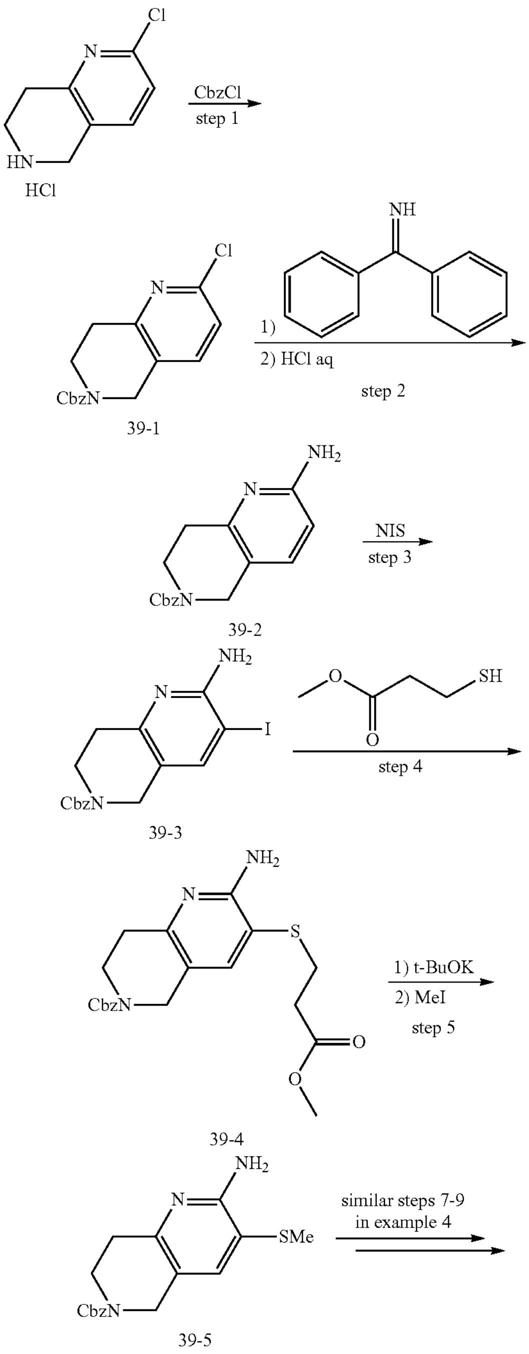

39-1

39-2

39-3

39-4

39-5

-continued

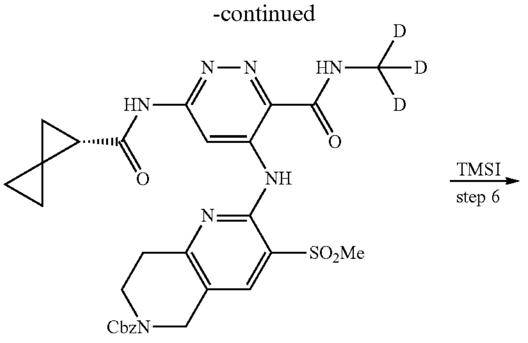

39

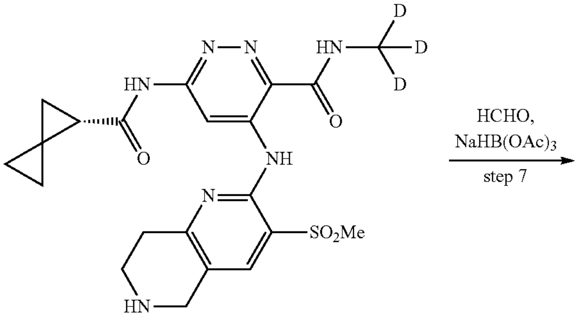

40

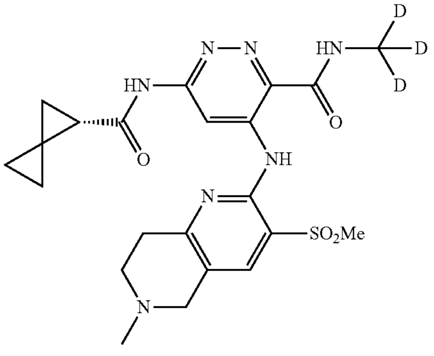

41

Step 1: To a suspension of 2-chloro-5,6,7,8-tetrahydro-1,6-naphthyridine hydrochloride (12.3 g, 60 mmol) in dioxane (100 mL) and saturated aqueous sodium bicarbonate (100 mL) was added benzyl chloroformate (11.29 g, 66 mmol) at 0° C. Then the reaction was stirred for 1 hour at room temperature. The mixture was diluted with ethyl acetate, washed with water and brine. The organic layer was dried over anhydrous sodium sulfate, filtered and concentrated. The residue was purified by column chromatography on silica gel (petroleum ether to petroleum ether/ethyl acetate=1/1) to afford 39-1.

Step 2: A mixture of 39-1 (12.1 g, 40 mmol), diphenylmethanimine (8.7 g, 48 mmol), cesium carbonate (19.6 g, 60 mmol), tris(dibenzylideneacetone)dipalladium (1.83 g, 2 mmol) and 4,5-bis(diphenylphosphino)-9,9-dimethylxanthene (2.3 g, 4 mmol) in dimethyl sulfoxide (200 mL) was stirred for 24 hours at 110° C. under $N_2$ atmosphere. The mixture was diluted with ethyl acetate, washed with water and brine. The organic layer was dried over anhydrous sodium sulfate, filtered and concentrated. The mixture was dissolved in dioxane (69 mL) and 3M hydrochloride acid (69 mL, 207 mmol). The reaction was stirred for 1 hour at room temperature. The mixture was adjusted to pH~8 with saturated aqueous sodium carbonate, and extracted with ethyl acetate. The combined organic layers were dried over anhydrous sodium sulfate, filtered and concentrated. The residue was purified by column chromatography on silica gel (petroleum ether to ethyl acetate) to afford 39-2.

Step 3: To a solution of 39-2 (4.25 g, 15 mmol) in acetic acid (50 mL) was added N-iodosuccinimide (4.05 g, 18 mmol) at room temperature. Then the reaction was stirred for 16 hours. The mixture was diluted with water, adjusted to pH~8 with saturated aqueous sodium carbonate, and extracted with ethyl acetate. The combined organic layers were dried over anhydrous sodium sulfate, filtered and concentrated. The residue was purified by column chromatography on silica gel (petroleum ether to ethyl acetate) to afford 39-3.

Step 4: To a mixture of 39-3 (4.9 g, 12 mmol) in dioxane (50 mL) was added methyl 3-sulfanylpropanoate (2.16 g, 18 mmol), tris(dibenzylideneacetone)dipalladium (550 mg, 0.6 mmol), ethyldiisopropylamine (3.1 g, 24 mmol) and 4,5-bis(diphenylphosphino)-9,9-dimethylxanthene (694 mg, 1.2 mmol). The mixture was stirred at 100° C. for 5 hours under $N_2$ atmosphere. The mixture was diluted with ethyl acetate, washed with water and brine. The organic layer was dried over anhydrous sodium sulfate, filtered and concentrated. The residue was purified by column chromatography on silica gel (petroleum ether to petroleum ether/ethyl acetate=1/4) to afford 39-4.

Step 5: To a mixture of 39-4 (4 g, 10 mmol) in tetrahydrofuran (40 mL) was added potassium tert-butanolate (3.36 g, 30 mmol) at 0° C. Then the reaction was stirred for 1 hour at room temperature. To above mixture was added a solution of sodium hydroxide (800 mg, 20 mmol) in methanol (40 mL) and iodomethane (2.84 g, 20 mmol), then stirred for 1 hour. The mixture was diluted with ethyl acetate, washed with water and brine. The organic layer was dried over anhydrous sodium sulfate, filtered and concentrated. The residue was purified by column chromatography on silica gel (petroleum ether to petroleum ether/ethyl acetate=1/3) to afford 39-5.

Compound 39 was prepared from 39-5 following the procedure for the synthesis of compound 5 in example 4. LCMS (ESI, m/z): $[M+H]^+$=609.3; $^1$H-NMR (400 MHz, DMSO-$d_6$, ppm): δ 12.06 (s, 1H), 11.19 (s, 1H), 9.72 (s, 1H), 9.15 (s, 1H), 8.14 (s, 1H), 7.50-7.29 (m, 5H), 5.13 (s, 2H), 4.77-4.59 (m, 2H), 3.85-3.72 (m, 2H), 3.30 (s, 3H), 2.96-2.92 (m, 2H), 2.49-2.43 (m, 1H), 1.45-1.35 (m, 2H), 0.95-0.70 (m, 4H).

Step 6: To a solution of 39 (152 mg, 0.25 mmol) in acetonitrile (10 mL) was added iodotrimethylsilane (300 mg, 1.5 mmol) at 0° C. under nitrogen atmosphere. Then the reaction was stirred for 1 hour at room temperature. The reaction was quenched with saturated aqueous sodium bicarbonate and extracted with dichloromethane. The organic layer was dried over anhydrous sodium sulfate, filtered and concentrated. The residue was purified by prep-HPLC (acetonitrile/0.1% formic acid in water: 5%~95%) to afford 40 as a 2.0 eq formic acid salt. LCMS (ESI, m/z): $[M+H]^+$=475.2; $^1$H-NMR (400 MHz, DMSO-$d_6$, ppm): δ 11.98 (s, 1H), 11.16 (s, 1H), 9.66 (s, 1H), 9.14 (s, 1H), 8.33 (s, 2H), 7.94 (s, 1H), 3.88 (s, 2H), 3.28 (s, 3H), 3.06-3.02 (m, 2H), 2.84-2.80 (m, 2H), 2.49-2.43 (m, 1H), 1.43-1.34 (m, 2H), 0.92-0.70 (m, 4H).

Step 7: To a solution of 40 (47 mg, 0.1 mmol) in 1,2-dichloroethane (3 mL) and N,N-dimethylacetamide (3 mL) was added acetic acid (12 mg, 0.2 mmol), 36% formaldehyde solution (83 mg, 1 mmol) and sodium triacetoxyborohydride (106 mg, 0.5 mmol). Then the reaction was stirred for 30 minutes. The reaction was quenched with saturated aqueous sodium bicarbonate and extracted with dichloromethane. The organic layer was dried over anhydrous sodium sulfate, filtered and concentrated. The residue was purified by prep-HPLC (acetonitrile/0.1% formic acid in water: 5%~95%) to afford 41. LCMS (ESI, m/z): $[M+H]^+$=489.3; $^1$H-NMR (400 MHz, DMSO-$d_6$, ppm): δ 12.00 (s, 1H), 11.18 (s, 1H), 9.66 (s, 1H), 9.15 (s, 1H), 7.96 (s, 1H), 3.54 (s, 2H), 3.29 (s, 3H), 2.93 (t, J=5.6 Hz, 2H), 2.72 (t, J=5.6 Hz, 2H), 2.47-2.42 (m, 1H), 2.37 (s, 3H), 1.43-1.34 (m, 2H), 0.92-0.70 (m, 4H).

Example 19 Synthesis of Compound 42

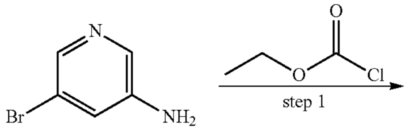

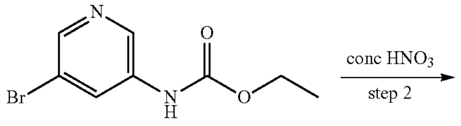

42-1

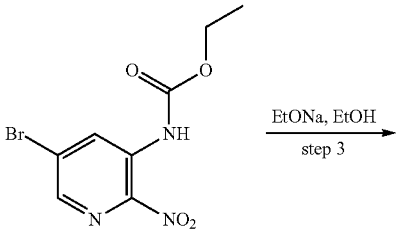

42-2

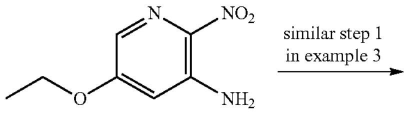

42-3

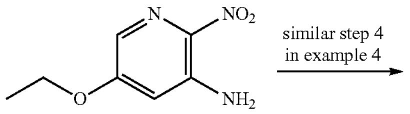

42-4

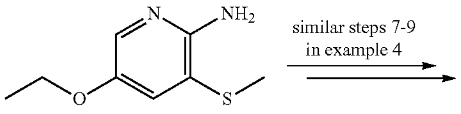

42-5

-continued

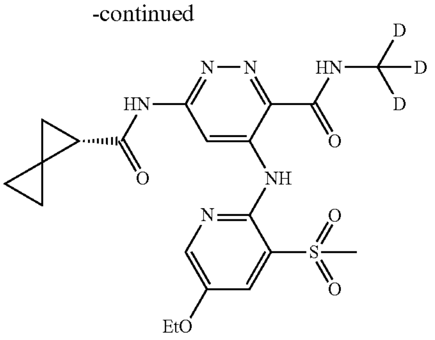

42

Step 1: To a solution of 5-bromopyridin-3-amine (20 g, 115.6 mmol) in pyridine (200 mL) was added ethyl carbonochloridate (15.05 g, 138.72 mmol) dropwise in an ice bath. The reaction mixture was stirred at room temperature for 2 hours. The solvent was removed in vacuo. The residue was dissolved in ethyl acetate and washed with water. The organic layer was dried over anhydrous sodium sulfate and concentrated. The crude was purified by silica gel chromatography (petroleum ether/ethyl acetate=7/3) to afford 42-1.

Step 2: To a mixture of concentrated sulfuric acid (35 mL, 609 mmol) and fuming nitric acid (23.5 mL, 487 mmol) was added 42-1 (10 g, 40.8 mmol) portion wise at 0° C. After being stirred at room temperature overnight, the mixture was poured onto ice water. The precipitate was filtered, washed with water and dried to afford 42-2.

Step 3: To a stirred mixture of 42-2 (3 g, 10.342 mmol) in ethanol (60 mL) was added sodium ethanolate (3.87 g, 56.881 mmol) under an $N_2$ atmosphere. The reaction was stirred at 50° C. for 17 hours. The reaction mixture was washed with water. The aqueous layer was extracted with dichloromethane. The combined organic layers were dried over anhydrous sodium sulfate and evaporated under vacuum. The residue was purified by column chromatography on silica (petroleum ether to petroleum ether/ethyl acetate=2:3) to afford 42-3.

Compound 42-4 was prepared from 42-3 following the procedure for the synthesis of compound 3-1 in example 3.

Compound 42-5 was prepared from 42-4 following the procedure for the synthesis of compound 5-4 in example 4.

Compound 42 was prepared from 42-5 following the procedure for the synthesis of compound 5 in example 4. LCMS (ESI, m/z): $[M+H]^+$=464.0; $^1$H-NMR (400 MHz, DMSO-$d_6$, ppm): δ 11.83 (s, 1H), 11.17 (s, 1H), 9.14 (s, 1H), 9.12 (s, 1H), 8.38 (d, J=3.2 Hz, 1H), 7.78 (d, J=2.8 Hz, 1H), 4.21 (q, J=6.8 Hz, 2H), 3.33 (s, 3H), 2.45-2.42 (m, 1H), 1.41-1.35 (m, 5H), 0.92-0.85 (m, 3H), 0.79-0.72 (m, 1H).

Example 20 Synthesis of Compound 43

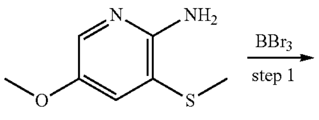

1-6

-continued

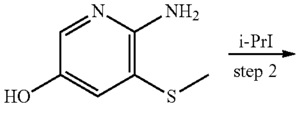

43-1

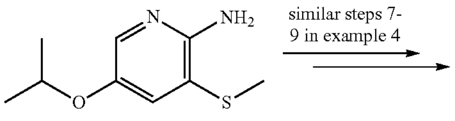

43-2

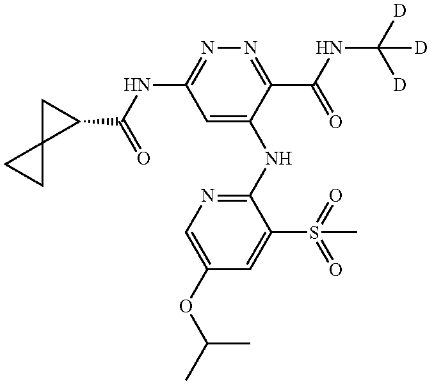

43

Step 1: To a solution of 1-6 (2 g, 11.7 mmol) in dichloromethane (20 mL) was added tribromoborane (35.2 mL, 35.2 mmol) at 0° C. The mixture was stirred for 2 hours at room temperature. After completion of the reaction, the solvent was removed in vacuo and ethyl acetate was added. The mixture was quenched with ice-cold water and aqueous sodium hydroxide solution was added to adjust pH to 12. The aqueous layer was extracted with ethyl acetate. The combined organic layers were concentrated. The residue was purified by column chromatography on silica (dichloromethane to dichloromethane/methane=10/1) to afford 43-1.

Step 2: To a solution of 1.42 g, 9.1 mmol) in N,N-dimethylformamide (15 mL) was added sodium hydride (436.34 mg, 10.9 mmol, 60% in mineral oil) at 0° C. and the mixture was stirred for 15 minutes. Then 2-iodopropane (1.7 g, 10.0 mmol) was added. The reaction mixture was stirred for 17 hours at room temperature. After completion of the reaction, the mixture was quenched with ice-cold water. The aqueous layer was extracted with dichloromethane. The combined organic layers were dried over anhydrous sodium sulfate, filtered and concentrated. The residue was purified by column chromatography on silica (petroleum ether to petroleum ether/ethyl acetate=1/1) to afford 43-2.

Compound 43 was prepared from 43-2 following the procedure for the synthesis of compound 5 in example 4. LCMS (ESI, m/z): $[M+H]^+$=478.1; $^1$H-NMR (400 MHz, DMSO-$d_6$, ppm): δ 11.83 (s, 1H), 11.17 (s, 1H), 9.14 (s, 1H), 9.11 (s, 1H), 8.36 (d, J=2.8 Hz, 1H), 7.76 (d, J=3.2 Hz, 1H), 4.81-4.74 (m, 1H), 3.34 (s, 3H), 2.46-2.42 (m, 1H), 1.42-1.35 (m, 2H), 1.32 (d, J=6.0 Hz, 6H), 0.94-0.82 (m, 3H), 0.79-0.73 (m, 1H).

Example 21 Synthesis of Compound 44

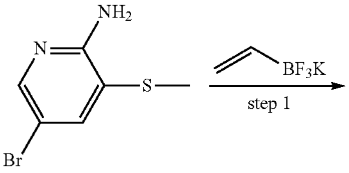

5-5

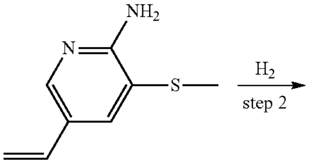

44-1

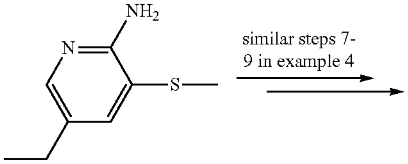

44-2

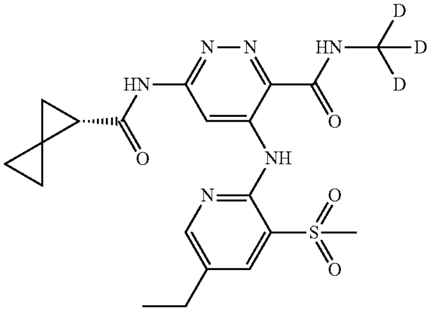

44

Step 1: A mixture of 5-5 (2.7 g, 12.3 mmol), potassium vinyltrifluoroborate (2.49 g, 18.5 mmol), sodium carbonate (2.6 g, 24.6 mmol) and [1,1'-bis(diphenylphosphino)ferrocene]dichloropalladium(II) (0.9 g, 1.23 mmol) in dioxane (48 mL) and water (12 mL) was stirred at 110° C. for 2 hours under $N_2$ atmosphere. The mixture was diluted with water and extracted with ethyl acetate. The combined organic layers were dried over anhydrous sodium sulfate, filtered and concentrated. The residue was purified by column chromatography on silica gel (petroleum ether to petroleum ether/ethyl acetate=1/1) to afford 44-1.

Step 2: To a solution of 44-1 (850 mg, 5.1 mmol) in methanol (10 mL) was added platinum (IV) oxide (85 mg). The reaction mixture was stirred at room temperature for 2 hours under $H_2$ atmosphere. The suspension was filtered and washed with methanol. The filtrate was concentrated to afford 44-2.

Compound 44 was prepared from 44-2 following the procedure for the synthesis of compound 5 in example 4. LCMS (ESI, m/z): $[M+H]^+$=448.2; $^1$H-NMR (400 MHz, DMSO-$d_6$, ppm): δ 12.01 (s, 1H), 11.21 (s, 1H), 9.42 (s, 1H), 9.17 (s, 1H), 8.51 (d, J=2.4 Hz, 1H), 8.11 (d, J=2.4 Hz, 1H), 3.32 (s, 3H), 2.71 (q, J=7.6 Hz, 2H), 2.47-2.44 (m, 1H), 1.41-1.35 (m, 2H), 1.21 (t, J=7.6 Hz, 3H), 0.91-0.83 (m, 3H), 0.78-0.74 (m, 1H).

Example 22 Synthesis of Compound 49

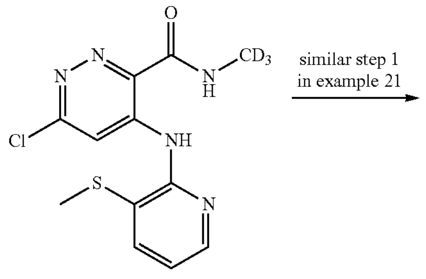

20-1

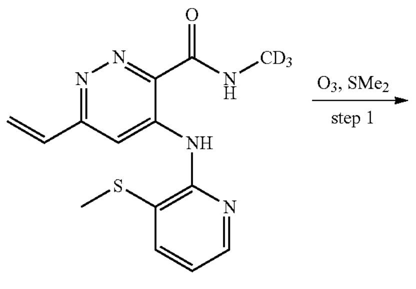

49-1

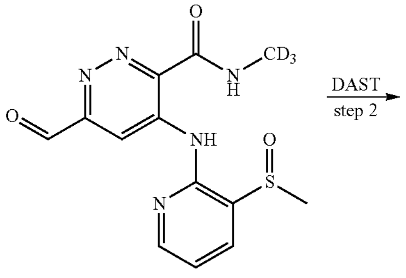

49-2

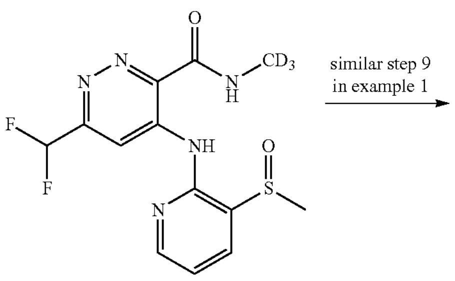

49-3

-continued

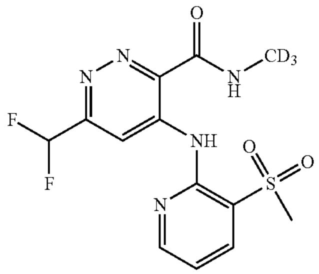

49

Compound 49-1 was prepared from 20-1 following the procedure for the synthesis of compound 44-1 in example 21.

Step 1: To a solution of 49-1 (1.05 g, 3.5 mmol) in dichloromethane (30 mL) was bubbled with ozone for 1 hour at −78° C. The reaction mixture was added dimethyl sulfide (2 mL), and stirred at room temperature for 1 hour. The reaction mixture was concentrated and purified by flash column (dichloromethane/methanol=20/1) to give 49-2.

Step 2: To a solution of 49-2 (248 mg, 0.75 mmol) in dichloromethane (20 mL) were added triethylamine trihydrofluoride (0.5 mL, 3.0 mmol) and diethylaminosulphur trifluoride (1.2 g, 7.5 mmol) at 0° C. The mixture was stirred at room temperature for 1 hour. The reaction mixture was added to ice water dropwise, extracted with dichloromethane. The organic layer was washed with brine, dried over anhydrous sodium sulfate, filtered and concentrated. The residue was purified by prep-TLC (dichloromethane/methanol=20/1) to give 49-3.

Compound 49 was prepared from 49-3 following the procedure for the synthesis of compound 1 in example 1. LCMS (ESI, m/z): $[M+H]^+$=361.2; $^1$H-NMR (400 MHz, DMSO-$d_6$, ppm): δ 12.33 (s, 1H), 9.49 (s, 1H), 9.01 (s, 1H), 8.71-8.66 (m, 1H), 8.32 (d, J=7.6 Hz, 1H), 7.44-7.15 (m, 2H), 3.37 (s, 3H).

Example 23 Synthesis of Compound 50

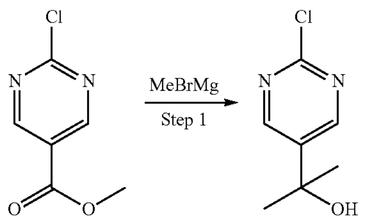

50-1

-continued

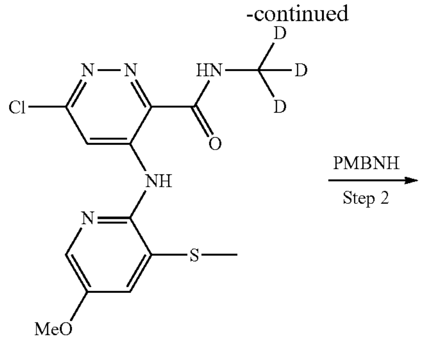

1-7

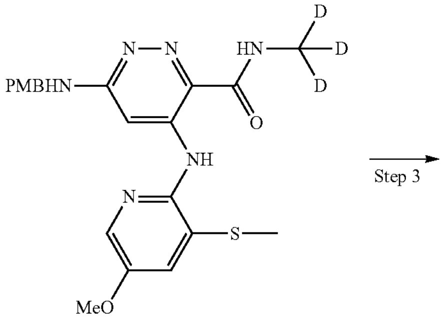

50-2

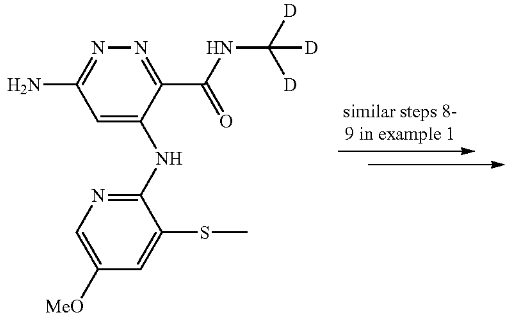

50-3

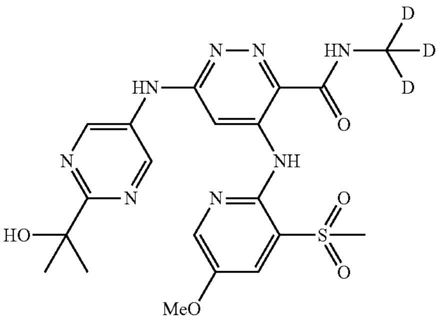

50

Step 1: To a solution of methyl 2-chloropyrimidine-5-carboxylate (250 mg, 1.449 mmol) in tetrahydrofuran (5 mL) was added methyl magnesium bromide (4.347 mL, 1M in hexanes) at −78° C. This solution was stirred at 0° C. for 30 minutes. The reaction mixture was stirred at room temperature for an additional 1 h. The mixture was quenched with saturated aqueous ammonium chloride, diluted with ether. The organic layer was washed with water, dried over sodium sulfate and concentrated to afford 50-1.

Step 2: A mixture of 1-7 (5 g, 14.6 mmol), 4-methoxybenzylamine (10 g, 72.9 mmol) and potassium fluoride (2.5 g, 43.7 mmol) in dimethyl sulfoxide (50 mL) was stirred at 120° C. for 16 hours. The reaction solution was poured into water. The precipitate was filtered, washed with water and dried to afford 50-2.

Step 3: A mixture of 50-2 (5 g, 11.3 mmol) in trifluoroacetic acid (30 mL) was stirred at 60° C. for 3 hours. The mixture was concentrated to remove trifluoroacetic acid. The result mixture was adjusted to pH~9 by saturated aqueous sodium bicarbonate. The result solution was extracted by dichloromethane. The combined organics were dried over sodium sulfate, filtered, concentrated, and purified by column chromatography on silica gel (0-10% methanol in dichloromethane) to afford 50-3.

Compound 50 was prepared from 50-3 and 50-1 following the procedure for the synthesis of compound 1 in example 1. LCMS (ESI, m/z): $[M+H]^+$=492.1; $^1$H-NMR (400 MHz, DMSO-$d_6$, ppm): δ 11.91 (s, 1H), 10.49 (s, 1H), 9.63 (s, 1H), 9.09 (s, 1H), 8.69 (s, 2H), 8.52-8.51 (m, 1H), 7.83-7.82 (m, 1H), 5.27 (s, 1H), 3.94 (s, 3H), 3.37 (s, 3H), 1.48 (s, 6H).

Example 24 Synthesis of Compound 51

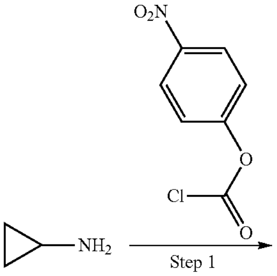

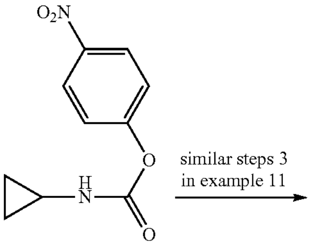

51-1

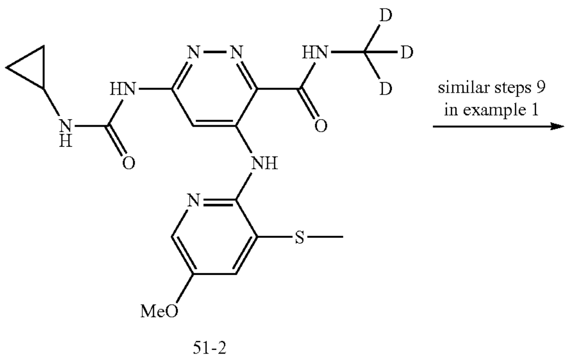

51-2

-continued

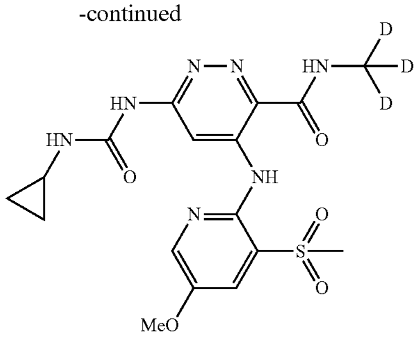

51

Step 1: To a solution of cyclopropylamine (2 g, 35 mmol) in acetonitrile (70 mL) was added 4-nitrophenyl chloroformate (7 g, 35 mmol) and triethylamine (5.3 g, 52.5 mmol). The reaction mixture was stirred at 20° C. for 2 hours. The resulting mixture was diluted with dichloromethane and water. The organic layer was concentrated and purified by column chromatography on silica gel (0-10% ethyl acetate in petroleum ether) to give 51-1.

Compound 51-2 was prepared from 50-3 and 51-1 following the procedure for the synthesis of compound 12-3 in example 11.

Compound 51 was prepared from 51-2 following the procedure for the synthesis of compound 1 in example 1. LCMS (ESI, m/z): $[M+H]^+$=439.6; $^1$H-NMR (400 MHz, DMSO-$d_6$, ppm): δ 11.82 (s, 1H), 9.47 (s, 1H), 9.12 (s, 1H), 8.77 (s, 1H), 8.40 (d, J=2.8 Hz, 1H), 7.81 (d, J=2.8 Hz, 1H), 7.56 (s, 1H), 3.94 (s, 3H), 3.34 (s, 3H), 2.62-2.58 (m, 1H), 0.71-0.62 (m, 2H), 0.46-0.37 (m, 2H).

Example 25 Synthesis of Compound 52

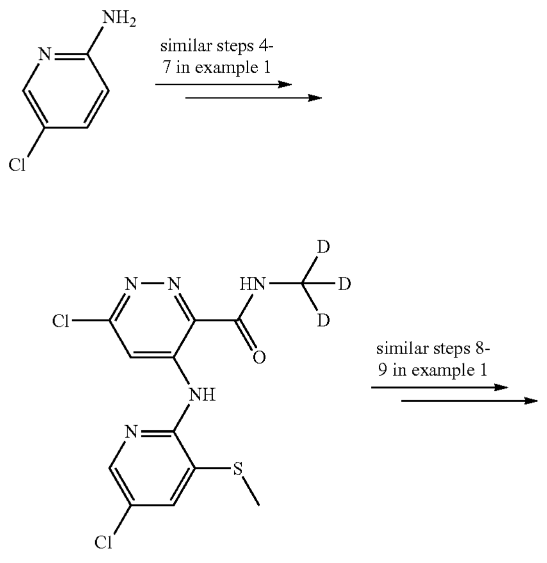

52-1

-continued

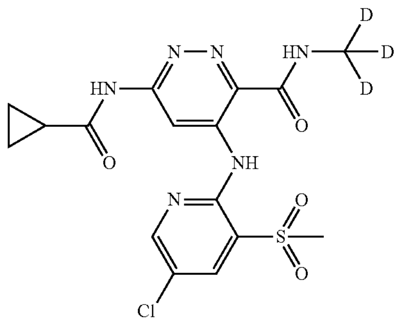

52

Compound 52-1 was prepared from 2-amino-5-chloropyridine following the procedure for the synthesis of compound 1-7 in example 1.

Compound 52 was prepared from 52-1 and cyclopropanecarboxamide following the procedure for the synthesis of compound 1 in example 1. LCMS (ESI, m/z): $[M+H]^+$=428.0; $^1$H-NMR (400 MHz, DMSO-$d_6$, ppm): δ 12.17 (s, 1H), 11.47 (s, 1H), 9.38 (s, 1H), 9.22 (s, 1H), 8.67 (s, 1H), 8.25 (s, 1H), 3.40 (s, 3H), 2.17-2.08 (m, 1H), 0.91-0.82 (m, 4H).

Example 26 Synthesis of Compound 53

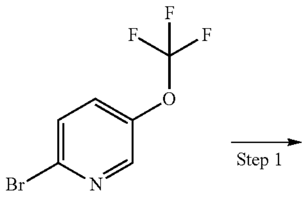

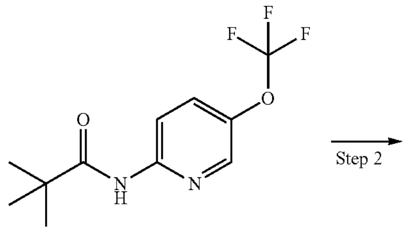

53-1

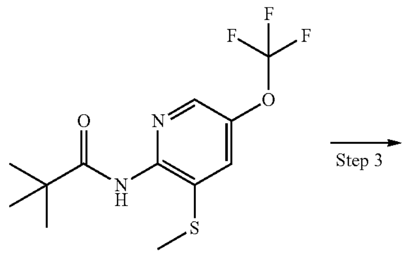

53-2

-continued

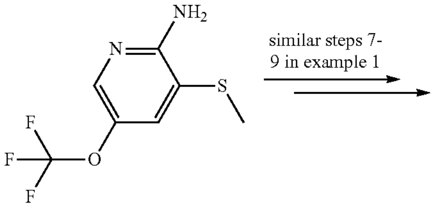

53-2

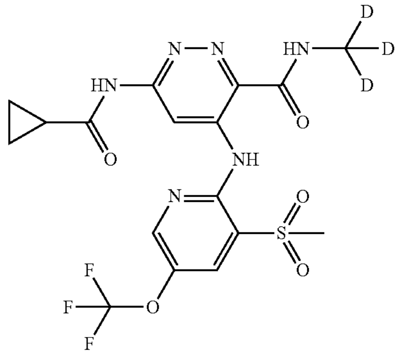

53

Step 1: To a solution of 2-bromo-5-(trifluoromethoxy) pyridine (2.1 g, 8.678 mmol) in dioxane (160 mL) was added 2,2-dimethylpropanamide (4.860 mL, 43.390 mmol), tris(dibenzylideneacetone)dipalladium (0.79 g, 0.868 mmol), 4,5-bis(diphenylphosphino)-9,9-dimethylxanthene (1.00 g, 1.736 mmol), cesium carbonate (8.48 g, 26.034 mmol) under a nitrogen atmosphere and heated to 110° C. for overnight. The mixture was concentrated and purified by column chromatography (Petroleum ether) to give 53-1.

Step 2: To the mixture of 53-1 (4 g, 15.254 mmol) in ether (150 mL) was added tert-butyllithium (33 mL, 2.5 eq) dropwise at −65° C. under a nitrogen atmosphere, then stirred for 3 hours. Then, (methyldisulfanyl)methane (2.028 mL, 22.881 mmol) was added to the mixture at −65° C. and stirred for 2 hours. The mixture was quenched by water and extracted with ethyl acetate. The combined organics were washed with brine, dried over anhydrous sodium sulfate, filtered, and concentrated to obtain 53-2.

Step 3: To the solution of 53-2 (3 g, 9.730 mmol) in water (40 mL) was added con. hydrochloric acid (36 wt %, 40 mL) and heated to 110° C. for 3 hours. The mixture was poured to saturated aqueous sodium bicarbonate and extracted with ethyl acetate. The organic phase was washed with brine, dried over anhydrous sodium sulfate, filtered, and concentrated. The residue was purified by column chromatography (ethyl acetate/petroleum ether=1:1) to give 53-3.

Compound 53 was prepared from 53-3 and 1-3 following the procedure for the synthesis of compound 1 in example 1. LCMS (ESI, m/z): $[M+H]^+$=478.1; $^1$H-NMR (400 MHz, DMSO-$d_6$, ppm): δ 12.27 (s, 1H), 11.49 (s, 1H), 9.45 (s, 1H), 9.25 (s, 1H), 8.76 (d, J=2.4 Hz, 1H), 8.23 (d, J=2.0 Hz, 1H), 3.45 (s, 3H), 2.18-2.08 (m, 1H), 0.93-0.82 (m, 4H). $^{19}$F-NMR (376 MHz, DMSO-$d_6$, ppm): δ −57.62 (3F).

Example 27 Synthesis of Compound 54

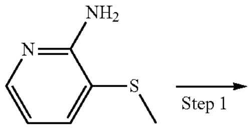

5-4

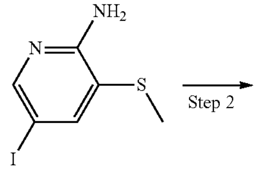

54-1

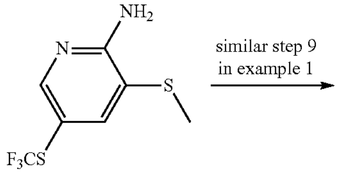

54-2

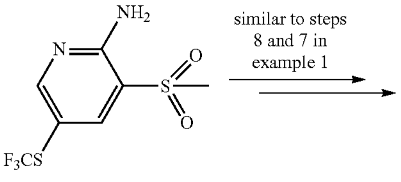

54-3

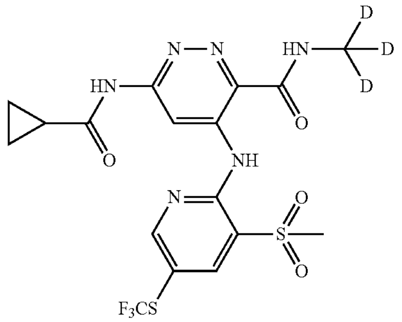

54

Step 1: A mixture of 5-4 (4.5 g, 32 mmol), p-toluenesulfonic acid (553 mg, 3.2 mmol) and N-iodosuccinimide (10.8 g, 48 mmol) in dimethyl sulfoxide (30 mL) was stirred at room temperature for 2 hours under $N_2$ atmosphere. The resulting mixture was quenched with water and adjusted to pH 8, extracted with ethyl acetate. The combined organic layers were washed with brine, dried over anhydrous sodium sulfate, filtered and concentrated. The residue was purified by column chromatography on silica gel (petroleum ether to petroleum ether/ethyl acetate=5/1) to give 54-1.

Step 2: A mixture of 54-1 (500 mg, 1.88 mmol) and trifluoromethylthiolato(2,2-bipyridine) copper(I) (724 mg, 2.06 mmol) in diglyme (6 mL) was stirred at 140° C. for 1.5 hours under $N_2$ atmosphere with the microwave condition. The resulting mixture was diluted with water and extracted with ethyl acetate. The combined organic layers were washed with brine, dried over anhydrous sodium sulfate, filtered and concentrated. The residue was purified by column chromatography on silica gel (petroleum ether to petroleum ether/ethyl acetate=5/1) to give 54-2.

Compound 54-3 was prepared from 54-2 following the procedure for the synthesis of compound 1 in example 1.

Compound 54 was prepared from 54-3 following the procedure for the synthesis of compound 1-8 in example 1. LCMS (ESI, m/z): $[M+H]^+$=494.1; $^1$H-NMR (400 MHz, DMSO-$d_6$, ppm): δ 12.42 (s, 1H), 11.53 (s, 1H), 9.56 (s, 1H), 9.27 (s, 1H), 8.80 (d, J=2.4 Hz, 1H), 8.40 (d, J=2.4 Hz, 1H), 3.43 (s, 3H), 2.15-2.03 (m, 1H), 0.90-0.83 (m, 4H). $^{19}$F-NMR (376 MHz, DMSO-$d_6$, ppm): δ −42.49 (3F).

Example 28 Synthesis of Compound 55

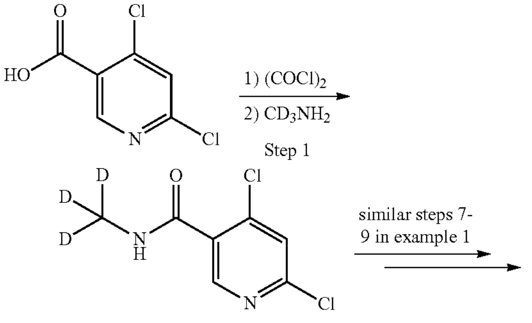

55-1

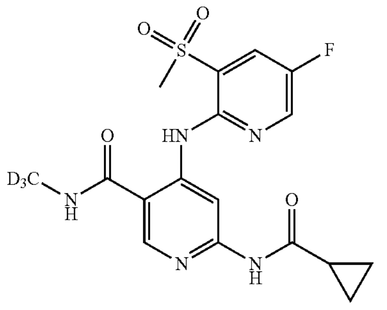

55

Step 1: To a mixture of 4,6-dichloronicotinic acid (7.0 g, 36.4 mmol) in chloroform (150 mL) was added oxalyl chloride (18.5 g, 146 mmol) and N,N-dimethylformamide (1 mL) at room temperature, then stirred for 2 hours at 60° C. The volatiles were removed under vacuum and co-evaporated with chloroform. The resulting mixture was added tetrahydrofuran (100 mL), methan-$d_3$-amine hydrochloride (3.1 g, 43 mmol) and N,N-diisopropylethylamine (14.1 g, 109 mmol) at 0° C., then stirred for 3 hours. The mixture was diluted with ethyl acetate, washed with saturated aqueous sodium bicarbonate and brine, dried over anhydrous sodium sulfate, filtered and concentrated. The residue was purified by column chromatography on silica gel (petroleum ether to petroleum ether/ethyl acetate=1/1) to give 55-1.

Compound 55 was prepared from 55-1 and 3-3 following the procedure for the synthesis of compound 1-8 in example 1. LCMS (ESI, m/z): $[M+H]^+$=411.1; $^1$H-NMR (400 MHz, DMSO-$d_6$, ppm): δ 11.43 (s, 1H), 10.82 (s, 1H), 8.83 (s, 1H), 8.63 (s, 1H), 8.60 (d, J=2.8 Hz, 1H), 8.56 (s, 1H), 8.10 (dd, J=7.6 Hz, 2.8 Hz, 1H), 3.34 (s, 3H), 2.00-1.96 (m, 1H), 0.79-0.75 (m, 4H).

Example 29 Synthesis of Compound 58

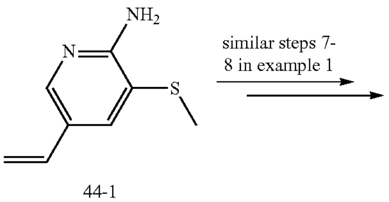

44-1

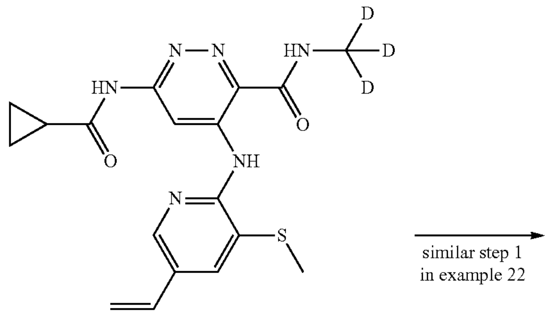

58-1

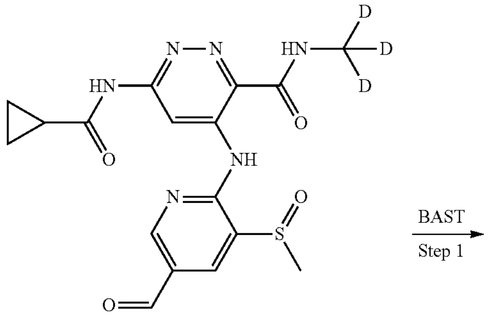

58-2

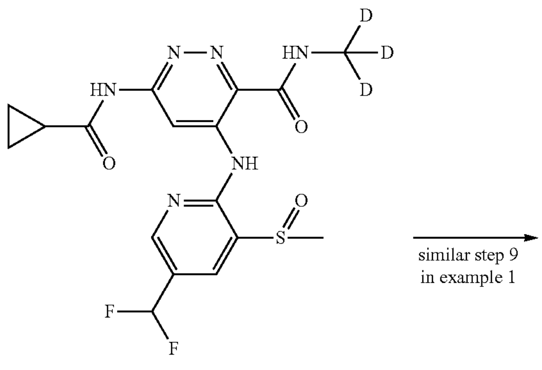

58-3

-continued

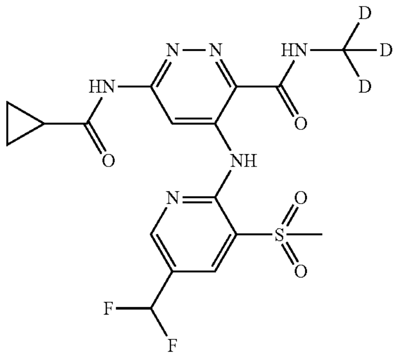

58

Compound 58-1 was prepared from 44-1 and 1-3 following the procedure for the synthesis of compound 1-8 in example 1.

Compound 58-2 was prepared from 58-1 following the procedure for the synthesis of compound 49-2 in example 22.

Step 1: To a solution of 58-2 (60 mg, 0.148 mmol) in dichloromethane (10 mL) was added bis(2-methoxyethyl)(trifluoro-λ4-sulfanyl)amine (0.136 mL, 0.740 mmol). The mixture was stirred at 20° C. for 16h. The reaction mixture was poured into ice water, washed with brine, dried over anhydrous sodium sulfate, filtered. The filtrate was concentrated to dryness under reduced pressure. The crude was purified by prep-TLC (dichloromethane/methanol=15/1) to give 58-3.

Compound 58 was prepared from 58-3 following the procedure for the synthesis of compound 1 in example 1. LCMS (ESI, m/z): $[M+H]^+$=444.2; $^1$H-NMR (400 MHz, DMSO-$d_6$, ppm): δ 12.34 (s, 1H), 11.50 (s, 1H), 9.58 (s, 1H), 9.25 (s, 1H), 8.80 (s, 1H), 8.40 (s, 1H), 7.40-7.08 (m, 1H), 3.42 (s, 3H), 2.19-2.03 (m, 1H), 0.89-0.82 (m, 4H). $^{19}$F-NMR (376 MHz, DMSO-$d_6$, ppm): δ −110.08 (2F).

Example 30 Synthesis of Compound 59

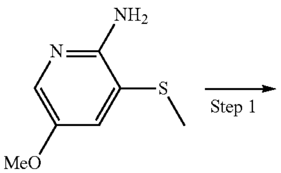

1-6

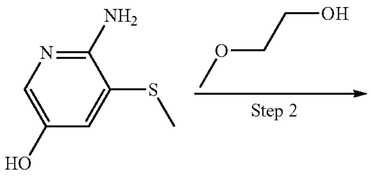

59-1

-continued

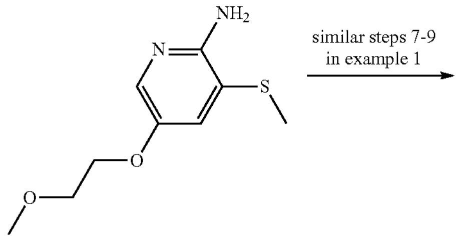

59-2

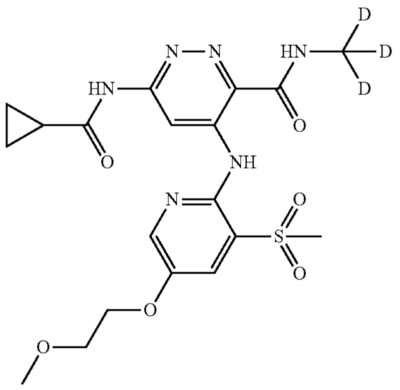

59

Step 1: To a mixture of 1-6 (5.1 g, 30 mmol) in dichloromethane (50 mL) was added boron tribromide (90 mL, 90 mmol, 1.0 M in dichloromethane) at 0° C. The reaction mixture was stirred at room temperature for 3 hours and cooled to 0° C. The mixture was quenched with methanol. The resulting mixture was adjusted to pH~9 with lithium hydroxide (1 M in water), extracted with dichloromethane/methanol=20/1. Organic layer was dried over anhydrous sodium sulfate, filtered and concentrated. The residue was purified by column chromatography on silica gel (dichloromethane to dichloromethane/methanol=20:1) to give 59-1.

Step 2: To a solution of 59-1 (1.0 g, 6.4 mmol) and 2-methoxyethan-1-ol (585 mg, 7.7 mmol) in tetrahydrofuran (40 mL) was added triphenylphosphine (2.02 g, 7.7 mmol) and N,N,N',N'-tetramethylazodicarboxamide (1.32 g, 7.7 mmol). The mixture was stirred at room temperature for 16 hours. The mixture was concentrated and purified by prep-HPLC (acetonitrile/0.05% TFA in water: 10%~95%) to give 59-2.

Compound 59 was prepared from 59-2 following the procedure for the synthesis of compound 1 in example 1. LCMS (ESI, m/z): $[M+H]^+$=468.2; $^1$H-NMR (400 MHz, DMSO-$d_6$, ppm): δ 11.84 (s, 1H), 11.39 (s, 1H), 9.17 (s, 1H), 9.13 (s, 1H), 8.38 (d, J=3.2 Hz, 1H), 7.81 (d, J=2.8 Hz, 1H), 4.29 (t, J=4.0 Hz, 2H), 3.68 (t, J=4.0 Hz, 2H), 3.33 (s, 3H), 3.32 (s, 3H), 2.15-2.07 (m, 1H), 0.86-0.82 (m, 4H).

Example 31 Synthesis of Compound 60

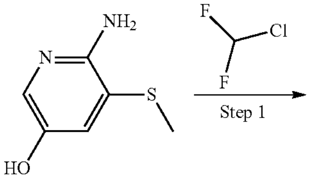

59-1

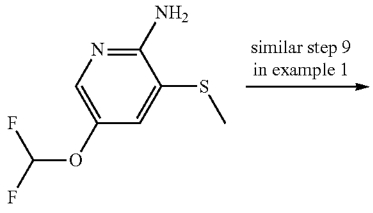

60-1

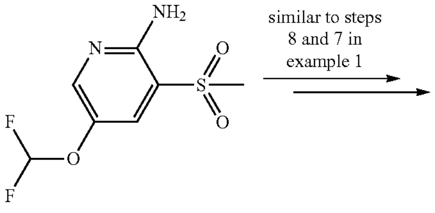

60-2

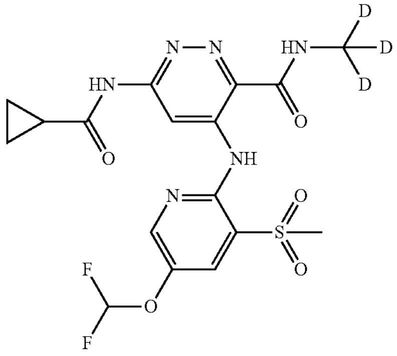

60

Step 1: To a mixture of 59-1 (2.00 g, 12.8 mmol) in 1,2-dimethoxyethane (20.0 mL) was added sodium hydroxide (1.64 g, 40.9 mmol) in water (10.0 mL) dropwise at 10~20° C., then bubbled with difluorochloromethane for 30 min, then stirred for 16 h. The reaction mixture was poured into water, extracted with ethyl acetate. The combined organic layers were washed with brine, dried over anhydrous sodium sulfate, and concentrated. The residue was purified by column chromatography (petroleum ether/ethyl acetate=1/0 to 0/1) to give 60-1.

Compound 60-2 was prepared from 60-1 following the procedure for the synthesis of compound 1 in example 1.

Compound 60 was prepared from 60-2 following the procedure for the synthesis of compound 1-8 in example 1. LCMS (ESI, m/z): $[M+H]^+$=460.2, $^1$H-NMR (400 MHz, DMSO-$d_6$, ppm): δ 12.14 (s, 1H), 11.46 (s, 1H), 9.38 (s, 1H), 9.22 (s, 1H), 8.56 (s, 1H), 8.07 (s, 1H), 7.55-7.15 (m, 1H), 3.40 (s, 3H), 2.14-2.08 (m, 1H), 0.90-0.82 (m, 4H). $^{19}$F-NMR (376 MHz, DMSO-$d_6$, ppm): δ −82.62 (2F).

Example 32 Synthesis of Compound 65

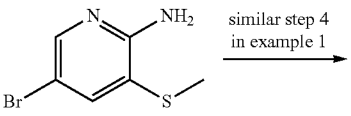

5-5

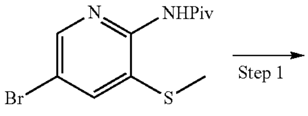

65-1

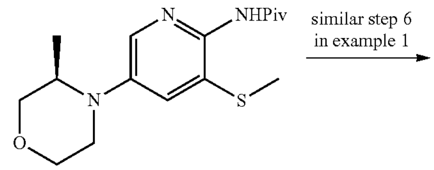

65-2

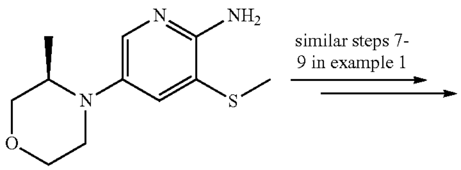

65-3

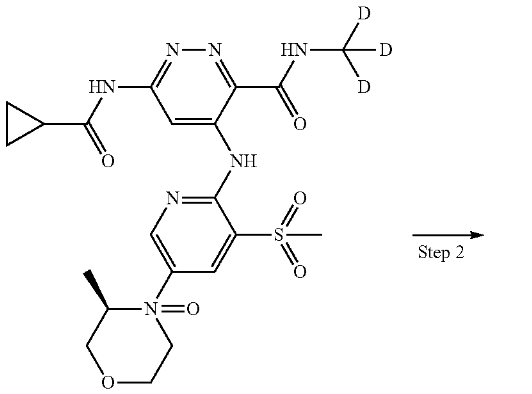

65-4

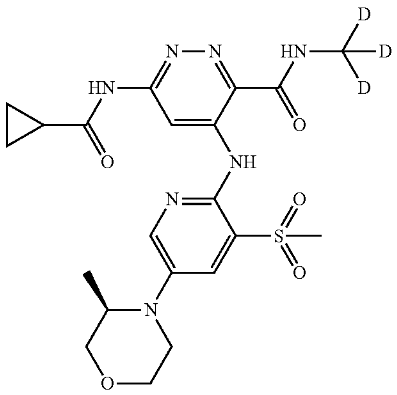

65

Compound 65-1 was prepared from 5-5 following the procedure for the synthesis of compound 1-4 in example 1.

Step 1: To a mixture of 65-1 (5 g, 22.820 mmol) in dioxane (250 mL) was added (3R)-3-methylmorpholine (6.92 g, 68.459 mmol), 2-(dicyclohexylphosphino)-2',4',6'-triisopropylbiphenyl (2.18 g, 4.564 mmol), lithium bis(trimethylsilyl)amide (38 mL, 38.3 mmol, 1M in tetrahydrofuran) and tris(dibenzylideneacetone)dipalladium (2.09 g, 2.282 mmol). Then the mixture was stirred at 110° C. for 18 hour under $N_2$ atmosphere. The reaction mixture was diluted with ethyl acetate, washed with saturated ammonium chloride solution, water and brine. The ethyl acetate layer was concentrated and purified by silica gel column chromatography eluting with ethyl acetate/petroleum ether 1:4 to afford 65-2.

Compound 65-3 was prepared from 65-2 following the procedure for the synthesis of compound 1-6 in example 1.

Compound 65-4 was prepared from 65-3 following the procedure for the synthesis of compound 1 in example 1.

Step 2: To a solution of 65-4 (60 mg, 0.11 mmol) in methanol (20 mL) was added sodium thiosulfate (187 mg, 1.18 mmol). The mixture was stirred for 24 hours at 20° C. The result mixture was diluted with water, extracted with dichloromethane/methanol=10/1. The combined organics were dried over anhydrous sodium sulfate, filtered and concentrated. The residue was purified by prep-HPLC (acetonitrile/0.1% formic acid in water=44-56%) to give 65. LCMS (ESI, m/z): $[M+H]^+=493.6$; $^1H$-NMR (400 MHz, DMSO-$d_6$, ppm): δ 11.73 (s, 1H), 11.33 (s, 1H), 9.12 (s, 1H), 9.08 (s, 1H), 8.31 (d, J=3.2 Hz, 1H), 7.66 (d, J=3.2 Hz, 1H), 4.01-3.90 (m, 2H), 3.75-3.67 (m, 2H), 3.59-3.55 (m, 1H), 3.30 (s, 3H), 3.17-3.08 (m, 2H), 2.14-2.05 (m, 1H), 1.06 (d, J=6.4 Hz, 3H), 0.87-0.81 (m, 4H).

Example 33 Synthesis of Compound 73 and 74

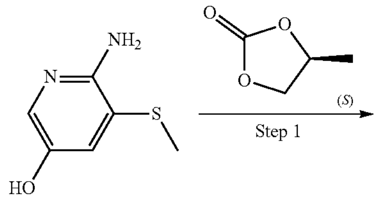

59-1

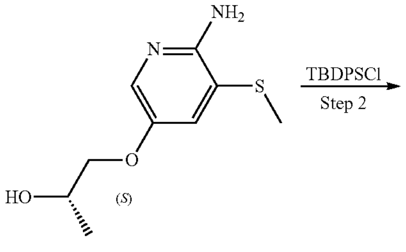

73-1

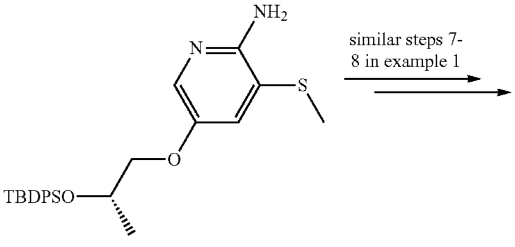

73-2

-continued

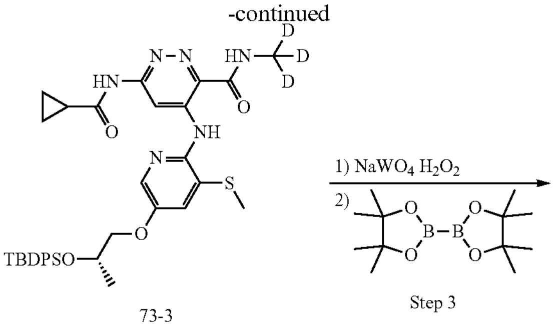

73-3

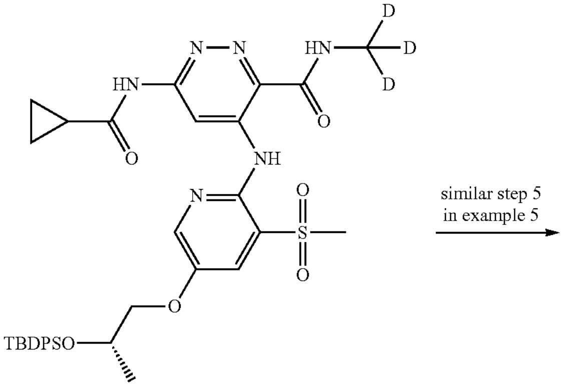

73-4

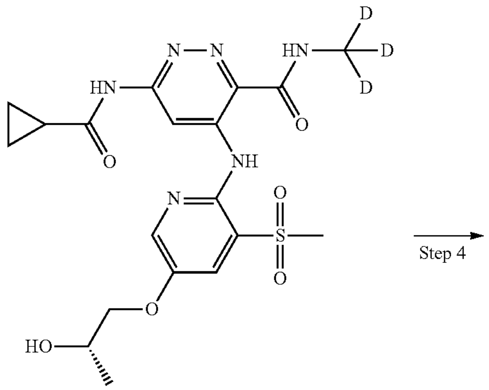

73-5

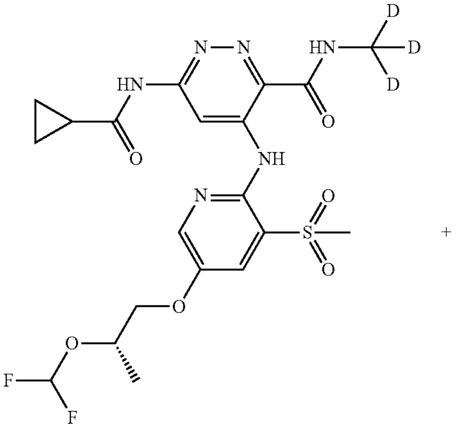

73

-continued

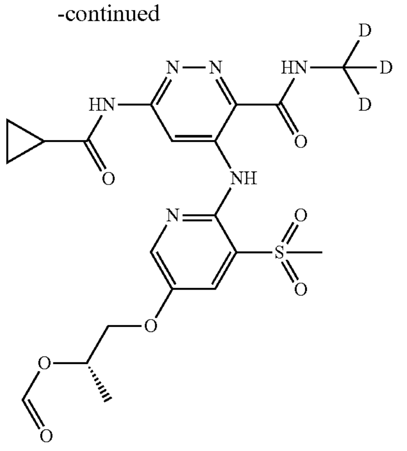

74

Step 1: A mixture of 59-1 (1.56 g, 10 mmol), cesium carbonate (6.52 g, 20 mmol) and (S)-4-methyl-1,3-dioxolan-2-one (1.53 g, 15 mmol) in N,N-dimethylformamide (40 mL) was stirred at 100° C. for 1 hour. The mixture was diluted with ethyl acetate, washed with water and brine, dried over anhydrous sodium sulfate, filtered and concentrated to give 73-1 (crude).

Step 2: To a mixture of 73-1 (crude, 10 mmol) and imidazole (2.04 g, 30 mmol) in N,N-dimethylformamide (40 mL) was added tert-butylchlorodiphenylsilane (4.13 g, 15 mmol) at 0° C., then stirred at room temperature for 3 hours. The mixture was diluted with ethyl acetate, washed with water and brine, dried over anhydrous sodium sulfate, filtered and concentrated. The residue was purified by column chromatography on silica gel (petroleum ether to petroleum ether/ethyl acetate=4/1) to give 73-2.

Compound 73-3 was prepared from 73-2 following the procedure for the synthesis of compound 1-8 in example 1.

Step 3: To a mixture of 73-3 (2.35 g, 3.5 mmol) in acetic acid (50 mL) was added sodium tungstate (1.03 g, 3.5 mmol), 30% hydrogen peroxide aqueous (5.93 g, 52.3 mmol) dropwise at room temperature. The reaction mixture was stirred for 3 hours. The result mixture was diluted with water, quenched with saturated sodium thiosulfate aqueous, adjusted to pH~9 with sodium carbonate solid. The mixture was extracted with dichloromethane/methanol=10/1. The combined organics were dried over anhydrous sodium sulfate, filtered and concentrated. The residue was added dioxane (50 mL) and bis(pinacolato)diboron (5.1 g, 20 mmol), then stirred at 100° C. for 3 hours. The result mixture was concentrated and diluted with petroleum ether, filtered and washed with petroleum ether. The collected solids were dried to afford 73-4.

Compound 73-5 was prepared from 73-4 following the procedure for the synthesis of compound 6 in example 5.

Step 4: To a mixture of 73-5 (200 mg, 0.43 mmol) and cuprous iodide (41 mg, 0.21 mmol) in acetonitrile (5 mL) was added 2,2-difluoro-2-(fluorosulfonyl)acetic acid (229 mg, 1.28 mmol), then stirred at 60° C. for 1 hour. The result mixture was quenched with saturated aqueous sodium bicarbonate, extracted with dichloromethane/methanol=20/1. The combined organics were dried over anhydrous sodium sulfate, filtered and concentrated. The residue was purified by prep-HPLC (acetonitrile/0.05% FA in water: 10%~95%) to give 73 and 74.

73: LCMS (ESI, m/z): $[M+H]^+$=518.2; $^1$H-NMR (400 MHz, DMSO-$d_6$, ppm): δ 11.86 (s, 1H), 11.38 (s, 1H), 9.24-9.05 (m, 2H), 8.38 (d, J=2.8 Hz, 1H), 7.81 (d, J=3.2 Hz, 1H), 7.03-6.55 (m, 1H), 4.63-4.48 (m, 1H), 4.28-4.12 (m, 2H), 3.32 (s, 3H), 2.16-2.05 (m, 1H), 1.30 (d, J=6.8 Hz, 3H), 0.86-0.79 (m, 4H); $^{19}$F-NMR (376 MHz, DMSO-$d_6$, ppm): δ -79.10 (2F).

74: LCMS (ESI, m/z): $[M+H]^+$=496.2; $^1$H-NMR (400 MHz, DMSO-$d_6$, ppm): δ 11.85 (s, 1H), 11.38 (s, 1H), 9.19-9.08 (m, 2H), 8.37 (d, J=2.8 Hz, 1H), 8.27 (s, 1H), 7.79 (d, J=2.8 Hz, 1H), 5.33-5.14 (m, 1H), 4.36-4.17 (m, 2H), 3.32 (s, 3H), 2.15-2.00 (m, 1H), 1.30 (d, J=6.4 Hz, 3H), 0.87-0.79 (m, 4H).

Example 33 Synthesis of Compound 86 and 87

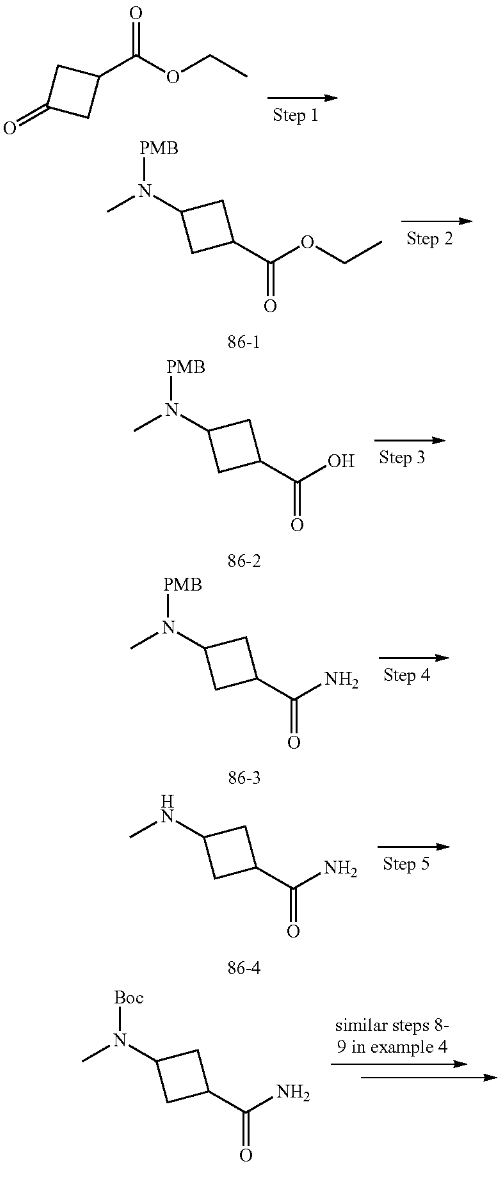

86-1

86-2

86-3

86-4

86-5

-continued

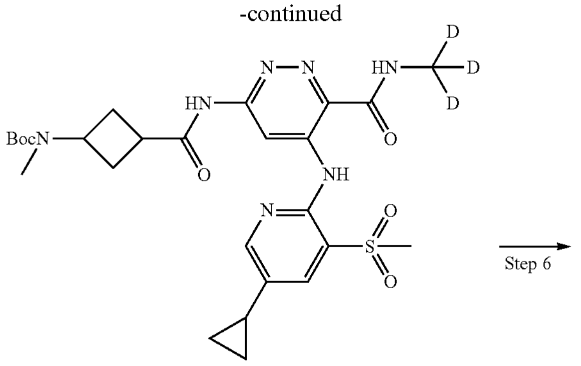

86-6

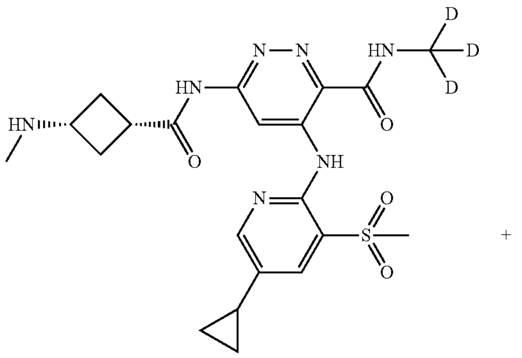

86

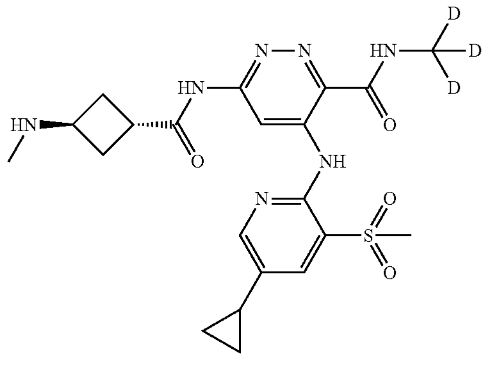

87

Step 1: To a solution of [(4-methoxyphenyl)methyl](methyl)amine (2.34 g, 15.477 mmol) in dichloroethane (30 mL) were added ethyl 3-oxocyclobutanecarboxylate (2 g, 14.070 mmol) and acetic acid (0.806 mL, 14.070 mmol), then stirred at room temperature for 1 hour. Sodium bis(acetyloxy)boranyl acetate (5.93 g, 28.139 mmol) was added and stirred at room temperature for 2 hours. The reaction was diluted with dichloromethane and washed with water. Organic layer was dried over anhydrous sodium sulfate, filtered and evaporated under vacuum. The residue was purified by column chromatography on silica (0-6% methanol in dichloromethane) to give 86-1.

Step 2: To a solution of 86-1 (2.9 g, 10.456 mmol) in tetrahydrofuran (20 mL) and water (20 mL) was added lithium hydroxide (0.581 mL, 20.911 mmol), then stirred at room temperature for 2 hours. The mixture was concentrated and poured into water. The aqueous phase was washed with ethyl acetate and the aqueous layer was acidified with saturated citric acid solution. The aqueous layer was extracted with chloroform and isopropyl alcohol (3:1). The combined organic layers were dried over anhydrous sodium sulfate and evaporated under vacuum to afford 86-2.

Step 3: To a solution of 86-2 (1000 mg, 4.011 mmol), 0-(7-azabenzotriazol-1-yl)-N,N,N',N'-tetramethyluronium hexafluorophosphate (2.28 g, 6.016 mmol), ethylbis(propan-2-yl)amine (1.989 mL, 12.033 mmol) in N,N-dimethylformamide (6 mL) was stirred 5 mins at room temperature. Then ammonium chloride (0.282 mL, 8.022 mmol) was added, stirred at room temperature for 2 hours. The reaction mixture was purified by prep-HPLC (Acetonitrile/ammonium bicarbonate in water) to give 86-3.

Step 4: To a solution of 86-3 (400 mg, 1.611 mmol) in methanol (30 mL) was added palladium carbon (10%, 80 mg). The mixture was stirred 17 hours at 50° C. under hydrogen. The mixture was filtered and concentrated to afford 86-4.

Step 5: A mixture of 86-4 (200 mg, 1.560 mmol), di-tert-butyl dicarbonate (0.501 mL, 2.340 mmol) and triethylamine (0.651 mL, 4.681 mmol) in tetrahydrofuran (20 mL) was stirred 2 hours at room temperature. The reaction mixture was concentrated and purified by prep-HPLC (Acetonitrile/ammonium bicarbonate in water) to give 86-5.

Compound 86-6 was prepared from 86-5 following the procedure for the synthesis of compound 5 in example 4.

Step 6: To a solution of 86-6 (97 mg, 0.168 mmol) in dichloromethane (4.5 mL) were added trifluoroacetic acid (2 mL), then stirred at room temperature for 1 hour. The reaction was diluted with dichloromethane and concentrated in vacuum. The residue was purified by Chiral Pre-SFC (DAICELCHIRALPAK® IG, eluting with supercritical $CO_2$/MeOH) to give 86 and crude 87. The crude 87 was further purified by prep-HPLC (Acetonitrile/0.1% trifluoroacetic acid in water=22%).

86: Chiral SFC analysis: >99% de. Retention time: 5.231 min on DAICELCHIRALPAK® IG 100*3 mm 3 μm (35° C.); mobile phase: MeOH (0.1% DEA) in $CO_2$, 1800 psi 2.0 mL/min.

LCMS (ESI, m/z): $[M+H]^+$=477.2; $^1$H-NMR (400 MHz, DMSO-$d_6$, ppm): δ 11.99 (s, 1H), 11.07 (s, 1H), 9.41 (s, 1H), 9.16 (s, 1H), 8.48 (d, J=2.0 Hz, 1H), 7.87 (d, J=2.0 Hz, 1H), 3.33 (s, 3H), 3.11-2.92 (m, 2H), 2.42-2.26 (m, 2H), 2.18 (s, 3H), 2.15-2.08 (m, 1H), 1.96-1.80 (m, 2H), 1.11-1.01 (m, 2H), 0.90-0.77 (m, 2H).

87: Chiral SFC analysis: 96.94% de. Retention time: 3.814 min on DAICELCHIRALPAK® IG 100*3 mm 3 μm (35° C.); mobile phase: MeOH (0.1% DEA) in $CO_2$, 1800 psi 2.0 mL/min.

LCMS (ESI, m/z): $[M+H]^+$=477.2; $^1$H-NMR (400 MHz, DMSO-$d_6$, ppm): δ 12.02 (s, 1H), 11.15 (s, 1H), 9.45 (s, 1H), 9.17 (s, 1H), 8.91-8.61 (m, 2H), 8.48 (d, J=2.0 Hz, 1H), 7.88 (d, J=2.4 Hz, 1H), 3.79-3.74 (m, 1H), 3.48-3.41 (m, 1H), 3.35 (s, 3H), 2.47-2.35 (m, 7H), 2.19-2.07 (m, 1H), 1.10-1.03 (m, 2H), 0.86-0.77 (m, 2H).

Example 34 Synthesis of Compound 94 and 95

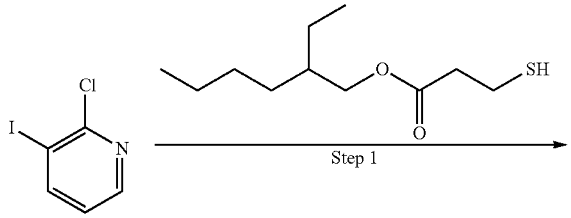

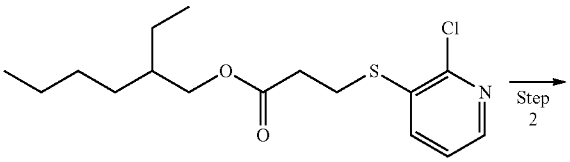

94-1

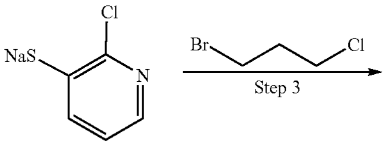

94-2

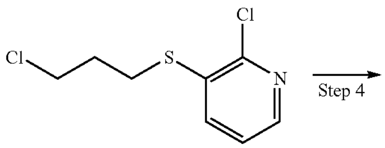

94-3

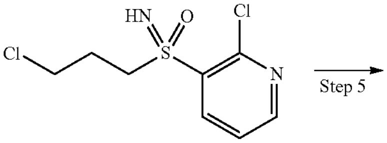

94-4

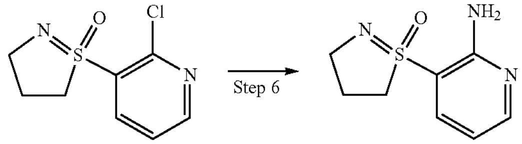

94-5 94-6

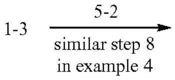

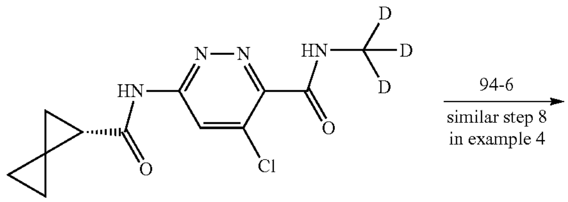

94-7

-continued

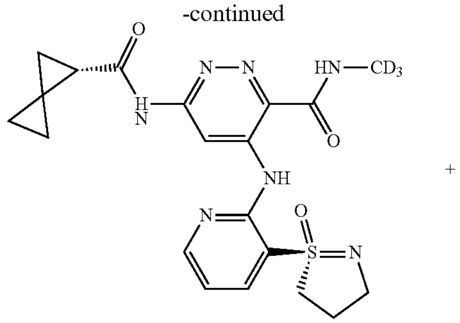

enantiomer 1
94

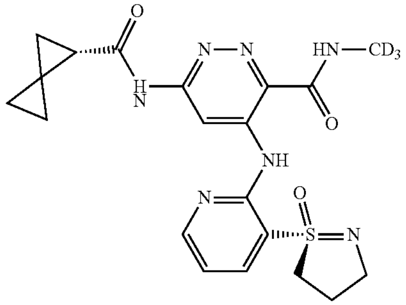

enantiomer 2
95

Step 1: In a 1 L flask was added 2-chloro-3-iodopyridine (10 g, 41.764 mmol), heptan-3-yl 3-sulfanylpropanoate (11.40 g, 52.205 mmol), tris(dibenzylideneacetone)dipalladium (3.82 g, 4.176 mmol), 4,5-bis(diphenylphosphino)-9,9-dimethylxanthene (4.83 g, 8.353 mmol), N,N-diisopropylethylamine (13.49 g, 104.410 mmol) and dioxane (300 mL). The mixture was stirred under $N_2$ at 100° C. for 18 hours. The reaction mixture was diluted with water and extracted with ethyl acetate, the combined organic layers were concentrated under vacuum. The residue was purified by phase column chromatography (0~20% of ethyl acetate/petroleum ether) to give 94-1.

Step 2: In a 100 mL flask was added 94-1 (500 mg, 1.516 mmol) and tetrahydrofuran (10 mL), sodium methanolate (122.79 mg, 2.273 mmol) at 0° C. The mixture was stirred at room temperature for 4 hours. The 94-2 was used for next step without purification.

Step 3: Into a 250 mL flask was added 94-2 (3.6 g, 31.989 mmol), 1-bromo-3-chloropropane (5.54 g, 35.188 mmol), triethylamine (2.27 g, 22.400 mmol) and tetrahydrofuran (50 mL). The mixture was stirred at room temperature for 18 hours. The reaction mixture was diluted with water and extracted with ethyl acetate. The combined organic layers were concentrated under vacuum. The residue was purified by column chromatography (0~30% of ethyl acetate/petroleum ether) to give 94-3.

Step 4: Into a 250 mL flask was added 94-3 (3.20 g, 14.405 mmol) and methanol (100 mL), iodobenzene diacetate (11.60 g, 36.013 mmol), ammonium carbamate (2.81 g, 36.013 mmol). The mixture was stirred at room temperature for 2 hours. The reaction mixture was concentrated under vacuum. The residue was purified by column chromatography (0~100% of Ethyl acetate/petroleum ether) to give 94-4.

Step 5: A solution of 94-4 (2.6 g, 10.271 mmol) in ammonium hydroxide solution (55 mL, 0.1 wt %) was stirred at 80° C. for 4 hours in a sealed tube. The cooled reaction mixture was concentrated to dryness under reduced pressure. The residue was purified by flash column chromatography (dichloromethane:methanol=20:1) to afford 94-5.

Step 6: A solution of 94-5 (1.5 g, 6.922 mmol) in ammonium hydroxide solution (25 mL, 28 wt %) was stirred at 120° C. in a sealed tube for 18 hours. The mixture was concentrated. The mixture was diluted with dichloromethane, filtered. The filtrate was concentrated to give 94-6.

Compound 94-7 was prepared from 1-3 and 5-2 following the procedure similar to the synthesis of compound 5-8 in example 4.

Compound 94 and 95 were prepared from 94-7 and 94-6 following the procedure for the synthesis of compound 5-8 in example 4.

Enantiomer 1 94 Chiral SFC analysis: 98.04% ee. Retention time 6.188 min on Reprosil Chiral-AM (Similar to Daicel CHIRALPAK® AD) 100*3 mm 3 μm (35° C.); mobile phase: MeOH (0.1% DEA) in $CO_2$, 1800 psi, 1.5 mL/min. LCMS (ESI, m/z): $[M+H]^+$=445.2; $^1$H-NMR (400 MHz, DMSO-$d_6$, ppm): δ 11.86 (s, 1H), 11.21 (s, 1H), 9.41 (s, 1H), 9.14 (s, 1H), 8.59 (dd, J=4.8 Hz, 1.6 Hz, 1H), 8.31 (dd, J=8.0 Hz, 1.6 Hz, 1H), 7.32 (dd, J=8.0 Hz, 4.8 Hz, 1H), 3.84-3.73 (m, 2H), 3.67-3.55 (m, 1H), 3.54-3.43 (m, 1H), 2.50-2.44 (m, 1H), 2.36-2.24 (m, 1H), 2.20-2.08 (m, 1H), 1.45-1.35 (m, 2H), 0.96-0.75 (m, 4H).

Enantiomer 2 95 Chiral SFC analysis: 98.88% ee. Retention time 7.186 min on Reprosil Chiral-AM (Similar to Daicel CHIRALPAK® AD) 100*3 mm 3 m (35° C.); mobile phase: MeOH (0.1% DEA) in $CO_2$, 1800 psi, 1.5 mL/min. LCMS (ESI, m/z): $[M+H]^+$=445.2; $^1$H-NMR (400 MHz, DMSO-$d_6$, ppm): δ 11.89 (s, 1H), 11.21 (s, 1H), 9.41 (s, 1H), 9.14 (s, 1H), 8.60-8.57 (m, 1H), 8.29 (dd, J=8.0 Hz, 1.2 Hz, 1H), 7.31 (dd, J=7.6, 4.8 Hz, 1H), 3.86-3.69 (m, 2H), 3.65-3.56 (m, 1H), 3.55-3.46 (m, 1H), 2.48-2.44 (m, 1H), 2.35-2.23 (m, 1H), 2.22-2.07 (m, 1H), 1.46-1.34 (m, 2H), 0.96-0.74 (m, 4H).

Example 35 Synthesis of Compound 96

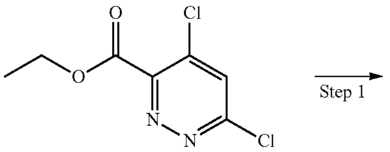

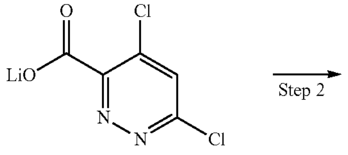

96-1

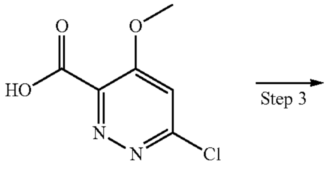

96-2

-continued

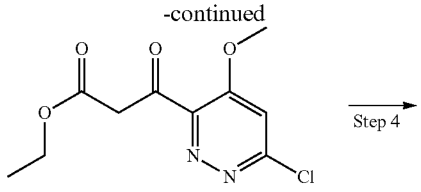

96-3

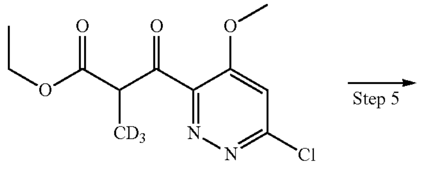

96-4

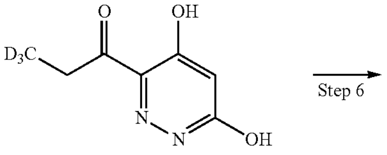

96-5

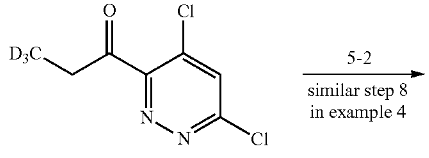

96-6

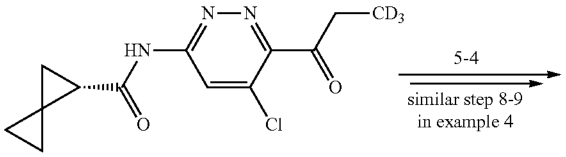

96-7

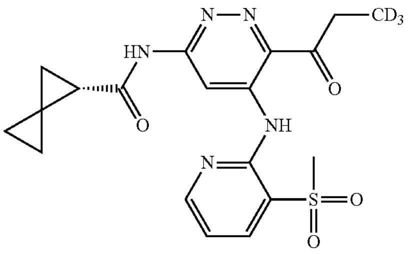

96

Step 1: To a solution of ethyl 4,6-dichloropyridazine-3-carboxylate (14.4 g, 65.16 mmol) in acetonitrile (75 mL) and water (11 mL) was added N-diisopropylethylamine (25.3 g, 195.48 mmol) and lithium bromide (17 g, 195.48 mmol) at 0° C., then stirred for 16 hours at room temperature. The mixture was filtered and rinsed with acetonitrile to give 96-1.

Step 2: To a solution of 96-1 (9 g, 45.24 mmol) in methanol (100 mL) was added sodium methanolate (3.66 g, 67.86 mmol) in portions at 0° C., then stirred for 16 hours at room temperature. Then sodium methanolate (2.44 g, 45.24 mmol) was added and stirred for 3 hours at room temperature. The mixture was adjusted to pH=2~3 with 2M aqueous hydrochloride and concentrated. The residue was purified by prep-HPLC (acetonitrile/0.05% trifluoroacetic acid in water: 0%~95%) to give 96-2 (crude, used for next step directly).

Step 3: A mixture of 96-2 (10.08 g, ~53.62 mmol) and N,N'-carbonyldiimidazole (13.03 g, 80.43 mmol) in tetrahydrofuran (200 mL) was stirred for 4 hours at 60° C. The result mixture was added into a pre-stirred mixture of potassium 3-ethoxy-3-oxopropanoate (21.88 g, 128.69 mmol), triethylamine (19.5 g, 193.03 mmol) and magnesium chloride (15.3 g, 160.86 mmol) in acetonitrile (400 mL) at 0° C. dropwise, then stirred for 16 hours at room temperature. The mixture was quenched with methanol, adjusted to pH~4 with 2M aqueous hydrochloride, extracted with ethyl acetate. The combined organic layers were washed with brine, dried over anhydrous sodium sulfate, filtered and concentrated. The residue was purified by column chromatography on silica gel (petroleum ether to petroleum ether/ethyl acetate=1/2) to give 96-3.

Step 4: To a solution of 96-3 (10.2 g, 39.43 mmol) and potassium carbonate (5.44 g, 39.43 mmol) in acetone (120 mL) was added trideuterio(iodo)methane (5.72 g, 39.43 mmol) dropwise at 0° C., then stirred for 16 hours at 30° C. The mixture was filtered and rinsed with ethyl acetate. The filtrate was concentrated and purified by column chromatography on silica gel (petroleum ether to petroleum ether/ethyl acetate=1/1) to give 96-4.

Step 5: A mixture of 96-4 (3.2 g, 11.61 mmol) in acetic acid (20 mL) and concentrated hydrochloric acid (10 mL) was stirred at 100° C. for 16 hours. Then cooled to room temperature and concentrated. The residue was diluted with water and filtered. The cake was slurried with acetonitrile and filtered to give 96-5.

Step 6: To a mixture of 96-5 (1.13 g, 6.61 mmol) in phosphorus oxychloride (10 mL) was added N,N-diethylaniline (985 mg, 6.61 mmol) at room temperature, then stirred for 1 hour at 100° C. Then cooled to room temperature and concentrated. The residue was dissolved in dichloromethane and slowly poured onto ice-water. The organic layer was washed with brine and concentrated. The residue was purified by column chromatography on silica gel (petroleum ether to petroleum ether/ethyl acetate=10/1) to give 96-6.

Compound 96-7 was prepared from 96-6 and 5-2 following the procedure for the synthesis of compound 5-8 in example 4.

Compound 96 was prepared from 96-7 and 5-4 following the procedure similar to the synthesis of compound 5 in example 4.

96 as a 1.0 eq formic acid salt. LCMS (ESI, m/z): $[M+H]^+$=419.1; $^1$H-NMR (400 MHz, DMSO-$d_6$, ppm): δ 11.61 (s, 1H), 11.38 (s, 1H), 9.44 (s, 1H), 8.63 (s, 1H), 8.43 (s, 1H), 8.28 (d, J=6.4 Hz, 1H), 7.36 (s, 1H), 3.32-3.24 (m, 5H), 2.47-2.43 (m, 1H), 1.45-1.36 (m, 2H), 0.94-0.71 (m, 4H).

Example 36 Synthesis of Compound 97 and 98

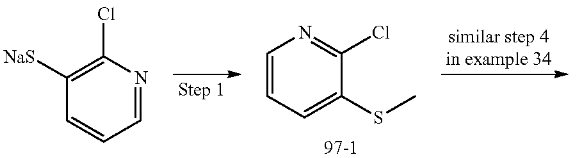

94-2 97-1

-continued

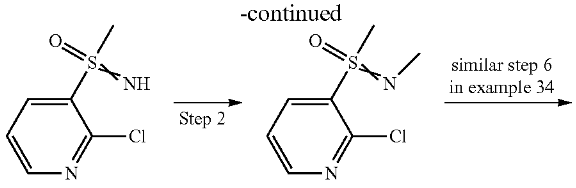

97-2 97-3

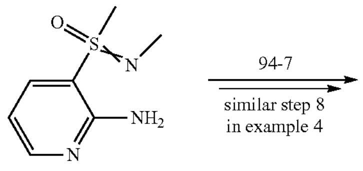

97-4

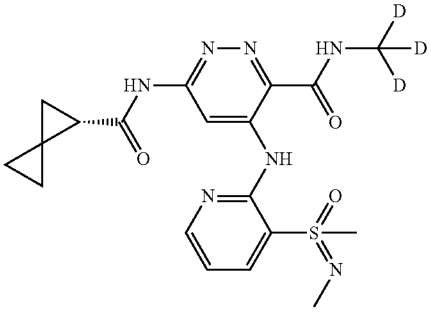

+ enantiomer 1
97

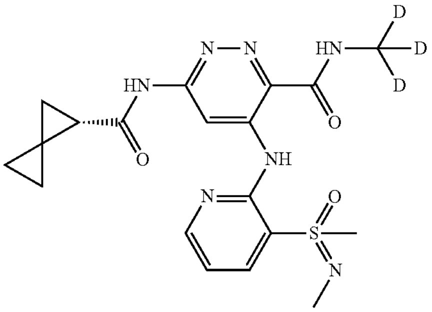

enantiomer 2
98

Step 1: In a 100 mL flask was added 94-2 (from Example 34, 2.666 mmol), iodomethane (0.166 mL, 2.666 mmol), triethylamine (0.371 mL, 2.666 mmol) and tetrahydrofuran (20 mL). The mixture was stirred at room temperature for 18 hours. The reaction mixture was diluted with water and extracted with ethyl acetate, the combined organic layers were concentrated under vacuum. The residue was purified by phase column chromatography (0~30% of Ethyl acetate/petroleum ether) to 97-1.

Compound 97-2 was prepared from 97-1 following the procedure for the synthesis of compound 94-4 in example 34.

Step 2: To the stirred solution of 97-2 (427 mg, 2.240 mmol) in 1,2-dimethoxyethane (6 mL), sodium hydride (179 mg, 7.458 mmol) was added at 0° C. and stirred for 15 min. Then iodomethane (0.418 mL, 6.719 mmol) was added to the reaction mixture and stirred for 3 hours at room temperature. After completion of the reaction, quenched with ice cold water and the aqueous layer was extracted with ethyl acetate. The combined organic layer was dried over anhydrous sodium sulfate and evaporated under vacuum. The residue purified by column chromatography on silica gel (0-75% ethyl acetate in petroleum ether) to give 97-3.

Step 3: A solution of 97-3 (1.3 g, 6.351 mmol) in ammonium hydroxide (25 mL) was stirred at 120° C. in a sealed tube for 18 hours. The solid was collected by filtered and washed with water to give 97-4.

Compound 97 and 98 were prepared from 94-7 and 97-4 following the procedure for the synthesis of compound 5-8 in example 4.

Enantiomer 1 97 Chiral SFC analysis: 98.62% ee. Retention time 3.490 min on DAICELCHIRALCEL® OJ 100*3 mm 3 μm (35° C.); mobile phase: MeOH (0.1% DEA) in $CO_2$, 1800 bar, 1.5 mL/min. LCMS (ESI, m/z): $[M+H]^+$=433.1; $^1$H-NMR (400 MHz, DMSO-$d_6$, ppm): δ 11.88 (s, 1H), 11.20 (s, 1H), 9.47 (s, 1H), 9.08 (s, 1H), 8.57 (dd, J=4.8, 1.6 Hz, 1H), 8.24 (dd, J=8.0, 1.6 Hz, 1H), 7.31 (dd, J=8.0, 4.8 Hz, 1H), 3.23 (s, 3H), 2.69 (s, 3H), 2.47-2.43 (m, 1H), 1.45-1.36 (m, 2H), 0.95-0.82 (m, 3H), 0.78-0.72 (m, 1H).

Enantiomer 2 98 Chiral SFC analysis: >99.5% ee. Retention time 3.862 min on DAICELCHIRALCEL® OJ 100*3 mm 3 m (35° C.); mobile phase: MeOH (0.1% DEA) in $CO_2$, 1800 bar, 1.5 mL/min. LCMS (ESI, m/z): $[M+H]^+$=433.2; $^1$H-NMR (400 MHz, DMSO-$d_6$, ppm): δ 11.88 (s, 1H), 11.20 (s, 1H), 9.48 (s, 1H), 9.08 (s, 1H), 8.57 (d, J=4.0 Hz, 1H), 8.24 (d, J=7.2 Hz, 1H), 7.30 (dd, J=7.6, 4.8 Hz, 1H), 3.24 (s, 3H), 2.68 (s, 3H), 2.48-2.44 (m, 1H), 1.45-1.35 (m, 2H), 0.96-0.77 (m, 4H).

Example 37 Synthesis of Compound 100

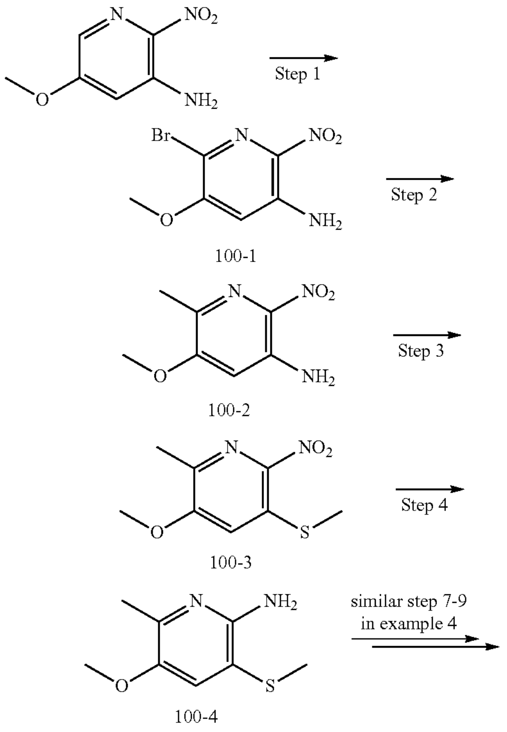

-continued

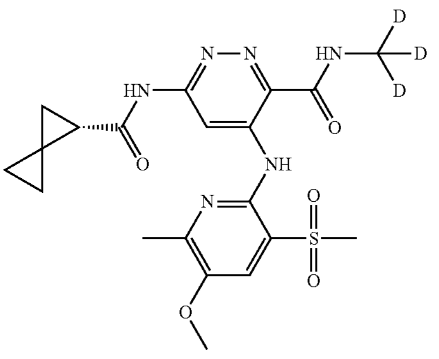

100

Step 1: To a solution of 5-methoxy-2-nitropyridin-3-amine (7.7 g, 45.524 mmol) in N,N-dimethylformamide (80 mL) was added N-bromosuccinimide (8.10 g, 45.524 mmol) portions at 0° C. The reaction mixture was stirred for 3 hours at 20~25° C. The aqueous phase was extracted with ethyl acetate. Organic layers were combined and washed with brine, dried over anhydrous sodium sulfate, filtered and concentrated to obtain 100-1.

Step 2: To the solution of 100-1 (8.3 g, 33.462 mmol) in dioxane (332 mL) was added methylboronic acid (10.02 g, 167.312 mmol), potassium carbonate (13.87 g, 100.387 mmol) and tetrakis(triphenylphosphane) palladium (3.87 g, 3.346 mmol) under $N_2$ protection, then heated to reflux for 4 hours. The reaction mixture was concentrated and purified by column chromatography on silica gel (eluting with petroleum ether: ethyl acetate=1:0~1:10) to obtain 100-2.

Step 3: To a solution of tert-butyl nitrite (3.437 mL, 28.662 mmol) in dichloromethane (360 mL) was added (methyldisulfanyl)methane (3.387 mL, 38.216 mmol) at 0° C., followed by dropwise added a solution of 100-2 (3.5 g, 19.108 mmol) in dichloromethane (20 mL) to the solution and allow to warm to room temperature for 4 hours. Then petroleum ether was added to the solution and filter through column chromatography silica gel eluting dichloromethane to obtain 100-3.

Step 4: To a solution of 100-3 (1.2 g, 5.601 mmol) in ethanol (12 mL) and water (6 mL) was added ammonium chloride (3 g, 56.009 mmol) and iron powder (0.94 g, 16.803 mmol). The mixture was t heated at 90° C. for 2 hours. The reaction mixture was concentrated and purified by column chromatography silica gel to obtain 100-4.

Compound 100 was prepared from 100-4 following the procedure for the synthesis of compound 5 in example 4. LCMS (ESI, m/z): $[M+H]^+$=464.1; $^1$H-NMR (400 MHz, DMSO-$d_6$, ppm): δ 11.88 (s, 1H), 11.14 (s, 1H), 9.57 (s, 1H), 9.13 (s, 1H), 7.70 (s, 1H), 3.91 (s, 3H), 3.31 (s, 3H), 2.47 (s, 3H), 2.46-2.43 (m, 1H), 1.43-1.35 (m, 2H), 0.98-0.83 (m, 3H), 0.80-0.70 (m, 1H).

Example 38 Synthesis of Compound 103

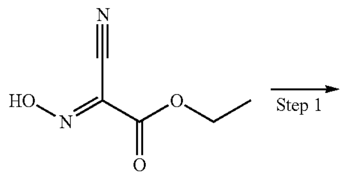

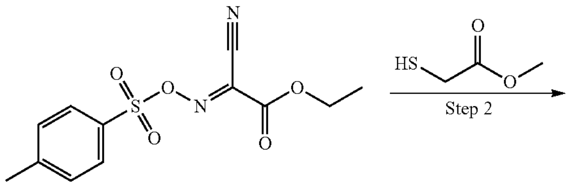

103-1

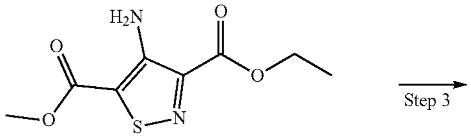

103-2

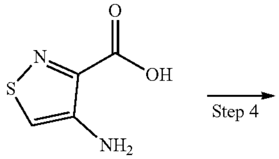

103-3

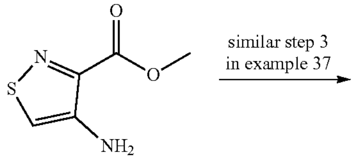

103-4

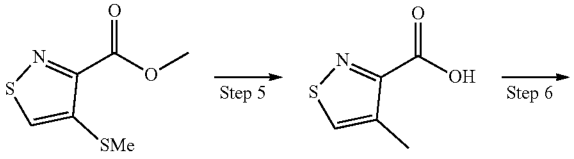

103-5

103-6

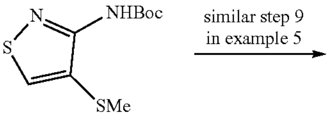

103-7

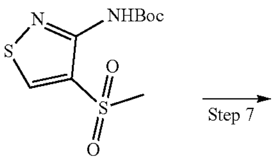

103-8

-continued

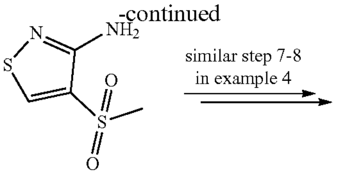

103-9

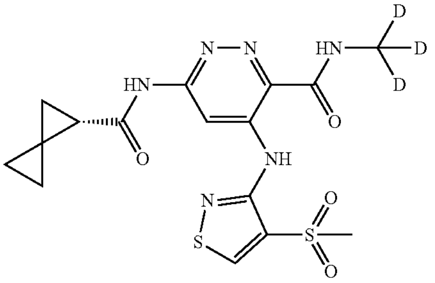

103

Step 1: To a solution of ethyl (E)-2-cyano-2-(hydroxyimino)acetate (1 g, 7.037 mmol) and triethylamine (1.09 g) in ethyl acetate (7.2 mL) was added p-toluenesulfonyl chloride (13.74 g) under ice cooling. The reaction was stirred at room temperature for 2 hours. The mixture was filtered, and the filtrate was concentrated under reduced pressure. Water was added to the residue, and the mixture was stirred for 15 minutes. The deposited precipitate was filtered and dried under reduced pressure to obtain 103-1.

Step 2: To a mixture of 103-1 (18.3 g, 61.76 mmol) and methylsulfanylacetate (8.4 mL, 93.931 mmol) in ethanol (54 mL) was added pyridine (6.94 mL) dropwise. The reaction was stirred for 30 minutes. Then the reaction mixture was partitioned between cold ether and ice water. The aqueous layer was extracted with cold ether. The combined ether layers were dried over anhydrous sodium sulfate, filtered and concentrated. To a solution of this material in absolute ethanol (20 mL) was added triethylamine (1.858 mL, 13.33 mmol) dropwise. The reaction was stirred for 30 minutes at room temperature. The reaction mixture was filtered and dried to afford 103-2.

Step 3: 103-2 (18 g, 78.176 mmol) in concentrated hydrochloric acid (100 mL) was heated to reflux for 16 hours. The mixture was cooled to 0° C. and filtered, the cake was washed by ether, dried in vacuo to get 103-3 (crude).

Step 4: To a solution of 103-3 (13.35 g, 92.605 mmol) in methanol (70 mL) was added thionyl chloride (10 mL) over 5 minutes at 0° C. This solution was stirred at 70° C. for 1 hours. The mixture was concentrated to afford 103-4.

Compound 103-5 was prepared from 103-4 following the procedure for the synthesis of compound 100-3 in example 37.

Step 5: To a solution of 103-5 (1.2 g, 6.340 mmol) in tetrahydrofuran (20 mL) and water (10 mL) was added lithium hydroxide (0.319 g, 9.510 mmol) at 0° C. This solution was stirred at room temperature for an additional 30 minutes. The mixture was extracted with ethyl acetate. The organic layer was dried over magnesium sulfate and concentrated, recrystallized with ethyl acetate: petroleum ether (10 mL: 5 mL) to afford 103-6.

Step 6: To a solution of 103-6 (254 mg, 1.450 mmol) in tert-butanol (5 mL) was added diphenylphosphoryl azide (0.405 mL) and triethylamine (0.404 mL) dropwise at 20° C. under nitrogen atmosphere. The mixture was stirred at 100° C. for 5 hours under nitrogen atmosphere. The mixture was quenched with saturated aqueous sodium bicarbonate and diluted with ether. The organic layer was dried over magnesium sulfate and concentrated. The residue was purified by silica gel chromatography (ethyl acetate: petroleum ether=1:10) to give 103-7.

Compound 103-8 was prepared from 103-7 following the procedure for the synthesis of compound 5 in example 4.

Step 7: To a solution of 103-8 (2 g, 7.185 mmol) in methanol (40 mL) was added 3M hydrochloric acid/methanol (40 mL). Then the reaction was stirred at 50° C. for 3 hours under nitrogen atmosphere. The mixture was cooled to room temperature and filtrated to give 103-9.

Compound 103 was prepared from 103-9 following the procedure for the synthesis of compound 5-8 in example 4. LCMS (ESI, m/z): $[M+H]^+=426.1$; $^1H$-NMR (400 MHz, DMSO-$d_6$, ppm): δ 12.45 (s, 1H), 11.26 (s, 1H), 9.72 (s, 1H), 9.69 (s, 1H), 9.21 (s, 1H), 3.38 (s, 3H), 2.49-2.45 (m, 1H), 1.48-1.37 (m, 2H), 0.94-0.74 (m, 4H).

Example 39 Synthesis of Compound 109

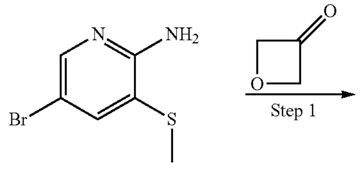

5-5

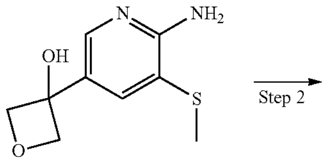

109-1

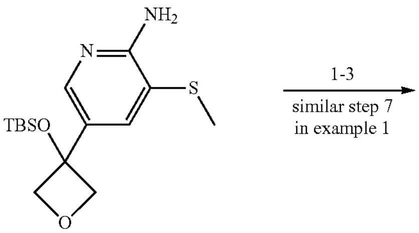

109-2

-continued

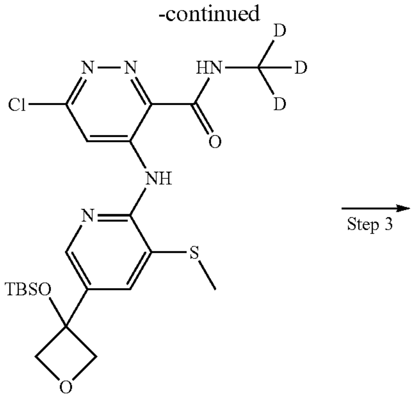

109-3

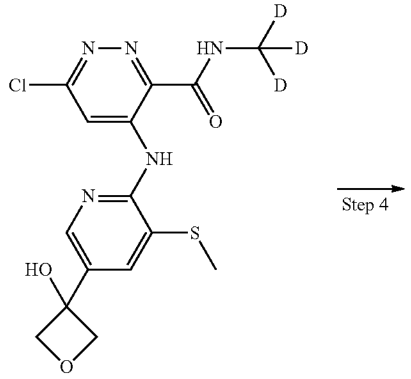

109-4

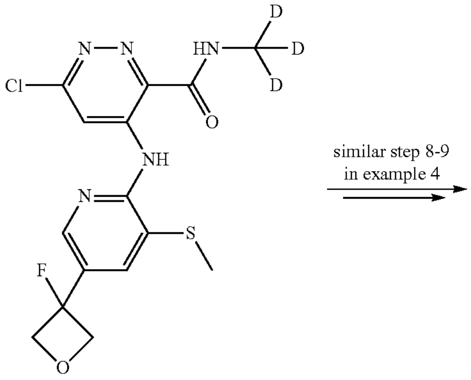

109-5

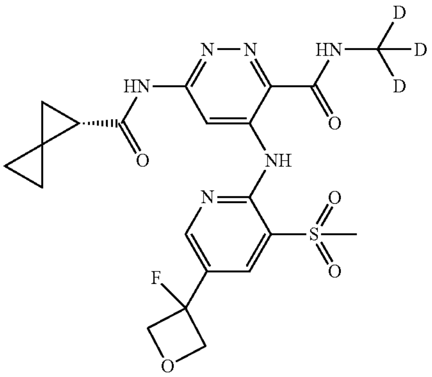

109

Step 1: To a mixture of 5-5 (2.75 g, 12.55 mmol) in tetrahydrofuran (100 mL) was added butyllithium (17.6 mL, 2.5 M solution in hexanes, 43.93 mmol) dropwise at −60° C. under $N_2$ atmosphere, then stirred for 0.5 hour. To above mixture was added a solution of oxetan-3-one (3.16 g, 43.93 mmol) in tetrahydrofuran (10 mL) dropwise at −60° C., then stirred for 1 hour. The mixture was quenched with saturated ammonium chloride aqueous, diluted with brine and extracted with tetrahydrofuran. The organic layer was dried over anhydrous sodium sulfate, filtered and concentrated. The residue was purified by column chromatography on silica gel (dichloromethane to dichloromethane/methanol/ammonium hydroxide=10/1/0.05) to give 109-1.

Step 2: To a mixture of 109-1 (1 g, 4.71 mmol) and tert-butyldimethylsilyl chloride (923 mg, 6.12 mmol) in dichloromethane (20 mL) was added 1,8-diazabicyclo[5.4.0]undec-7-ene (932 mg, 6.12 mmol) at 0° C. under $N_2$ atmosphere, then stirred for 16 hours at room temperature. The mixture was diluted with water and extracted with dichloromethane. The organic layer was washed with brine, dried over anhydrous sodium sulfate, filtered and concentrated. The residue was purified by column chromatography on silica gel (petroleum ether to petroleum ether/ethyl acetate=1/1) to give 109-2.

Compound 109-3 was prepared from 109-2 and 1-3 following the procedure for the synthesis of compound 1-7 in example 1.

Step 3: To a solution of 109-3 (570 mg, 1.14 mmol) in tetrahydrofuran (15 mL) was added tetrabutylammonium fluoride (1.26 mL, 1.26 mmol, 1M in THF) at room temperature, then stirred for 1 hour. The mixture was diluted with water and stirred for 5 minutes. The mixture was filtered and rinsed with water and acetonitrile to give 109-4.

Step 4: To a mixture of 109-4 (390 mg, 1.01 mmol) in dichloromethane (20 mL) was added diethylaminosulfur trifluoride (403 mg, 2.50 mmol) dropwise at −70° C. under $N_2$ atmosphere, then stirred for 2 hours. The mixture was warmed to −10° C., then stirred for 2 hours. The mixture was stirred at 5° C. for 16 hours. The result mixture was quenched with saturated aqueous sodium bicarbonate and extracted with dichloromethane. The organic layer was washed with brine, dried over anhydrous sodium sulfate, filtered and concentrated. The residue was purified by column chromatography on silica gel (dichloromethane to dichloromethane/ethyl acetate=2/1) to give 109-5.

Compound 109 was prepared from 109-5 following the procedure for the synthesis of compound 5 in example 4. 109 as a 2.0 eq formic acid salt. LCMS (ESI, m/z): [M+H]=494.2; $^1$H-NMR (400 MHz, DMSO-$d_6$, ppm): δ 12.25 (s, 1H), 11.27 (s, 1H), 9.55 (s, 1H), 9.21 (s, 1H), 8.90-8.67 (m, 1H), 8.42 (s, 2H), 8.36-8.23 (m, 1H), 5.07-4.93 (m, 4H), 3.38 (s, 3H), 2.47-2.42 (m, 1H), 1.44-1.35 (m, 2H), 0.93-0.82 (m, 3H), 0.78-0.73 (m, 1H). $^{19}$F-NMR (376 MHz, DMSO-$d_6$, ppm): δ −143.83 (1F).

Example 40 Synthesis of Compound 120

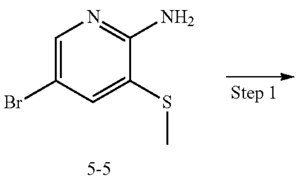

5-5

-continued

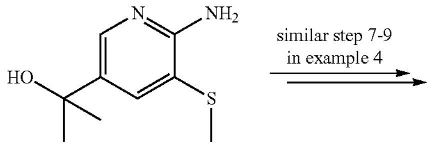

120-1

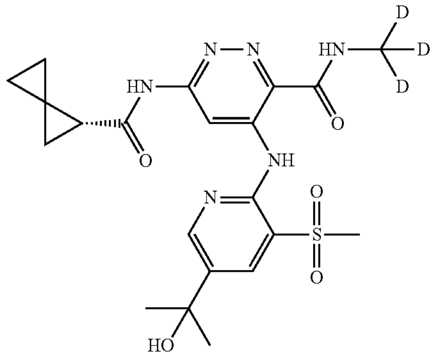
120

Step 1: To a mixture of 5-5 (1.3 g, 5.96 mmol) in tetrahydrofuran (60 mL) was added n-butyllithium (13 mL, 3.5 eq, 1.3 M) dropwise at −65° C. under nitrogen atmosphere, then stirred for 10 min at −65° C. To result mixture was added acetone (2 g, 6.0 eq) at −65° C., then stirred for 5 min at −65° C. The reaction was quenched with brine, extracted with tetrahydrofuran. The organic phase was washed with brine, dried over anhydrous sodium sulfate and evaporated under vacuum. The residue was purified by silica gel column chromatography eluting with dichloromethane/methanol=100:0~50:1 to give 120-1.

Compound 120 was prepared from 120-1 following the procedure for the synthesis of compound 5 in example 4. LCMS (ESI, m/z): $[M+H]^+$=478.4; $^1$H-NMR (400 MHz, DMSO-$d_6$, ppm): δ 12.08 (s, 1H), 11.21 (s, 1H), 9.50 (s, 1H), 9.18 (s, 1H), 8.70 (d, J=2.4 Hz, 1H), 8.34 (d, J=2.4 Hz, 1H), 5.46 (s, 1H), 3.36 (s, 3H), 2.50-2.45 (m, 1H), 1.51 (s, 6H), 1.47-1.36 (m, 2H), 1.00-0.73 (m, 4H).

Example 41 Synthesis of Compound 123

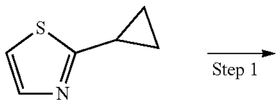

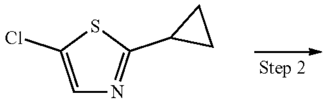

123-1

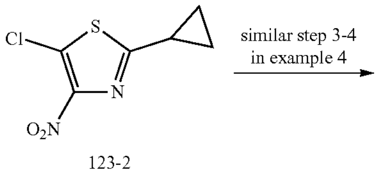

123-2

-continued

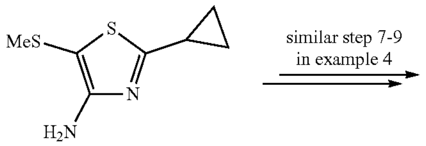

123-3

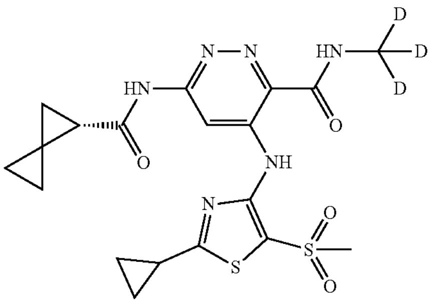

123

Step 1: To a −78° C. solution of 2-cyclopropylthiazole (2 g, 15.974 mmol) in tetrahydrofuran (50 mL) was added n-butyllithium (7.688 mL, 19.169 mmol, 2.5M in hexanes) at −65° C., then stirred at −78° C. for 30 minutes, after which hexachloroethane (2.170 mL, 19.169 mmol) was added portionwise over 30 minutes. The reaction mixture was stirred at −78° C. for 30 minutes when warmed to room temperature. The mixture was quenched with saturated aqueous ammonium chloride. The mixture was diluted with ethyl acetate. The mixture was washed with brine. The organic layer was dried over anhydrous sodium sulfate and concentrated to afford 123-1.

Step 2: A solution of 123-1 (2 g, 12.528 mmol) in sulfuric acid (10 mL) was slowly added to a mixture of sulfuric acid (15 mL) and nitric acid (7 mL) at 0° C. The reaction mixture was warmed up to room temperature and stirred for 2 hours. The mixture was poured in to ice water and stirred for 1 hour. The organic was dried washed by aqueous 1M sodium bicarbonate and brine. The organic phase was concentrated to obtain 123-2.

Compound 123-3 was prepared from 123-2 following the procedure for the synthesis of compound 5-4 in example 4.

Compound 123 was prepared from 123-3 following the procedure for the synthesis of compound 5 in example 4. LCMS (ESI, m/z): $[M+H]^+$=466.1; $^1$H-NMR (400 MHz, $CDCl_3$, ppm): δ 12.33 (s, 1H), 9.45 (s, 1H), 8.88 (s, 1H), 8.10 (s, 1H), 3.21 (s, 3H), 2.26-2.18 (m, 2H), 1.64-1.61 (m, 1H), 1.58-1.44 (m, 3H), 1.28-1.27 (m, 2H), 1.15-1.09 (m, 1H), 1.07-0.97 (m, 3H).

Example 42 Synthesis of Compound 124

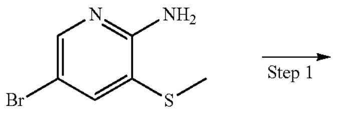

5-5

-continued

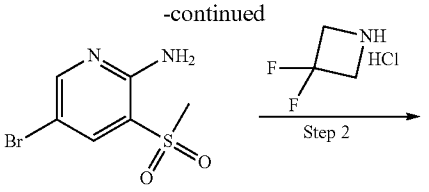

124-1

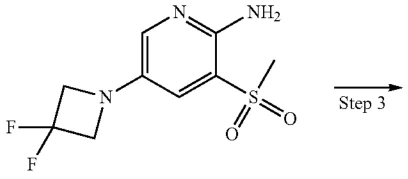

124-2

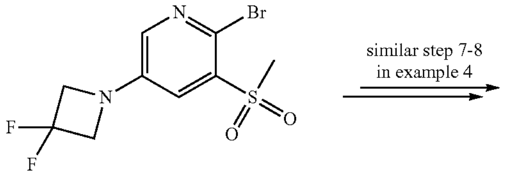

124-3

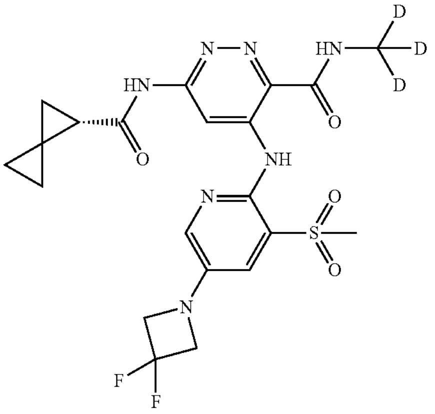

124

Step 1: To a solution of 5-5 (5 g, 22.820 mmol) in dichloromethane (200 mL) was added 3-chloroperoxybenzoic acid (11.54 g, 57.05 mmol) at room temperature. The reaction mixture was stirred at room temperature for 1 hour. The reaction was quenched with aqueous solution of sodium hydroxide (1 N), extracted with dichloromethane. The combined organic layers were dried over anhydrous sodium sulfate, filtered and concentrated under reduced pressure. The crude product was purified by column chromatography on silica gel (dichloromethane) to afford 124-1.

Step 2: A mixture of 124-1 (1.8 g, 7.168 mmol), 3-difluoroazetidine (2.79 g, 21.505 mmol), tris(dibenzylideneacetone)dipalladium (0.66 g, 0.717 mmol), cesium carbonate (389.03 mg, 1.194 mmol) and 2-(dicyclohexylphosphino)-2',4',6'-tri-i-propyl-1,1'-biphenyl (75.94 mg, 0.159 mmol) in dioxane (150 mL) was stirred at 110° C. for 6 hours under $N_2$ atmosphere. The mixture was poured into water, extracted with ethyl acetate. The organic layer was washed with brine, dried over anhydrous sodium sulfate, filtered and concentrated. The residue was purified by flash column (petroleum ether/ethyl acetate=1/1) to give 124-2.

Step 3: A solution of 124-2 (1.5 g, 5.698 mmol) in dibromomethane (50 mL) was treated with tetrabutylammonium bromide (2446.16 mg, 7.597 mmol) and t-butylnitrite (6.769 mL, 56.976 mmol) and stirred at room temperature for 2 hours. The mixture was diluted with ethyl acetate, washed with saturated aqueous sodium bicarbonate, water and brine, dried over anhydrous sodium sulfate and concentrated to afford 124-3.

Compound 124 was prepared from 124-3 following the procedure for the synthesis of compound 5-8 in example 4. LCMS (ESI, m/z): $[M+H]^+=511.1$; $^1H$-NMR (400 MHz, DMSO-$d_6$, ppm): δ 11.78 (s, 1H), 11.15 (s, 1H), 9.14-9.11 (m, 2H), 8.06 (d, J=3.2 Hz, 1H), 7.46 (d, J=3.2 Hz, 1H), 4.47 (t, J=12.0 Hz, 4H), 3.30 (s, 3H), 2.47-2.41 (m, 1H), 1.47-1.32 (m, 2H), 0.95-0.71 (m, 4H). $^{19}F$-NMR (376 MHz, DMSO-$d_6$, ppm): δ −98.27 (2F).

Example 43 Synthesis of Compound 126

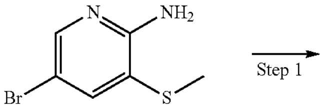

5-5

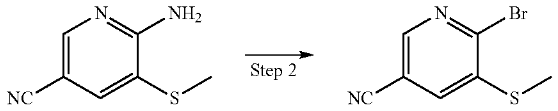

126-1 126-2

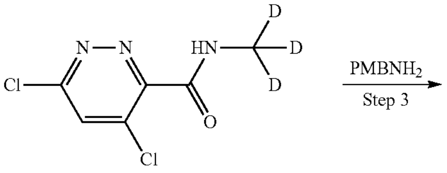

1-3

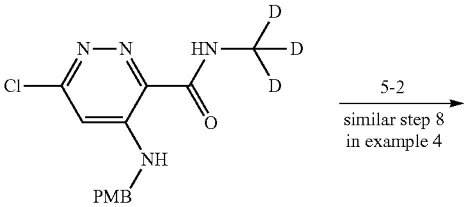

126-3

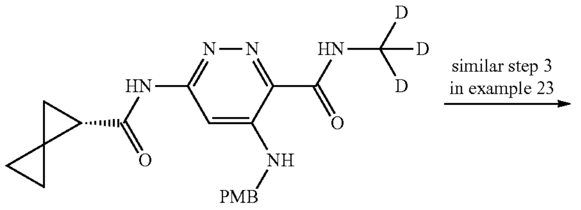

126-4

-continued

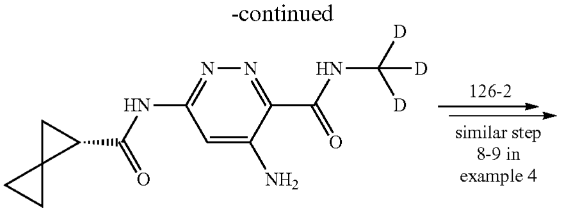

126-5

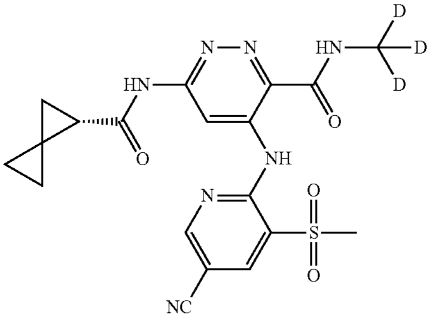

126

Step 1: A suspension of 5-5 (1 g, 219.1 mmol) and copper cyanide (820 mg, 89.56 mmol) in N,N-dimethylformamide (10 mL) was stirred at 155° C. in for 12 hours. The mixture was poured into ammonium chloride aqueous (50 mL) and extracted with ethyl acetate. The combined organic layers were dried over anhydrous sodium sulfate, filtered and concentrated. The residue was purified by silica gel column chromatography (petroleum ether/ethyl acetate=1/1) to give 126-1.

Step 2: A solution of 126-1 (200 mg, 1.211 mmol) in dibromomethane (5 mL) was added tetrabutylammonium bromide (1560.92 mg, 4.842 mmol) and t-butylnitrite (1.440 mL, 12.105 mmol) at room temperature, then stirred for 4 hours. The mixture was diluted with ethyl acetate, washed with water and brine. Organic layer was dried over anhydrous sodium sulfate, filtrated and concentrated. The residue was purified by silica gel column chromatography (petroleum ether: ethyl acetate=0-50%) to afford 126-2.

Step 3: To a solution of 1-3 (10 g, 48.537 mmol) in dimethyl sulfoxide (100 mL) was added 4-methoxybenzylamine (7.32 g, 53.391 mmol) and potassium fluoride (8.46 g, 145.611 mmol. The reaction mixture was stirred at 120° C. for 3 hours. The mixture was cooled to room temperature and poured into water. The solid was collected by filtered and dried in vacuo to give 126-3.

Compound 126-4 was prepared from 126-3 and 5-2 following the procedure for the synthesis of compound 5-8 in example 4.

Compound 126-5 was prepared from 126-4 following the procedure for the synthesis of compound 50-3 in example 23.

Compound 126 was prepared from 126-5 and 126-2 following the procedure for the synthesis of compound 5 in example 4. LCMS (ESI, m/z): $[M+H]^+=445.1$; $^1H$-NMR (400 MHz, DMSO-$d_6$, ppm): δ 12.49 (s, 1H), 11.36 (s, 1H), 9.54 (s, 1H), 9.28 (s, 1H), 9.03 (s, 1H), 8.61 (s, 1H), 3.42 (s, 3H), 2.50-2.46 (m, 1H), 1.46-1.39 (m, 2H), 0.98-0.74 (m, 4H).

Example 44 Synthesis of Compound 129 and 130

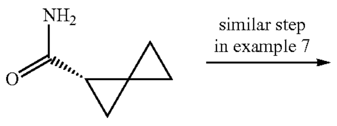

5-2

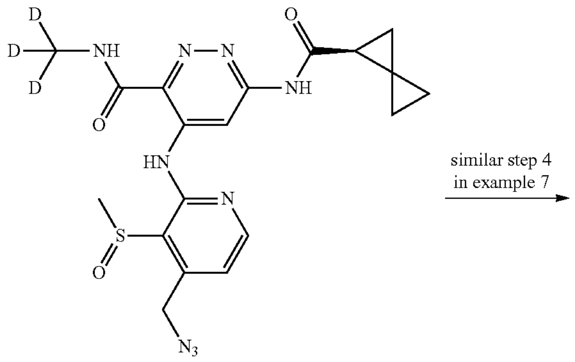

129-1

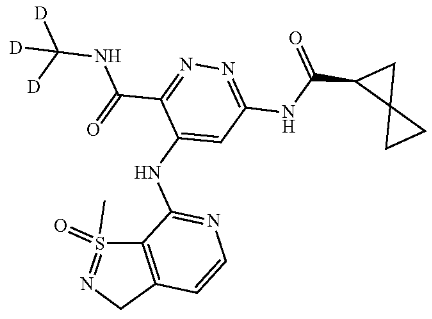

enantiomer 1
129

+

-continued

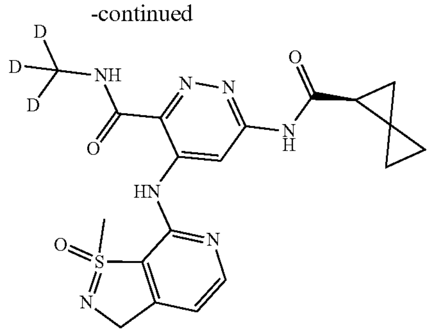

enantiomer 2
130

Compound 129-1 was prepared from 5-2 following the procedure for the synthesis of compound 8-3 in example 7.

Compound 129 and 130 were prepared from 129-1 following the procedure for the synthesis of compound 8 in example 7. Compound 129 and 130 were purified by preparative SFC (DAICELCHIRALPAK® AD with MeOH/$CO_2$).

129: Chiral SFC analysis: 99.44% ee. Retention time 2.420 min on DAICEL CHIRALPAK® AD-3 100*3 mm 3 μm column (35° C.); mobile phase: MeOH (0.1% DEA) in $CO_2$, 1800 psi, 1.5 mL/min.

129: LCMS (ESI, m/z): $[M+H]^+$=431.2; $^1$H-NMR (400 MHz, $CDCl_3$, ppm): δ 12.76 (s, 1H), 10.14 (s, 1H), 9.32 (br s, 1H), 8.60 (d, J=4.4 Hz, 1H), 8.19 (s, 1H), 7.11 (d, J=5.2 Hz, 1H), 4.95-4.74 (m, 2H), 3.71 (s, 3H), 2.27-2.17 (m, 1H), 1.73-1.65 (m, 1H), 1.61-1.52 (m, 1H), 1.20-1.12 (m, 1H), 1.10-0.96 (m, 3H).

130: Chiral SFC analysis: >99.5% ee. Retention time 3.892 min on DAICEL CHIRALPAK® AD-3 100*3 mm 3 μm column (35° C.); mobile phase: MeOH (0.1% DEA) in $CO_2$, 1800 psi, 1.5 mL/min.

130: LCMS (ESI, m/z): $[M+H]^+$=431.2; $^1$H-NMR (400 MHz, $CDCl_3$, ppm): δ 12.71 (s, 1H), 10.12 (s, 1H), 9.33 (br s, 1H), 8.59 (d, J=5.2 Hz, 1H), 8.21 (s, 1H), 7.10 (d, J=5.2 Hz, 1H), 4.95-4.73 (m, 2H), 3.69 (s, 3H), 2.28-2.25 (m, 1H), 1.74-1.65 (m, 1H), 1.57-1.49 (m, 1H), 1.17-1.08 (m, 1H), 1.07-0.94 (m, 3H).

Compounds of the present disclosure can be prepared following similar procedures and methods described hereinabove. Table 1 shows characterizations of representative compounds that were prepared.

TABLE 1

Characterization of representative compounds of the present disclosure

| Compound No. | Structure | $[M + H]^+$ | $^1$H-NMR and $^{19}$F-NMR; optical rotation |
|---|---|---|---|
| 4 | 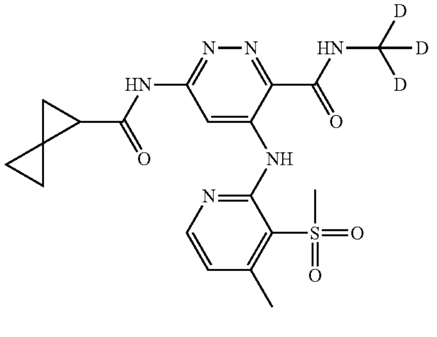 [SMILES: [2H]C([2H])([2H])NC(=O)c1nnc(NC(=O)C2CC23CC3)cc1Nc1nccc(C)c1S(C)(=O)=O] | 434.1 | $^1$H-NMR (400 HHz, DMSO-$d_6$, ppm): δ 11.87 (s, 1H), 11.14 (s, 1H), 9.07 (s, 1H), 9.04 (s, 1H), 8.34 (d, J = 4.8 Hz, 1H), 7.11 (d, J = 5.2 Hz, 1H), 3.36 (s, 3H), 2.63 (s, 3H), 2.43-2.37 (m, 1H), 1.38-1.27 (m, 2H), 0.92-0.78 (m, 3H), 0.76-0.68 (m, 1H). |

TABLE 1-continued

Characterization of representative compounds of the present disclosure

| Compound No. | Structure | $[M + H]^+$ | $^1$H-NMR and $^{19}$F-NMR; optical rotation |
|---|---|---|---|
| 14 | 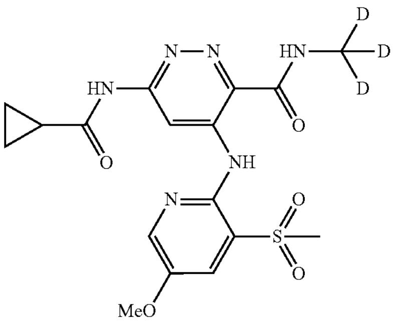 [SMILES: [2H]C([2H])([2H])NC(=O)c1nnc(NC(=O)C2CC2)cc1Nc1ncc(OC)cc1S(C)(=O)=O] | 424.2 | $^1$H-NMR (400 HHz, DMSO-$d_6$, ppm): δ 11.80 (s, 1H), 11.32 (s, 1H), 9.10 (m, 2H), 8.34 (d, J = 2.8 Hz, 1H), 7.76 (d, J = 2.8 Hz, 1H), 3.88 (s, 3H), 3.29 (s, 3H), 2.08-2.04 (m, 1H), 0.86-0.77 (m, 4H). |
| 15 | 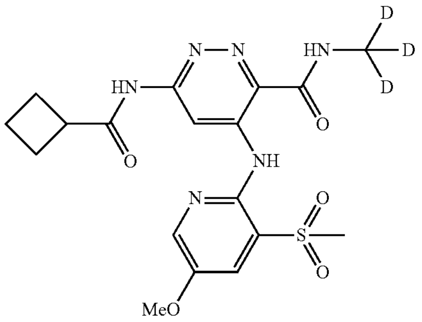 [SMILES: [2H]C([2H])([2H])NC(=O)c1nnc(NC(=O)C2CCC2)cc1Nc1ncc(OC)cc1S(C)(=O)=O] | 438.2 | $^1$H-NMR (400 HHz, DMSO-$d_6$, ppm): δ 11.80 (s, 1H), 10.84 (s, 1H), 9.16 (s, 1H), 9.08 (s, 1H), 8.38 (d, J = 2.8 Hz, 1H), 7.77 (d, J = 2.8 Hz, 1H), 3.90 (s, 3H), 3.32-3.29 (m, 4H), 2.19-2.03 (m, 4H), 1.93-1.86 (m, 1H), 1.79-1.74 (m, 1H). |
| 17 | 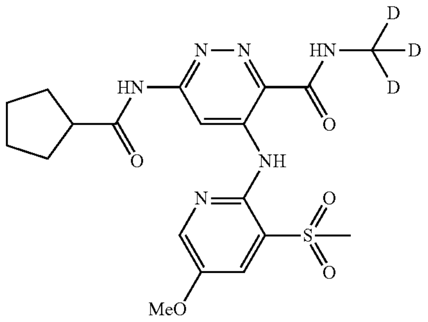 [SMILES: [2H]C([2H])([2H])NC(=O)c1nnc(NC(=O)C2CCCC2)cc1Nc1ncc(OC)cc1S(C)(=O)=O] | 452.2 | $^1$H-NMR (400 HHz, DMSO-$d_6$, ppm): δ 11.80 (s, 1H), 10.97 (s, 1H), 9.13 (s, 1H), 9.09 (s, 1H), 8.37 (d, J = 2.8 Hz, 1H), 7.76 (d, J = 3.2 Hz, 1H), 3.90 (s, 3H), 3.30 (s, 3H), 3.04-2.93 (m, 1H), 1.88-1.45 (m, 8H). |
| 18 | 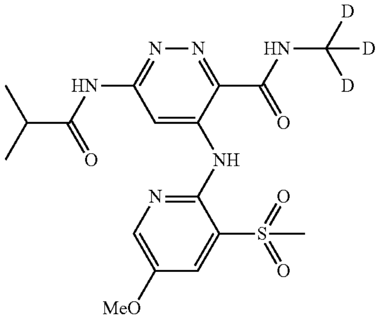 [SMILES: [2H]C([2H])([2H])NC(=O)c1nnc(NC(=O)C(C)C)cc1Nc1ncc(OC)cc1S(C)(=O)=O] | 426.2 | $^1$H-NMR (400 HHz, DMSO-$d_6$, ppm): δ 11.81 (s, 1H), 10.97 (s, 1H), 9.15 (s, 1H), 9.09 (s, 1H), 8.38 (d, J = 2.8 Hz, 1H), 7.76 (d, J = 2.8 Hz, 1H), 3.90 (s, 3H), 3.33-3.30 (m, 3H), 2.82-2.79 (m, 1H), 1.06 (d, J = 6.8 Hz, 6H). |

TABLE 1-continued

Characterization of representative compounds of the present disclosure

| Compound No. | Structure | [M + H]$^+$ | $^1$H-NMR and $^{19}$F-NMR; optical rotation |
|---|---|---|---|
| 19 | 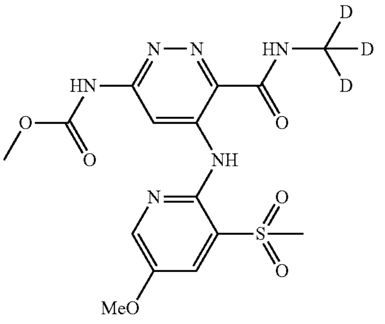 [SMILES: [2H]C([2H])([2H])NC(=O)c1nnc(NC(=O)OC)cc1Nc1ncc(OC)cc1S(C)(=O)=O] | 414.1 | $^1$H-NMR (400 HHz, DMSO-$d_6$, ppm): δ 11.83 (s, 1H), 10.84 (s, 1H), 9.09 (s, 1H), 8.95 (s, 1H), 8.36 (d, J = 3.2 Hz, 1H), 7.77 (d, J = 3.2 Hz, 1H), 3.89 (s, 3H), 3.66 (s, 3H), 3.31 (s, 3H). |
| 23 | 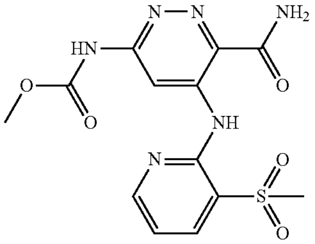 | 367.1 | $^1$H-NMR (400 HHz, DMSO-$d_6$, ppm): δ 12.17 (s, 1H), 10.91 (s, 1H), 9.36 (s, 1H), 8.60 (d, J = 3.6 Hz, 1H), 8.54 (s, 1H), 8.24 (d, J = 6.4 Hz, 1H), 7.91 (s, 1H), 7.31-7.27 (m, 1H), 3.68 (s, 3H), 3.32 (s, 3H). |
| 24 | 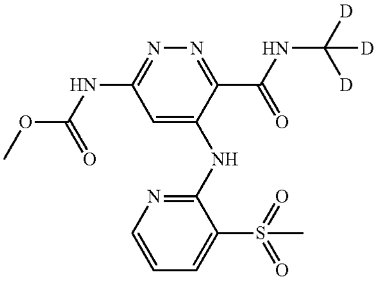 [SMILES: [2H]C([2H])([2H])NC(=O)c1nnc(NC(=O)OC)cc1Nc1ncccc1S(C)(=O)=O] | 384.1 | $^1$H-NMR (400 HHz, DMSO-$d_6$, ppm): δ 12.08 (s, 1H), 10.91 (s, 1H), 9.30 (s, 1H), 9.14 (s, 1H), 8.59 (dd, J = 4.8, 1.2 Hz, 1H), 8.25 (dd, J = 8.0, 1.6 Hz, 1H), 7.30 (dd, J = 8.0, 4.8 Hz, 1H), 3.68 (s, 3H), 3.33 (s, 3H). |
| 26 | 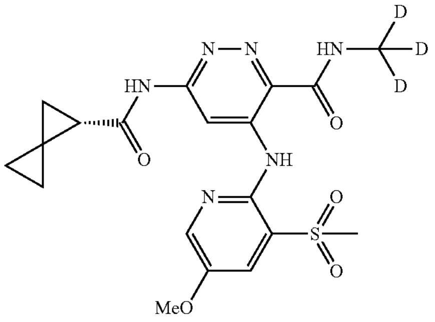 [SMILES: [2H]C([2H])([2H])NC(=O)c1nnc(NC(=O)[C@H]2CC23CC3)cc1Nc1ncc(OC)cc1S(C)(=O)=O] | 450.2 | $^1$H-NMR (400 HHz, DMSO-$d_6$, ppm): δ 11.82 (s, 1H), 11.15 (s, 1H), 9.12 (s, 1H), 9.11 (s, 1H), 8.37 (d, J = 2.8 Hz, 1H), 7.77 (d, J = 3.2 Hz, 1H), 3.90 (s, 3H), 3.30 (s, 3H), 2.44-2.40 (m, 1H), 1.40-1.32 (m, 2H), 0.90-0.79 (m, 3H), 0.76-0.69 (m, 1H). |
| 27 | 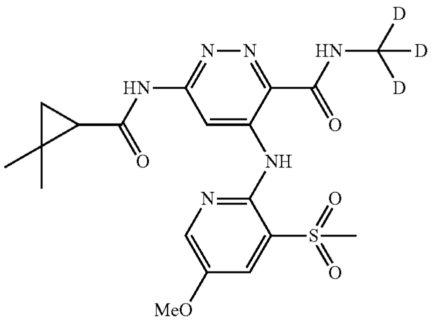 [SMILES: [2H]C([2H])([2H])NC(=O)c1nnc(NC(=O)C2CC2(C)C)cc1Nc1ncc(OC)cc1S(C)(=O)=O] | 452.2 | $^1$H-NMR (400 HHz, DMSO-$d_6$, ppm): δ 11.86 (s, 1H), 11.20 (s, 1H), 9.15 (s, 1H), 9.14 (s, 1H), 8.38 (d, J = 3.2 Hz, 1H), 7.80 (d, J = 3.2 Hz, 1H), 3.93 (s, 3H), 3.35 (s, 3H), 2.01-1.97 (m, 1H), 1.16 (s, 3H), 1.13 (s, 3H), 1.02-0.98 (m, 1H), 0.87-0.83 (m, 1H). |

TABLE 1-continued

Characterization of representative compounds of the present disclosure

| Compound No. | Structure | [M + H]$^+$ | $^1$H-NMR and $^{19}$F-NMR; optical rotation |
|---|---|---|---|
| 28 | 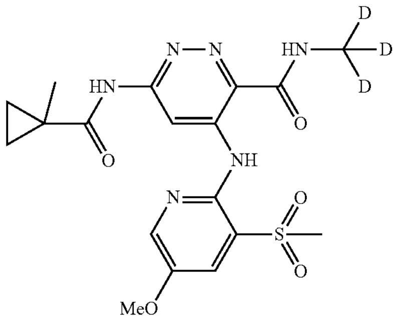 [SMILES: [2H]C([2H])([2H])NC(=O)c1nnc(NC(=O)C2(C)CC2)cc1Nc1ncc(OC)cc1S(C)(=O)=O] | 438.1 | $^1$H-NMR (400 HHz, DMSO-$d_6$, ppm): δ 11.84 (s, 1H), 10.13 (s, 1H), 9.12 (s, 1H), 9.07 (s, 1H), 8.40 (d, J = 2.8 Hz, 1H), 7.80 (d, J = 2.8 Hz, 1H), 3.93 (s, 3H), 3.34 (s, 3H), 1.45 (s, 3H), 1.17-1.14 (m, 2H), 0.72-0.68 (m, 2H). |
| 29 | 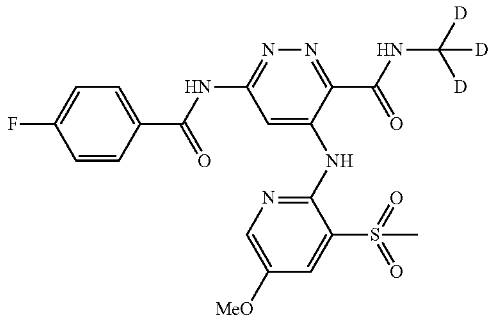 [SMILES: [2H]C([2H])([2H])NC(=O)c1nnc(NC(=O)c2ccc(F)cc2)cc1Nc1ncc(OC)cc1S(C)(=O)=O] | 478.1 | $^1$H-NMR (400 HHz, DMSO-$d_6$, ppm): δ 11.91 (s, 1H), 11.37 (s, 1H), 9.29 (s, 1H), 9.18 (s, 1H), 8.43 (s, 1H), 8.14-8.10 (m, 2H), 7.83 (s, 1H), 7.39-7.34 (m, 2H), 3.94 (s, 3H), 3.38 (s, 3H). |
| 30 | 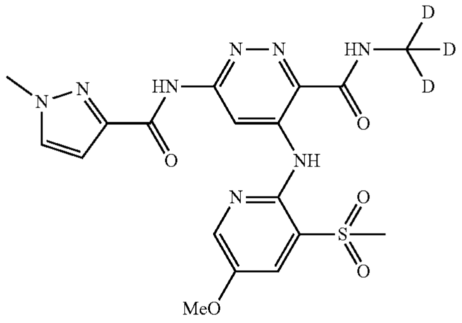 [SMILES: [2H]C([2H])([2H])NC(=O)c1nnc(NC(=O)c2ccn(C)n2)cc1Nc1ncc(OC)cc1S(C)(=O)=O] | 464.1 | $^1$H-NMR (400 HHz, DMSO-$d_6$, ppm): δ 11.98 (s, 1H), 10.02 (s, 1H), 9.34 (s, 1H), 9.24 (s, 1H), 8.44 (d, J = 1.6 Hz, 1H), 7.92 (s, 1H), 7.83 (d, J = 1.6 Hz, 1H), 6.89 (s, 1H), 3.99 (s, 3H), 3.95 (s, 3H), 3.38 (s, 3H). |
| 31 | 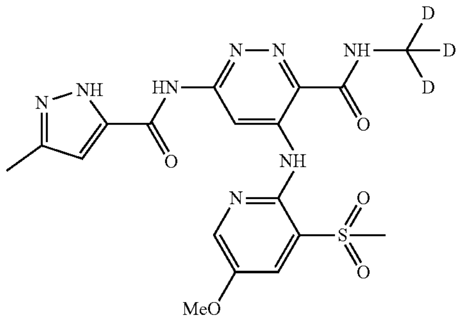 [SMILES: [2H]C([2H])([2H])NC(=O)c1nnc(NC(=O)c2cc(C)n[nH]2)cc1Nc1ncc(OC)cc1S(C)(=O)=O] | 421.1 | 1 eq formic acid salt, $^1$H-NMR (400 HHz, DMSO-$d_6$, ppm): δ 12.99 (s, 1H), 11.87 (s, 1H), 9.32 (s, 1H), 8.87 (s, 1H), 8.47-8.45 (m, 2H), 7.80 (d, J = 3.2 Hz, 1H), 6.74 (s, 1H), 3.92 (s, 3H), 3.33 (s, 3H), 2.30 (s, 3H). |

TABLE 1-continued

| Characterization of representative compounds of the present disclosure | | | |
|---|---|---|---|
| Compound No. | Structure | [M + H]+ | $^1$H-NMR and $^{19}$F-NMR; optical rotation |
| 32 | 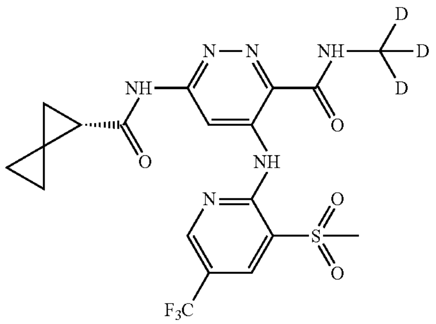 [SMILES: [2H]C([2H])([2H])NC(=O)c1nnc(NC(=O)[C@H]2CC23CC3)cc1Nc1ncc(C(F)(F)F)cc1S(C)(=O)=O] | 488.2 | $^1$H-NMR (400 HHz, DMSO-$d_6$, ppm): δ 12.44 (s, 1H), 11.33 (s, 1H), 9.55 (s, 1H), 9.26 (s, 1H), 8.98 (s, 1H), 8.41 (d, J = 1.6 Hz, 1H), 3.45 (s, 3H), 2.47-2.41 (m, 1H), 1.46-1.35 (m, 2H), 0.96-0.80 (m, 4H). $^{19}$F-NMR (376 HHz, DMSO-$d_6$, ppm): δ −60.15 (3F) |
| 33 | 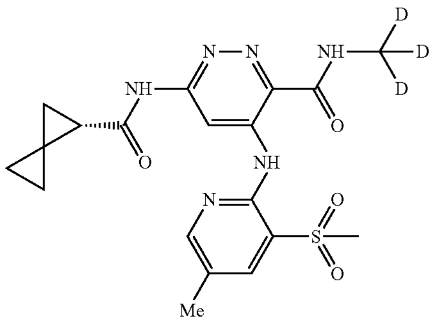 [SMILES: [2H]C([2H])([2H])NC(=O)c1nnc(NC(=O)[C@H]2CC23CC3)cc1Nc1ncc(C)cc1S(C)(=O)=O] | 434.2 | $^1$H-NMR (400 HHz, DMSO-$d_6$, ppm): δ 11.98 (s, 1H), 11.21 (s, 1H), 9.39 (s, 1H), 9.16 (s, 1H), 8.48 (d, J = 2.0 Hz, 1H), 8.10 (d, J = 2.0 Hz, 1H), 3.31 (s, 3H), 2.46-2.43 (m, 1H), 2.36 (s, 3H), 1.41-1.34 (m, 2H), 0.91-0.73 (m, 4H). |
| 34 | 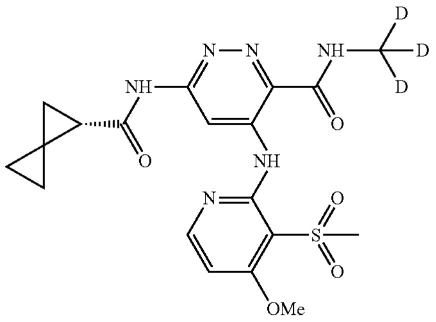 [SMILES: [2H]C([2H])([2H])NC(=O)c1nnc(NC(=O)[C@H]2CC23CC3)cc1Nc1nccc(OC)c1S(C)(=O)=O] | 450.1 | $^1$H-NMR (400 HHz, TFA-d, ppm): δ 9.05 (d, J = 7.2 Hz, 1H), 8.20 (s, 1H), 7.88 (d, J = 7.2 Hz, 1H), 4.67 (s, 3H), 3.80 (s, 3H), 2.60-2.57 (m, 1H), 2.19-2.09 (m, 2H), 1.43-1.24 (m, 4H). |
| 35 | 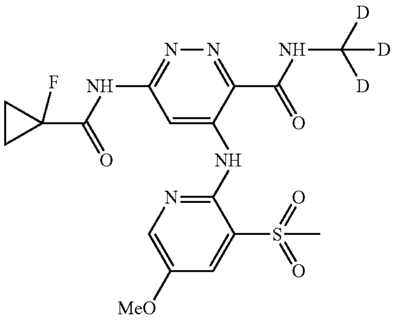 [SMILES: [2H]C([2H])([2H])NC(=O)c1nnc(NC(=O)C2(F)CC2)cc1Nc1ncc(OC)cc1S(C)(=O)=O] | 442.0 | $^1$H-NMR (400 HHz, DMSO-$d_6$, ppm): δ 11.91 (s, 1H), 10.48 (br s, 1H), 9.22 (s, 1H), 9.12 (s, 1H), 8.39 (d, J = 2.8 Hz, 1H), 7.81 (d, J = 3.2 Hz, 1H), 3.93 (s, 3H), 3.35 (s, 3H), 1.58-1.45 (m, 2H), 1.44-1.29 (m, 2H). $^{19}$F-NMR (376 HHz, DMSO-$d_6$, ppm): δ −195.26 (1F). |

TABLE 1-continued

| Compound No. | Structure | [M + H]+ | $^{1}$H-NMR and $^{19}$F-NMR; optical rotation |
|---|---|---|---|
| Characterization of representative compounds of the present disclosure | | | |
| 36 | 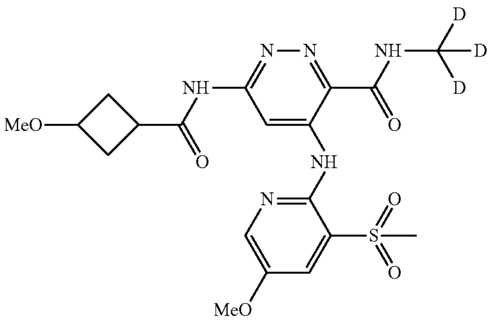 [SMILES: [2H]C([2H])([2H])NC(=O)c1nnc(NC(=O)C2CC(OC)C2)cc1Nc1ncc(OC)cc1S(C)(=O)=O] | 468.2 | $^{1}$H-NMR (400 HHz, DMSO-$d_6$, ppm): δ 11.87 (s, 1H), 11.04 (s, 1H), 9.22 (s, 1H), 9.15 (s, 1H), 8.44 (s, 1H), 7.82 (s, 1H), 3.95 (s, 3H), 3.86-3.73 (m, 1H), 3.35 (s, 3H), 3.13 (s, 3H), 3.04-2.91 (m, 1H), 2.46-2.34 (m, 2H), 2.19-1.94 (m, 2H). |
| 38 | 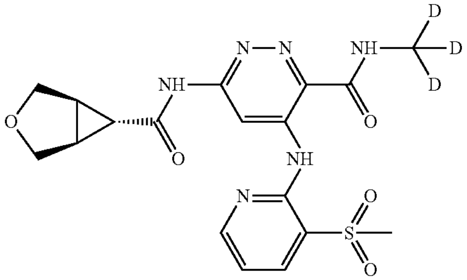 [SMILES: [2H]C([2H])([2H])NC(=O)c1nnc(NC(=O)[C@H]2[C@@H]3COC[C@@H]32)cc1Nc1ncccc1S(C)(=O)=O] | 436.1 | $^{1}$H-NMR (400 HHz, DMSO-$d_6$, ppm): δ 12.09 (s, 1H), 11.36 (s, 1H), 9.47 (s, 1H), 9.21 (s, 1H), 8.61 (d, J = 3.6 Hz, 1H), 8.28 (d, J = 6.8 Hz, 1H), 7.33 (dd, J = 7.2, 4.8 Hz, 1H), 3.84 (d, J = 8.8 Hz, 2H), 3.67 (d, J = 8.4 Hz, 2H), 3.35 (s, 3H), 2.23-1.98 (m, 3H). |
| 45 | 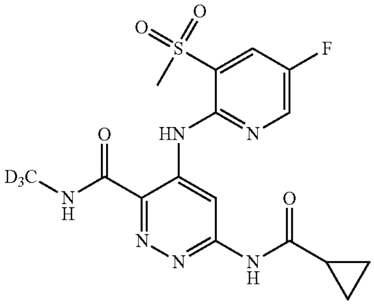 [SMILES: [2H]C([2H])([2H])NC(=O)c1nnc(NC(=O)C2CC2)cc1Nc1ncc(F)cc1S(C)(=O)=O] | 412.1 | $^{1}$H-NMR (400 HHz, DMSO-$d_6$, ppm): δ 12.05 (s, 1H), 11.42 (s, 1H), 9.29 (s, 1H), 9.19 (s, 1H), 8.67 (d, J = 2.8 Hz, 1H), 8.16 (dd, J = 7.6, J = 3.2 Hz, 1H), 3.37 (s, 3H), 2.13-2.06 (m, 1H), 0.86-0.83 (m, 4H). |
| 46 | 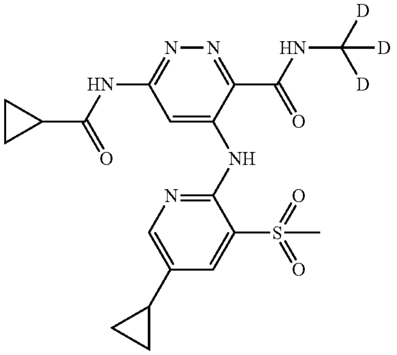 [SMILES: [2H]C([2H])([2H])NC(=O)c1nnc(NC(=O)C2CC2)cc1Nc1ncc(C2CC2)cc1S(C)(=O)=O] | 434.1 | $^{1}$H-NMR (400 HHz, DMSO-$d_6$, ppm): δ 11.96 (s, 1H), 11.38 (s, 1H), 9.35 (s, 1H), 9.15 (s, 1H), 8.43 (d, J = 2.4 Hz, 1H), 7.84 (d, J = 2.4 Hz, 1H), 3.31 (s, 3H), 2.14-2.04 (m, 2H), 1.06-0.99 (m, 2H), 0.88-0.75 (m, 6H). |

TABLE 1-continued

Characterization of representative compounds of the present disclosure

| Compound No. | Structure | [M + H]+ | 1H-NMR and 19F-NMR; optical rotation |
|---|---|---|---|
| 47 | 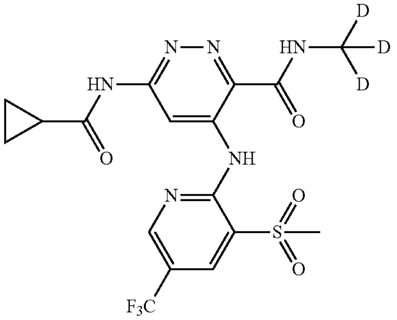 [SMILES: [2H]C([2H])([2H])NC(=O)c1nnc(NC(=O)C2CC2)cc1Nc1ncc(C(F)(F)F)cc1S(C)(=O)=O] | 462.2 | $^1$H-NMR (400 HHz, DMSO-$d_6$, ppm): δ 12.45 (s, 1H), 11.54 (s, 1H), 9.55 (s, 1H), 9.28 (s, 1H), 8.96 (s, 1H), 8.40 (d, J = 2.0 Hz, 1H), 3.44 (s, 3H), 2.17-2.07 (m, 1H), 0.91-0.82 (m, 4H). $^{19}$F-NMR (376 HHz, DMSO-$d_6$, ppm): δ −60.18 (3F). |
| 48 | 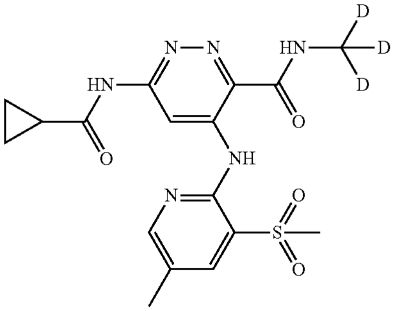 [SMILES: [2H]C([2H])([2H])NC(=O)c1nnc(NC(=O)C2CC2)cc1Nc1ncc(C)cc1S(C)(=O)=O] | 408.2 | $^1$H-NMR (400 HHz, DMSO-$d_6$, ppm): δ 11.97 (s, 1H), 11.40 (s, 1H), 9.39 (s, 1H), 9.17 (s, 1H), 8.45 (d, J = 2.0 Hz, 1H), 8.10 (d, J = 2.0 Hz, 1H), 3.31 (s, 3H), 2.35 (s, 3H), 2.11-2.06 (m, 1H), 0.88-0.79 (m, 4H). |
| 56 | 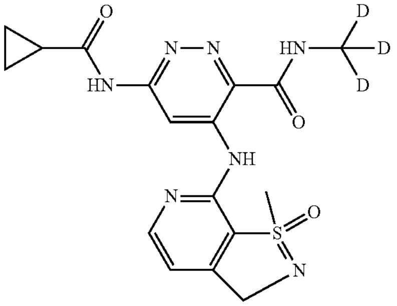 enantiomer 1 | 405.1 | $^1$H-NMR (400 HHz, DMSO-$d_6$, ppm): δ 12.48 (s, 1H), 11.46 (s, 1H), 9.92 (s, 1H), 9.38 (s, 1H), 8.48 (d, J = 4.8 Hz, 1H), 7.29 (d, J = 4.8 Hz, 1H), 4.78-4.60 (m, 2H), 3.64 (s, 3H), 2.15-2.09 (m, 1H), 0.88-0.86 (m, 4H). >99.5% ee. |
| 57 | 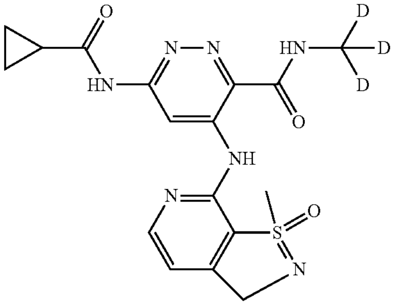 enantiomer 2 | 405.1 | $^1$H-NMR (400 HHz, DMSO-$d_6$, ppm): δ 12.48 (s, 1H), 11.46 (s, 1H), 9.92 (s, 1H), 9.38 (s, 1H), 8.48 (d, J = 4.8 Hz, 1H), 7.29 (d, J = 4.8 Hz, 1H), 4.78-4.60 (m, 2H), 3.64 (s, 3H), 2.13-2.09 (m, 1H), 0.88-0.86 (m, 4H). >99.5% ee. |

TABLE 1-continued

Characterization of representative compounds of the present disclosure

| Compound No. | Structure | $[M + H]^+$ | $^1$H-NMR and $^{19}$F-NMR; optical rotation |
|---|---|---|---|
| 61 | 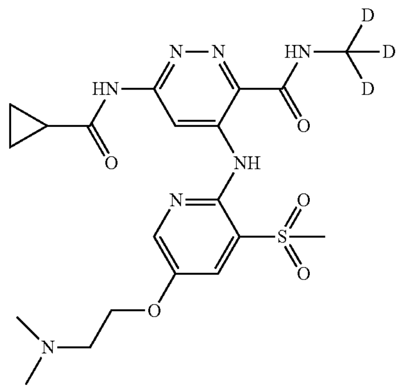 [SMILES: [2H]C([2H])([2H])NC(=O)c1nnc(NC(=O)C2CC2)cc1Nc1ncc(OCCN(C)C)cc1S(C)(=O)=O] | 481.2 | 1 eq formic acid salt, $^1$H-NMR (400 HHz, DMSO-$d_6$, ppm): δ 11.82 (s, 1H), 11.37 (s, 1H), 9.14 (s, 1H), 9.11 (s, 1H), 8.40 (s, 1H), 8.36 (d, J = 3.2 Hz, 1H), 7.78 (d, J = 3.2 Hz, 1H), 4.21 (t, J = 5.6 Hz, 2H), 3.31 (s, 3H), 2.63 (t, J = 5.6 Hz, 2H), 2.20 (s, 6H), 2.12-2.05 (m, 1H), 0.84-0.81 (m, 4H). |
| 62 | 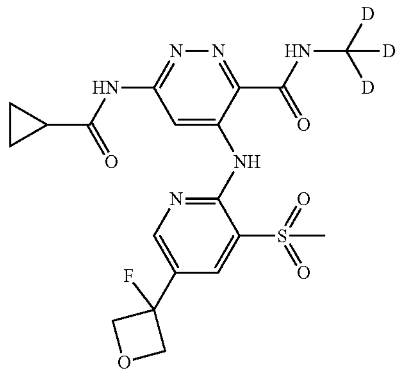 [SMILES: [2H]C([2H])([2H])NC(=O)c1nnc(NC(=O)C2CC2)cc1Nc1ncc(C2(F)COC2)cc1S(C)(=O)=O] | 468.2 | $^1$H-NMR (400 HHz, DMSO-$d_6$, ppm): δ 12.25 (s, 1H), 11.47 (s, 1H), 9.55 (s, 1H), 9.22 (s, 1H), 8.81-8.76 (m, 1H), 8.29 (d, J = 2.0 Hz, 1H), 5.07-4.92 (m, 4H), 3.39 (s, 3H), 2.15-2.07 (m, 1H), 0.91-0.82 (m, 4H). $^{19}$F-NMR (376 HHz, DMSO-$d_6$, ppm): δ −143.92 (1F). |
| 63 | 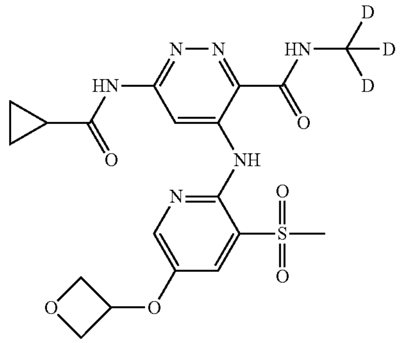 [SMILES: [2H]C([2H])([2H])NC(=O)c1nnc(NC(=O)C2CC2)cc1Nc1ncc(OC2COC2)cc1S(C)(=O)=O] | 466.2 | $^1$H-NMR (400 HHz, DMSO-$d_6$, ppm): δ 11.87 (s, 1H), 11.36 (s, 1H), 9.13 (s, 2H), 8.25 (d, J = 2.8 Hz, 1H), 7.63 (d, J = 2.8 Hz, 1H), 5.50-5.44 (m, 1H), 4.95-4.91 (m, 2H), 4.60-4.56 (m, 2H), 3.32 (s, 3H), 2.10-2.05 (m, 1H), 0.87-0.81 (m, 4H). |
| 64 | 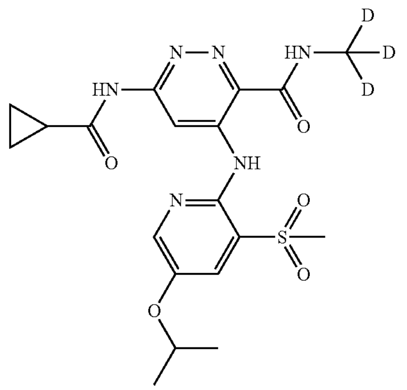 [SMILES: [2H]C([2H])([2H])NC(=O)c1nnc(NC(=O)C2CC2)cc1Nc1ncc(OC(C)C)cc1S(C)(=O)=O] | 452.2 | $^1$H-NMR (400 HHz, DMSO-$d_6$, ppm): δ 11.83 (s, 1H), 11.37 (s, 1H), 9.15 (s, 1H), 9.13 (s, 1H), 8.35 (d, J = 2.8 Hz, 1H), 7.77 (d, J = 3.2 Hz, 1H), 4.81-4.74 (m, 1H), 3.34 (s, 3H), 2.15-2.09 (m, 1H), 1.32 (d, J = 6.0 Hz, 6H), 0.88-0.80 (m, 4H). |

TABLE 1-continued

| Characterization of representative compounds of the present disclosure | | | |
|---|---|---|---|
| Compound No. | Structure | $[M + H]^+$ | $^1H$-NMR and $^{19}F$-NMR; optical rotation |
| 66 | 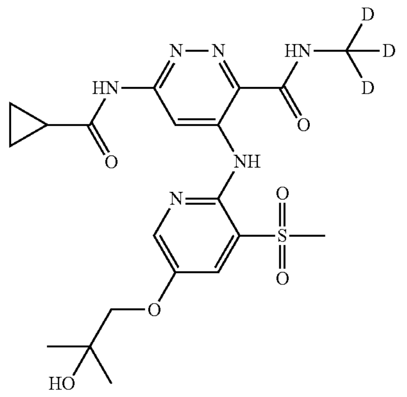 [SMILES: [2H]C([2H])([2H])NC(=O)c1nnc(NC(=O)C2CC2)cc1Nc1ncc(OCC(C)(C)O)cc1S(C)(=O)=O] | 482.2 | $^1H$-NMR (400 HHz, DMSO-$d_6$, ppm): δ 11.82 (s, 1H), 11.36 (s, 1H), 9.14 (s, 1H), 9.12 (s, 1H), 8.36 (d, J = 2.8 Hz, 1H), 7.80 (d, J = 3.2 Hz, 1H), 4.71 (s, 1H), 3.88 (s, 2H), 3.32 (s, 3H), 2.12-2.05 (m, 1H), 1.20 (s, 6H), 0.84-0.81 (m, 4H). |
| 67 | 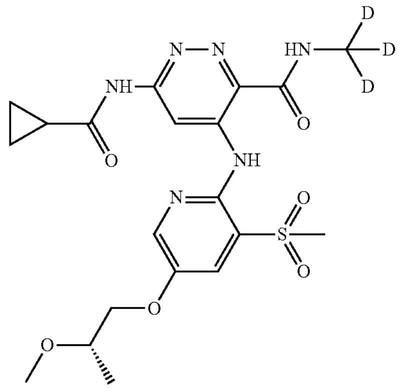 [SMILES: [2H]C([2H])([2H])NC(=O)c1nnc(NC(=O)C2CC2)cc1Nc1ncc(OC[C@H](C)OC)cc1S(C)(=O)=O] | 482.2 | $^1H$-NMR (400 HHz, DMSO-$d_6$, ppm): δ 11.82 (s, 1H), 11.35 (s, 1H), 9.13 (s, 1H), 9.12 (s, 1H), 8.36 (d, J = 3.2 Hz, 1H), 7.79 (d, J = 3.2 Hz, 1H), 4.16-4.05 (m, 2H), 3.70-3.65 (m, 1H), 3.32 (s, 3H), 3.30 (s, 3H), 2.12-2.05 (m, 1H), 1.17 (d, J = 6.4 Hz, 3H), 0.85-0.81 (m, 4H). |
| 68 | 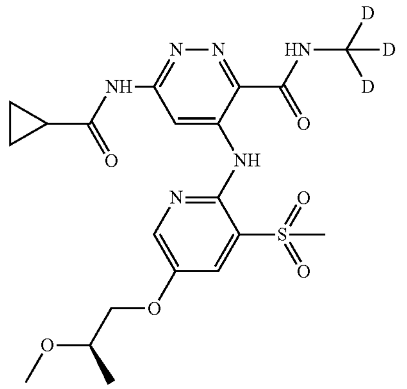 [SMILES: [2H]C([2H])([2H])NC(=O)c1nnc(NC(=O)C2CC2)cc1Nc1ncc(OC[C@@H](C)OC)cc1S(C)(=O)=O] | 482.2 | $^1H$-NMR (400 HHz, DMSO-$d_6$, ppm): δ 11.82 (s, 1H), 11.35 (s, 1H), 9.13 (s, 1H), 9.12 (s, 1H), 8.36 (d, J = 3.2 Hz, 1H), 7.79 (d, J = 2.8 Hz, 1H), 4.15-4.05 (m, 2H), 3.71-3.64 (m, 1H), 3.31 (s, 3H), 3.30 (s, 3H), 2.12-2.05 (m, 1H), 1.17 (d, J = 6.4 Hz, 3H), 0.85-0.82 (m, 4H). |

TABLE 1-continued

Characterization of representative compounds of the present disclosure

| Compound No. | Structure | [M + H]+ | $^1$H-NMR and $^{19}$F-NMR; optical rotation |
|---|---|---|---|
| 69 | 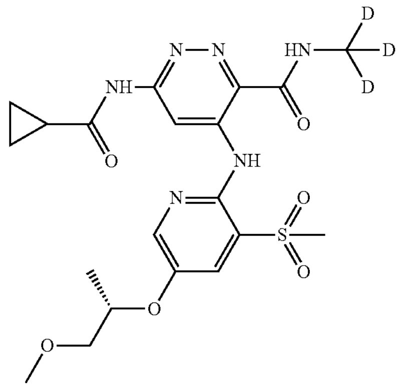 [SMILES: [2H]C([2H])([2H])NC(=O)c1nnc(NC(=O)C2CC2)cc1Nc1ncc(O[C@@H](C)COC)cc1S(C)(=O)=O] | 482.2 | $^1$H-NMR (400 HHz, DMSO-$d_6$, ppm): δ 11.82 (s, 1H), 11.35 (s, 1H), 9.13 (s, 1H), 9.11 (s, 1H), 8.34 (d, J = 2.8 Hz, 1H), 7.79 (d, J = 3.2 Hz, 1H), 4.79-4.72 (m, 1H), 3.51-3.47 (m, 2H), 3.32 (s, 3H), 3.28 (s, 3H), 2.12-2.06 (m, 1H), 1.24 (d, J = 6.0 Hz, 3H), 0.84-0.82 (m, 4H). |
| 70 | 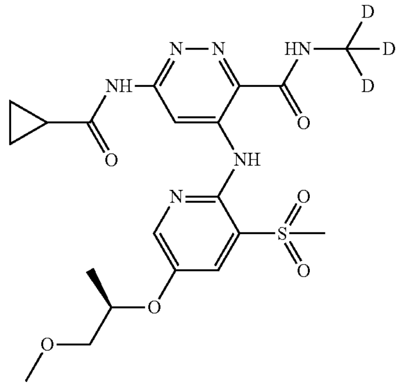 [SMILES: [2H]C([2H])([2H])NC(=O)c1nnc(NC(=O)C2CC2)cc1Nc1ncc(O[C@H](C)COC)cc1S(C)(=O)=O] | 482.2 | $^1$H-NMR (400 HHz, DMSO-$d_6$, ppm): δ 11.82 (s, 1H), 11.36 (s, 1H), 9.14 (s, 1H), 9.11 (s, 1H), 8.34 (d, J = 2.8 Hz, 1H), 7.79 (d, J = 3.2 Hz, 1H), 4.78-4.71 (m, 1H), 3.51-3.48 (m, 2H), 3.32 (s, 3H), 3.28 (s, 3H), 2.12-2.05 (m, 1H), 1.24 (d, J = 6.0 Hz, 3H), 0.84-0.82 (m, 4H). |
| 71 | 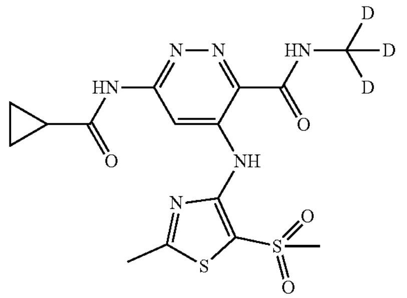 [SMILES: [2H]C([2H])([2H])NC(=O)c1nnc(NC(=O)C2CC2)cc1Nc1nc(C)sc1S(C)(=O)=O] | 414.3 | $^1$H-NMR (400 HHz, DMSO-$d_6$, ppm): δ 12.15 (s, 1H), 11.38 (s, 1H), 9.30 (s, 1H), 9.18 (s, 1H), 3.34 (s, 3H), 2.74 (s, 3H), 2.14-2.11 (m, 1H), 0.89-0.85 (m, 4H). |
| 72 | 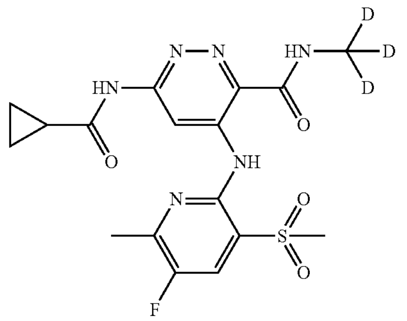 [SMILES: [2H]C([2H])([2H])NC(=O)c1nnc(NC(=O)C2CC2)cc1Nc1nc(C)c(F)cc1S(C)(=O)=O] | 426.1 | $^1$H-NMR (400 HHz, DMSO-$d_6$, ppm): δ 12.13 (s, 1H), 11.42 (s, 1H), 9.78 (s, 1H), 9.19 (s, 1H), 8.03 (d, J = 8.0 Hz, 1H), 3.32 (s, 3H), 2.56-2.52 (m, 3H), 2.19-2.07 (m, 1H), 0.90-0.82 (m, 4H). $^{19}$F-NMR (376 HHz, DMSO-$d_6$, ppm): δ −132.05 (1F). |

TABLE 1-continued

Characterization of representative compounds of the present disclosure

| Compound No. | Structure | $[M + H]^+$ | $^1$H-NMR and $^{19}$F-NMR; optical rotation |
| --- | --- | --- | --- |
| 75 | 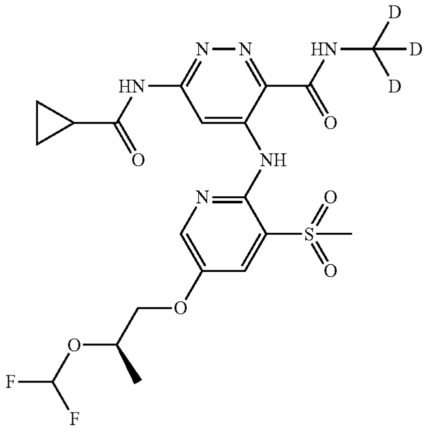 [SMILES: [2H]C([2H])([2H])NC(=O)c1nnc(NC(=O)C2CC2)cc1Nc1ncc(OC[C@@H](C)OC(F)F)cc1S(C)(=O)=O] | 518.2 | $^1$H-NMR (400 HHz, DMSO-$d_6$, ppm): δ 11.86 (s, 1H), 11.38 (s, 1H), 9.21-9.10 (m, 2H), 8.38 (d, J = 2.8 Hz, 1H), 7.81 (d, J = 2.8 Hz, 1H), 6.99-6.60 (m, 1H), 4.61-4.46 (m, 1H), 4.29-4.11 (m, 2H), 3.32 (s, 3H), 2.16-1.99 (m, 1H), 1.35-1.22 (m, 3H), 0.91-0.72 (m, 4H); $^{19}$F-NMR (376 HHz, DMSO-$d_6$, ppm): δ −78.41 (1F), −79.83 (1F). |
| 76 | 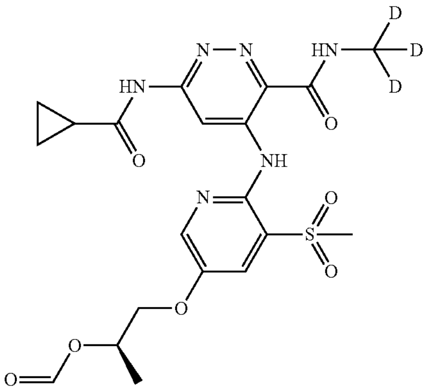 [SMILES: [2H]C([2H])([2H])NC(=O)c1nnc(NC(=O)C2CC2)cc1Nc1ncc(OC[C@@H](C)OC=O)cc1S(C)(=O)=O] | 496.1 | $^1$H-NMR (400 HHz, DMSO-$d_6$, ppm): δ 11.86 (s, 1H), 11.38 (s, 1H), 9.17-9.13 (m, 2H), 8.37 (d, J = 2.8 Hz, 1H), 8.27 (s, 1H), 7.79 (d, J = 2.8 Hz, 1H), 5.33-5.08 (m, 1H), 4.42-4.15 (m, 2H), 3.32 (s, 3H), 2.19-2.02 (m, 1H), 1.30 (d, J-6.4 Hz, 3H), 0.94-0.78 (m, 4H). |
| 77 | 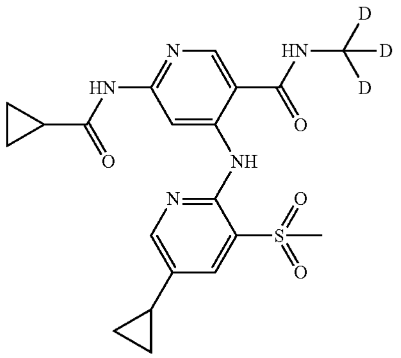 [SMILES: [2H]C([2H])([2H])NC(=O)c1cnc(NC(=O)C2CC2)cc1Nc1ncc(C2CC2)cc1S(C)(=O)=O] | 433.2 | $^1$H-NMR (400 HHz, DMSO-$d_6$, ppm): δ 11.34 (s, 1H), 10.80 (s, 1H), 8.87 (s, 1H), 8.60 (s, 1H), 8.53 (s, 1H), 8.38 (d, J = 2.4 Hz, 1H), 7.78 (d, J = 2.4 Hz, 1H), 3.27 (s, 3H), 2.11-1.92 (m, 2H), 1.05-0.93 (m, 2H), 0.83-0.70 (m, 6H). |
| 78 | 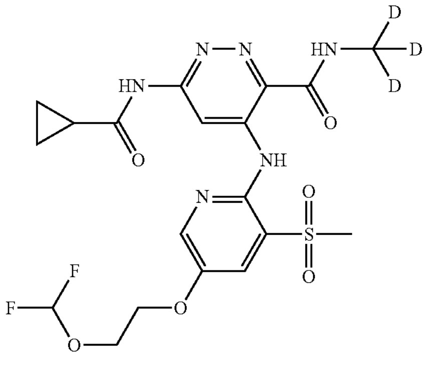 [SMILES: [2H]C([2H])([2H])NC(=O)c1nnc(NC(=O)C2CC2)cc1Nc1ncc(OCCOC(F)F)cc1S(C)(=O)=O] | 504.2 | $^1$H-NMR (400 HHz, DMSO-$d_6$, ppm): δ 11.85 (s, 1H), 11.37 (s, 1H), 9.19-9.07 (m, 2H), 8.39 (d, J = 2.8 Hz, 1H), 7.81 (d, J = 3.2 Hz, 1H), 6.97-6.54 (m, 1H), 4.40-4.32 (m, 2H), 4.22-4.12 (m, 2H), 3.32 (s, 3H), 2.13-2.04 (m, 1H), 0.87-0.80 (m, 4H); $^{19}$F-NMR (376 HHz, DMSO-$d_6$, ppm): δ −82.55 (2F). |

TABLE 1-continued

Characterization of representative compounds of the present disclosure

| Compound No. | Structure | [M + H]+ | $^1$H-NMR and $^{19}$F-NMR; optical rotation |
|---|---|---|---|
| 79 | 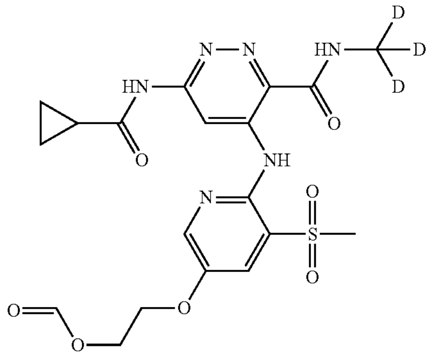 [SMILES: [2H]C([2H])([2H])NC(=O)c1nnc(NC(=O)C2CC2)cc1Nc1ncc(OCCOC=O)cc1S(C)(=O)=O] | 482.2 | $^1$H-NMR (400 HHz, DMSO-$d_6$, ppm): δ 11.85 (s, 1H), 11.37 (s, 1H), 9.19-9.08 (m, 2H), 8.38 (d, J = 2.8 Hz, 1H), 8.29 (s, 1H), 7.81 (d, J = 2.8 Hz, 1H), 4.49-4.35 (m, 4H), 3.32 (s, 3H), 2.13-2.04 (m, 1H), 0.87-0.76 (m, 4H). |
| 80 | 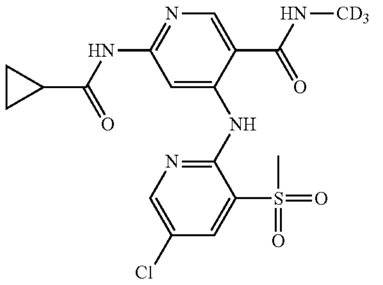 [SMILES: [2H]C([2H])([2H])NC(=O)c1cnc(NC(=O)C2CC2)cc1Nc1ncc(Cl)cc1S(C)(=O)=O] | 427.1 | $^1$H-NMR (400 HHz, DMSO-$d_6$, ppm): δ 11.53 (s, 1H), 10.87 (s, 1H), 8.90 (s, 1H), 8.67 (s, 1H), 8.60-8.57 (m, 2H), 8.18 (d, J = 2.4 Hz, 1H), 3.36 (s, 3H), 2.02-1.95 (m, 1H), 0.81-0.77 (m, 4H). |
| 81 | 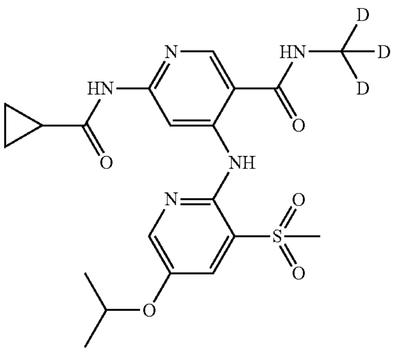 [SMILES: [2H]C([2H])([2H])NC(=O)c1cnc(NC(=O)C2CC2)cc1Nc1ncc(OC(C)C)cc1S(C)(=O)=O] | 451.2 | $^1$H-NMR (400 HHz, DMSO-$d_6$, ppm): δ 11.25 (s, 1H), 10.77 (s, 1H), 8.65 (s, 1H), 8.59 (s, 1H), 8.53 (s, 1H), 8.28 (d, J = 2.8 Hz, 1H), 7.70 (d, J = 2.8 Hz, 1H), 4.78-4.64 (m, 1H), 3.29 (s, 3H), 2.02-1.92 (m, 1H), 1.28 (d, J = 6.0 Hz, 6H), 0.82-0.73 (m, 4H). |
| 82 | 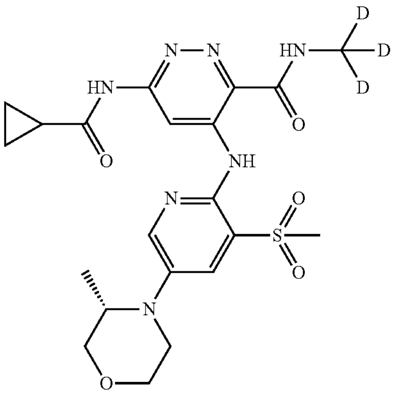 [SMILES: [2H]C([2H])([2H])NC(=O)c1nnc(NC(=O)C2CC2)cc1Nc1ncc(N2CCOC[C@@H]2C)cc1S(C)(=O)=O] | 493.1 | $^1$H-NMR (400 HHz, DMSO-$d_6$, ppm): δ 11.73 (s, 1H), 11.33 (s, 1H), 9.11 (s, 1H), 9.08 (s, 1H), 8.31 (d, J = 3.2 Hz, 1H), 7.66 (d, J = 3.2 Hz, 1H), 4.00-3.90 (m, 2H), 3.76-3.66 (m, 2H), 3.64-3.52 (m, 1H), 3.30 (s, 3H), 3.20-3.05 (m, 2H), 2.15-2.05 (m, 1H), 1.06 (d, J = 6.4 Hz, 3H), 0.87-0.80 (m, 4H). |

TABLE 1-continued

Characterization of representative compounds of the present disclosure

| Compound No. | Structure | $[M + H]^+$ | $^1H$-NMR and $^{19}F$-NMR; optical rotation |
|---|---|---|---|
| 83 | 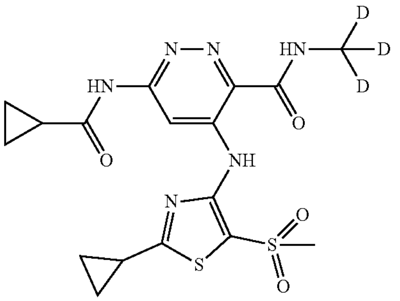 [SMILES: [2H]C([2H])([2H])NC(=O)c1nnc(NC(=O)C2CC2)cc1Nc1nc(C2CC2)sc1S(C)(=O)=O] | 440.1 | $^1H$-NMR (400 HHz, DMSO-$d_6$, ppm): δ 12.12 (s, 1H), 11.42 (s, 1H), 9.24 (s, 1H), 9.16 (s, 1H), 3.32 (s, 3H), 2.51-2.47 (m, 1H), 2.18-2.08 (m, 1H), 1.40-1.30 (m, 2H), 1.25-1.15 (m, 2H), 0.91-0.84 (m, 4H). |
| 84 | 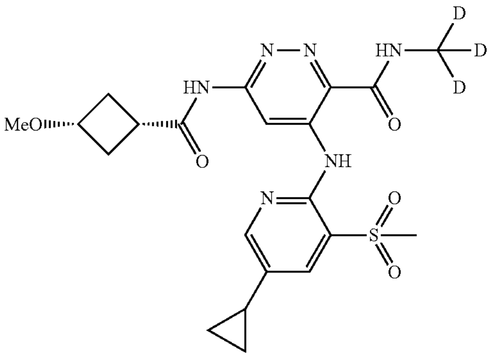 [SMILES: [2H]C([2H])([2H])NC(=O)c1nnc(NC(=O)[C@H]2C[C@@H](OC)C2)cc1Nc1ncc(C2CC2)cc1S(C)(=O)=O] | 478.2 | $^1H$-NMR (400 HHz, DMSO-$d_6$, ppm): δ 12.00 (s, 1H), 11.07 (s, 1H), 9.43 (s, 1H), 9.16 (s, 1H), 8.49 (d, J = 1.6 Hz, 1H), 7.88 (d, J = 2.0 Hz, 1H), 3.89-3.75 (m, 1H), 3.33 (s, 3H), 3.13 (s, 3H), 3.03-2.91 (m, 1H), 2.45-2.34 (m, 2H), 2.16-1.97 (m, 3H), 1.10-0.99 (m, 2H), 0.90-0.77 (m, 2H). |
| 85 | 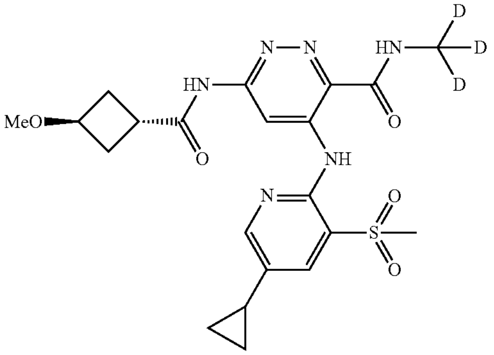 [SMILES: [2H]C([2H])([2H])NC(=O)c1nnc(NC(=O)[C@H]2C[C@H](OC)C2)cc1Nc1ncc(C2CC2)cc1S(C)(=O)=O] | 478.3 | $^1H$-NMR (400 HHz, DMSO-$d_6$, ppm): δ 11.99 (s, 1H), 11.04 (s, 1H), 9.42 (s, 1H), 9.16 (s, 1H), 8.50 (d, J = 2.4 Hz, 1H), 7.87 (d, J = 2.4 Hz, 1H), 4.03-3.91 (m, 1H), 3.41-3.34 (m, 1H), 3.33 (s, 3H), 3.14 (s, 3H), 2.45-2.35 (m, 2H), 2.22-2.08 (m, 3H), 1.11-1.01 (m, 2H), 0.90-0.74 (m, 2H). |
| 88 | 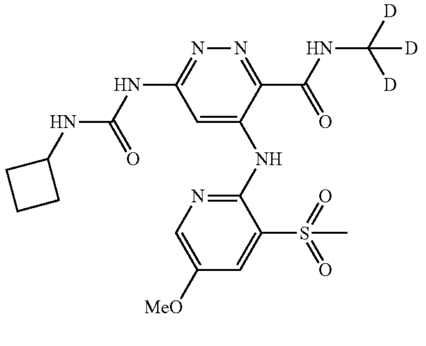 [SMILES: [2H]C([2H])([2H])NC(=O)c1nnc(NC(=O)NC2CCC2)cc1Nc1ncc(OC)cc1S(C)(=O)=O] | 453.2 | $^1H$-NMR (400 HHz, DMSO-$d_6$, ppm): δ 11.82 (s, 1H), 9.49 (s, 1H), 9.13 (s, 1H), 8.72 (s, 1H), 8.38 (d, J = 3.2 Hz, 1H), 7.81-7.73 (m, 2H), 4.19-4.12 (m, 1H), 3.93 (s, 3H), 3.33 (s, 3H), 2.24-2.21 (m, 2H), 1.91-1.77 (m, 2H), 1.68-1.60 (m, 2H). |

TABLE 1-continued

| Characterization of representative compounds of the present disclosure | | | |
|---|---|---|---|
| Compound No. | Structure | $[M + H]^+$ | $^1$H-NMR and $^{19}$F-NMR; optical rotation |
| 89 | 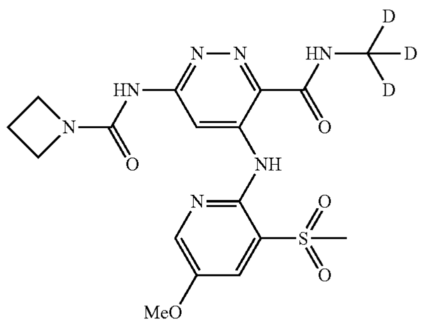 | 439.2 | $^1$H-NMR (400 HHz, DMSO-$d_6$, ppm): δ 11.77 (s, 1H), 9.67 (s, 1H), 9.04 (s, 1H), 8.98 (s, 1H), 8.44-8.36 (m, 1H), 7.80 (d, J = 3.2 Hz, 1H), 4.10-3.98 (s, 4H), 3.93 (s, 3H), 3.34 (s, 3H), 2.24-2.08 (m, 2H). |
| 90 | 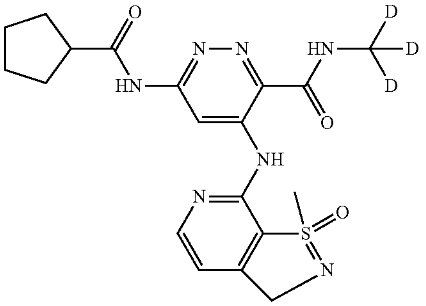 enantiomer 1 | 433.1 | $^1$H-NMR (400 HHz, DMSO-$d_6$, ppm): δ 12.49 (s, 1H), 11.12 (s, 1H), 9.95 (s, 1H), 9.38 (s, 1H), 8.51 (d, J = 4.8 Hz, 1H), 7.30 (d, J = 5.2 Hz, 1H), 4.79-4.60 (m, 2H), 3.64 (s, 3H), 3.06-2.99 (m, 1H), 1.88-1.53 (m, 8H). >99.5% ee. |
| 91 | 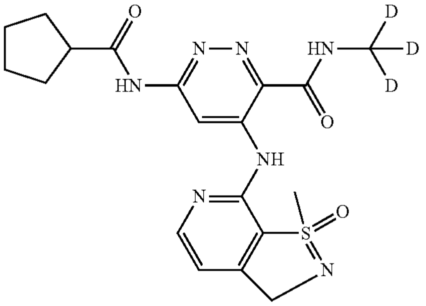 enantiomer 2 | 433.2 | $^1$H-NMR (400 HHz, DMSO-$d_6$, ppm): δ 12.49 (s, 1H), 11.13 (s, 1H), 9.95 (s, 1H), 9.39 (s, 1H), 8.51 (d, J = 5.2 Hz, 1H), 7.30 (d, J = 4.8 Hz, 1H), 4.79-4.60 (m, 2H), 3.64 (s, 3H), 3.08-2.99 (m, 1H), 1.90-0.1.53 (m, 8H). >99.5% ee. |
| 92 | 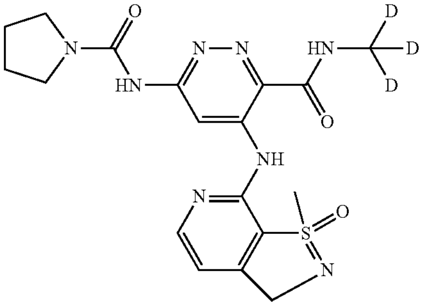 enantiomer 1 | 434.2 | $^1$H-NMR (400 HHz, DMSO-$d_6$, ppm): δ 12.40 (s, 1H), 9.66 (s, 1H), 9.42 (s, 1H), 9.26 (s, 1H), 8.48 (d, J = 5.2 Hz, 1H), 7.28 (d, J = 5.2 Hz, 1H), 4.78-4.60 (m, 2H), 3.64 (s, 3H), 3.52-3.40 (m, 4H), 1.88-1.80 (m, 4H). >99.5% ee. |

TABLE 1-continued

| Compound No. | Structure | [M + H]$^+$ | $^1$H-NMR and $^{19}$F-NMR; optical rotation |
|---|---|---|---|
| Characterization of representative compounds of the present disclosure | | | |
| 93 | 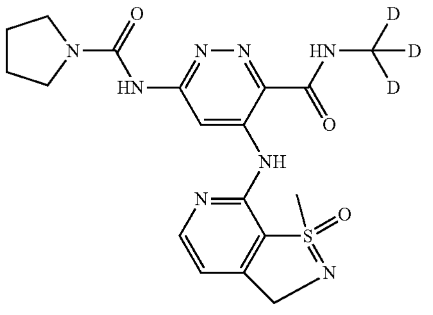 enantiomer 2 | 434.2 | $^1$H-NMR (400 HHz, DMSO-$d_6$, ppm): δ 12.40 (s, 1H), 9.66 (s, 1H), 9.42 (s, 1H), 9.26 (s, 1H), 8.48 (d, J = 5.2 Hz, 1H), 7.28 (d, J = 5.2 Hz, 1H), 4.78-4.60 (m, 2H), 3.64 (s, 3H), 3.51-3.40 (m, 4H), 1.88-1.81 (m, 4H). >99.5% ee. |
| 99 | 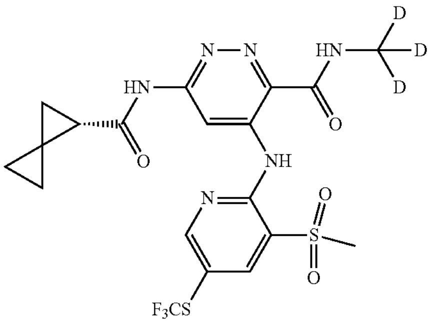 | 520.1 | $^1$H-NMR (400 HHz, DMSO-$d_6$, ppm): δ 12.42 (s, 1H), 11.34 (s, 1H), 9.56 (s, 1H), 9.27 (s, 1H), 8.83 (d, J = 2.4 Hz, 1H), 8.40 (d, J = 2.4 Hz, 1H), 3.43 (s, 3H), 2.47-2.42 (m, 1H), 1.46-1.33 (m, 2H), 0.92-0.79 (m, 4H).$^{19}$F-NMR (376 HHz, DMSO-$d_6$, ppm): δ −42.49 (3F). |
| 101 | 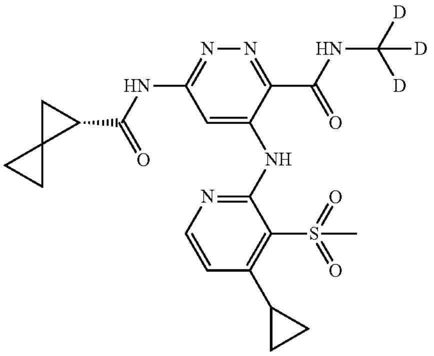 [SMILES: [2H]C([2H])([2H])NC(=O)c1nnc(NC(=O)[C@H]2CC23CC3)cc1Nc1nccc(C2CC2)c1S(C)(=O)=O] | 460.2 | $^1$H-NMR (400 HHz, DMSO-$d_6$, ppm): δ 11.87 (s, 1H), 11.25 (s, 1H), 9.15-9.13 (m, 2H), 8.09 (d, J = 8.0 Hz, 1H), 7.26 (d, J = 8.0 Hz, 1H), 3.29 (s, 3H), 2.49-2.42 (m, 1H), 2.23-2.11 (m, 1H), 1.43-1.37 (m, 2H), 1.17-1.02 (m, 2H), 1.00-0.76 (m, 6H). |
| 102 | 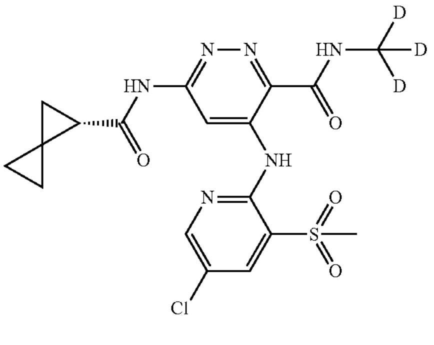 [SMILES: [2H]C([2H])([2H])NC(=O)c1nnc(NC(=O)[C@H]2CC23CC3)cc1Nc1ncc(Cl)cc1S(C)(=O)=O] | 454.0 | $^1$H-NMR (400 HHz, DMSO-$d_6$, ppm): δ 12.16 (s, 1H), 11.27 (s, 1H), 9.38 (s, 1H), 9.21 (s, 1H), 8.69 (d, J = 2.4 Hz, 1H), 8.26 (d, J = 2.4 Hz, 1H), 3.40 (s, 3H), 2.46-2.44 (m, 1H), 1.45-1.35 (m, 2H), 0.95-0.85 (m, 3H), 0.81-0.75 (m, 1H). |

TABLE 1-continued

| Compound No. | Structure | [M + H]$^+$ | $^1$H-NMR and $^{19}$F-NMR; optical rotation |
|---|---|---|---|
| Characterization of representative compounds of the present disclosure | | | |
| 104 | 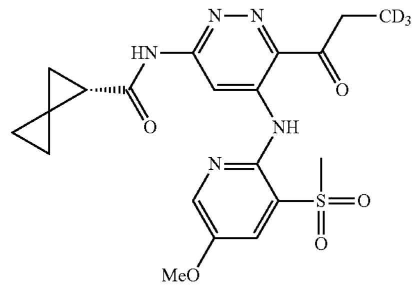 [SMILES: [2H]C([2H])([2H])CC(=O)c1nnc(NC(=O)[C@H]2CC23CC3)cc1Nc1ncc(OC)cc1S(C)(=O)=O] | 449.2 | $^1$H-NMR (400 HHz, DMSO-$d_6$, ppm): δ 11.43 (s, 1H), 11.32 (s, 1H), 9.11 (s, 1H), 8.41 (s, 1H), 7.80 (s, 1H), 3.93 (s, 3H), 3.32-3.27 (m, 5H), 2.47-2.41 (m, 1H), 1.43-1.34 (m, 2H), 0.94-0.69 (m, 4H). |
| 105 | 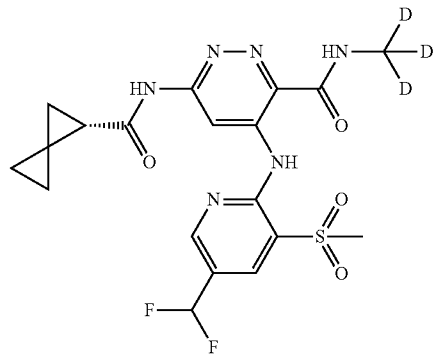 [SMILES: [2H]C([2H])([2H])NC(=O)c1nnc(NC(=O)[C@H]2CC23CC3)cc1Nc1ncc(C(F)F)cc1S(C)(=O)=O] | 470.2 | $^1$H-NMR (400 HHz, DMSO-$d_6$, ppm): δ 12.34 (s, 1H), 11.30 (s, 1H), 9.60 (s, 1H), 9.24 (s, 1H), 8.83 (s, 1H), 8.40 (s, 1H), 7.37-7.09 (m, 1H), 3.43 (s, 3H), 2.48-2.45 (m, 1H), 1.48-1.36 (m, 2H), 0.95-0.75 (m, 4H). $^{19}$F-NMR (376 HHz, DMSO-$d_6$, ppm): δ −110.49 (2F). |
| 106 | 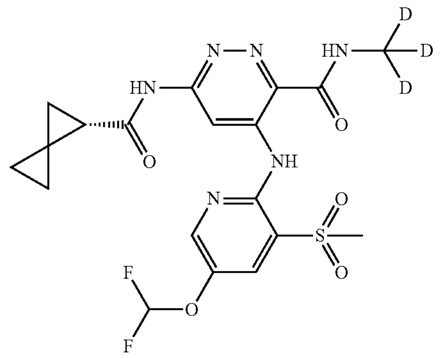 [SMILES: [2H]C([2H])([2H])NC(=O)c1nnc(NC(=O)[C@H]2CC23CC3)cc1Nc1ncc(OC(F)F)cc1S(C)(=O)=O] | 486.1 | $^1$H-NMR (400 HHz, DMSO-$d_6$, ppm): δ 12.14 (s, 1H), 11.25 (s, 1H), 9.38 (s, 1H), 9.21 (s, 1H), 8.58 (d, J = 2.4 Hz, 1H), 8.08 (d, J = 2.8 Hz, 1H), 7.56-7.18 (m, 1H), 3.40 (s, 3H), 2.48-2.44 (m, 1H), 1.48-1.32 (m, 2H), 0.95-0.75 (m, 4H). $^{19}$F-NMR (376 HHz, DMSO-$d_6$, ppm): δ −82.81 (2F). |
| 107 | 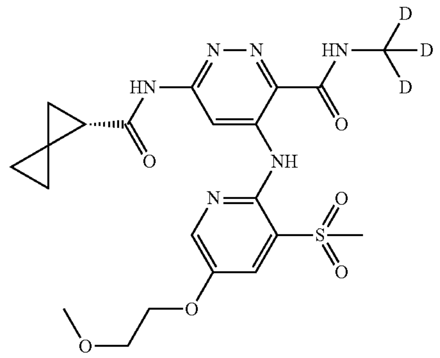 [SMILES: [2H]C([2H])([2H])NC(=O)c1nnc(NC(=O)[C@H]2CC23CC3)cc1Nc1ncc(OCCOC)cc1S(C)(=O)=O] | 494.2 | $^1$H-NMR (400 HHz, DMSO-$d_6$, ppm): δ 11.83 (s, 1H), 11.19 (s, 1H), 9.15 (s, 1H), 9.11 (s, 1H), 8.39 (d, J = 2.8 Hz, 1H), 7.80 (d, J = 2.8 Hz, 1H), 4.28 (t, J = 4.0 Hz, 2H), 3.68 (t, J = 4.0 Hz, 2H), 3.32 (s, 3H), 3.30 (s, 3H), 2.47-2.40 (m, 1H), 1.42-1.31 (m, 2H), 0.93-0.79 (m, 3H), 0.78-0.69 (m, 1H). |

TABLE 1-continued

| Compound No. | Structure | [M + H]+ | $^{1}$H-NMR and $^{19}$F-NMR; optical rotation |
|---|---|---|---|
| | Characterization of representative compounds of the present disclosure | | |
| 108 | 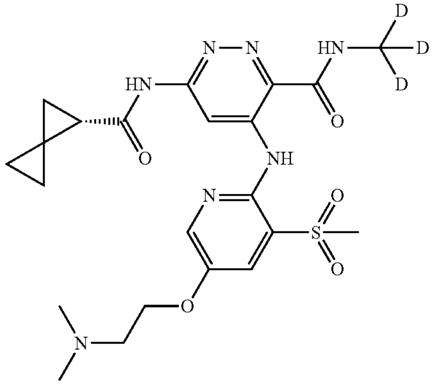 [SMILES: [2H]C([2H])([2H])NC(=O)c1nnc(NC(=O)[C@H]2CC23CC3)cc1Nc1ncc(OCCN(C)C)cc1S(C)(=O)=O] | 507.3 | $^{1}$H-NMR (400 HHz, DMSO-$d_6$, ppm): δ 11.82 (s, 1H), 11.17 (s, 1H), 9.14 (s, 1H), 9.11 (s, 1H), 8.38 (d, J = 2.8 Hz, 1H), 7.79 (d, J = 2.8 Hz, 1H), 4.22 (t, J = 5.6 Hz, 2H), 3.32 (s, 3H), 2.66-2.63 (m, 2H), 2.45-2.41 (m, 1H), 2.22 (s, 6H), 1.41-1.32 (m, 2H), 0.92-0.71 (m, 4H). |
| 110 | 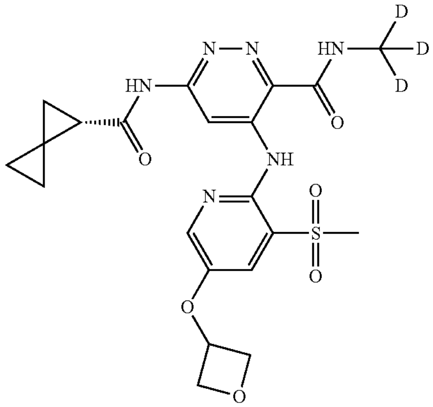 [SMILES: [2H]C([2H])([2H])NC(=O)c1nnc(NC(=O)[C@H]2CC23CC3)cc1Nc1ncc(OC2COC2)cc1S(C)(=O)=O] | 492.2 | $^{1}$H-NMR (400 HHz, DMSO-$d_6$, ppm): δ 11.87 (s, 1H), 11.17 (s, 1H), 9.14 (s, 1H), 9.13 (s, 1H), 8.27 (d, J = 2.8 Hz, 1H), 7.63 (d, J = 2.4 Hz, 1H), 5.58-5.40 (m, 1H), 5.00-4.85 (m, 2H), 4.67-4.46 (m, 2H), 3.33 (s, 3H), 2.46-2.40 (m, 1H), 1.43-1.31 (m, 2H), 0.94-0.79 (m, 3H), 0.78-0.69 (m, 1H). |
| 111 | 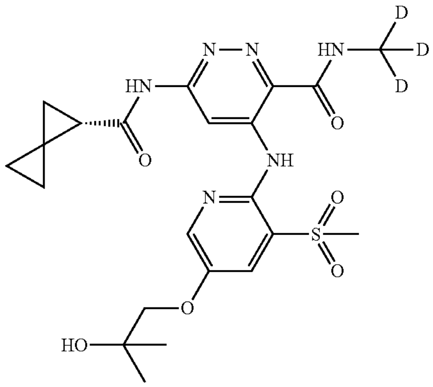 [SMILES: [2H]C([2H])([2H])NC(=O)c1nnc(NC(=O)[C@H]2CC23CC3)cc1Nc1ncc(OCC(C)(C)O)cc1S(C)(=O)=O] | 508.3 | $^{1}$H-NMR (400 HHz, DMSO-$d_6$, ppm): δ 11.82 (s, 1H), 11.16 (s, 1H), 9.12 (s, 2H), 8.38 (d, J = 2.8 Hz, 1H), 7.81 (d, J = 2.8 Hz, 1H), 4.71 (s, 1H), 3.89 (s, 2H), 3.31 (s, 3H), 2.46-2.40 (m, 1H), 1.41-1.32 (m, 2H), 1.21 (s, 6H), 0.92-0.81 (m, 3H), 0.79-0.69 (m, 1H). |

TABLE 1-continued
| Compound No. | Structure | [M + H]+ | $^1$H-NMR and $^{19}$F-NMR; optical rotation |
|---|---|---|---|
| 112 | 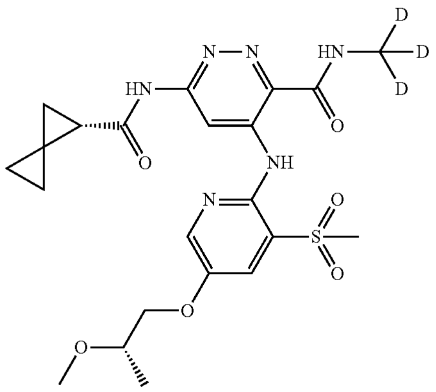 [SMILES: [2H]C([2H])([2H])NC(=O)c1nnc(NC(=O)[C@H]2CC23CC3)cc1Nc1ncc(OC[C@H](C)OC)cc1S(C)(=O)=O] | 508.2 | $^1$H-NMR (400 HHz, DMSO-$d_6$, ppm): δ 11.82 (s, 1H), 11.16 (s, 1H), 9.15-9.10 (m, 2H), 8.39 (d, J = 3.2 Hz, 1H), 7.80 (d, J = 3.2 Hz, 1H), 4.19-4.05 (m, 2H), 3.74-3.63 (m, 1H), 3.32 (s, 3H), 3.31 (s, 3H), 2.47-2.42 (m, 1H), 1.44-1.33 (m, 2H), 1.17 (d, J = 6.4 Hz, 3H), 0.91-0.81 (m, 3H), 0.78-0.71 (m, 1H). |
| 113 | 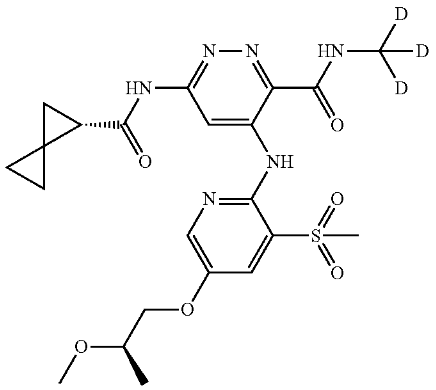 [SMILES: [2H]C([2H])([2H])NC(=O)c1nnc(NC(=O)[C@H]2CC23CC3)cc1Nc1ncc(OC[C@@H](C)OC)cc1S(C)(=O)=O] | 508.2 | $^1$H-NMR (400 HHz, DMSO-$d_6$, ppm): δ 11.83 (s, 1H), 11.16 (s, 1H), 9.13-9.11 (m, 2H), 8.39 (d, J = 3.0 Hz, 1H), 7.80 (d, J = 3.0 Hz, 1H), 4.20-4.04 (m, 2H), 3.79-3.64 (m, 1H), 3.32 (s, 3H), 3.31 (s, 3H), 2.47-2.39 (m, 1H), 1.43-1.31 (m, 2H), 1.17 (d, J = 6.4 Hz, 3H), 0.94-0.80 (m, 3H), 0.79-0.69 (m, 1H). |
| 114 | 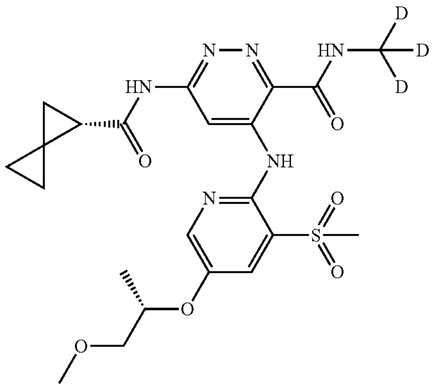 [SMILES: [2H]C([2H])([2H])NC(=O)c1nnc(NC(=O)[C@H]2CC23CC3)cc1Nc1ncc(O[C@@H](C)COC)cc1S(C)(=O)=O] | 508.2 | $^1$H-NMR (400 HHz, DMSO-$d_6$, ppm): δ 11.81 (s, 1H), 11.15 (s, 1H), 9.12 (s, 1H), 9.11 (s, 1H), 8.36 (d, J = 2.8 Hz, 1H), 7.80 (d, J = 2.8 Hz, 1H), 4.78-4.74 (m, 1H), 3.51-3.49 (m, 2H), 3.32 (s, 3H), 3.28 (s, 3H), 2.45-2.42 (m, 1H), 1.40-1.31 (m, 2H), 1.24 (d, J = 6.4 Hz, 3H), 0.90-0.80 (m, 3H), 0.76-0.72 (m, 1H). |

TABLE 1-continued

| Compound No. | Structure | [M + H]$^+$ | $^1$H-NMR and $^{19}$F-NMR; optical rotation |
|---|---|---|---|
| 115 | 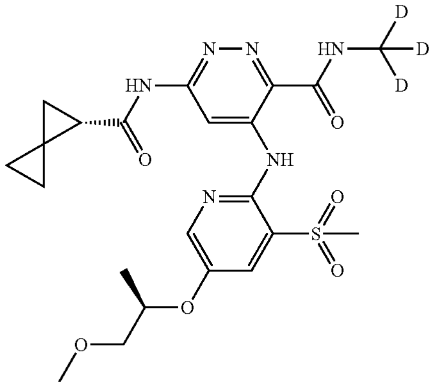 [SMILES: [2H]C([2H])([2H])NC(=O)c1nnc(NC(=O)[C@H]2CC23CC3)cc1Nc1ncc(O[C@H](C)COC)cc1S(C)(=O)=O] | 508.3 | $^1$H-NMR (400 HHz, DMSO-$d_6$, ppm): δ 11.81 (s, 1H), 11.14 (s, 1H), 9.16-9.07 (m, 2H), 8.36 (d, J = 3.2 Hz, 1H), 7.80 (d, J = 3.2 Hz, 1H), 4.80-4.72 (m, 1H), 3.55-3.44 (m, 2H), 3.36 (s, 3H), 3.28 (s, 3H), 2.45-2.41 (m, 1H), 1.40-1.33 (m, 2H), 1.24 (d, J = 6.4 Hz, 3H), 0.93-0.79 (m, 3H), 0.78-0.71 (m, 1H). |
| 116 | 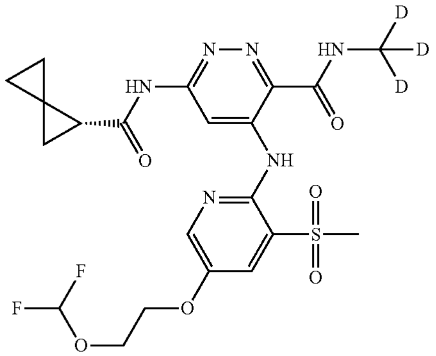 [SMILES: [2H]C([2H])([2H])NC(=O)c1nnc(NC(=O)[C@@H]2CC23CC3)cc1Nc1ncc(OCCOC(F)F)cc1S(C)(=O)=O] | 530.2 | 2 eq formic acid salt, $^1$H-NMR (400 HHz, DMSO-$d_6$, ppm): δ 11.85 (s, 1H), 11.18 (s, 1H), 9.14 (s, 2H), 8.44-8.40 (m, 3H), 7.81 (d, J = 2.8 Hz, 1H), 6.95-6.56 (m, 1H), 4.38-4.35 (m, 2H), 4.19-4.16 (m, 2H), 3.34 (s, 3H), 2.45-2.42 (m, 1H), 1.39-1.34 (m, 2H), 0.90-0.81 (m, 3H), 0.75-0.72 (m, 1H); $^{19}$F-NMR (376 HHz, DMSO-$d_6$, ppm): δ −82.56 (2F). |
| 117 | 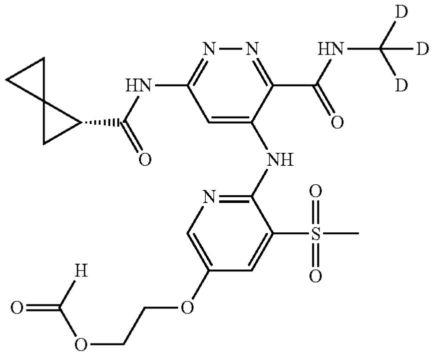 [SMILES: [2H]C([2H])([2H])NC(=O)c1nnc(NC(=O)[C@@H]2CC23CC3)cc1Nc1ncc(OCCOC=O)cc1S(C)(=O)=O] | 508.1 | 1 eq formic acid salt, $^1$H-NMR (400 HHz, DMSO-$d_6$, ppm): δ 11.85 (s, 1H), 11.17 (s, 1H), 9.14 (s, 2H), 8.47 (s, 1H), 8.40 (d, J = 3.2 Hz, 1H), 8.29 (s, 1H), 7.80 (d, J = 2.8 Hz, 1H), 4.46-4.41 (m, 4H), 3.32 (s, 3H), 2.45-2.42 (m, 1H), 1.39-1.35 (m, 2H), 0.90-0.83 (m, 3H), 0.76-0.72 (m, 1H) |
| 118 | 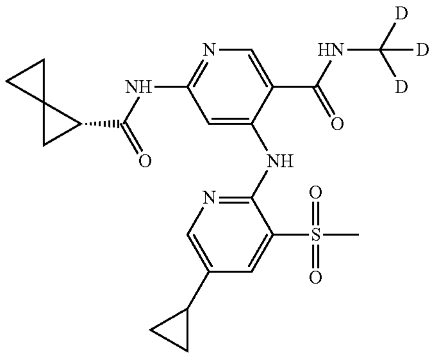 [SMILES: [2H]C([2H])([2H])NC(=O)c1cnc(NC(=O)[C@@H]2CC23CC3)cc1Nc1ncc(C2CC2)cc1S(C)(=O)=O] | 459.2 | $^1$H-NMR (400 HHz, DMSO-$d_6$, ppm): δ 11.35 (s, 1H), 10.60 (s, 1H), 8.87 (s, 1H), 8.60 (s, 1H), 8.52 (s, 1H), 8.40 (d, J = 2.4 Hz, 1H), 7.78 (d, J = 2.8 Hz, 1H), 3.28 (s, 3H), 2.35-2.32 (m, 1H), 2.10-2.04 (m, 1H), 1.35-1.33 (m, 1H), 1.30-1.28 (m, 1H), 1.02-0.98 (m, 2H), 0.87-0.69 (m, 6H). |

TABLE 1-continued

| Characterization of representative compounds of the present disclosure | | | |
|---|---|---|---|
| Compound No. | Structure | [M + H]$^+$ | $^1$H-NMR and $^{19}$F-NMR; optical rotation |
| 119 | 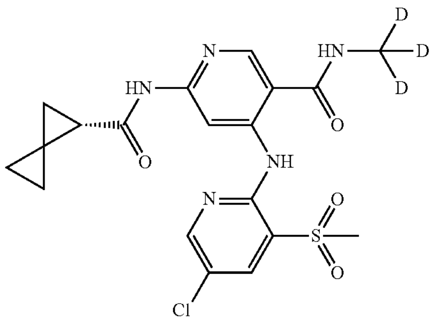 [SMILES: [2H]C([2H])([2H])NC(=O)c1cnc(NC(=O)[C@H]2CC23CC3)cc1Nc1ncc(Cl)cc1S(C)(=O)=O] | 453.1 | $^1$H-NMR (400 HHz, DMSO-d$_6$, ppm): δ 11.54 (s, 1H), 10.65 (s, 1H), 8.87 (s, 1H), 8.78-8.56 (m, 3H), 8.15 (s, 1H), 3.35 (s, 3H), 2.36-2.31 (m, 1H), 1.35-1.29 (m, 2H), 0.88-0.78 (m, 3H), 0.74-0.70 (m, 1H). |
| 121 | 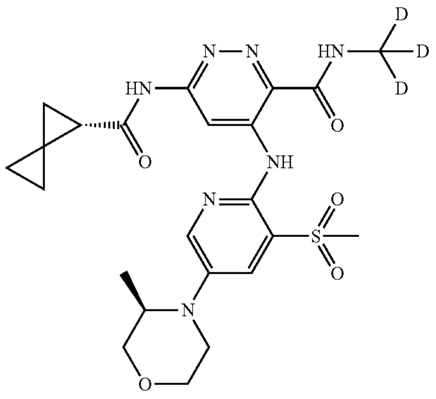 [SMILES: [2H]C([2H])([2H])NC(=O)c1nnc(NC(=O)[C@H]2CC23CC3)cc1Nc1ncc(N2CCOC[C@H]2C)cc1S(C)(=O)=O] | 519.5 | $^1$H-NMR (400 HHz, DMSO-d$_6$, ppm): δ 11.75 (s, 1H), 11.14 (s, 1H), 9.12 (s, 1H), 9.09 (s, 1H), 8.33 (d, J = 2.4 Hz, 1H), 7.67 (d, J = 2.4 Hz, 1H), 4.05-3.85 (m, 2H), 3.78-3.66 (m, 2H), 3.62-3.54 (m, 1H), 3.38-3.34 (m, 1H), 3.31 (s, 3H), 3.18-3.06 (m, 1H), 2.48-2.43 (m, 1H), 1.44-1.32 (m, 2H), 1.07 (d, J = 6.4 Hz, 3H), 0.97-0.62 (m, 4H). |
| 122 | 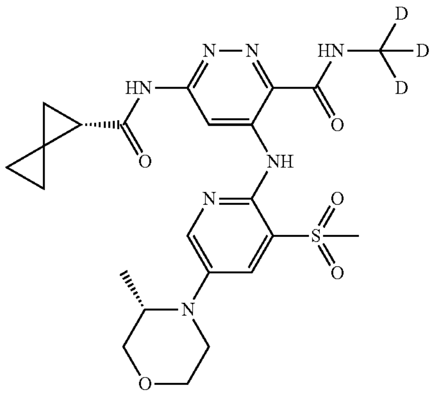 [SMILES: [2H]C([2H])([2H])NC(=O)c1nnc(NC(=O)[C@H]2CC23CC3)cc1Nc1ncc(N2CCOC[C@@H]2C)cc1S(C)(=O)=O] | 519.3 | $^1$H-NMR (400 HHz, DMSO-d$_6$, ppm): δ 11.74 (s, 1H), 11.13 (s, 1H), 9.12 (s, 1H), 9.07 (s, 1H), 8.33 (d, J = 2.8 Hz, 1H), 7.67 (d, J = 2.8 Hz, 1H), 4.05-3.85 (m, 2H), 3.76-3.66 (m, 2H), 3.62-3.54 (m, 1H), 3.38-3.34 (m, 1H), 3.31 (s, 3H), 3.18-3.06 (m, 1H), 2.48-2.43 (m, 1H), 1.43-1.32 (m, 2H), 1.07 (d, J = 6.4 Hz, 3H), 0.94-0.70 (m, 4H). |
| 125 | 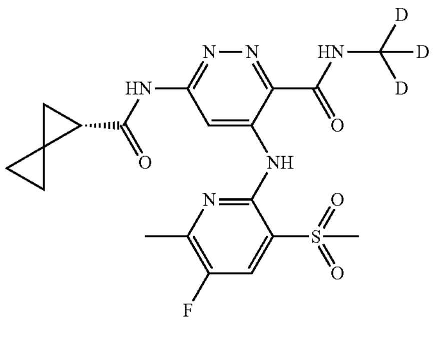 [SMILES: [2H]C([2H])([2H])NC(=O)c1nnc(NC(=O)[C@H]2CC23CC3)cc1Nc1nc(C)c(F)cc1S(C)(=O)=O] | 452.1 | $^1$H-NMR (400 HHz, DMSO-d$_6$, ppm): δ 12.12 (s, 1H), 11.22 (s, 1H), 9.77 (s, 1H), 9.18 (s, 1H), 8.04 (d, J = 8.4 Hz, 1H), 3.37 (s, 3H), 2.57-2.53 (m, 3H), 2.49-2.43 (m, 1H), 1.46-1.37 (m, 2H), 1.00-0.82 (m, 3H), 0.81-0.73 (m, 1H). $^{19}$F-NMR (376 HHz, DMSO-d$_6$, ppm): δ −132.00 (1F). |

TABLE 1-continued

| Characterization of representative compounds of the present disclosure | | | |
|---|---|---|---|
| Compound No. | Structure | [M + H]$^+$ | $^1$H-NMR and $^{19}$F-NMR; optical rotation |
| 127 | 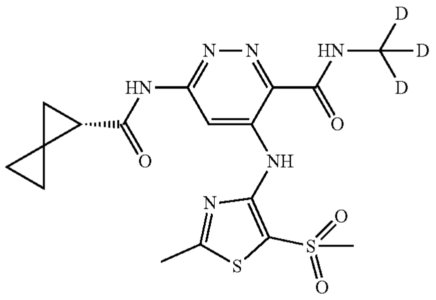 [SMILES: [2H]C([2H])([2H])NC(=O)c1nnc(NC(=O)[C@H]2CC23CC3)cc1Nc1nc(C)sc1S(C)(=O)=O] | 440.0 | $^1$H-NMR (400 HHz, DMSO-$d_6$, ppm): δ 12.20 (s, 1H), 11.25 (s, 1H), 9.35 (s, 1H), 9.23 (s, 1H), 3.43 (s, 3H), 2.80 (s, 3H), 2.56-2.51 (m, 1H), 1.50-1.43 (m, 2H), 0.98-0.83 (m, 4H). |
| 128 | 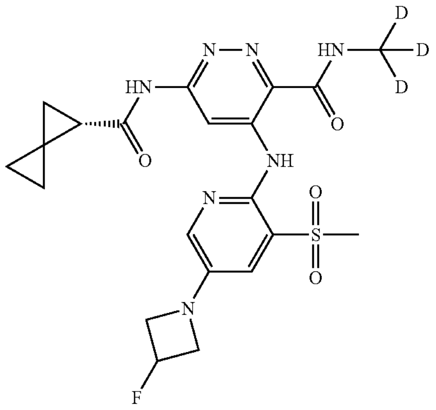 [SMILES: [2H]C([2H])([2H])NC(=O)c1nnc(NC(=O)[C@H]2CC23CC3)cc1Nc1ncc(N2CC(F)C2)cc1S(C)(=O)=O] | 493.1 | $^1$H-NMR (400 HHz, DMSO-$d_6$, ppm): δ 11.69 (s, 1H), 11.11 (s, 1H), 9.10 (s, 1H), 9.02 (s, 1H), 7.98 (d, J = 3.2 Hz, 1H), 7.34 (d, J = 3.2 Hz, 1H), 5.60-5.43 (m, 1H), 4.37-4.27 (m, 2H), 4.13-4.04 (m, 2H), 3.28 (s, 3H), 2.47-2.41 (m, 1H), 1.41-1.34 (m, 2H), 0.91-0.71 (m, 4H). $^{19}$F-NMR (376 HHz, DMSO-$d_6$, ppm): δ −178.90 (1F). |
| 131 | 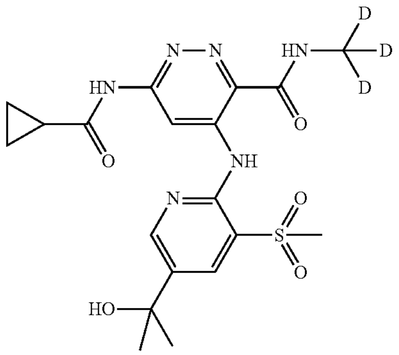 [SMILES: [2H]C([2H])([2H])NC(=O)c1nnc(NC(=O)C2CC2)cc1Nc1ncc(C(C)(C)O)cc1S(C)(=O)=O] | 452.2 | $^1$H-NMR (400 HHz, DMSO-$d_6$, ppm): § 12.08 (s, 1H), 11.42 (s, 1H), 9.50 (s, 1H), 9.19 (s, 1H), 8.67 (d, J = 2.0 Hz, 1H), 8.33 (d, J = 2.0 Hz, 1H), 5.46 (s, 1H), 3.36 (s, 3H), 2.20-2.04 (m, 1H), 1.50 (s, 6H), 0.89-0.85 (m, 4H). |
| 132 | 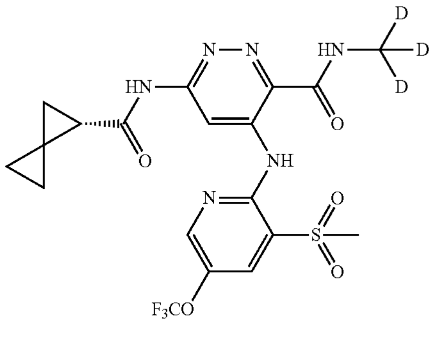 [SMILES: [2H]C([2H])([2H])NC(=O)c1nnc(NC(=O)[C@H]2CC23CC3)cc1Nc1ncc(OC(F)(F)F)cc1S(C)(=O)=O] | 504.1 | $^1$H-NMR (400 HHz, DMSO-$d_6$, ppm): § 12.27 (s, 1H), 11.28 (s, 1H), 9.43 (s, 1H), 9.25 (s, 1H), 8.77 (s, 1H), 8.22 (s, 1H), 3.44 (s, 3H), 2.48-2.45 (m, 1H), 1.47-1.33 (m, 2H), 0.97-0.74 (m, 4H). $^{19}$F-NMR (376 HHz, DMSO-$d_6$, ppm): δ −57.53 (3F). |

TABLE 1-continued

| Characterization of representative compounds of the present disclosure | | | |
|---|---|---|---|
| Compound No. | Structure | $[M + H]^+$ | $^1$H-NMR and $^{19}$F-NMR; optical rotation |
| 133 | 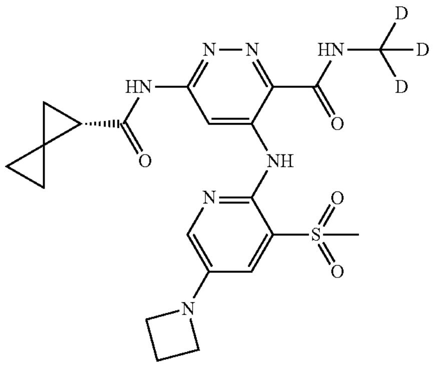 [SMILES: [2H]C([2H])([2H])NC(=O)c1nnc(NC(=O)[C@H]2CC23CC3)cc1Nc1ncc(N2CCC2)cc1S(C)(=O)=O] | 475.2 | $^1$H-NMR (400 HHz, DMSO-$d_6$, ppm): δ 11.64 (s, 1H), 11.11 (s, 1H), 9.10 (s, 1H), 8.96 (s, 1H), 7.89 (d, J = 2.8 Hz, 1H), 7.25 (d, J = 2.8 Hz, 1H), 3.99-3.95 (m, 4H), 4.39-3.27 (s, 3H), 2.50-2.35 (m, 3H), 1.41-1.34 (m, 2H), 0.91-0.84 (m, 3H), 0.78-0.71 (m, 1H). |

HEK-Blue IL-23 STAT3 Reporter Assay

HEK-Blue IL23 cells (InvivoGen catalog #HKB-IL23) are designed for the detection of bioactive IL-23 by monitoring the activation of the STAT3 pathway. They were generated by stably introducing the genes for the human IL-23 receptor, STAT3, and the SEAP (secreted embryonic alkaline phosphatase) reporter gene into human HEK293 cell line.

Briefly, around 50,000 cells in DMEM medium supplemented with 10% heat inactivated FBS (~180 ul) were seeded into each well and incubate for 48 hours at 37° C. with 5% $CO_2$ in air. On day 3, one microliter of compound and 20 ul IL-23 were transferred to the assay plate respectively. The plate was left in the 37° C. incubator overnight. Two microliter of cell supernatant was transferred to a 384-well plate, and 18 ul of resuspended QUANTI-Blue solution was added to each well. SLAP levels were determined using Tecan Spark at $OD_{655}$.

Cells with no IL23 added were used as Low control. Cells stimulated with IL23 were used as High control. Inhibition rate was calculated with the formula of % inhibition=100*(High control−Treated Well)/(High Control−Low control). IL-23 reporter assay inhibition $IC_{50}$ was calculated with the equation of Y=Bottom+(Top-Bottom)/(1+10^((Log $IC_{50}$−X)*HillSlope)).

TABLE 2

| Inhibition of HEK-Blue IL23 Reporter by Representative Compounds | |
|---|---|
| Compound | HEK Blue IL23 $IC_{50}$ (nM) |
| 1 | 3.5 |
| 2 | 4.3 |
| 3 | 7.1 |
| 4 | 39.3 |
| 5 | 1.7 |
| 6 | 18.8 |
| 7 | 14.4 |
| 8 | 2.6 |
| 9 | 51.0 |
| 10 | 1817.0 |
| 11 | 121.0 |
| 12 | 140.0 |
| 13 | 346.4 |
| 14 | 1.3 |

TABLE 2-continued

| Inhibition of HEK-Blue IL23 Reporter by Representative Compounds | |
|---|---|
| Compound | HEK Blue IL23 $IC_{50}$ (nM) |
| 15 | 9.1 |
| 16 | 182.4 |
| 17 | 13.8 |
| 18 | 38.9 |
| 19 | 20.9 |
| 20 | 195.2 |
| 21 | 8.9 |
| 22 | 105.7 |
| 23 | 58.5 |
| 24 | 25.4 |
| 25 | 1000 |
| 26 | 2.3 |
| 27 | 24.2 |
| 28 | 35.1 |
| 29 | 350.2 |
| 30 | 440.4 |
| 31 | >1000 |
| 32 | 5.3 |
| 33 | 0.9 |
| 34 | 548 |
| 35 | 11 |
| 36 | 5.6 |
| 37 | 10.2 |
| 38 | 15.3 |
| 39 | 3.2 |
| 40 | 54.4 |
| 41 | 12.7 |
| 42 | 0.58 |
| 43 | 0.34 |
| 44 | 1.0 |
| 45 | 1.5 |
| 46 | 0.2 |
| 47 | 1.4 |
| 48 | 0.46 |
| 49 | >1000 |
| 50 | 9.3 |
| 51 | 6.2 |
| 52 | 2.5 |
| 53 | 1.9 |
| 54 | 1.5 |
| 55 | 1.5 |
| 56 | 0.3 |
| 57 | 51.7 |
| 58 | 2.7 |
| 59 | 0.4 |
| 60 | 1.7 |
| 61 | 19.9 |

TABLE 2-continued

| Inhibition of HEK-Blue IL23 Reporter by Representative Compounds | |
|---|---|
| Compound | HEK Blue IL23 $IC_{50}$ (nM) |
| 62 | 71.9 |
| 63 | 1.9 |
| 64 | 0.6 |
| 65 | 0.5 |
| 66 | 5.7 |
| 67 | 1.0 |
| 68 | 0.6 |
| 69 | 0.2 |
| 70 | 1.3 |
| 71 | 5.4 |
| 72 | 1.6 |
| 73 | 1.1 |
| 74 | 2.2 |
| 75 | 1.6 |
| 76 | 2.5 |
| 77 | 1.1 |
| 78 | 0.8 |
| 79 | 3.3 |
| 80 | 1.5 |
| 81 | 0.9 |
| 82 | 9.0 |
| 83 | 7.4 |
| 84 | 4.1 |
| 85 | 2.1 |
| 86 | 30.8 |
| 87 | 19.9 |
| 88 | 0.6 |
| 89 | 7.9 |
| 90 | 4.2 |
| 91 | 1000 |
| 92 | 1000 |
| 93 | 13.6 |
| 94 | 137.4 |
| 95 | 19.5 |
| 96 | 189.4 |
| 97 | 1.4 |
| 98 | 187.8 |
| 99 | 15.6 |
| 100 | 2.1 |
| 101 | 11.5 |
| 102 | 3.7 |
| 103 | 5.7 |
| 104 | 119 |
| 105 | 6.7 |
| 106 | 3.6 |
| 107 | 0.8 |
| 108 | 19.5 |
| 109 | 284.2 |
| 110 | 2.7 |
| 111 | 7.5 |
| 112 | 2.7 |
| 113 | 1.2 |
| 114 | 1.0 |
| 115 | 3.5 |
| 116 | 3.0 |
| 117 | 5.7 |
| 118 | 0.6 |
| 119 | 6.2 |
| 120 | 14.7 |
| 121 | 1.2 |
| 122 | 16.1 |
| 123 | 19.8 |
| 124 | 1.9 |
| 125 | 7.3 |
| 126 | 17.4 |
| 127 | 6.4 |
| 128 | 1.0 |
| 129 | 0.4 |
| 130 | 59.9 |
| 131 | 9.0 |
| 132 | 6.5 |
| 133 | 1.2 |

The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound, or a pharmaceutically acceptable salt thereof, wherein the compound is

52

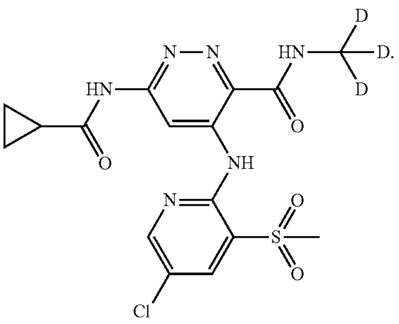

2. A pharmaceutical composition comprising the compound of claim 1, or the pharmaceutically acceptable salt thereof.

* * * * *